(12) United States Patent
Peck et al.

(10) Patent No.: US 12,357,959 B2
(45) Date of Patent: Jul. 15, 2025

(54) HIGHLY ACCURATE DE NOVO POLYNUCLEOTIDE SYNTHESIS

(71) Applicant: Twist Bioscience Corporation, San Francisco, CA (US)

(72) Inventors: Bill James Peck, Santa Clara, CA (US); Mary Noe, San Francisco, CA (US); Stefan Pitsch, Stein am Rhein (CH); Patrick A. Weiss, Daly City, CA (US)

(73) Assignee: Twist Bioscience Corporation, South San Francisco, CA (US)

( * ) Notice: Subject to any disclaimer, the term of this patent is extended or adjusted under 35 U.S.C. 154(b) by 418 days.

(21) Appl. No.: 16/726,073

(22) Filed: Dec. 23, 2019

(65) Prior Publication Data
US 2020/0222875 A1 Jul. 16, 2020

Related U.S. Application Data

(60) Provisional application No. 62/785,015, filed on Dec. 26, 2018.

(51) Int. Cl.
*B01J 19/00* (2006.01)
*C07H 21/04* (2006.01)
(Continued)

(52) U.S. Cl.
CPC .......... *B01J 19/0046* (2013.01); *C07H 21/04* (2013.01); *B01J 2219/00596* (2013.01);
(Continued)

(58) Field of Classification Search
CPC .......... B01J 19/0046; B01J 2219/00596; B01J 2219/00722; C07H 21/00; C07H 21/02; C07H 21/04; C40B 50/14
See application file for complete search history.

(56) References Cited

U.S. PATENT DOCUMENTS

| 3,549,368 A | 12/1970 | Robert et al. |
| 3,920,714 A | 11/1975 | Streck |

(Continued)

FOREIGN PATENT DOCUMENTS

| AU | 3157000 A | 9/2000 |
| CA | 2362939 A1 | 8/2000 |

(Continued)

OTHER PUBLICATIONS

Damha et al., "An improved procedure for derivatization of controlled-pore glass beads for solid-phase oligonucleotide synthesis" Nucleic Acids Research vol. 18 No. 13 pp. 3813-3821 (Year: 1990).*

(Continued)

*Primary Examiner* — Eric Olson
(74) *Attorney, Agent, or Firm* — Bookoff McAndrews, PLLC

(57) ABSTRACT

Methods, systems, compositions, and devices for the manufacturing of high-quality building blocks, such as polynucleotides, are described herein. Processes described herein provide for efficient washing of residual reagents, solvents, or byproducts from previous synthetic steps to allow for the generation of polynucleotides with low error rates. Processes described herein also provide for reduction in deletion rates during chemical nucleic acid synthesis. Further, methods and devices described herein allow for the rapid construction and assembly of large libraries of highly accurate polynucleotides.

22 Claims, 25 Drawing Sheets

(51) Int. Cl.
  *C07C 53/02*    (2006.01)
  *C07C 53/08*    (2006.01)
  *C07C 53/12*    (2006.01)
  *C07C 53/122*   (2006.01)
  *C07C 53/134*   (2006.01)
  *C07D 213/16*   (2006.01)
  *C07D 213/74*   (2006.01)
  *C07D 233/58*   (2006.01)

(52) U.S. Cl.
  CPC ..... *B01J 2219/00722* (2013.01); *C07C 53/02* (2013.01); *C07C 53/08* (2013.01); *C07C 53/12* (2013.01); *C07C 53/122* (2013.01); *C07C 53/134* (2013.01); *C07D 213/16* (2013.01); *C07D 213/74* (2013.01); *C07D 233/58* (2013.01)

(56) References Cited

U.S. PATENT DOCUMENTS

| | | |
|---|---|---|
| 4,123,661 A | 10/1978 | Wolf et al. |
| 4,415,732 A | 11/1983 | Caruthers et al. |
| 4,613,398 A | 9/1986 | Chiong et al. |
| 4,726,877 A | 2/1988 | Fryd et al. |
| 4,808,511 A | 2/1989 | Holmes |
| 4,837,401 A | 6/1989 | Hirose et al. |
| 4,863,557 A | 9/1989 | Kokaku et al. |
| 4,981,797 A | 1/1991 | Jessee et al. |
| 4,988,617 A | 1/1991 | Landegren et al. |
| 5,102,797 A | 4/1992 | Tucker et al. |
| 5,118,605 A | 6/1992 | Urdea |
| 5,137,814 A | 8/1992 | Rashtchian et al. |
| 5,143,854 A | 9/1992 | Pirrung et al. |
| 5,242,794 A | 9/1993 | Whiteley et al. |
| 5,242,974 A | 9/1993 | Holmes |
| 5,288,514 A | 2/1994 | Ellman |
| 5,299,491 A | 4/1994 | Kawada |
| 5,368,823 A | 11/1994 | McGraw et al. |
| 5,384,261 A | 1/1995 | Winkler et al. |
| 5,387,541 A | 2/1995 | Hodge et al. |
| 5,395,753 A | 3/1995 | Prakash |
| 5,431,720 A | 7/1995 | Nagai et al. |
| 5,445,934 A | 8/1995 | Fodor et al. |
| 5,449,754 A | 9/1995 | Nishioka |
| 5,459,039 A | 10/1995 | Modrich et al. |
| 5,474,796 A | 12/1995 | Brennan |
| 5,476,930 A | 12/1995 | Letsinger et al. |
| 5,487,993 A | 1/1996 | Herrnstadt et al. |
| 5,494,810 A | 2/1996 | Barany et al. |
| 5,501,893 A | 3/1996 | Laermer et al. |
| 5,508,169 A | 4/1996 | Deugau et al. |
| 5,510,270 A | 4/1996 | Fodor et al. |
| 5,514,789 A | 5/1996 | Kempe |
| 5,527,681 A | 6/1996 | Holmes |
| 5,530,516 A | 6/1996 | Sheets |
| 5,534,507 A | 7/1996 | Cama et al. |
| 5,556,750 A | 9/1996 | Modrich et al. |
| 5,586,211 A | 12/1996 | Dumitrou et al. |
| 5,641,658 A | 6/1997 | Adams et al. |
| 5,677,195 A | 10/1997 | Winkler et al. |
| 5,679,522 A | 10/1997 | Modrich et al. |
| 5,683,879 A | 11/1997 | Laney et al. |
| 5,688,642 A | 11/1997 | Chrisey et al. |
| 5,700,637 A | 12/1997 | Southern |
| 5,700,642 A | 12/1997 | Monforte et al. |
| 5,702,894 A | 12/1997 | Modrich et al. |
| 5,707,806 A | 1/1998 | Shuber |
| 5,712,124 A | 1/1998 | Walker |
| 5,712,126 A | 1/1998 | Weissman et al. |
| 5,717,085 A | 2/1998 | Lyttle et al. |
| 5,739,386 A | 4/1998 | Holmes |
| 5,750,672 A | 5/1998 | Kempe |
| 5,780,613 A | 7/1998 | Letsinger et al. |
| 5,830,643 A | 11/1998 | Yamamoto et al. |
| 5,830,655 A | 11/1998 | Monforte et al. |
| 5,830,662 A | 11/1998 | Soares et al. |
| 5,834,252 A | 11/1998 | Stemmer et al. |
| 5,843,669 A | 12/1998 | Kaiser et al. |
| 5,843,767 A | 12/1998 | Beattie |
| 5,846,717 A | 12/1998 | Brow et al. |
| 5,854,033 A | 12/1998 | Lizardi |
| 5,858,754 A | 1/1999 | Modrich et al. |
| 5,861,482 A | 1/1999 | Modrich et al. |
| 5,863,801 A | 1/1999 | Southgate et al. |
| 5,869,245 A | 2/1999 | Yeung |
| 5,877,280 A | 3/1999 | Wetmur |
| 5,882,496 A | 3/1999 | Northrup et al. |
| 5,922,539 A | 7/1999 | Modrich et al. |
| 5,922,593 A | 7/1999 | Livingston |
| 5,928,907 A | 7/1999 | Woudenberg et al. |
| 5,962,272 A | 10/1999 | Chenchik et al. |
| 5,976,842 A | 11/1999 | Wurst |
| 5,976,846 A | 11/1999 | Passmore et al. |
| 5,989,872 A | 11/1999 | Luo et al. |
| 5,994,069 A | 11/1999 | Hall et al. |
| 6,001,567 A | 12/1999 | Brow et al. |
| 6,008,031 A | 12/1999 | Modrich et al. |
| 6,013,440 A | 1/2000 | Lipshutz et al. |
| 6,015,674 A | 1/2000 | Woudenberg et al. |
| 6,017,434 A | 1/2000 | Simpson et al. |
| 6,020,481 A | 2/2000 | Benson et al. |
| 6,027,898 A | 2/2000 | Gjerde et al. |
| 6,028,189 A | 2/2000 | Blanchard |
| 6,028,198 A | 2/2000 | Liu et al. |
| 6,040,138 A | 3/2000 | Lockhart et al. |
| 6,077,674 A | 6/2000 | Schleifer et al. |
| 6,087,482 A | 7/2000 | Teng et al. |
| 6,090,543 A | 7/2000 | Prudent et al. |
| 6,090,606 A | 7/2000 | Kaiser et al. |
| 6,103,474 A | 8/2000 | Dellinger et al. |
| 6,107,038 A | 8/2000 | Choudhary et al. |
| 6,110,682 A | 8/2000 | Dellinger et al. |
| 6,114,115 A | 9/2000 | Wagner, Jr. |
| 6,130,045 A | 10/2000 | Wurst et al. |
| 6,132,997 A | 10/2000 | Shannon |
| 6,136,568 A | 10/2000 | Hiatt et al. |
| 6,171,797 B1 | 1/2001 | Perbost |
| 6,180,351 B1 | 1/2001 | Cattell |
| 6,201,112 B1 | 3/2001 | Ach |
| 6,218,118 B1 | 4/2001 | Sampson et al. |
| 6,221,653 B1 | 4/2001 | Caren et al. |
| 6,222,030 B1 | 4/2001 | Dellinger et al. |
| 6,232,072 B1 | 5/2001 | Fisher |
| 6,235,483 B1 | 5/2001 | Wolber et al. |
| 6,242,266 B1 | 6/2001 | Schleifer et al. |
| 6,248,877 B1 | 6/2001 | Bonner et al. |
| 6,251,588 B1 | 6/2001 | Shannon et al. |
| 6,251,595 B1 | 6/2001 | Gordon et al. |
| 6,251,685 B1 | 6/2001 | Dorsel et al. |
| 6,258,454 B1 | 7/2001 | Lefkowitz et al. |
| 6,262,490 B1 | 7/2001 | Hsu et al. |
| 6,274,725 B1 | 8/2001 | Sanghvi et al. |
| 6,284,465 B1 | 9/2001 | Wolber |
| 6,287,776 B1 | 9/2001 | Hefti |
| 6,287,824 B1 | 9/2001 | Lizardi |
| 6,297,017 B1 | 10/2001 | Schmidt et al. |
| 6,300,137 B1 | 10/2001 | Earhart et al. |
| 6,306,599 B1 | 10/2001 | Perbost |
| 6,309,822 B1 | 10/2001 | Fodor et al. |
| 6,309,828 B1 | 10/2001 | Schleifer et al. |
| 6,312,911 B1 | 11/2001 | Bancroft et al. |
| 6,319,674 B1 | 11/2001 | Fulcrand et al. |
| 6,323,043 B1 | 11/2001 | Caren et al. |
| 6,329,210 B1 | 12/2001 | Schleifer |
| 6,346,423 B1 | 2/2002 | Schembri |
| 6,365,355 B1 | 4/2002 | McCutchen-Maloney |
| 6,372,483 B2 | 4/2002 | Schleifer et al. |
| 6,375,903 B1 | 4/2002 | Cerrina et al. |
| 6,376,285 B1 | 4/2002 | Joyner et al. |
| 6,384,210 B1 | 5/2002 | Blanchard |
| 6,387,636 B1 | 5/2002 | Perbost et al. |
| 6,399,394 B1 | 6/2002 | Dahm et al. |
| 6,399,516 B1 | 6/2002 | Ayon |

(56) References Cited

U.S. PATENT DOCUMENTS

| | | |
|---|---|---|
| 6,403,314 B1 | 6/2002 | Lange et al. |
| 6,406,849 B1 | 6/2002 | Dorsel et al. |
| 6,406,851 B1 | 6/2002 | Bass |
| 6,408,308 B1 | 6/2002 | Maslyn et al. |
| 6,419,883 B1 | 7/2002 | Blanchard |
| 6,428,957 B1 | 8/2002 | Delenstarr |
| 6,440,669 B1 | 8/2002 | Bass et al. |
| 6,444,268 B2 | 9/2002 | Lefkowitz et al. |
| 6,446,642 B1 | 9/2002 | Caren et al. |
| 6,446,682 B1 | 9/2002 | Viken |
| 6,451,998 B1 | 9/2002 | Perbost |
| 6,458,526 B1 | 10/2002 | Schembri et al. |
| 6,458,535 B1 | 10/2002 | Hall et al. |
| 6,458,583 B1 | 10/2002 | Bruhn et al. |
| 6,461,812 B2 | 10/2002 | Barth et al. |
| 6,461,816 B1 | 10/2002 | Wolber et al. |
| 6,469,156 B1 | 10/2002 | Schafer et al. |
| 6,472,147 B1 | 10/2002 | Janda et al. |
| 6,492,107 B1 | 12/2002 | Kauffman et al. |
| 6,518,056 B2 | 2/2003 | Schembri et al. |
| 6,521,427 B1 | 2/2003 | Evans |
| 6,521,453 B1 | 2/2003 | Crameri et al. |
| 6,555,357 B1 | 4/2003 | Kaiser et al. |
| 6,558,908 B2 | 5/2003 | Wolber et al. |
| 6,562,611 B1 | 5/2003 | Kaiser et al. |
| 6,566,495 B1 | 5/2003 | Fodor et al. |
| 6,582,908 B2 | 6/2003 | Fodor et al. |
| 6,582,938 B1 | 6/2003 | Su et al. |
| 6,586,211 B1 | 7/2003 | Staehler et al. |
| 6,587,579 B1 | 7/2003 | Bass |
| 6,589,739 B2 | 7/2003 | Fisher |
| 6,599,693 B1 | 7/2003 | Webb |
| 6,602,472 B1 | 8/2003 | Zimmermann et al. |
| 6,610,978 B2 | 8/2003 | Yin et al. |
| 6,613,513 B1 | 9/2003 | Parce et al. |
| 6,613,523 B2 | 9/2003 | Fischer |
| 6,613,560 B1 | 9/2003 | Tso et al. |
| 6,613,893 B1 | 9/2003 | Webb |
| 6,621,076 B1 | 9/2003 | Van et al. |
| 6,630,581 B2 | 10/2003 | Dellinger et al. |
| 6,632,641 B1 | 10/2003 | Brennan et al. |
| 6,635,226 B1 | 10/2003 | Tso et al. |
| 6,642,373 B2 | 11/2003 | Manoharan et al. |
| 6,649,348 B2 | 11/2003 | Bass et al. |
| 6,660,338 B1 | 12/2003 | Hargreaves |
| 6,664,112 B2 | 12/2003 | Mulligan et al. |
| 6,670,127 B2 | 12/2003 | Evans |
| 6,670,461 B1 | 12/2003 | Wengel et al. |
| 6,673,552 B2 | 1/2004 | Frey |
| 6,682,702 B2 | 1/2004 | Barth et al. |
| 6,689,319 B1 | 2/2004 | Fisher et al. |
| 6,692,917 B2 | 2/2004 | Neri et al. |
| 6,702,256 B2 | 3/2004 | Killeen et al. |
| 6,706,471 B1 | 3/2004 | Brow et al. |
| 6,706,875 B1 | 3/2004 | Goldberg et al. |
| 6,709,841 B2 | 3/2004 | Short |
| 6,709,852 B1 | 3/2004 | Bloom et al. |
| 6,709,854 B2 | 3/2004 | Donahue et al. |
| 6,713,262 B2 | 3/2004 | Gillibolian et al. |
| 6,716,629 B2 | 4/2004 | Hess et al. |
| 6,716,634 B1 | 4/2004 | Myerson |
| 6,723,509 B2 | 4/2004 | Ach |
| 6,728,129 B2 | 4/2004 | Lindsey et al. |
| 6,743,585 B2 | 6/2004 | Dellinger et al. |
| 6,753,145 B2 | 6/2004 | Holcomb et al. |
| 6,768,005 B2 | 7/2004 | Mellor et al. |
| 6,770,748 B2 | 8/2004 | Imanishi et al. |
| 6,770,892 B2 | 8/2004 | Corson et al. |
| 6,773,676 B2 | 8/2004 | Schembri |
| 6,773,888 B2 | 8/2004 | Li et al. |
| 6,780,982 B2 | 8/2004 | Lyamichev et al. |
| 6,787,308 B2 | 9/2004 | Balasubramanian et al. |
| 6,789,965 B2 | 9/2004 | Barth et al. |
| 6,790,620 B2 | 9/2004 | Bass et al. |
| 6,794,499 B2 | 9/2004 | Wengel et al. |
| 6,796,634 B2 | 9/2004 | Caren et al. |
| 6,800,439 B1 | 10/2004 | McGall et al. |
| 6,814,846 B1 | 11/2004 | Berndt |
| 6,815,218 B1 | 11/2004 | Jacobson et al. |
| 6,824,866 B1 | 11/2004 | Glazer et al. |
| 6,830,890 B2 | 12/2004 | Lockhart et al. |
| 6,833,246 B2 | 12/2004 | Balasubramanian |
| 6,833,450 B1 | 12/2004 | McGall et al. |
| 6,835,938 B2 | 12/2004 | Ghosh et al. |
| 6,838,888 B2 | 1/2005 | Peck |
| 6,841,131 B2 | 1/2005 | Zimmermann et al. |
| 6,845,968 B2 | 1/2005 | Killeen et al. |
| 6,846,454 B2 | 1/2005 | Peck |
| 6,846,922 B1 | 1/2005 | Manoharan et al. |
| 6,852,850 B2 | 2/2005 | Myerson et al. |
| 6,858,720 B2 | 2/2005 | Myerson et al. |
| 6,879,915 B2 | 4/2005 | Cattell |
| 6,880,576 B2 | 4/2005 | Karp et al. |
| 6,884,580 B2 | 4/2005 | Caren et al. |
| 6,887,715 B2 | 5/2005 | Schembri |
| 6,890,723 B2 | 5/2005 | Perbost et al. |
| 6,890,760 B1 | 5/2005 | Webb |
| 6,893,816 B1 | 5/2005 | Beattie |
| 6,897,023 B2 | 5/2005 | Fu et al. |
| 6,900,047 B2 | 5/2005 | Bass |
| 6,900,048 B2 | 5/2005 | Perbost |
| 6,911,611 B2 | 6/2005 | Wong et al. |
| 6,914,229 B2 | 7/2005 | Corson et al. |
| 6,916,113 B2 | 7/2005 | De et al. |
| 6,916,633 B1 | 7/2005 | Shannon |
| 6,919,181 B2 | 7/2005 | Hargreaves |
| 6,927,029 B2 | 8/2005 | Lefkowitz et al. |
| 6,929,951 B2 | 8/2005 | Corson et al. |
| 6,936,472 B2 | 8/2005 | Earhart et al. |
| 6,938,476 B2 | 9/2005 | Chesk |
| 6,939,673 B2 | 9/2005 | Bass et al. |
| 6,943,036 B2 | 9/2005 | Bass |
| 6,946,285 B2 | 9/2005 | Bass |
| 6,950,756 B2 | 9/2005 | Kincaid |
| 6,951,719 B1 | 10/2005 | Dupret et al. |
| 6,958,119 B2 | 10/2005 | Yin et al. |
| 6,960,464 B2 | 11/2005 | Jessee et al. |
| 6,969,449 B2 | 11/2005 | Maher et al. |
| 6,969,488 B2 | 11/2005 | Bridgham et al. |
| 6,976,384 B2 | 12/2005 | Hobbs et al. |
| 6,977,223 B2 | 12/2005 | George et al. |
| 6,987,263 B2 | 1/2006 | Hobbs et al. |
| 6,989,267 B2 | 1/2006 | Kim et al. |
| 6,991,922 B2 | 1/2006 | Dupret et al. |
| 7,008,037 B2 | 3/2006 | Caren et al. |
| 7,025,324 B1 | 4/2006 | Slocum et al. |
| 7,026,124 B2 | 4/2006 | Barth et al. |
| 7,027,930 B2 | 4/2006 | Cattell |
| 7,028,536 B2 | 4/2006 | Karp et al. |
| 7,029,854 B2 | 4/2006 | Collins et al. |
| 7,034,290 B2 | 4/2006 | Lu et al. |
| 7,041,445 B2 | 5/2006 | Chenchik et al. |
| 7,045,289 B2 | 5/2006 | Allawi et al. |
| 7,051,574 B2 | 5/2006 | Peck |
| 7,052,841 B2 | 5/2006 | Delenstarr |
| 7,062,385 B2 | 6/2006 | White et al. |
| 7,064,197 B1 | 6/2006 | Rabbani et al. |
| 7,070,932 B2 | 7/2006 | Leproust et al. |
| 7,075,161 B2 | 7/2006 | Barth |
| 7,078,167 B2 | 7/2006 | Delenstarr et al. |
| 7,078,505 B2 * | 7/2006 | Bass ............... C03C 17/002 536/23.1 |
| 7,094,537 B2 | 8/2006 | Leproust et al. |
| 7,097,974 B1 | 8/2006 | Stahler et al. |
| 7,101,508 B2 | 9/2006 | Thompson et al. |
| 7,101,986 B2 | 9/2006 | Dellinger et al. |
| 7,105,295 B2 | 9/2006 | Bass et al. |
| 7,115,423 B1 | 10/2006 | Mitchell |
| 7,122,303 B2 | 10/2006 | Delenstarr et al. |
| 7,122,364 B1 | 10/2006 | Lyamichev et al. |
| 7,125,488 B2 | 10/2006 | Li |
| 7,125,523 B2 | 10/2006 | Sillman |
| 7,128,876 B2 | 10/2006 | Yin et al. |
| 7,129,075 B2 | 10/2006 | Gerard et al. |

(56) References Cited

U.S. PATENT DOCUMENTS

| | | |
|---|---|---|
| 7,135,565 B2 | 11/2006 | Dellinger et al. |
| 7,138,062 B2 | 11/2006 | Yin et al. |
| 7,141,368 B2 | 11/2006 | Fisher et al. |
| 7,141,807 B2 | 11/2006 | Joyce et al. |
| 7,147,362 B2 | 12/2006 | Caren et al. |
| 7,150,982 B2 | 12/2006 | Allawi et al. |
| 7,153,689 B2 | 12/2006 | Tolosko et al. |
| 7,163,660 B2 | 1/2007 | Lehmann |
| 7,166,258 B2 | 1/2007 | Bass et al. |
| 7,179,659 B2 | 2/2007 | Stolowitz et al. |
| 7,183,406 B2 | 2/2007 | Belshaw et al. |
| 7,192,710 B2 | 3/2007 | Gellibolian et al. |
| 7,193,077 B2 | 3/2007 | Dellinger et al. |
| 7,195,872 B2 | 3/2007 | Agrawal et al. |
| 7,198,939 B2 | 4/2007 | Dorsel et al. |
| 7,202,264 B2 | 4/2007 | Ravikumar et al. |
| 7,202,358 B2 | 4/2007 | Hargreaves |
| 7,205,128 B2 | 4/2007 | Ilsley et al. |
| 7,205,399 B1 | 4/2007 | Vargeese et al. |
| 7,205,400 B2 | 4/2007 | Webb |
| 7,206,439 B2 | 4/2007 | Zhou et al. |
| 7,208,322 B2 | 4/2007 | Stolowitz et al. |
| 7,217,522 B2 | 5/2007 | Brenner |
| 7,220,573 B2 | 5/2007 | Shea et al. |
| 7,221,785 B2 | 5/2007 | Curry et al. |
| 7,226,862 B2 | 6/2007 | Staehler et al. |
| 7,227,017 B2 | 6/2007 | Mellor et al. |
| 7,229,497 B2 | 6/2007 | Stott et al. |
| 7,247,337 B1 | 7/2007 | Leproust et al. |
| 7,247,497 B2 | 7/2007 | Dahm et al. |
| 7,252,938 B2 | 8/2007 | Leproust et al. |
| 7,269,518 B2 | 9/2007 | Corson |
| 7,271,258 B2 | 9/2007 | Dellinger et al. |
| 7,276,336 B1 | 10/2007 | Webb et al. |
| 7,276,378 B2 | 10/2007 | Myerson |
| 7,276,599 B2 | 10/2007 | Moore et al. |
| 7,282,183 B2 | 10/2007 | Peck |
| 7,282,332 B2 | 10/2007 | Caren et al. |
| 7,282,705 B2 | 10/2007 | Brennen |
| 7,291,471 B2 | 11/2007 | Sampson et al. |
| 7,302,348 B2 | 11/2007 | Ghosh et al. |
| 7,306,917 B2 | 12/2007 | Prudent et al. |
| 7,314,599 B2 | 1/2008 | Roitman et al. |
| 7,323,320 B2 | 1/2008 | Oleinikov |
| 7,344,831 B2 | 3/2008 | Wolber et al. |
| 7,348,144 B2 | 3/2008 | Minor |
| 7,351,379 B2 | 4/2008 | Schleifer |
| 7,353,116 B2 | 4/2008 | Webb et al. |
| 7,361,906 B2 | 4/2008 | Ghosh et al. |
| 7,364,896 B2 | 4/2008 | Schembri |
| 7,368,550 B2 | 5/2008 | Dellinger et al. |
| 7,371,348 B2 | 5/2008 | Schleifer et al. |
| 7,371,519 B2 | 5/2008 | Wolber et al. |
| 7,371,580 B2 | 5/2008 | Yakhini et al. |
| 7,372,982 B2 | 5/2008 | Le |
| 7,384,746 B2 | 6/2008 | Lyamichev et al. |
| 7,385,050 B2 | 6/2008 | Dellinger et al. |
| 7,390,457 B2 | 6/2008 | Schembri |
| 7,393,665 B2 | 7/2008 | Brenner |
| 7,396,676 B2 | 7/2008 | Robotti et al. |
| 7,399,844 B2 | 7/2008 | Sampson et al. |
| 7,402,279 B2 | 7/2008 | Schembri |
| 7,411,061 B2 | 8/2008 | Myerson et al. |
| 7,413,709 B2 | 8/2008 | Roitman et al. |
| 7,417,139 B2 | 8/2008 | Dellinger et al. |
| 7,422,911 B2 | 9/2008 | Schembri |
| 7,427,679 B2 | 9/2008 | Dellinger et al. |
| 7,432,048 B2 | 10/2008 | Neri et al. |
| 7,435,810 B2 | 10/2008 | Myerson et al. |
| 7,439,272 B2 | 10/2008 | Xu |
| 7,476,709 B2 | 1/2009 | Moody et al. |
| 7,482,118 B2 | 1/2009 | Allawi et al. |
| 7,488,607 B2 | 2/2009 | Tom-Moy et al. |
| 7,504,213 B2 | 3/2009 | Sana et al. |
| 7,514,369 B2 | 4/2009 | Li et al. |
| 7,517,979 B2 | 4/2009 | Wolber |
| 7,524,942 B2 | 4/2009 | Wang et al. |
| 7,524,950 B2 | 4/2009 | Dellinger et al. |
| 7,527,928 B2 | 5/2009 | Neri et al. |
| 7,531,303 B2 | 5/2009 | Dorsel et al. |
| 7,534,561 B2 | 5/2009 | Sana et al. |
| 7,534,563 B2 | 5/2009 | Hargreaves |
| 7,537,936 B2 | 5/2009 | Dahm et al. |
| 7,541,145 B2 | 6/2009 | Prudent et al. |
| 7,544,473 B2 | 6/2009 | Brenner |
| 7,556,919 B2 | 7/2009 | Chenchik et al. |
| 7,563,600 B2 | 7/2009 | Oleinikov |
| 7,572,585 B2 | 8/2009 | Wang |
| 7,572,907 B2 | 8/2009 | Dellinger et al. |
| 7,572,908 B2 | 8/2009 | Dellinger et al. |
| 7,585,970 B2 | 9/2009 | Dellinger et al. |
| 7,588,889 B2 | 9/2009 | Wolber et al. |
| 7,595,350 B2 | 9/2009 | Xu |
| 7,604,941 B2 | 10/2009 | Jacobson |
| 7,604,996 B1 | 10/2009 | Stuelpnagel et al. |
| 7,608,396 B2 | 10/2009 | Delenstarr |
| 7,618,777 B2 | 11/2009 | Myerson et al. |
| 7,629,120 B2 | 12/2009 | Bennett et al. |
| 7,635,772 B2 | 12/2009 | McCormac |
| 7,648,832 B2 | 1/2010 | Jessee et al. |
| 7,651,762 B2 | 1/2010 | Xu et al. |
| 7,659,069 B2 | 2/2010 | Belyaev et al. |
| 7,678,542 B2 | 3/2010 | Lyamichev et al. |
| 7,682,809 B2 | 3/2010 | Sampson |
| 7,709,197 B2 | 5/2010 | Drmanac |
| 7,718,365 B2 | 5/2010 | Wang |
| 7,718,786 B2 | 5/2010 | Dupret et al. |
| 7,723,077 B2 | 5/2010 | Young et al. |
| 7,737,088 B1 | 6/2010 | Stahler et al. |
| 7,737,089 B2 | 6/2010 | Guimil et al. |
| 7,741,463 B2 | 6/2010 | Gormley et al. |
| 7,749,701 B2 | 7/2010 | Leproust et al. |
| 7,759,471 B2 | 7/2010 | Dellinger et al. |
| 7,776,021 B2 | 8/2010 | Borenstein et al. |
| 7,776,532 B2 | 8/2010 | Gibson et al. |
| 7,790,369 B2 | 9/2010 | Stahler et al. |
| 7,790,387 B2 | 9/2010 | Dellinger et al. |
| 7,807,356 B2 | 10/2010 | Sampson et al. |
| 7,807,806 B2 | 10/2010 | Allawi et al. |
| 7,811,753 B2 | 10/2010 | Eshoo |
| 7,816,079 B2 | 10/2010 | Fischer |
| 7,820,387 B2 | 10/2010 | Neri et al. |
| 7,829,314 B2 | 11/2010 | Prudent et al. |
| 7,855,281 B2 | 12/2010 | Dellinger et al. |
| 7,862,999 B2 | 1/2011 | Zheng et al. |
| 7,867,782 B2 | 1/2011 | Barth |
| 7,875,463 B2 | 1/2011 | Adaskin et al. |
| 7,879,541 B2 | 2/2011 | Kincaid |
| 7,879,580 B2 | 2/2011 | Carr et al. |
| 7,894,998 B2 | 2/2011 | Kincaid |
| 7,919,239 B2 | 4/2011 | Wang |
| 7,919,308 B2 | 4/2011 | Schleifer |
| 7,927,797 B2 | 4/2011 | Nobile et al. |
| 7,927,838 B2 | 4/2011 | Shannon |
| 7,932,025 B2 | 4/2011 | Carr et al. |
| 7,932,070 B2 | 4/2011 | Hogrefe et al. |
| 7,935,800 B2 | 5/2011 | Allawi et al. |
| 7,939,645 B2 | 5/2011 | Borns |
| 7,943,046 B2 | 5/2011 | Martosella et al. |
| 7,943,358 B2 | 5/2011 | Hogrefe et al. |
| 7,960,157 B2 | 6/2011 | Borns |
| 7,977,119 B2 | 7/2011 | Kronick et al. |
| 7,979,215 B2 | 7/2011 | Sampas |
| 7,998,437 B2 | 8/2011 | Berndt et al. |
| 7,999,087 B2 | 8/2011 | Dellinger et al. |
| 8,021,842 B2 | 9/2011 | Brenner |
| 8,021,844 B2 | 9/2011 | Wang |
| 8,034,917 B2 | 10/2011 | Yamada |
| 8,036,835 B2 | 10/2011 | Sampas et al. |
| 8,048,664 B2 | 11/2011 | Guan et al. |
| 8,053,191 B2 | 11/2011 | Blake |
| 8,058,001 B2 | 11/2011 | Crameri et al. |
| 8,058,004 B2 | 11/2011 | Oleinikov |
| 8,058,055 B2 | 11/2011 | Barrett et al. |

(56) References Cited

U.S. PATENT DOCUMENTS

| | | |
|---|---|---|
| 8,063,184 B2 | 11/2011 | Allawi et al. |
| 8,067,556 B2 | 11/2011 | Hogrefe et al. |
| 8,073,626 B2 | 12/2011 | Troup et al. |
| 8,076,064 B2 | 12/2011 | Wang |
| 8,076,152 B2 | 12/2011 | Robotti |
| 8,097,711 B2 | 1/2012 | Timar et al. |
| 8,137,936 B2 | 3/2012 | Macevicz |
| 8,148,068 B2 | 4/2012 | Brenner |
| 8,154,729 B2 | 4/2012 | Baldo et al. |
| 8,168,385 B2 | 5/2012 | Brenner |
| 8,168,388 B2 | 5/2012 | Gormley et al. |
| 8,173,368 B2 | 5/2012 | Staehler et al. |
| 8,182,991 B1 | 5/2012 | Kaiser et al. |
| 8,194,244 B2 | 6/2012 | Wang et al. |
| 8,198,071 B2 | 6/2012 | Goshoo et al. |
| 8,202,983 B2 | 6/2012 | Dellinger et al. |
| 8,202,985 B2 | 6/2012 | Dellinger et al. |
| 8,206,952 B2 | 6/2012 | Carr et al. |
| 8,213,015 B2 | 7/2012 | Kraiczek et al. |
| 8,242,258 B2 | 8/2012 | Dellinger et al. |
| 8,247,221 B2 | 8/2012 | Fawcett et al. |
| 8,263,335 B2 | 9/2012 | Carr et al. |
| 8,268,605 B2 | 9/2012 | Sorge et al. |
| 8,283,148 B2 | 10/2012 | Sorge et al. |
| 8,288,093 B2 | 10/2012 | Hall et al. |
| 8,298,767 B2 | 10/2012 | Brenner et al. |
| 8,304,273 B2 | 11/2012 | Stellacci et al. |
| 8,309,307 B2 | 11/2012 | Barrett et al. |
| 8,309,706 B2 | 11/2012 | Dellinger et al. |
| 8,309,710 B2 | 11/2012 | Sierzchala et al. |
| 8,314,220 B2 | 11/2012 | Mullinax et al. |
| 8,318,433 B2 | 11/2012 | Brenner |
| 8,318,479 B2 | 11/2012 | Domansky et al. |
| 8,357,489 B2 | 1/2013 | Chua et al. |
| 8,357,490 B2 | 1/2013 | Froehlich et al. |
| 8,367,016 B2 | 2/2013 | Quan et al. |
| 8,367,335 B2 | 2/2013 | Staehler et al. |
| 8,380,441 B2 | 2/2013 | Webb et al. |
| 8,383,338 B2 | 2/2013 | Kitzman et al. |
| 8,415,138 B2 | 4/2013 | Leproust |
| 8,435,736 B2 | 5/2013 | Gibson et al. |
| 8,445,205 B2 | 5/2013 | Brenner |
| 8,445,206 B2 | 5/2013 | Bergmann et al. |
| 8,470,996 B2 | 6/2013 | Brenner |
| 8,476,018 B2 | 7/2013 | Brenner |
| 8,476,598 B1 | 7/2013 | Pralle et al. |
| 8,481,292 B2 | 7/2013 | Casbon et al. |
| 8,481,309 B2 | 7/2013 | Zhang et al. |
| 8,491,561 B2 | 7/2013 | Borenstein et al. |
| 8,497,069 B2 | 7/2013 | Hutchison et al. |
| 8,500,979 B2 | 8/2013 | Elibol et al. |
| 8,501,454 B2 | 8/2013 | Liu et al. |
| 8,507,226 B2 | 8/2013 | Carr et al. |
| 8,507,239 B2 | 8/2013 | Lubys et al. |
| 8,507,272 B2 | 8/2013 | Zhang et al. |
| 8,530,197 B2 | 9/2013 | Li et al. |
| 8,552,174 B2 | 10/2013 | Dellinger et al. |
| 8,563,478 B2 | 10/2013 | Gormley et al. |
| 8,569,046 B2 | 10/2013 | Love et al. |
| 8,577,621 B2 | 11/2013 | Troup et al. |
| 8,586,310 B2 | 11/2013 | Mitra et al. |
| 8,614,092 B2 | 12/2013 | Zhang et al. |
| 8,642,755 B2 | 2/2014 | Sierzchala et al. |
| 8,664,164 B2 | 3/2014 | Ericsson et al. |
| 8,669,053 B2 | 3/2014 | Stuelpnagel et al. |
| 8,679,756 B1 | 3/2014 | Brenner et al. |
| 8,685,642 B2 | 4/2014 | Sampas |
| 8,685,676 B2 | 4/2014 | Hogrefe et al. |
| 8,685,678 B2 | 4/2014 | Casbon et al. |
| 8,715,933 B2 | 5/2014 | Oliver |
| 8,715,967 B2 | 5/2014 | Casbon et al. |
| 8,716,467 B2 | 5/2014 | Jacobson |
| 8,722,368 B2 | 5/2014 | Casbon et al. |
| 8,722,585 B2 | 5/2014 | Wang |
| 8,728,766 B2 | 5/2014 | Casbon et al. |
| 8,741,606 B2 | 6/2014 | Casbon et al. |
| 8,808,896 B2 | 8/2014 | Choo et al. |
| 8,808,986 B2 | 8/2014 | Jacobson et al. |
| 8,815,600 B2 | 8/2014 | Liu et al. |
| 8,889,851 B2 | 11/2014 | Leproust et al. |
| 8,932,994 B2 | 1/2015 | Gormley et al. |
| 8,962,532 B2 | 2/2015 | Shapiro et al. |
| 8,968,999 B2 | 3/2015 | Gibson et al. |
| 8,980,563 B2 | 3/2015 | Zheng et al. |
| 9,018,365 B2 | 4/2015 | Brenner |
| 9,023,601 B2 | 5/2015 | Oleinikov |
| 9,051,666 B2 | 6/2015 | Oleinikov |
| 9,073,962 B2 | 7/2015 | Fracchia et al. |
| 9,074,204 B2 | 7/2015 | Anderson et al. |
| 9,085,797 B2 | 7/2015 | Gebeyehu et al. |
| 9,102,731 B2 | 8/2015 | Boone et al. |
| 9,133,510 B2 | 9/2015 | Andersen et al. |
| 9,139,874 B2 | 9/2015 | Myers et al. |
| 9,150,853 B2 | 10/2015 | Hudson et al. |
| 9,187,777 B2 | 11/2015 | Jacobson et al. |
| 9,194,001 B2 | 11/2015 | Brenner |
| 9,216,414 B2 | 12/2015 | Chu |
| 9,217,144 B2 | 12/2015 | Jacobson et al. |
| 9,279,149 B2 | 3/2016 | Efcavitch et al. |
| 9,286,439 B2 | 3/2016 | Shapiro et al. |
| 9,295,965 B2 | 3/2016 | Jacobson et al. |
| 9,315,861 B2 | 4/2016 | Hendricks et al. |
| 9,328,378 B2 | 5/2016 | Earnshaw et al. |
| 9,347,091 B2 | 5/2016 | Bergmann et al. |
| 9,375,748 B2 | 6/2016 | Harumoto et al. |
| 9,376,677 B2 | 6/2016 | Mir |
| 9,376,678 B2 | 6/2016 | Gormley et al. |
| 9,384,320 B2 | 7/2016 | Church |
| 9,384,920 B1 | 7/2016 | Bakulich |
| 9,388,407 B2 | 7/2016 | Jacobson |
| 9,394,333 B2 | 7/2016 | Wada et al. |
| 9,403,141 B2 | 8/2016 | Banyai et al. |
| 9,409,139 B2 * | 8/2016 | Banyai .................. C12N 15/66 |
| 9,410,149 B2 | 8/2016 | Brenner et al. |
| 9,410,173 B2 | 8/2016 | Betts et al. |
| 9,416,411 B2 | 8/2016 | Stuelpnagel et al. |
| 9,422,600 B2 | 8/2016 | Ramu et al. |
| 9,487,824 B2 | 11/2016 | Kutyavin |
| 9,499,848 B2 | 11/2016 | Carr et al. |
| 9,523,122 B2 | 12/2016 | Zheng et al. |
| 9,528,148 B2 | 12/2016 | Zheng et al. |
| 9,534,251 B2 | 1/2017 | Young et al. |
| 9,555,388 B2 | 1/2017 | Banyai et al. |
| 9,568,839 B2 | 2/2017 | Stahler et al. |
| 9,580,746 B2 | 2/2017 | Leproust et al. |
| 9,670,529 B2 | 6/2017 | Osborne et al. |
| 9,670,536 B2 | 6/2017 | Casbon et al. |
| 9,677,067 B2 | 6/2017 | Toro et al. |
| 9,695,211 B2 | 7/2017 | Wada et al. |
| 9,718,060 B2 | 8/2017 | Venter et al. |
| 9,745,573 B2 | 8/2017 | Stuelpnagel et al. |
| 9,745,619 B2 | 8/2017 | Rabbani et al. |
| 9,765,387 B2 | 9/2017 | Rabbani et al. |
| 9,771,576 B2 | 9/2017 | Gibson et al. |
| 9,833,761 B2 * | 12/2017 | Banyai ............... C12N 15/1096 |
| 9,834,774 B2 | 12/2017 | Carstens |
| 9,839,894 B2 | 12/2017 | Banyai et al. |
| 9,879,283 B2 | 1/2018 | Ravinder et al. |
| 9,889,423 B2 | 2/2018 | Banyai et al. |
| 9,895,673 B2 | 2/2018 | Peck et al. |
| 9,925,510 B2 | 3/2018 | Jacobson et al. |
| 9,932,576 B2 | 4/2018 | Raymond et al. |
| 9,981,239 B2 * | 5/2018 | Banyai ............... C12N 15/1093 |
| 10,053,688 B2 | 8/2018 | Cox |
| 10,272,410 B2 | 4/2019 | Banyai et al. |
| 10,384,188 B2 | 8/2019 | Banyai et al. |
| 10,384,189 B2 | 8/2019 | Peck |
| 10,417,457 B2 | 9/2019 | Peck |
| 10,583,415 B2 * | 3/2020 | Banyai ................. B01J 19/0046 |
| 10,639,609 B2 * | 5/2020 | Banyai .................. C40B 50/18 |
| 10,754,994 B2 | 8/2020 | Peck |
| 10,773,232 B2 * | 9/2020 | Banyai .................. C12N 15/74 |
| 10,936,953 B2 | 3/2021 | Bramlett et al. |
| 10,963,953 B2 * | 3/2021 | Sweeder ................ G06Q 30/08 |

(56) References Cited

U.S. PATENT DOCUMENTS

| | | |
|---|---|---|
| 10,975,372 B2 * | 4/2021 | Cox .................. C12N 15/1093 |
| 11,214,798 B2 | 1/2022 | Brown |
| 11,236,393 B2 | 2/2022 | Dubinsky et al. |
| 11,268,149 B2 | 3/2022 | Targan et al. |
| 2001/0018512 A1 | 8/2001 | Blanchard |
| 2001/0039014 A1 | 11/2001 | Bass et al. |
| 2001/0055761 A1 | 12/2001 | Kanemoto et al. |
| 2002/0012930 A1 | 1/2002 | Rothberg et al. |
| 2002/0025561 A1 | 2/2002 | Hodgson |
| 2002/0028455 A1 | 3/2002 | Laibinis et al. |
| 2002/0058802 A1 | 5/2002 | Dellinger et al. |
| 2002/0076716 A1 | 6/2002 | Sabanayagam et al. |
| 2002/0081582 A1 | 6/2002 | Gao et al. |
| 2002/0094533 A1 | 7/2002 | Hess et al. |
| 2002/0095073 A1 | 7/2002 | Jacobs et al. |
| 2002/0119459 A1 | 8/2002 | Griffiths |
| 2002/0132308 A1 | 9/2002 | Liu et al. |
| 2002/0155439 A1 | 10/2002 | Rodriguez et al. |
| 2002/0160536 A1 | 10/2002 | Regnier et al. |
| 2002/0164824 A1 | 11/2002 | Xiao et al. |
| 2003/0008411 A1 | 1/2003 | Van et al. |
| 2003/0022207 A1 | 1/2003 | Balasubramanian et al. |
| 2003/0022240 A1 | 1/2003 | Luo et al. |
| 2003/0022317 A1 | 1/2003 | Jack et al. |
| 2003/0044781 A1 | 3/2003 | Korlach et al. |
| 2003/0058629 A1 | 3/2003 | Hirai et al. |
| 2003/0064398 A1 | 4/2003 | Barnes |
| 2003/0068633 A1 | 4/2003 | Belshaw et al. |
| 2003/0082618 A1 | 5/2003 | Li et al. |
| 2003/0082719 A1 | 5/2003 | Schumacher et al. |
| 2003/0100102 A1 | 5/2003 | Rothberg et al. |
| 2003/0108903 A1 | 6/2003 | Wang et al. |
| 2003/0120035 A1 | 6/2003 | Gao et al. |
| 2003/0130827 A1 | 7/2003 | Bentzien et al. |
| 2003/0138782 A1 | 7/2003 | Evans |
| 2003/0143605 A1 | 7/2003 | Lok et al. |
| 2003/0148291 A1 | 8/2003 | Robotti |
| 2003/0148344 A1 | 8/2003 | Rothberg et al. |
| 2003/0148401 A1 | 8/2003 | Agrawal et al. |
| 2003/0171325 A1 | 9/2003 | Gascoyne et al. |
| 2003/0186226 A1 | 10/2003 | Brennan et al. |
| 2003/0228602 A1 | 12/2003 | Parker et al. |
| 2003/0228620 A1 | 12/2003 | Du |
| 2004/0009498 A1 | 1/2004 | Short |
| 2004/0043509 A1 | 3/2004 | Stahler et al. |
| 2004/0053362 A1 | 3/2004 | De et al. |
| 2004/0086892 A1 | 5/2004 | Crothers et al. |
| 2004/0087008 A1 | 5/2004 | Schembri |
| 2004/0106130 A1 | 6/2004 | Besemer et al. |
| 2004/0106728 A1 * | 6/2004 | McGall ................ C07F 9/2408 558/186 |
| 2004/0110133 A1 | 6/2004 | Xu et al. |
| 2004/0143114 A1 | 7/2004 | Imanishi et al. |
| 2004/0175710 A1 | 9/2004 | Haushalter |
| 2004/0175734 A1 | 9/2004 | Stahler et al. |
| 2004/0191810 A1 | 9/2004 | Yamamoto |
| 2004/0213795 A1 | 10/2004 | Collins et al. |
| 2004/0219663 A1 | 11/2004 | Page et al. |
| 2004/0236027 A1 | 11/2004 | Maeji et al. |
| 2004/0248161 A1 | 12/2004 | Rothberg et al. |
| 2004/0253242 A1 | 12/2004 | Bowdish et al. |
| 2004/0259146 A1 | 12/2004 | Friend et al. |
| 2005/0022895 A1 | 2/2005 | Barth et al. |
| 2005/0049402 A1 | 3/2005 | Babcook et al. |
| 2005/0049796 A1 | 3/2005 | Webb et al. |
| 2005/0053968 A1 | 3/2005 | Bharadwaj et al. |
| 2005/0079510 A1 | 4/2005 | Berka et al. |
| 2005/0100932 A1 | 5/2005 | Lapidus et al. |
| 2005/0112608 A1 | 5/2005 | Grossman et al. |
| 2005/0112636 A1 | 5/2005 | Hurt et al. |
| 2005/0112679 A1 | 5/2005 | Myerson et al. |
| 2005/0118706 A1 | 6/2005 | Pirrung et al. |
| 2005/0124022 A1 | 6/2005 | Srinivasan et al. |
| 2005/0137805 A1 | 6/2005 | Lewin et al. |
| 2005/0208513 A1 | 9/2005 | Agbo et al. |
| 2005/0214778 A1 | 9/2005 | Peck et al. |
| 2005/0214779 A1 | 9/2005 | Peck et al. |
| 2005/0227235 A1 | 10/2005 | Carr et al. |
| 2005/0255477 A1 | 11/2005 | Carr et al. |
| 2005/0266045 A1 | 12/2005 | Canham et al. |
| 2005/0277125 A1 | 12/2005 | Benn et al. |
| 2005/0282158 A1 | 12/2005 | Landegren |
| 2005/0287585 A1 | 12/2005 | Oleinikov |
| 2006/0003381 A1 | 1/2006 | Gilmore et al. |
| 2006/0003958 A1 | 1/2006 | Melville et al. |
| 2006/0012784 A1 | 1/2006 | Ulmer |
| 2006/0012793 A1 | 1/2006 | Harris |
| 2006/0019084 A1 | 1/2006 | Pearson |
| 2006/0024678 A1 | 2/2006 | Buzby |
| 2006/0024711 A1 | 2/2006 | Lapidus et al. |
| 2006/0024721 A1 | 2/2006 | Pedersen |
| 2006/0076482 A1 | 4/2006 | Hobbs et al. |
| 2006/0078909 A1 | 4/2006 | Srinivasan et al. |
| 2006/0078927 A1 | 4/2006 | Peck et al. |
| 2006/0078937 A1 | 4/2006 | Korlach et al. |
| 2006/0127920 A1 | 6/2006 | Church et al. |
| 2006/0134638 A1 | 6/2006 | Mulligan et al. |
| 2006/0149046 A1 * | 7/2006 | Arar .................... C07H 21/04 536/23.2 |
| 2006/0160138 A1 | 7/2006 | Church |
| 2006/0171855 A1 | 8/2006 | Yin et al. |
| 2006/0202330 A1 | 9/2006 | Reinhardt et al. |
| 2006/0203236 A1 | 9/2006 | Ji et al. |
| 2006/0203237 A1 | 9/2006 | Ji et al. |
| 2006/0207923 A1 | 9/2006 | Li |
| 2006/0219637 A1 | 10/2006 | Killeen et al. |
| 2006/0286569 A1 | 12/2006 | Bar-Or et al. |
| 2007/0031857 A1 | 2/2007 | Makarov et al. |
| 2007/0031877 A1 | 2/2007 | Stahler et al. |
| 2007/0043516 A1 | 2/2007 | Gustafsson et al. |
| 2007/0054127 A1 | 3/2007 | Hergenrother et al. |
| 2007/0059692 A1 | 3/2007 | Gao et al. |
| 2007/0087349 A1 | 4/2007 | Staehler et al. |
| 2007/0099196 A1 | 5/2007 | Kauppinen et al. |
| 2007/0099208 A1 | 5/2007 | Drmanac et al. |
| 2007/0122817 A1 | 5/2007 | Church et al. |
| 2007/0128635 A1 | 6/2007 | Macevicz |
| 2007/0141557 A1 | 6/2007 | Raab et al. |
| 2007/0196834 A1 | 8/2007 | Cerrina et al. |
| 2007/0196854 A1 | 8/2007 | Stahler et al. |
| 2007/0207482 A1 | 9/2007 | Church et al. |
| 2007/0207487 A1 | 9/2007 | Emig et al. |
| 2007/0231800 A1 | 10/2007 | Roberts et al. |
| 2007/0238104 A1 | 10/2007 | Barrett et al. |
| 2007/0238106 A1 | 10/2007 | Barrett et al. |
| 2007/0238108 A1 | 10/2007 | Barrett et al. |
| 2007/0259344 A1 | 11/2007 | Leproust et al. |
| 2007/0259345 A1 | 11/2007 | Sampas |
| 2007/0259346 A1 | 11/2007 | Gordon et al. |
| 2007/0259347 A1 | 11/2007 | Gordon et al. |
| 2007/0269870 A1 | 11/2007 | Church et al. |
| 2008/0085511 A1 | 4/2008 | Peck et al. |
| 2008/0085514 A1 | 4/2008 | Peck et al. |
| 2008/0087545 A1 | 4/2008 | Jensen et al. |
| 2008/0161200 A1 | 7/2008 | Yu et al. |
| 2008/0182296 A1 | 7/2008 | Chanda et al. |
| 2008/0214412 A1 | 9/2008 | Stahler et al. |
| 2008/0227160 A1 | 9/2008 | Kool |
| 2008/0233616 A1 | 9/2008 | Liss |
| 2008/0287320 A1 | 11/2008 | Baynes et al. |
| 2008/0300842 A1 | 12/2008 | Govindarajan et al. |
| 2008/0308884 A1 | 12/2008 | Kalvesten |
| 2008/0311628 A1 | 12/2008 | Shoemaker |
| 2009/0036664 A1 | 2/2009 | Peter |
| 2009/0053704 A1 | 2/2009 | Novoradovskaya et al. |
| 2009/0062129 A1 | 3/2009 | McKernan et al. |
| 2009/0074771 A1 | 3/2009 | Koenig et al. |
| 2009/0087840 A1 | 4/2009 | Baynes et al. |
| 2009/0088679 A1 | 4/2009 | Wood et al. |
| 2009/0105094 A1 | 4/2009 | Heiner et al. |
| 2009/0170802 A1 | 7/2009 | Stahler et al. |
| 2009/0176280 A1 | 7/2009 | Hutchison, III et al. |
| 2009/0181861 A1 | 7/2009 | Li et al. |
| 2009/0194483 A1 | 8/2009 | Robotti et al. |

(56) References Cited

U.S. PATENT DOCUMENTS

| | | |
|---|---|---|
| 2009/0230044 A1 | 9/2009 | Bek |
| 2009/0238722 A1 | 9/2009 | Mora-Fillat et al. |
| 2009/0239759 A1 | 9/2009 | Balch |
| 2009/0246788 A1 | 10/2009 | Albert et al. |
| 2009/0263802 A1 | 10/2009 | Drmanac |
| 2009/0285825 A1 | 11/2009 | Kini et al. |
| 2009/0324546 A1 | 12/2009 | Notka et al. |
| 2010/0004143 A1 | 1/2010 | Shibahara |
| 2010/0008851 A1 | 1/2010 | Nicolaides et al. |
| 2010/0009872 A1 | 1/2010 | Eid et al. |
| 2010/0047805 A1 | 2/2010 | Wang |
| 2010/0051967 A1 | 3/2010 | Bradley et al. |
| 2010/0069250 A1 | 3/2010 | White, III et al. |
| 2010/0090341 A1 | 4/2010 | Wan et al. |
| 2010/0099103 A1 | 4/2010 | Hsieh et al. |
| 2010/0111768 A1 | 5/2010 | Banerjee et al. |
| 2010/0160463 A1 | 6/2010 | Wang et al. |
| 2010/0167950 A1 | 7/2010 | Juang et al. |
| 2010/0173364 A1 | 7/2010 | Evans, Jr. et al. |
| 2010/0216648 A1 | 8/2010 | Staehler et al. |
| 2010/0256017 A1 | 10/2010 | Larman et al. |
| 2010/0258487 A1 | 10/2010 | Zelechonok et al. |
| 2010/0272711 A1 | 10/2010 | Feldman et al. |
| 2010/0286290 A1 | 11/2010 | Lohmann et al. |
| 2010/0292102 A1 | 11/2010 | Nouri |
| 2010/0300882 A1 | 12/2010 | Zhang et al. |
| 2010/0311960 A1 | 12/2010 | Dellinger |
| 2010/0323404 A1 | 12/2010 | Lathrop |
| 2011/0009607 A1 | 1/2011 | Komiyama et al. |
| 2011/0082055 A1 | 4/2011 | Fox et al. |
| 2011/0114244 A1 | 5/2011 | Yoo et al. |
| 2011/0114549 A1 | 5/2011 | Yin et al. |
| 2011/0124049 A1 | 5/2011 | Li et al. |
| 2011/0124055 A1 | 5/2011 | Carr et al. |
| 2011/0126929 A1 | 6/2011 | Velasquez-Garcia et al. |
| 2011/0171651 A1 | 7/2011 | Richmond |
| 2011/0172127 A1 | 7/2011 | Jacobson et al. |
| 2011/0201057 A1 | 8/2011 | Carr et al. |
| 2011/0201528 A1 | 8/2011 | Baek et al. |
| 2011/0217738 A1 | 9/2011 | Jacobson |
| 2011/0229975 A1 | 9/2011 | Matthiesen et al. |
| 2011/0230653 A1 | 9/2011 | Novoradovskaya et al. |
| 2011/0254107 A1 | 10/2011 | Bulovic et al. |
| 2011/0287435 A1 | 11/2011 | Grunenwald et al. |
| 2012/0003713 A1 | 1/2012 | Hansen et al. |
| 2012/0021932 A1 | 1/2012 | Mershin et al. |
| 2012/0027786 A1 | 2/2012 | Gupta et al. |
| 2012/0028843 A1 | 2/2012 | Ramu et al. |
| 2012/0032366 A1 | 2/2012 | Ivniski et al. |
| 2012/0046175 A1 | 2/2012 | Rodesch et al. |
| 2012/0050411 A1 | 3/2012 | Mabritto et al. |
| 2012/0094847 A1 | 4/2012 | Warthmann et al. |
| 2012/0128548 A1 | 5/2012 | West et al. |
| 2012/0129704 A1 | 5/2012 | Gunderson et al. |
| 2012/0149602 A1 | 6/2012 | Friend et al. |
| 2012/0164127 A1 | 6/2012 | Short et al. |
| 2012/0164633 A1 | 6/2012 | Laffler |
| 2012/0164691 A1 | 6/2012 | Eshoo et al. |
| 2012/0184724 A1 | 7/2012 | Sierzchala et al. |
| 2012/0220497 A1 | 8/2012 | Jacobson et al. |
| 2012/0231968 A1 | 9/2012 | Bruhn et al. |
| 2012/0238737 A1 | 9/2012 | Dellinger et al. |
| 2012/0258487 A1 | 10/2012 | Chang et al. |
| 2012/0264653 A1 | 10/2012 | Carr et al. |
| 2012/0270750 A1 | 10/2012 | Oleinikov |
| 2012/0270754 A1 | 10/2012 | Blake |
| 2012/0283140 A1 | 11/2012 | Chu |
| 2012/0288476 A1 | 11/2012 | Hartmann et al. |
| 2012/0289691 A1 | 11/2012 | Dellinger et al. |
| 2012/0315670 A1 | 12/2012 | Jacobson et al. |
| 2012/0322681 A1 | 12/2012 | Kung et al. |
| 2013/0005585 A1 | 1/2013 | Anderson et al. |
| 2013/0005612 A1 | 1/2013 | Carr et al. |
| 2013/0017642 A1 | 1/2013 | Milgrew et al. |
| 2013/0017977 A1 | 1/2013 | Oleinikov |
| 2013/0017978 A1 | 1/2013 | Kavanagh et al. |
| 2013/0035261 A1 | 2/2013 | Sierzchala et al. |
| 2013/0040836 A1 | 2/2013 | Himmler et al. |
| 2013/0045483 A1 | 2/2013 | Treusch et al. |
| 2013/0053252 A1 | 2/2013 | Xie et al. |
| 2013/0059296 A1 | 3/2013 | Jacobson et al. |
| 2013/0059761 A1 | 3/2013 | Jacobson et al. |
| 2013/0065017 A1 | 3/2013 | Sieber |
| 2013/0109595 A1 | 5/2013 | Routenberg |
| 2013/0109596 A1 | 5/2013 | Peterson et al. |
| 2013/0123129 A1 | 5/2013 | Zeiner et al. |
| 2013/0130321 A1 | 5/2013 | Staehler et al. |
| 2013/0137161 A1 | 5/2013 | Zhang et al. |
| 2013/0137173 A1 | 5/2013 | Zhang et al. |
| 2013/0137174 A1 | 5/2013 | Zhang et al. |
| 2013/0137861 A1 | 5/2013 | Leproust et al. |
| 2013/0164308 A1 | 6/2013 | Foletti et al. |
| 2013/0165328 A1 | 6/2013 | Previte et al. |
| 2013/0196864 A1 | 8/2013 | Govindarajan et al. |
| 2013/0217071 A1 | 8/2013 | Montesclaros et al. |
| 2013/0225421 A1 | 8/2013 | Li et al. |
| 2013/0244884 A1 | 9/2013 | Jacobson et al. |
| 2013/0252849 A1 | 9/2013 | Hudson et al. |
| 2013/0261027 A1 | 10/2013 | Li et al. |
| 2013/0281308 A1 | 10/2013 | Kung et al. |
| 2013/0289246 A1 | 10/2013 | Crowe et al. |
| 2013/0296192 A1 | 11/2013 | Jacobson et al. |
| 2013/0296194 A1 | 11/2013 | Jacobson et al. |
| 2013/0298265 A1 | 11/2013 | Cunnac et al. |
| 2013/0309725 A1 | 11/2013 | Jacobson et al. |
| 2013/0323725 A1 | 12/2013 | Peter et al. |
| 2013/0330778 A1 | 12/2013 | Zeiner et al. |
| 2014/0011226 A1 | 1/2014 | Bernick et al. |
| 2014/0018441 A1 | 1/2014 | Fracchia et al. |
| 2014/0031240 A1 | 1/2014 | Behlke et al. |
| 2014/0038240 A1 | 2/2014 | Temme et al. |
| 2014/0106394 A1 | 4/2014 | Ko et al. |
| 2014/0141982 A1 | 5/2014 | Jacobson et al. |
| 2014/0170665 A1 | 6/2014 | Hiddessen et al. |
| 2014/0178992 A1 | 6/2014 | Nakashima et al. |
| 2014/0221250 A1 | 8/2014 | Vasquez et al. |
| 2014/0274729 A1 | 9/2014 | Kurn et al. |
| 2014/0274741 A1 | 9/2014 | Hunter et al. |
| 2014/0303000 A1 | 10/2014 | Armour et al. |
| 2014/0309119 A1 | 10/2014 | Jacobson et al. |
| 2014/0309142 A1 | 10/2014 | Tian |
| 2015/0010953 A1 | 1/2015 | Lindstrom et al. |
| 2015/0012723 A1 | 1/2015 | Park et al. |
| 2015/0031089 A1 | 1/2015 | Lindstrom |
| 2015/0038373 A1 | 2/2015 | Banyai et al. |
| 2015/0056609 A1 | 2/2015 | Daum et al. |
| 2015/0057625 A1 | 2/2015 | Coulthard |
| 2015/0065357 A1 | 3/2015 | Fox |
| 2015/0065393 A1 | 3/2015 | Jacobson |
| 2015/0099870 A1 | 4/2015 | Bennett et al. |
| 2015/0119293 A1 | 4/2015 | Short |
| 2015/0120265 A1 | 4/2015 | Amirav-Drory |
| 2015/0159152 A1 | 6/2015 | Allen et al. |
| 2015/0183853 A1 | 7/2015 | Sharma et al. |
| 2015/0191524 A1 | 7/2015 | Smith et al. |
| 2015/0191624 A1 | 7/2015 | Scheibel et al. |
| 2015/0191719 A1 | 7/2015 | Hudson et al. |
| 2015/0196917 A1 | 7/2015 | Kay et al. |
| 2015/0203839 A1 | 7/2015 | Jacobson et al. |
| 2015/0211047 A1 | 7/2015 | Borns |
| 2015/0225782 A1 | 8/2015 | Walder et al. |
| 2015/0240232 A1 | 8/2015 | Zamore et al. |
| 2015/0240280 A1 | 8/2015 | Gibson et al. |
| 2015/0261664 A1 | 9/2015 | Goldman et al. |
| 2015/0269313 A1 | 9/2015 | Church |
| 2015/0293102 A1 | 10/2015 | Shim |
| 2015/0307875 A1 | 10/2015 | Happe et al. |
| 2015/0321191 A1 | 11/2015 | Kendall et al. |
| 2015/0322504 A1 | 11/2015 | Lao et al. |
| 2015/0344927 A1 | 12/2015 | Sampson et al. |
| 2015/0353921 A9 | 12/2015 | Tian |
| 2015/0353994 A1 | 12/2015 | Myers et al. |
| 2015/0361420 A1 | 12/2015 | Hudson et al. |
| 2015/0361422 A1 | 12/2015 | Sampson et al. |

(56) References Cited

U.S. PATENT DOCUMENTS

| | | |
|---|---|---|
| 2015/0361423 A1 | 12/2015 | Sampson et al. |
| 2015/0368687 A1 | 12/2015 | Saaem et al. |
| 2015/0376602 A1 | 12/2015 | Jacobson et al. |
| 2016/0001247 A1 | 1/2016 | Oleinikov |
| 2016/0002621 A1 | 1/2016 | Nelson et al. |
| 2016/0002622 A1 | 1/2016 | Nelson et al. |
| 2016/0010045 A1 | 1/2016 | Cohen et al. |
| 2016/0017394 A1 | 1/2016 | Liang et al. |
| 2016/0017425 A1 | 1/2016 | Ruvolo et al. |
| 2016/0019341 A1 | 1/2016 | Harris et al. |
| 2016/0024138 A1 | 1/2016 | Gebeyehu et al. |
| 2016/0024576 A1 | 1/2016 | Chee |
| 2016/0026753 A1 | 1/2016 | Krishnaswami et al. |
| 2016/0026758 A1 | 1/2016 | Jabara et al. |
| 2016/0032396 A1 | 2/2016 | Diehn et al. |
| 2016/0046973 A1 | 2/2016 | Efcavitch et al. |
| 2016/0046974 A1 | 2/2016 | Efcavitch et al. |
| 2016/0082472 A1 | 3/2016 | Perego et al. |
| 2016/0089651 A1 | 3/2016 | Banyai |
| 2016/0090422 A1 | 3/2016 | Reif et al. |
| 2016/0090592 A1 | 3/2016 | Banyai et al. |
| 2016/0096160 A1 | 4/2016 | Banyai et al. |
| 2016/0097051 A1 | 4/2016 | Jacobson et al. |
| 2016/0102322 A1 | 4/2016 | Ravinder et al. |
| 2016/0108466 A1 | 4/2016 | Nazarenko et al. |
| 2016/0122755 A1 | 5/2016 | Hall et al. |
| 2016/0122800 A1 | 5/2016 | Bernick et al. |
| 2016/0152972 A1 | 6/2016 | Stapleton et al. |
| 2016/0168611 A1 | 6/2016 | Efcavitch et al. |
| 2016/0184788 A1 | 6/2016 | Hall et al. |
| 2016/0200759 A1 | 7/2016 | Srivastava et al. |
| 2016/0215283 A1 | 7/2016 | Braman et al. |
| 2016/0229884 A1 | 8/2016 | Indermuhle |
| 2016/0230175 A1 | 8/2016 | Carstens |
| 2016/0230221 A1 | 8/2016 | Bergmann et al. |
| 2016/0251651 A1 | 9/2016 | Banyai |
| 2016/0256846 A1 | 9/2016 | Smith et al. |
| 2016/0264958 A1 | 9/2016 | Toro et al. |
| 2016/0289758 A1 | 10/2016 | Akeson et al. |
| 2016/0289839 A1 | 10/2016 | Harumoto et al. |
| 2016/0297883 A1 | 10/2016 | Gallo et al. |
| 2016/0303535 A1 | 10/2016 | Banyai et al. |
| 2016/0304862 A1 | 10/2016 | Igawa et al. |
| 2016/0304946 A1 | 10/2016 | Betts et al. |
| 2016/0310426 A1 | 10/2016 | Wu |
| 2016/0310927 A1 | 10/2016 | Banyai et al. |
| 2016/0318016 A1 | 11/2016 | Hou et al. |
| 2016/0333340 A1 | 11/2016 | Wu |
| 2016/0339409 A1 | 11/2016 | Banyai |
| 2016/0340672 A1 | 11/2016 | Banyai et al. |
| 2016/0348098 A1 | 12/2016 | Stuelpnagel et al. |
| 2016/0354752 A1 | 12/2016 | Banyai et al. |
| 2016/0355880 A1 | 12/2016 | Gormley et al. |
| 2017/0017436 A1 | 1/2017 | Church |
| 2017/0066844 A1 | 3/2017 | Glanville |
| 2017/0067047 A1 | 3/2017 | Link et al. |
| 2017/0067099 A1 | 3/2017 | Zheng et al. |
| 2017/0073664 A1 | 3/2017 | McCafferty et al. |
| 2017/0073731 A1 | 3/2017 | Zheng et al. |
| 2017/0081660 A1 | 3/2017 | Cox |
| 2017/0081716 A1 | 3/2017 | Peck |
| 2017/0088887 A1 | 3/2017 | Makarov et al. |
| 2017/0095785 A1 | 4/2017 | Banyai et al. |
| 2017/0096706 A1 | 4/2017 | Behlke et al. |
| 2017/0114404 A1 | 4/2017 | Behlke et al. |
| 2017/0141793 A1 | 5/2017 | Strauss et al. |
| 2017/0147748 A1 | 5/2017 | Staehler et al. |
| 2017/0151546 A1 | 6/2017 | Peck et al. |
| 2017/0159044 A1 | 6/2017 | Toro et al. |
| 2017/0175110 A1 | 6/2017 | Jacobson et al. |
| 2017/0218537 A1 | 8/2017 | Olivares |
| 2017/0233764 A1 | 8/2017 | Young et al. |
| 2017/0247473 A1 | 8/2017 | Short |
| 2017/0249345 A1 | 8/2017 | Malik et al. |
| 2017/0253644 A1 | 9/2017 | Steyaert et al. |
| 2017/0298432 A1 | 10/2017 | Holt |
| 2017/0320061 A1 | 11/2017 | Venter et al. |
| 2017/0327819 A1 | 11/2017 | Banyai |
| 2017/0355984 A1 | 12/2017 | Evans et al. |
| 2017/0357752 A1 | 12/2017 | Diggans |
| 2017/0362589 A1 | 12/2017 | Banyai |
| 2018/0029001 A1 | 2/2018 | Banyai |
| 2018/0051278 A1 | 2/2018 | Cox et al. |
| 2018/0051280 A1 | 2/2018 | Gibson et al. |
| 2018/0068060 A1 | 3/2018 | Ceze et al. |
| 2018/0104664 A1 | 4/2018 | Fernandez |
| 2018/0126355 A1 | 5/2018 | Peck et al. |
| 2018/0142289 A1 | 5/2018 | Zeitoun |
| 2018/0171509 A1 | 6/2018 | Cox |
| 2018/0230459 A1 | 8/2018 | Gill et al. |
| 2018/0236425 A1 | 8/2018 | Banyai et al. |
| 2018/0253563 A1 | 9/2018 | Peck et al. |
| 2018/0264428 A1 | 9/2018 | Banyai et al. |
| 2018/0273936 A1 | 9/2018 | Cox et al. |
| 2018/0282721 A1 | 10/2018 | Cox et al. |
| 2018/0291445 A1 | 10/2018 | Betts et al. |
| 2018/0312834 A1 | 11/2018 | Cox et al. |
| 2018/0326388 A1 | 11/2018 | Banyai et al. |
| 2018/0334712 A1 | 11/2018 | Singer et al. |
| 2018/0346585 A1 | 12/2018 | Zhang et al. |
| 2018/0355351 A1 | 12/2018 | Nugent et al. |
| 2019/0060345 A1 | 2/2019 | Harrison et al. |
| 2019/0083596 A1 | 3/2019 | Orentas et al. |
| 2019/0118154 A1 | 4/2019 | Eugene et al. |
| 2019/0135926 A1 | 5/2019 | Glanville |
| 2019/0224711 A1 | 7/2019 | Demeris, Jr. |
| 2019/0240636 A1 | 8/2019 | Peck et al. |
| 2019/0314783 A1 | 10/2019 | Banyai et al. |
| 2019/0352635 A1 | 11/2019 | Toro et al. |
| 2019/0366293 A1 | 12/2019 | Banyai et al. |
| 2019/0366294 A1 | 12/2019 | Banyai et al. |
| 2020/0017907 A1 | 1/2020 | Zeitoun et al. |
| 2020/0056229 A1 | 2/2020 | Mir |
| 2020/0102611 A1 | 4/2020 | Zeitoun et al. |
| 2020/0156037 A1 | 5/2020 | Banyai et al. |
| 2020/0181667 A1 | 6/2020 | Wu et al. |
| 2020/0283760 A1 | 9/2020 | Nugent et al. |
| 2020/0299322 A1 | 9/2020 | Indermuhle et al. |
| 2020/0299684 A1 | 9/2020 | Toro et al. |
| 2020/0308575 A1 | 10/2020 | Sato |
| 2020/0325235 A1 | 10/2020 | Tabibiazar et al. |
| 2020/0342143 A1 | 10/2020 | Peck |
| 2021/0002710 A1 | 1/2021 | Gantt et al. |
| 2021/0040476 A1 | 2/2021 | Cox et al. |
| 2021/0071168 A1 | 3/2021 | Nugent et al. |
| 2021/0102192 A1 | 4/2021 | Tabibiazar et al. |
| 2021/0102195 A1 | 4/2021 | Sato et al. |
| 2021/0102198 A1 | 4/2021 | Cox et al. |
| 2021/0115594 A1 | 4/2021 | Cox et al. |
| 2021/0129108 A1 | 5/2021 | Marsh et al. |
| 2021/0142182 A1 | 5/2021 | Bramlett et al. |
| 2021/0147830 A1 | 5/2021 | Liss |
| 2021/0170356 A1 | 6/2021 | Peck et al. |
| 2021/0179724 A1 | 6/2021 | Sato et al. |
| 2021/0207197 A1 | 7/2021 | Gantt et al. |
| 2021/0332078 A1 | 10/2021 | Wu |
| 2021/0348220 A1 | 11/2021 | Zeitoun et al. |
| 2021/0355194 A1 | 11/2021 | Sato et al. |
| 2021/0395344 A1 | 12/2021 | Sato et al. |
| 2022/0032256 A1 | 2/2022 | Lackey et al. |
| 2022/0064206 A1 | 3/2022 | Fernandez et al. |
| 2022/0064313 A1 | 3/2022 | Sato et al. |
| 2022/0064628 A1 | 3/2022 | Toro et al. |
| 2022/0106586 A1 | 4/2022 | Nugent et al. |
| 2022/0106590 A1 | 4/2022 | Arbiza et al. |
| 2022/0135690 A1 | 5/2022 | Sato et al. |
| 2022/0135965 A1 | 5/2022 | Gantt et al. |
| 2022/0138354 A1 | 5/2022 | Peck |
| 2022/0145289 A1 | 5/2022 | Lackey et al. |
| 2022/0206001 A1 | 6/2022 | Sato |
| 2022/0243195 A1 | 8/2022 | Nugent et al. |
| 2022/0246236 A1 | 8/2022 | Amirav-Drory |
| 2022/0259319 A1 | 8/2022 | Sato et al. |
| 2022/0259638 A1 | 8/2022 | Brown |

(56) References Cited

U.S. PATENT DOCUMENTS

| | | |
|---|---|---|
| 2022/0277808 A1 | 9/2022 | Arbiza et al. |
| 2022/0281989 A1 | 9/2022 | Glanville |
| 2022/0307010 A1 | 9/2022 | Sato et al. |
| 2022/0315971 A1 | 10/2022 | Wu et al. |
| 2022/0323924 A1 | 10/2022 | Lackey et al. |
| 2022/0325276 A2 | 10/2022 | Banyai et al. |
| 2022/0325278 A1 | 10/2022 | Nugent et al. |
| 2022/0348659 A1 | 11/2022 | Sato et al. |
| 2022/0356463 A1 | 11/2022 | Shen et al. |
| 2022/0356468 A1 | 11/2022 | Sato et al. |
| 2022/0411784 A1 | 12/2022 | Sato et al. |
| 2023/0002478 A1 | 1/2023 | Sato et al. |
| 2023/0054232 A1 | 2/2023 | Peck |
| 2023/0086062 A1 | 3/2023 | Banyai et al. |
| 2023/0096464 A1 | 3/2023 | Sato |
| 2023/0115861 A1 | 4/2023 | Nugent et al. |

FOREIGN PATENT DOCUMENTS

| | | | |
|---|---|---|---|
| CA | 2720587 A1 | 10/2009 | |
| CN | 1771336 A | 5/2006 | |
| CN | 101277758 A | 10/2008 | |
| CN | 102159726 A | 8/2011 | |
| CN | 103003431 A | 3/2013 | |
| CN | 103907117 A | 7/2014 | |
| CN | 104520864 A | 4/2015 | |
| CN | 104562213 A | 4/2015 | |
| CN | 104734848 A | 6/2015 | |
| CN | 104974929 A | 10/2015 | |
| CN | 204714802 U | 10/2015 | |
| CN | 105637097 A | 6/2016 | |
| DE | 10260805 A1 | 7/2004 | |
| EA | 201890763 A1 | 8/2018 | |
| EP | 0090789 A1 | 10/1983 | |
| EP | 0126621 B1 | 8/1990 | |
| EP | 0753057 A1 | 1/1997 | |
| EP | 1314783 A1 | 5/2003 | |
| EP | 1363125 A2 | 11/2003 | |
| EP | 1546387 A2 | 6/2005 | |
| EP | 1153127 B1 | 7/2006 | |
| EP | 1728860 A1 | 12/2006 | |
| EP | 1072010 B1 | 4/2010 | |
| EP | 2175021 A2 | 4/2010 | |
| EP | 2330216 A1 | 6/2011 | |
| EP | 1343802 B1 | 5/2012 | |
| EP | 2504449 A1 | 10/2012 | |
| EP | 2751729 A1 | 7/2014 | |
| EP | 2872629 A1 | 5/2015 | |
| EP | 2928500 A1 | 10/2015 | |
| EP | 2971034 A1 | 1/2016 | |
| EP | 3030682 A2 | 6/2016 | |
| EP | 3044228 A4 | 4/2017 | |
| EP | 2994509 B1 | 6/2017 | |
| EP | 3204518 A1 | 8/2017 | |
| JP | H07505530 A | 6/1995 | |
| JP | 2001518086 A | 10/2001 | |
| JP | 2002511276 A | 4/2002 | |
| JP | 2002536977 A | 11/2002 | |
| JP | 2002538790 A | 11/2002 | |
| JP | 2003522119 A | 7/2003 | |
| JP | 2004521628 A | 7/2004 | |
| JP | 2004268394 A | 9/2004 | |
| JP | 2006503586 A | 2/2006 | |
| JP | 2006238724 A | 9/2006 | |
| JP | 2007314746 A | 12/2007 | |
| JP | 2008505642 A | 2/2008 | |
| JP | 2008097189 A | 4/2008 | |
| JP | 2008523786 A | 7/2008 | |
| JP | 2008214343 A | 9/2008 | |
| JP | 2009294195 A | 12/2009 | |
| JP | 2010-248084 | * 11/2010 | ............ C07H 21/04 |
| JP | 2012507513 A | 3/2012 | |
| JP | 2015521472 A | 7/2015 | |
| JP | 2016527313 A | 9/2016 | |
| KR | 101339064 B1 | 1/2014 | |
| WO | WO-9015070 A1 | 12/1990 | |
| WO | WO-9210092 A1 | 6/1992 | |
| WO | WO-9210588 A1 | 6/1992 | |
| WO | WO-9220823 A1 | 11/1992 | |
| WO | WO-9309668 A1 | 5/1993 | |
| WO | WO-9320242 A1 | 10/1993 | |
| WO | WO-9525116 A1 | 9/1995 | |
| WO | WO-9526397 A1 | 10/1995 | |
| WO | WO-9615861 A1 | 5/1996 | |
| WO | WO-9710365 A1 | 3/1997 | |
| WO | WO-9822541 A2 | 5/1998 | |
| WO | WO-9841531 A2 | 9/1998 | |
| WO | WO-9942813 A1 | 8/1999 | |
| WO | WO-9953101 A1 | 10/1999 | |
| WO | WO-0013017 A2 | 3/2000 | |
| WO | WO-0018957 A1 | 4/2000 | |
| WO | WO-0042559 A1 | 7/2000 | |
| WO | WO-0042560 A2 | 7/2000 | |
| WO | WO-0042561 A2 | 7/2000 | |
| WO | WO-0049142 A1 | 8/2000 | |
| WO | WO-0053617 A1 | 9/2000 | |
| WO | WO-0079006 A1 | 12/2000 | |
| WO | WO-0156216 A2 | 8/2001 | |
| WO | WO-0210443 A1 | 2/2002 | |
| WO | WO-0156216 A3 | 3/2002 | |
| WO | WO-0220537 A2 | 3/2002 | |
| WO | WO-0224597 A2 | 3/2002 | |
| WO | WO-0227638 A1 | 4/2002 | |
| WO | WO-0233669 A1 | 4/2002 | |
| WO | WO-0246205 A2 | 6/2002 | |
| WO | WO-02072791 A2 | 9/2002 | |
| WO | WO-02072864 A2 | 9/2002 | |
| WO | WO-03040410 A1 | 5/2003 | |
| WO | WO-03046223 A1 | 6/2003 | |
| WO | WO-03054232 A2 | 7/2003 | |
| WO | WO-03060084 A2 | 7/2003 | |
| WO | WO-03064026 A1 | 8/2003 | |
| WO | WO-03064027 A2 | 8/2003 | |
| WO | WO-03064699 A2 | 8/2003 | |
| WO | WO-03065038 A2 | 8/2003 | |
| WO | WO-03066212 A2 | 8/2003 | |
| WO | WO-03089605 A2 | 10/2003 | |
| WO | WO-03093504 A1 | 11/2003 | |
| WO | WO-03100012 A2 | 12/2003 | |
| WO | WO-2004024886 A2 | 3/2004 | |
| WO | WO-2004029220 A2 | 4/2004 | |
| WO | WO-2004029586 A1 | 4/2004 | |
| WO | WO-2004031351 A2 | 4/2004 | |
| WO | WO-2004031399 A2 | 4/2004 | |
| WO | WO-2004039953 A2 | 5/2004 | |
| WO | WO-2004059556 A2 | 7/2004 | |
| WO | WO-03060084 A3 | 8/2004 | |
| WO | WO-2005014850 A2 | 2/2005 | |
| WO | WO-2005051970 A2 | 6/2005 | |
| WO | WO-2005059096 A2 | 6/2005 | |
| WO | WO-2005059097 A2 | 6/2005 | |
| WO | WO-2005093092 A2 | 10/2005 | |
| WO | WO-2006023144 | 3/2006 | |
| WO | WO-2006044956 A1 | 4/2006 | |
| WO | WO-2006076679 A1 | 7/2006 | |
| WO | WO-2006116476 A1 | 11/2006 | |
| WO | WO-2007073171 A2 | 6/2007 | |
| WO | WO-2007109221 A2 | 9/2007 | |
| WO | WO-2007118214 A2 | 10/2007 | |
| WO | WO-2007120627 A2 | 10/2007 | |
| WO | WO-2007137242 A2 | 11/2007 | |
| WO | WO-2008003116 A2 | 1/2008 | |
| WO | WO-2008006078 A2 | 1/2008 | |
| WO | WO-2008027558 A2 | 3/2008 | |
| WO | WO-2008045380 | 4/2008 | |
| WO | WO-2008054543 A2 | 5/2008 | |
| WO | WO-2008063134 A1 | 5/2008 | |
| WO | WO-2008063135 A1 | 5/2008 | |
| WO | WO-2008068280 A1 | 6/2008 | |
| WO | WO-2008103474 A1 | 8/2008 | |
| WO | WO-2008109176 A2 | 9/2008 | |
| WO | WO-2009132876 A1 | 11/2009 | |
| WO | WO-2009126290 A3 | 12/2009 | |
| WO | WO-2010001251 A2 | 1/2010 | |

(56) References Cited

FOREIGN PATENT DOCUMENTS

| | | |
|---|---|---|
| WO | WO-2010025310 A2 | 3/2010 |
| WO | WO-2010025566 A1 | 3/2010 |
| WO | WO-2010027512 A2 | 3/2010 |
| WO | WO-2010053443 A1 | 5/2010 |
| WO | WO-2010089412 A1 | 8/2010 |
| WO | WO-2010141249 A2 | 12/2010 |
| WO | WO-2010141433 A2 | 12/2010 |
| WO | WO-2011020529 A2 | 2/2011 |
| WO | WO-2010141433 A3 | 4/2011 |
| WO | WO-2011053957 A2 | 5/2011 |
| WO | WO-2011056644 A2 | 5/2011 |
| WO | WO-2011056872 A2 | 5/2011 |
| WO | WO-2011066185 A1 | 6/2011 |
| WO | WO-2011066186 A1 | 6/2011 |
| WO | WO-2011085075 A2 | 7/2011 |
| WO | WO-2011103468 A2 | 8/2011 |
| WO | WO-2011109031 A1 | 9/2011 |
| WO | WO-2011143556 A1 | 11/2011 |
| WO | WO-2011150168 A1 | 12/2011 |
| WO | WO-2011161413 A2 | 12/2011 |
| WO | WO-2012013913 A1 | 2/2012 |
| WO | WO-2012061832 A1 | 5/2012 |
| WO | WO-2012078312 A2 | 6/2012 |
| WO | WO-2012149171 A1 | 11/2012 |
| WO | WO-2012154201 A1 | 11/2012 |
| WO | WO-2013010062 A2 | 1/2013 |
| WO | WO-2013030827 A1 | 3/2013 |
| WO | WO-2013032850 A2 | 3/2013 |
| WO | WO-2013036668 A1 | 3/2013 |
| WO | WO-2013049227 A2 | 4/2013 |
| WO | WO-2013101896 A1 | 7/2013 |
| WO | WO-2013134881 A1 | 9/2013 |
| WO | WO-2013154770 A1 | 10/2013 |
| WO | WO-2013170168 A1 | 11/2013 |
| WO | WO-2013177220 A1 | 11/2013 |
| WO | WO-2014004393 A1 | 1/2014 |
| WO | WO-2014008447 A1 | 1/2014 |
| WO | WO-2014021938 A1 | 2/2014 |
| WO | WO-2014035693 A2 | 3/2014 |
| WO | WO-2014088693 A1 | 6/2014 |
| WO | WO-2014089160 A1 | 6/2014 |
| WO | WO-2014093330 A1 | 6/2014 |
| WO | WO-2014093694 A1 | 6/2014 |
| WO | WO-2014151117 A1 | 9/2014 |
| WO | WO-2014151696 A1 | 9/2014 |
| WO | WO-2014160004 A1 | 10/2014 |
| WO | WO-2014160059 A1 | 10/2014 |
| WO | WO-2014206304 A1 | 12/2014 |
| WO | WO-2015017527 A2 | 2/2015 |
| WO | WO-2015021080 A2 | 2/2015 |
| WO | WO-2015021280 A1 | 2/2015 |
| WO | WO-2015031689 A1 | 3/2015 |
| WO | WO-2015040075 A1 | 3/2015 |
| WO | WO-2015054292 A1 | 4/2015 |
| WO | WO-2015066174 A1 | 5/2015 |
| WO | WO-2015081114 A2 | 6/2015 |
| WO | WO-2015081142 A1 | 6/2015 |
| WO | WO-2015081440 A1 | 6/2015 |
| WO | WO-2015090879 A1 | 6/2015 |
| WO | WO-2015095404 A2 | 6/2015 |
| WO | WO-2015120403 A1 | 8/2015 |
| WO | WO-2015136072 A1 | 9/2015 |
| WO | WO-2015160004 A1 | 10/2015 |
| WO | WO-2015175832 A1 | 11/2015 |
| WO | WO-2016007604 A1 | 1/2016 |
| WO | WO-2016011080 A2 | 1/2016 |
| WO | WO-2016022557 A1 | 2/2016 |
| WO | WO-2016053883 A1 | 4/2016 |
| WO | WO-2016055956 A1 | 4/2016 |
| WO | WO-2016065056 A1 | 4/2016 |
| WO | WO-2016126882 A1 | 8/2016 |
| WO | WO-2016126987 A1 | 8/2016 |
| WO | WO-2016130868 A2 | 8/2016 |
| WO | WO-2016161244 A2 | 10/2016 |
| WO | WO-2016162127 A1 | 10/2016 |
| WO | WO-2016164779 A1 | 10/2016 |
| WO | WO-2016172377 A1 | 10/2016 |
| WO | WO-2016173719 A1 | 11/2016 |
| WO | WO-2016183100 A1 | 11/2016 |
| WO | WO-2017049231 A1 | 3/2017 |
| WO | WO-2017053450 A1 | 3/2017 |
| WO | WO-2017059399 A1 | 4/2017 |
| WO | WO-2017095958 A1 | 6/2017 |
| WO | WO-2017100441 A1 | 6/2017 |
| WO | WO-2017118761 A1 | 7/2017 |
| WO | WO-2017158103 A1 | 9/2017 |
| WO | WO-2017214574 A1 | 12/2017 |
| WO | WO-2018026920 A1 | 2/2018 |
| WO | WO-2018038772 A1 | 3/2018 |
| WO | WO-2018057526 A2 | 3/2018 |
| WO | WO-2018094263 A1 | 5/2018 |
| WO | WO-2018112426 A1 | 6/2018 |
| WO | WO-2018119246 A1 | 6/2018 |
| WO | WO-2018156792 A1 | 8/2018 |
| WO | WO-2018170164 A1 | 9/2018 |
| WO | WO-2018170169 A1 | 9/2018 |
| WO | WO-2018170559 A1 | 9/2018 |
| WO | WO-2018200380 A1 | 11/2018 |
| WO | WO-2018231872 A1 | 12/2018 |
| WO | WO-2019014781 A1 | 1/2019 |
| WO | WO-2019051501 A1 | 3/2019 |
| WO | WO-2019079769 A1 | 4/2019 |
| WO | WO-2019084500 A1 | 5/2019 |
| WO | WO-2019136175 A1 | 7/2019 |
| WO | WO-2019222706 A1 | 11/2019 |
| WO | WO-2020139871 A1 | 7/2020 |
| WO | WO-2020176362 A1 | 9/2020 |
| WO | WO-2020176678 A1 | 9/2020 |
| WO | WO-2020176680 A1 | 9/2020 |
| WO | WO-2020257612 A1 | 12/2020 |
| WO | WO-2021046655 A1 | 3/2021 |
| WO | WO-2021119193 A2 | 6/2021 |
| WO | WO-2022010934 A2 | 1/2022 |
| WO | WO-2022046797 A1 | 3/2022 |
| WO | WO-2022046944 A2 | 3/2022 |
| WO | WO-2022047076 A1 | 3/2022 |
| WO | WO-2022076326 A1 | 4/2022 |
| WO | WO-2022086866 A1 | 4/2022 |
| WO | WO-2022087293 A1 | 4/2022 |
| WO | WO-2022098662 A2 | 5/2022 |
| WO | WO-2022159620 A1 | 7/2022 |
| WO | WO-2022178137 A1 | 8/2022 |
| WO | WO-2022204309 A1 | 9/2022 |
| WO | WO-2022204316 A2 | 9/2022 |
| WO | WO-2022217004 A1 | 10/2022 |
| WO | WO-2022235579 A1 | 11/2022 |
| WO | WO-2022235584 A1 | 11/2022 |
| WO | WO-2022271884 A2 | 12/2022 |
| WO | WO-2023023183 A2 | 2/2023 |
| WO | WO-2023023190 A2 | 2/2023 |
| WO | WO-2023023285 A2 | 2/2023 |
| WO | WO-2023069367 A1 | 4/2023 |
| WO | WO-2023076419 A2 | 5/2023 |
| WO | WO-2023076420 A2 | 5/2023 |
| WO | WO-2023076687 A1 | 5/2023 |

OTHER PUBLICATIONS

English machine translation of JP2010-248084 above, downloaded from worldwide.espacenet.org (Year: 2010).*
Froehler et al., "Synthesis of DNA via deoxynndeodde H-phosphonale Intermediates" Nucleic Acids Research vol. 14 No. 13 pp. 5399-5407 (Year: 1986).*
Kamaike et al., "Oligonucleotide Synthesis by the Use of a 2-(Levulinyloxymethyi)-5-nitrobenzoyl Group as the Novel Base-labile Protecting Group for the 5'-Hydroxyl Groups of Ribonucleoside and 2'-Deoxyribonucleoside 3'-Phosphoramidites" Tetrahedron Letters vol. 38 No. 39 pp. 6857-6860 (Year: 1997).*
Kosuri et al., "Large-scale de novo DNA synthesis: technologies and applications" Nature Methods vol. 11 No. 5 pp. 499-507 (Year: 2014).*
"Electrophile", downloaded from Chemistry Learner at www.chemistrylearner.com/electrophile.html (Year: 2024).*

(56) References Cited

OTHER PUBLICATIONS

Wong et al., "Surface characterization of 3-glycidoxypropyltrimethoxysilane films on silicon-based substrates" Anal Bioanal Chem vol. 383 pp. 187-200, DOI 10.1007/s00216-005-3414-y (Year: 2005).*
Krotz et al., "Large-Scale Synthesis of Antisense Oligonucleotides without Chlorinated Solvents" Organic Process Research and Development vol. 4 pp. 190-193, DOI 10.1021/op990183d (Year: 2000).*
Abudayyeh et al.: C2c2 is a single-component programmable RNA-guided RNA-targeting CRISPR effector. Science, available on line, Jun. 13, 2016, at: http://zlab.mit.edu/assets/reprints/Abudayyeh_OO_Science_2016.pdf , 17 pages.
Acevedo-Rocha et al:. Directed evolution of stereoselective enzymes based on genetic selection as opposed to screening systems. J. Biotechnol. 191:3-10 (2014).
Adessi et al.: Solid phase DNA amplification: characterisation of primer attachment and amplification mechanisms. Nucleic Acids Res. 28(20):E87, 2000.
Alexeyev et al.: Gene synthesis, bacterial expression and purification of the Rickettsia prowazekii ATP/ADP translocase, Biochimica et Biophysics Acta, 1419:299-306, 1999.
Ai-Housseiny et al.: Control of interfacial instabilities using flow geometry Nature Physics, 8:747-750, 2012.
Amblard et al.: A magnetic manipulator for studying local rheology and micromechanical properties of biological systems, Rev. Sci. Instrum., 67(3):18-827, 1996.
Andoni and Indyk. Near-Optimal Hashing Algorithms for Approximate Nearest Neighbor in High Dimensions, Communications of the ACM, 51(1):117-122, 2008.
Arand et al.: Structure of Rhodococcus erythropolis limonene-1,2-epoxide hydrolase reveals a novel active site. EMBO J. 22:2583-2592 (2003).
Arkles et al.: The Role of Polarity in the Structure of Silanes Employed in Surface Modification. Silanes and Other Coupling Agents. 5:51-64, 2009.
Arkles. Hydrophobicity, Hydrophilicity Reprinted with permission from the Oct. 2006 issue of Paint & Coatings Industry magazine, Retrieved on Mar. 19, 2016, 10 pages.
Assembly manual for the POSaM: The ISB Piezoelectric Oligonucleotide Synthesizer and Microarrayer, The Institute for Systems Biology, May 28, 2004 (50 pages).
Assi et al.: Massive-parallel adhesion and reactivity-measurements using simple and inexpensive magnetic tweezers. J. Appl. Phys. 92(9):5584-5586 (2002).
ATDBio. Nucleic Acid Structure, Nucleic Acids Book, 9 pages, published on Jan. 22, 2005. from: http://www.atdbio.com/content/5/Nucleic-acid-structure.
ATDBio. Solid-Phase Oligonucleotide Synthesis, Nucleic Acids Book, 20 pages, Published on Jul. 31, 2011. from: http://www.atdbio.com/content/17/Solid-phase-oligonucleotide-synthesis.
Au et al.: Gene synthesis by a LCR-based approach: high level production of Leptin-L54 using synthetic gene in *Escherichia coli*. Biochemical and Biophysical Research Communications 248:200-203 (1998).
Baedeker et al.: Overexpression of a designed 2.2kb gene of eukaryotic phenylalanine ammonialyase in *Escherichia coli•*. FEBS Letters, 457:57-60, 1999.
Barbee et al.: Magnetic Assembly of High-Density DNA Arrays for Genomic Analyses. Anal Chem. 80(6):2149-2154, 2008.
Barton et al.: A desk electrohydrodynamic jet printing system. Mechatronics, 20:611-616, 2010.
Beaucage et al.: Advances in the synthesis of oligonucleotides by the phosphoramidite approach. Tetrahedron. 48:2223-2311, 1992.
Beaucage et al.: Deoxynucleoside phosphoramidites—A new class of key intermediates for deoxypolynucleotide synthesis. Tetrahedron Lett. 22(20):1859-1862, 1981.
Beaucage et al.: The Chemical synthesis of DNA/RNA Chapter 2 in: Encyclopedia of Cell Biology, 1:36-53, 2016.

Beaulieu et al.: PCR candidate region mismatch scanning adaptation to quantitative, high-throughput genotyping, Nucleic Acids Research, 29(5):1114-1124, 2001.
Beigelman et al.: Base-modified phosphoramidite analogs of pyrimidine ribonucleosides for RNA structure-activity studies. Methods Enzymol. 317:39-65, 2000.
Bethge et al.: Reverse synthesis and 3'-modification of RNA. Jan. 1, 2011, pp. 64-64, XP055353420. Retrieved from the Internet: URL:http://www.is3na.org/assets/events/Category%202-Medicinal %20Chemistry%20of%20oligonucleotides%20%2864-108%29.pdf.
Binkowski et al.: Correcting errors in synthetic DNA through consensus shuffling. Nucleic Acids Research, 33(6):e55, 8 pages, 2005.
Biswas et al.: Identification and characterization of a thermostable MutS homolog from Thennus aquaticus, The Journal of Biological Chemistry, 271(9):5040-5048, 1996.
Biswas et al.: Interaction of MutS protein with the major and minor grooves of a heteroduplex DNA, The Journal of Biological Chemistry, 272(20):13355-13364, 1997.
Bjornson et al.: Differential and simultaneous adenosine Di- and Triphosphate binding by MutS, The Journal of Biological Chemistry, 278(20):18557-18562, 2003.
Blanchard et al.: High-Density Oligonucleotide Arrays, Biosensors & Bioelectronics, 11(6/7):687-690, 1996.
Blanchard: Genetic Engineering, Principles and Methods, vol. 20, Ed. J. Sedlow, New York: Plenum Press, p. 111-124, 1979.
Blawat et al.: Forward error correction for DNA data storage. Procedia Computer Science, 80:1011-1022, 2016.
Bonini and Mondino. Adoptive T-cell therapy for cancer: The era of engineered T cells. European Journal of Immunology, 45:2457-2469, 2015.
Bornholt et al.: A DNA-Based Archival Storage System, in International Conference on Architectural Support for Programming Languages and Operating Systems (ASPLOS), Apr. 2-6, 2016, Atlanta, GA, 2016, 637-649.
Borovkov et al.: High-quality gene assembly directly from unpurified mixtures of microassay-synthesized oligonucleotides. Nucleic Acid Research, 38(19):e180, 10 pages, 2010.
Brunet. Aims and methods of biosteganography. Journal of Biotechnology, 226:56-64, 2016.
Buermans et al.: Next Generation sequencing technology: Advances and applications, Biochimica et Biophysica Acta (BBA)— Molecular Basis of Disease, 1842:1931-1941, 2014.
Butler et al.: In situ synthesis of oligonucleotide arrays by using surface tension. J Am Chem Soc. 123(37):8887-94, 2001.
Calvert. Lithographically patterned self-assembled films. In: Organic Thin Films and Surfaces: Directions for the Nineties, vol. 20, p. 109, ed. by Abraham Ulman, San Diego: Academic Press, 1995.
Cardelli. Two-Domain DNA Strand Displacement, Electron. Proc. Theor. Comput. Sci., 26:47-61, 2010.
Carlson. Time for New DNA Synthesis and Sequencing Cost Curves, 2014. [Online]. Available: http://www.synthesis.cc/synthesis/2014/02/time_for_new_cost_curves_2014. 10 pages.
Carr et al.: Protein-mediated error correction for de novo DNA synthesis. Nucleic Acids Res. 32(20):e162, 9 pages, 2004.
Carter and Friedman. DNA synthesis and Biosecurity: Lessons learned and options for the future. J. Craig Venter Institute, La Jolla, CA, 28 pages, Oct. 2015.
Caruthers. Chemical synthesis of deoxyoligonucleotides by the phosphoramidite method. In Methods in Enzymology, Chapter 15, 154:287-313, 1987.
Caruthers. Gene synthesis machines: DNA chemistry and its uses. Science 230(4723):281-285 (1985).
Caruthers. The Chemical Synthesis of DNA/RNA: Our Gift to Science. J. Biol. Chem., 288(2):1420-1427, 2013.
Casmiro et al.: PCR-based gene synthesis and protein NMR spectroscopy, Structure, 5(11):1407-1412, 1997.
CeGaT. Tech Note available at https://www.cegat.de/web/wp-content/uploads/2018/06/Twist-Exome-Tech-Note.pdf (4 pgs.) (2018).
Cello et al.: Chemical synthesis of poliovirus cDNA: generation of infectious virus in the absence of natural template. Science. 297(5583):1016-8, 2000.

(56) References Cited

OTHER PUBLICATIONS

Chalmers et al.: Scaling up the ligase chain reaction-based approach to gene synthesis. Biotechniques. 30(2):249-52, 2001.
Chan et al.: Natural and engineered nicking endonucleases—from cleavage mechanism to engineering of strand-specificity. Nucleic Acids Res. 39(1):1-18, 2011.
Chen et al.: Chemical modification of gene silencing oligonucleotides for drug discovery and development. Drug Discov Today. 10(8):587-93 2005.
Chen et al.: Programmable chemical controllers made from DNA, Nat. Nanotechnol., 8(10):755-762, 2013.
Cheng et al.: High throughput parallel synthesis of oligonucleotides with 1536 channel synthesizer. Nucleic Acids Res. 30(18):e93, 2002.
Chilamakuri et al.: Performance comparison of four exome capture systems for deep sequencing. BMC Genomics 15(1):449 (2014).
Cho et al.: Capillary passive valve in microfluidic systems. NSTI-Nanotech. 2004; 1:263-266.
Chrisey et al.: Fabrication of patterned DNA surfaces Nucleic Acids Research, 24(15):3040-3047 (1996).
Chung et al.: One-step preparation of competent *Escherichia coli*: Transformation and storage of bacterial cells in the same solution. Proc Natl Acad Sci U S A. Apr. 1989;86(7):2172-2175.
Church et al.: Next-generation digital information storage in DNA. Science, 337:6102, 1628-1629, 2012.
Cleary et al.: Production of complex nucleic acid libraries using highly parallel in situ oligonucleotide synthesis. Nat Methods 1(3):241-248 (2004).
Cohen et al.: Human population: The next half century. Science, 302:1172-1175, 2003.
Crick. On protein synthesis. Symp Soc Exp Biol12:138-163, 1958.
Cruse et al.: Atlas of Immunology, Third Edition. Boca Raton:CRC Press (pp. 282-283) (2010).
Cutler et al.: High-throughput variation detection and genotyping using microarrays, Genome Research, vol. 11, 1913-19 (2001).
Dahl et al.: Circle-to-circle amplification for precise and sensitive DNA analysis. Proc Natl Acad Sci U S A. Mar. 30, 2004;101(13):4548-53. Epub Mar. 15, 2004.
De Mesmaeker et al.: Backbone modifications in oligonucleotides and peptide nucleic acid systems. Curr Opin Struct Biol. Jun. 1995;5(3):343-55.
De Silva et al.: New Trends of Digital Data Storage in DNA. BioMed Res Int. 2016:8072463 (2016).
Deamer et al.: Characterization of nucleic acids by nanopore analysis, Ace. Cham. Res., vol. 35, No. 10, 817-825 (2002).
Deaven. The Human Genome Project: Recombinant clones for mapping and sequencing DNA. Los Alamos Science, 20:218-249, 1992.
Deng et al.: Targeted bisulfite sequencing reveals changes in DNA methylation associated with nuclear reprogramming Nature Biotechnology, 27:352-360 (2009).
Dietrich et al.: Gene assembly based on blunt-ended double-stranded DNA-modules, Biotechnology Techniques, vol. 12, No. 1, 49-54 (Jan. 1998).
Dillon et al.: Exome sequencing has higher diagnostic yield compared to simulated disease-specific panels in children with suspected monogenic disorders. Eur J Hum Genet 26(5):644-651 (2018).
Dormitzer et al.: Synthetic generation of influenza vaccine viruses for rapid response to pandemics. Sci Translational Medicine, 5(185):185ra68, 14 pages, 2013.
Doudna et al.: Genome editing. The new frontier of genome engineering with CRISPR-Cas9. Science 346(6213):1258096-1-1258096-9, 2014.
Douthwaite et al.: Affinity maturation of a novel antagonistic human monoclonal antibody with a long VH CDR3 targeting the Class A GPCR formyl-peptide receptor 1; mAbs, vol. 7, Iss. 1, pp. 152-166 (Jan. 1, 2015).
Dower et al.: High efficiency transformation of *E.coli* by high voltage electroporation. Nucleic Acids Res. 16(13):6127-45 (1988).
Dressman et al.: Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Drmanac et al.: Human genome sequencing using unchained base reads on self-assembling DNA nanoarrays. Science. Jan. 1, 2010;327(5961):78-81. doi: 10.1126/science.1181498. Epub Nov. 5, 2009.
Droege and Hill. The Genome Sequencer FLXTM System-Longer reads, more applications, straight forward bioinformatics and more complete data sets Journal of Biotechnology, 136:3-10, 2008.
Duffy et al.: Rapid Prototyping of Microfluidic Systems in Poly(dimethylsiloxane). Anal Chem. Dec. 1, 1998;70(23):4974-84. doi: 10.1021/ac980656z.
Duggan et al.: Expression profiling using cDNA microarrays. Nat Genet. Jan. 1999;21(1 Suppl):10-4.
Dvorsky. Living Bacteria Can Now Store Data. GIZMODO internet publication. Retrieved from https://gizmodo.com/living-bacteria-can-now-store-data-1781773517 (4 pgs) (Jun. 10, 2016).
Eadie et al.: Guanine modification during chemical DNA synthesis. Nucleic Acids Res. Oct. 26, 1987;15(20):8333-49.
Eisen. A phylogenomic study of the MutS family of proteins, Nucleic Acids Research, vol. 26, No. 18, 4291-4300 (1998).
Ellis et al.: DNA assembly for synthetic biology: from parts to pathways and beyond. Integr Biol (Camb). Feb. 2011;3(2):109-18. doi: 10.1039/c0ib00070a. Epub Jan. 19, 2011.
El-Sagheer et al.: Biocompatible artificial DNA linker that is read through by DNA polymerases and is functional in *Escherichia coli*. Proc Natl Acad Sci U S A. Jul. 12, 2011;108(28):11338-43. doi: 10.1073/pnas.1101519108. Epub Jun. 27, 2011.
Elsik et al.: The Genome sequence of taurine cattle: A window of ruminant biology and evolution. Science, 324:522-528, 2009.
Elsner et al.: 172 nm excimer VUV-triggered photodegradation and micropatterning of aminosilane films, Thin Solid Films, 517:6772-6776 (2009).
Engler et al.: A one pot, one step, precision cloning method with high throughput capability. PLoS One. 2008;3(11):e3647. doi: 10.1371/journal.pone.0003647. Epub Nov. 5, 2008.
Engler et al.: Golden gate shuffling: a one-pot DNA shuffling method based on type IIs restriction enzymes. PLoS One. 2009;4(5):e5553. doi: 10.1371/journal.pone.0005553. Epub May 14, 2009.
Erlich and Zielinski, DNA fountain enables a robust and efficient storage architecture. Science, 355(6328):950-054, 2017.
Eroshenko et al.: Gene Assembly from Chip-Synthesized Oligonucleotides; Current Protocols in Chemical biology 4: 1-17 (2012).
European Patent Application No. 12827479.2 Extended European Search Report dated May 18, 2015.
European Patent Application No. 12827479.2 Partial European Search Report dated Jan. 29, 2015.
European Patent Application No. 14834665.3 Communication dated Jan. 16, 2018.
European Patent Application No. 14834665.3 extended European Search Report dated Apr. 28, 2017 .
European Patent Application No. 14834665.3 Further Examination Report dated Nov. 28, 2018.
European Patent Application No. 14834665.3 Office Action dated May 2, 2018.
European Patent Application No. 16847497.1 Extended European Search Report dated Jan. 9, 2019.
European Patent Application No. 16871446.7 European Search Report dated Apr. 10, 2019.
European Patent Application No. 16871446.7 First Official Action dated Nov. 13, 2019.
Evans et al.: DNA Repair Enzymes. Current Protocols in Molecular Biology 84:III:3.9:3.9.1-3.9.12 http://www.ncbi.nlm.nih.gov/pubmed/18972391 (Published online Oct. 1, 2008 Abstract only provided).
Fahy et al.: Self-sustained sequence replication (3SR): an isothermal transcription-based amplification system alternative to Pcr. Pcr Methods Appl. Aug. 1991;1(1):25-33.
Fedoryak, Olesya D. et al.: Brominated hydroxyquinoline as a photolabile protecting group with sensitivity to multiphoton excitation, Org. Lett., vol. 4, No. 2, 3419-3422 (2002).

(56) References Cited

OTHER PUBLICATIONS

Ferretti et al.: Total synthesis of a gene for bovine rhodopsin. PNAS, 83:599-603 (1986).
Finger et al.: The wonders of Flap Endonucleases: Structure, function, mechanism and regulation. Subcell Biochem., 62:301-326, 2012.
Fodor et al.: Light-directed, spatially addressable parallel chemical synthesis. Science. 251(4995):767-773 (1991).
Fogg et al.: Structural basis for uracil recognition by archaeal family B DNA polymerases. Nature Structural Biology, 9(12):922-927, 2002.
Foldesi et al.: The synthesis of deuterionucleosides. Nucleosides Nucleotides Nucleic Acids. Oct.-Dec. 2000;19(10-12):1615-56.
Frandsen et al.: Efficient four fragment cloning for the construction of vectors for targeted gene replacement in filamentous fungi. BMC Molecular Biology 2008, 9:70.
Frandsen. Experimental setup. Dec. 7, 2010, 3 pages. http://www.rasmusfrandsen.dk/experimental_setup.htm.
Frandsen. The User Friendly technology. User cloning. Oct. 7, 2010, 2 pages. http://www.rasmusfrandsen.dk/user_cloning.htm.
Fullwood et al.: Next-generation DNA sequencing of paired-end tags [PET] for transcriptome and genome analysis Genome Research, 19:521-532, 2009.
Galka et al.: QuickLib, a method for building fully synthetic plasmid libraries by seamless cloning of degenerate oligonucleotides. Plos One, 12, e0175146:1-9 (2017).
Galka et al.: QuickLib, a method for building fully synthetic plasmid libraries by seamless cloning of degenerate oligonucleotides. Plos One, 12, e0175146:S1 figure (2017).
Galka et al.: QuickLib, a method for building fully synthetic plasmid libraries by seamless cloning of degenerate oligonucleotides. Plos One, 12, e0175146:S1 Table (2017).
Galka et al.: QuickLib, a method for building fully synthetic plasmid libraries by seamless cloning of degenerate oligonucleotides. Plos One, 12, e0175146:S2 figure (2017).
Galneder et al.: Microelectrophoresis of a bilayer-coated silica bead in an optical trap: application to enzymology. Biophysical Journal, vol. 80, No. 5, 2298-2309 (May 2001).
Gao et al.: A flexible light-directed DNA chip synthesis gated by deprotection using solution photogenerated acids. Nucleic Acids Res. Nov. 15, 2001;29(22):4744-50.
Gao et al.: A method for the generation of combinatorial antibody libraries using pIX phage display. PNAS 99(20):12612-12616 (2002).
Gao et al.: Thermodynamically balanced inside-out (TBIO) PCR-based gene synthesis: a novel method of primer design for high-fidelity assembly of longer gene sequences. Nucleic Acids Res. Nov. 15, 2003;31(22):e143.
Garaj et al.: Graphene as a subnanometre trans-electrode membrane. Nature. Sep. 9, 2010;467(7312):190-3. doi: 10.1038/nature09379.
Garbow et al.: Optical tweezing electrophoresisof isolated, highly charged colloidal spheres, Colloids and Surfaces A: Physiochem. Eng. Aspects, vol. 195, 227-241 (2001).
Gaytan et al.: Chemical synthesis of oligonucleotides using acetone as a washing solvent. Bio Techniques 47:701-702 (2009).
GeneArt Seamless Cloning and Assembly Kits. Life Technologies Synthetic Biology. 8 pages, available online Jun. 15, 2012.
Genomics 101. An Introduction to the Genomic Workflow. 2016 edition, 64 pages. Available at: http://www.frontlinegenomics.com/magazine/6757/genomics-101/.
Geu-Flores et al.: User fusion: a rapid and efficient method for simultaneous fusion and cloning of multiple PCR products. Nucleic Acids Res. 2007;35(7):e55. Epub Mar. 27, 2007.
Gibson Assembly. Product Listing. Application Overview. 2 pages, available online Dec. 16, 2014.
Gibson et al.: Complete chemical synthesis, assembly, and cloning of a Mycoplasma genitalium genome. Science. Feb. 29, 2008;319(5867):1215-20. doi: 10.1126/science.1151721. Epub Jan. 24, 2008.
Gibson et al.: Creation of a Bacterial Cell Controlled by a Chemically Synthesized Genome. Science 329(5989):52-56 (2010).
Goldfeder et al.: Medical implications of technical accuracy in genome sequencing. Genome Med 8(1):24 (2016).
Goldman et al.: Towards practical, high-capacity, low-maintenance information storage in synthesized DNA, Nature, 494(7435):77-80, 2013.
Gosse et al.: Magnetic tweezers: micromanipulation and force measurement at the molecular level, Biophysical Journal, vol. 8, 3314-3329 (Jun. 2002).
Grass et al.: Robust chemical preservation of digital information on DNA in silica with error-correcting codes, Angew. Chemie—Int. Ed., 54(8):2552-2555, 2015.
Greagg et al.: A read-ahead function in archaeal DNA polymerases detects promutagenic template-strand uracil. Proc. Nat. Acad. Sci. USA, 96:9045-9050, 1999.
Grovenor. Microelectronic materials. Graduate Student Series in Materials Science and Engineering. Bristol, England: Adam Hilger, 1989; p. 113-123.
Gu et al.: Depletion of abundant sequences by hybridization (DASH): using Cas9 to remove unwanted high-abundance species in sequencing libraries and molecular counting applications. Genome Biology, 17:41, 13 pages, 2016.
Haber et al.: Magnetic tweezers for DNA micromanipulation, Rev. Sci. Instrum., vol. 71, No. 12, 4561-4570 (Dec. 2000).
Han et al.: Linking T-cell receptor sequence to functional phenotype at the single-cell level. Nat Biotechnol 32(7):684-692 (2014).
Hanahan and Cold Spring Harbor Laboratory. Studies on transformation of *Escherichia coli* with plasmids J. Mol. Biol. 166:557-580 (1983).
Hanahan et al.: Plasmid transformation of *Escherichia coli* and other bacteria. Methods Enzymol, vol. 204, p. 63-113 (1991).
Harada et al.: Unexpected substrate specificity of T4 DNA ligase revealed by in vitro selection. Nucleic Acids Res. May 25, 1993;21(10):2287-91.
Heckers et al.: Error analysis of chemically synthesized polynucleotides, BioTechniques, vol. 24, No. 2, 256-260 (1998).
Herzer et al.: Fabrication of patterned silane based self-assembled monolayers by photolithography and surface reactions on silicon-oxide substrates Chem. Commun., 46:5634-5652 (2010).
Hoover et al.: DNAWorks: an automated method for designing oligonucleotides for PCR-based gene synthesis, Nucleic Acids Research, vol. 30, No. 10, e43, 7 pages (2002).
Hosu et al.: Magnetic tweezers for intracellular applications•, Rev. Sci. Instrum., vol. 74, No. 9, 4158-4163 (Sep. 2003).
Huang et al.: Three-dimensional cellular deformation analysis with a two-photon magnetic manipulator workstation, Biophysical Journal, vol. 82, No. 4, 2211•2223 (Apr. 2002).
Hughes et al.: Expression profiling using microarrays fabricated by an ink-jet oligonucleotide synthesizer Nat Biotech 4:342-347 (2001).
Hughes et al.: Principles of early drug discovery. Br J Pharmacol 162(2):1239-1249, 2011.
Hutchison et al.: Cell-free cloning using phi29 DNA polymerase. Proc Natl Acad Sci U S A. Nov. 29, 2005;102(48):17332-6. Epub Nov. 14, 2005.
Imgur: The magic of the internet. Uploaded May 10, 2012, 2 pages, retrieved from: https://imgur.com/mEWuW.
In-Fusion Cloning: Accuracy, Not Background. Cloning & Competent Cells, ClonTech Laboratories, 3 pages, available online Jul. 6, 2014.
International Application No. PCT/US2017/026232 International Preliminary Report on Patentability dated Feb. 26, 2019.
International Application No. PCT/US2017/045105 International Preliminary Report on Patentability dated Feb. 5, 2019.
International Application No. PCT/US2017/052305 International Preliminary Report on Patentability dated Apr. 30, 2019.
International Application No. PCT/US2017/062391 International Preliminary Report on Patentability dated May 21, 2019.
International Application No. PCT/US2018/019268 International Preliminary Report on Patentability dated Sep. 6, 2019.
International Application No. PCT/US2018/050511 International Search Report and Written Opinion dated Jan. 11, 2019.
International Application No. PCT/US2018/057857 International Search Report and Written Opinion dated Mar. 18, 2019.

(56) References Cited

OTHER PUBLICATIONS

International Application No. PCT/US2019/012218 International Search Report and Written Opinion dated Mar. 21, 2019.
International Application No. PCT/US2019/032992 International Search Report and Written Opinion dated Oct. 28, 2019.
International Application No. PCT/US2019/032992 Invitation to Pay Additional Fees dated Sep. 6, 2019.
Jackson et al.: Recognition of DNA base mismatches by a rhodium intercalator, J. Am. Chem. Soc., vol. 19, 12986-12987 (1997).
Jacobs et al.: DNA glycosylases: In DNA repair and beyond. Chromosoma 121:1-20 (2012)—http://www.ncbi.nlm.nih.gov/pmc/articles/PMC3260424/.
Jacobus et al.: Optimal cloning of PCR fragments by homologous recombination in *Escherichia soli*. PLoS One 10(3):e0119221 (2015).
Jager et al.: Simultaneous Humoral and Cellular: Immune Response against Cancer-Testis Antigen NY-ES0-1: Definition of Human Histocompatibility Leukocyte Antigen (HLA)-A2—binding Peptide Epitopes. J. Exp. Med. 187(2):265-270 (1998).
Jinek et al.: A Programmable dual-RNA-guided DNA endonuclease in adaptive bacterial immunity. Science, 337:816-821, 2012.
Karagiannis and Ei-Osta. RNA interference and potential therapeutic applications of short interfering RNAs Cancer Gene Therapy, 12:787-795, 2005.
Ke et al.: Influence of neighboring base pairs on the stability of single base bulges and base pairs in a DNA fragment, Biochemistry, Vo. 34, 4593-4600 (1995).
Kelley et al.: Single-base mismatch detection based on charge transduction through DNA, Nucleic Acids Research, vol. 27, No. 24, 4830-4837 (1999).
Kim et al.: High-resolution patterns of quantum dots formed by electrohydrodynamic jet printing for light-emitting diodes. Nano Letters, 15:969-973, 2015.
Kim et al.: Chimeric restriction endonuclease, Proc. Natl. Acad. Sci. USA, vol. 91, 883-887 (Feb. 1994).
KIM. The interaction between Z-ONA and the Zab domain of double-stranded RNA adenosine deaminase characterized using fusion nucleases, The Journal of Biological Chemistry, vol. 274, No. 27, 19081-19086 (1999).
Kim et al.: Site-specific cleavage of DNA-RNA hybrids by zinc finger/Fok I cleavage domain fusions Gene, vol. 203, 43-49 (1997).
Kinde et al.: Detection and quantification of rare mutations with massively parallel sequencing. Proc Natl Acad Sci U S A. Jun. 7, 2011;108(23):9530-5. Epub May 17, 2011.
Kodumal et al.: Total synthesis of long DNA sequences: synthesis of a contiguous 32-kb polyketide synthase gene cluster. Proc Natl Acad Sci U S A. Nov. 2, 2004;101(44):15573-8. Epub Oct. 20, 2004.
Koike-Yusa et al.: Genome-wide recessive genetic screening in mammalian cells with a lentiviral CRISPR-guide RNA library. Nature Biotechnology, 32:267-273, 2014 (with three pages of supplemental Online Methods).
Kong et al.: Parallel gene synthesis in a microfluidic device. Nucleic Acids Res., 35(8):e61 (2007).
Kong. Microfluidic Gene Synthesis. MIT Thesis. Submitted to the program in Media Arts and Sciences, School of Architecture and Planning, in partial fulfillment of the requirements for the degree of Doctor of Philosophy in Media Arts and Sciences at the Massachusetts Institute of Technology. 143 pages Jun. 2008.
Kopp et al.: Chemical amplification: continuous-flow PCR on a chip, Science, vol. 280, 1046-1048 (May 15, 1998).
Kosuri and Church. Large-scale de novo DNA synthesis: technologies and applications, Nature Methods, 11:499-507, 2014. Available at: http://www.nature.com/nmeth/journal/v11/n5/full/nmeth.2918.html.
Kosuri et al.: A scalable gene synthesis by selective amplification of DNA pools from high-fidelity microchips. Nature Biotechnology. 2010; 28:1295-1299.
Krayden, Inc .: A Guide to Silane Solutions. Silane coupling agents. 7 pages. Published on May 31, 2005 at: http://krayden.com/pdf/xia_silane_chemistry.pdf.

Lagally et al.: Single-Molecule DNA Amplification and Analysis in an Integrated Microfluidic Device. Analytical Chemistry. 2001;73(3): 565-570.
Lahue et al.: DNA mismatch correction in a defined system, Science, vol. 425; No. 4914, 160-164 (Jul. 14, 1989).
Lambrinakos et al.: Reactivity of potassium permanganate and tetraethylammonium chloride with mismatched bases and a simple mutation detection protocol, Nucleic Acids Research, vol. 27, No. 8, 1866-1874 (1999).
Landegren et al.: A ligase-mediated gene detection technique. Science. Aug. 26, 1988;241(4869):1077-80.
Lang et al.: An automated two-dimensional optical force clamp for single molecule studies, Biophysical Journal, vol. 83, 491.501 (Jul. 2002).
Lashkari et al.: An automated multiplex oligonucleotide synthesizer: development of high-throughput, low-cost DNA synthesis. Proc Natl Acad Sci U S A. Aug. 15, 1995;92(17):7912-5.
Lausted et al.: POSaM: a fast, flexible, open-source, inkjet oligonucleotide synthesizer and microarrayer, Genome Biology, 5:R58, 17 pages, 2004. available at https://www.ncbi.nlm.nih.gov/pmc/articles/PMC507883/.
Leamon et al.: A massively parallel PicoTiterPlate based platform for discrete picoliter-scale polymerase chain reactions. Electrophoresis. Nov. 2003;24(21):3769-77.
Lee: Covalent End-Immobilization of Oligonucleotides onto Solid Surfaces; Thesis, Massachusetts Institute of Technology, Aug. 2001 (315 pages).
Lee et al.: Microelectromagnets for the control of magnetic nanoparticles, Appl. Phys. Lett., vol. 79, No. 20, 3308-3310 (Nov. 12, 2001).
Lee et al.: A microfluidic oligonucleotide synthesizer. Nucleic Acids Research 2010 vol. 38(8):2514-2521. DOI: 10.1093/nar/gkq092.
Leproust et al.: Agilent's Microarray Platform: How High-Fidelity DNA Synthesis Maximizes the Dynamic Range of Gene Expression Measurements. 2008; 1-12. http://www.miltenyibiotec.com/~/media/Files/Navigation/Genomic%20Services/Agilent_DNA_Microarray_Platform.ashx.
Leproust et al.: Synthesis of high-quality libraries of long (150mer) oligonucleotides by a novel depurination controlled process. Nucleic Acids Research. 2010; 38(8):2522-2540.
Lesnikowski et al.: Nucleic acids and nucleosides containing carboranes. J. Organometallic Chem. 1999; 581:156-169.
Leumann. DNA analogues: from supramolecular principles to biological properties. Bioorg Med Chem. Apr. 2002; 10(4):841-54.
Levene et al.: Zero-mode waveguides for single-molecule analysis at high concentrations. Science. Jan. 31, 2003;299(5607):682-6.
Lewontin and Harti. Population genetics in forensic DNA typing. Science, 254:1745-1750, 1991.
Li et al.: Beating bias in the directed evolution of proteins: Combining high-fidelity on-chip solid-phase gene synthesis with efficient gene assembly for combinatorial library construction. First published Nov. 24, 2017, 2 pages. retrieved from: https://doi.org/10.1002/cbic.201700540.
Li et al.: Beating Bias in the Directed Evolution of Proteins: Combining High-Fidelity on-Chip Solid-Phase Gene Synthesis with Efficient Gene Assembly for Combinatorial Library Construction. ChemBioChem 19:221-228 (2018).
Light source unit for printable patterning VUV-Aligner / USHIO Inc., Link here: https://www.ushio.co.jp/en/products/1005.html, published Apr. 25, 2016, printed from the internet on Aug. 2, 2016, 3 pages.
Limbachiya et al.: Natural data storage: A review on sending information from now to then via Nature. ACM Journal on Emerging Technologies in Computing Systems, V(N):Article A, May 19, 2015, 17 pages.
Link Technologies. Product Guide 2010. Nov. 27, 2009, 136 pages. XP055353191. Retrieved from the Internet: URL:http://www.linktech.co.uk/documents/517/517.pdf.
Lipshutz et al.: High density synthetic oligonucleotide arrays, Nature Genetics Supplement, vol. 21, 20-24 (Jan. 1999).
Lishanski et al.: Mutation detection by mismatch binding protein, MutS, in amplified DNA: application to the cystic fibrosis gene, Proc. Natl. Acad. Sci. USA, vol. 91, 2674-2678 (Mar. 1994).

(56) References Cited

OTHER PUBLICATIONS

Liu et al.: Comparison of Next-Generation Sequencing Systems. J Biomed Biotechnol 2012: 251364 (2012).
Liu et al.: Enhanced Signals and Fast Nucleic Acid Hybridization by Microfluidic Chaotic Mixing. Angew. Chem. Int. Ed. 2006; 45:3618-3623.
Liu et al.: Rational design of CXCR4 specific antibodies with elongated CDRs. JACS, 136:10557-10560, 2014.
Lizardi et al.: Mutation detection and single-molecule counting using isothermal rolling-circle amplification. Nat Genet. Jul. 1998; 19(3):225-32.
Li et al.: Functional domains in Fok I restriction endonuclease, Proc. Natl. Acad. Sci. USA, 89:4275-4279, 1992.
Lu et al.: Methyl-directed repair of DNA base-pair mismatches in vitro, Proc. Natl. Acad. Sci. USA, 80:4639-4643, 1983.
Lund et al.: A validated system for ligation-free uracilexcision based assembly of expression vectors for mammalian cell engineering. DTU Systems of Biology. 2011. 1 page. http://www.lepublicsystemepco.com/files/modules/gestion_rubriques/REF-B036-Lund_Anne%20Mathilde.pdf.
Ma et al.: DNA synthesis, assembly and application in synthetic biology. Current Opinion in Chemical Biology. 16:260-267, 2012.
Ma et al.: Versatile surface functionalization of cyclic olefin copolymer (COC) with sputtered SiO2 thin film for potential BioMEMS applications. Journal of Materials Chemistry, 11 pages, 2009.
Mahato et al.: Modulation of gene expression by antisense and antigene oligodeoxynucleotides and small interfering RNA Expert Opin. Drug Delivery, 2(1):3-28, 2005.
Margulies et al.: Genome sequencing in open microfabricated high-density picolitre reactors. Nature. 437(7057):376-80, 2005.
Martinez-Torrecuadrada et al.: Targeting the Extracellular Domain of Fibroblast Growth Factor Receptor 3 with Human Single-Chain Fv Antibodies Inhibits Bladder Carcinoma Cell Line Proliferation; Clinical Cancer Research; vol. 11; pp. 6282-6290 (2005).
Matteucci et al.: Synthesis of deoxyoligonucleotides on a polymer support. J. Am. Chem. Soc. 103(11):3185-3191, 1981.
Matzas et al.: Next generation gene synthesis by targeted retrieval of bead-immobilized, sequence verified DNA clones from a high throughput pyrosequencing device. Nat. Biotechnol., 28(12):1291-1294, 2010.
Mazor et al.: Isolation of Full-Length IgG Antibodies from Combinatorial Libraries Expressed in *Escherichia coli*; Antony S. Dimitrov (ed.), Therapeutic Antibodies: Methods and Protocols, vol. 525, Chapter 11, pp. 217-239 (2009).
McBride & Caruthers. An investigation of several deoxynucleoside phosphoramidites useful for synthesizing deoxyoligonucleotides. Tetrahedron Lett. 24: 245-248, 1983.
McGall et al.: Light-directed synthesis of high-density oligonucleotide arrays using semiconductor photoresists. Proc Natl Acad Sci U S A. 93(24):13555-60, 1996.
McGall et al.: The Efficiency of Light-Directed Synthesis of DNA Arrays on Glass Substrates. J. Am. Chem. Soc. 119(22):5081-5090, 1997.
Mei et al.: Cell-free protein synthesis in microfluidic array devices Biotechnol. Prog., 23(6):1305-1311, 2007.
Mendel-Hartvig. Padlock probes and rolling circle amplification. New possibilities for sensitive gene detection. Comprehensive Summaries of Uppsala Dissertations from the Faculty of Medicine 1175. Uppsala University. 2002, 39 pages. http://www.diva-portal.org/smash/get/diva2:161926/FULLTEXT01.pdf.
Meyers and Friedland. Knowledge-based simulation of genetic regulation in bacteriophage lambda. Nucl. Acids Research, 12(1):1-16, 1984.
Meynert et al.: Quantifying single nucleotide variant detection sensitivity in exome sequencing. BMC Bioinformatics 14:195 (2013).
Meynert et al.: Variant detection sensitivity and biases in whole genome and exome sequencing. BMC Bioinformatics 15:247 (2014).
Milo and Phillips. Numbers here reflect the number of protein coding genes and excludes tRNA and non-coding RNA. Cell Biology by the Numbers, p. 286, 2015.
Mitra et al.: In situ localized amplification and contact replication of many individual DNA molecules. Nucleic Acids Res. 27(24):e34, 1999.
Morin et al.: Profiling the HeLa S3 transcriptome using randomly primed cDNA and massively parallel short-read sequencing. Biotechniques, 45:81-94, 2008.
Morris and Stauss. Optimizing T-cell receptor gene therapy for hematologic malignancies. Blood, 127(26):3305-3311, 2016.
Muller et al.: Protection and labelling of thymidine by a fluorescent photolabile group, Helvetica Chimica Acta, vol. 84, 3735-3741 (2001).
Mulligan. Commercial Gene Synthesis Technology PowerPoint presentation. BlueHeron® Biotechnology. Apr. 5, 2006 (48 pgs).
Nakatani et al.: Recognition of a single guanine bulge by 2-Acylamino-1,8-naphthyridine, J. Am. Chem. Soc., vol. 122, 2172-2177 (2000).
Jo et al.: Engineering therapeutic antibodies targeting G-protein-coupled receptors; Experimental & Molecular Medicine; 48; 9 pages (2016).
Neiman M.S.: Negentropy principle in information processing systems. Radiotekhnika, 1966, No. 11, p. 2-9.
Neiman M.S.: On the bases of the theory of information retrieval. Radiotekhnika, 1967, No. 5, p. 2-10.
Neiman M.S.: On the molecular memory systems and the directed mutations. Radiotekhnika, 1965, No. 6, pp. 1-8.
Neiman M.S.: On the relationships between the reliability, performance and degree of microminiaturization at the molecular-atomic level. Radiotekhnika, 1965, No. 1, pp. 1-9.
Neiman M.S.: Some fundamental issues of microminiaturization. Radiotekhnika, 1964, No. 1, pp. 3-12.
Nishikura. A short primer on RNAi: RNA-directed RNA polymerase acts as a key catalyst Cell, 107:415-418, 2001.
Nour-Eldin et al.: User Cloning and User Fusion: The Ideal Cloning Techniques for Small and Big Laboratories. Plant Secondary Metabolism Engineering. Methods in Molecular Biology vol. 643, 2010, pp. 185-200.
Ochman et al.: Genetic applications of an inverse polymerase chain reaction. Genetics. Nov. 1988;120(3):621-3.
Organick et al.: Random access in large-scale DNA data storage. Nature Biotechnology, Advance Online Publication, 8 pages, 2018.
Organick et al.: Scaling up DNA data storage and random access retrieval, bioRxiv, preprint first posted online Mar. 7, 2017, 14 pages.
Pan et al.: An approach for global scanning of single nucleotide variations. Proc Natl Acad Sci USA. Jul. 9, 2002;99(14):9346-51.
Pankiewicz. Fluorinated nucleosides. Carbohydr Res. Jul. 10, 2000;327(1-2):87-105.
Paul et al.: Acid binding and detritylation during oligonucleotide synthesis. Nucleic Acids Research. 15. pp. 3048-3052 (1996).
PCT/IL2012/000326 International Preliminary Report on Patentability dated Dec. 5, 2013.
PCT/IL2012/000326 International Search Report dated Jan. 29, 2013.
PCT/US14/049834 International Preliminary Report on Patentability dated Feb. 18, 2016.
PCT/US2014/049834 International Search Report and Written Opinion mailed Mar. 19, 2015.
PCT/US2014/049834, Invitation to Pay Additional Fees and, where applicable, protest fee, mailed Jan. 5, 2015.
PCT/US2015/043605 International Preliminary Report on Patentability dated Feb. 16, 2017.
PCT/US2015/043605 International Search Report and Written Opinion dated Jan. 6, 2016.
PCT/US2015/043605 Invitation To Pay Additional Fees dated Oct. 28, 2015.
PCT/US2016/016459 International Preliminary Report on Patentability dated Aug. 17, 2017.
PCT/US2016/016459 International Search Report and Written Opinion dated Apr. 13, 2016.
PCT/US2016/016636 International Preliminary Report on Patentability dated Aug. 17, 2017.
PCT/US2016/016636 International Search Report and Written Opinion dated May 2, 2016.

(56) References Cited

OTHER PUBLICATIONS

PCT/US2016/028699 International Preliminary Report on Patentability dated Nov. 2, 2017.
PCT/US2016/028699 International Search Report and Written Opinion dated Jul. 29, 2016.
PCT/US2016/031674 International Preliminary Report on Patentability dated Nov. 23, 2017.
PCT/US2016/031674 International Search Report and Written Opinion dated Aug. 11, 2016.
PCT/US2016/052336 International Preliminary Report on Patentability dated Mar. 29, 2018.
PCT/US2016/052336 International Search Report and Written Opinion dated Dec. 7, 2016.
PCT/US2016/052916 International Preliminary Report on Patentability dated Apr. 5, 2018.
PCT/US2016/052916 International Search Report and Written Opinion dated Dec. 30, 2016.
PCT/US2016/064270 International Preliminary Report on Patentability dated Jun. 14, 2018.
PCT/US2016/064270 International Search Report and Written Opinion dated Apr. 28, 2017.
PCT/US2017/026232 International Search Report and Written Opinion dated Aug. 28, 2017.
PCT/US2017/036868 International Search Report and Written Opinion dated Aug. 11, 2017.
PCT/US2017/045105 International Search Report and Written Opinion dated Oct. 20, 2017.
PCT/US2017/052305 International Search Report and Written Opinion dated Feb. 2, 2018.
PCT/US2017/062391 International Search Report and Written Opinion dated Mar. 28, 2018.
PCT/US2017/066847 International Search Report and Written Opinion dated May 4, 2018.
PCT/US2018/022487 International Search Report and Written Opinion dated Aug. 1, 2018.
PCT/US2018/022493 International Search Report and Written Opinion dated Aug. 1, 2018.
PCT/US2018/037152 International Search Report and Written Opinion dated Aug. 28, 2018.
PCT/US2018/037161 International Search Report and Written Opinion dated Oct. 22, 2018.
PCT/US2018/037161 Invitation to Pay Additional Fees dated Aug. 27, 2018.
PCT/US2018/056783 International Search Report and Written Opinion of the International Searching Authority dated Dec. 20, 2018.
PCT/US2018/19268 International Search Report and Written Opinion dated Jun. 26, 2018.
PCT/US2018/19268 Invitation to Pay Additional Fees and, where applicable, protest fee dated May 2, 2018.
PCT/US2018/22487 Invitation to Pay Additional Fees and, where applicable, protest fee dated May 31, 2018.
PCT/US2018/22493 Invitation to Pay Additional Fees and, where applicable, protest fee dated May 31, 2018.
Pease et al.: Light-generated oligonucleotide arrays for rapid DNA sequence analysis. Proc Natl Acad Sci U S A. May 24, 1994;91(11):5022-6.
Peisajovich et al.: BBF RFC 28: A method for combinatorial multi-part assembly based on the type-IIs restriction enzyme aarI. Sep. 16, 2009, 7 pages.
Pellois et al.: Individually addressable parallel peptide synthesis on microchips, Nature Biotechnology, vol. 20 , 922-926 (Sep. 2002).
Petersen et al.: LNA: a versatile tool for therapeutics and genomics. Trends Biotechnol. Feb. 2003;21(2):74-81.
Pierce and Wangh. Linear-after-the-exponential polymerase chain reaction and allied technologies Real-time detection strategies for rapid, reliable diagnosis from single cells Methods Mol. Med. 132:65-85 (2007) (Abstract only).
Pierce et al.: Linear-after-the-exponential polymerase chain reaction and allied technologies. Real-time detection strategies for rapid, reliable diagnosis from single cells. Methods Mol Med. 2007;132:65-85.
Pirrung. How to make a DNA chip. Angew. Chem. Int. Ed., 41:1276-1289, 2002.
Plesa et al.: Multiplexed gene synthesis in emulsions for exploring protein functional landscapes. Science, 10.1126/science.aao5167, 10 pages, 2018.
Pon. Solid-phase supports for oligonucleotide synthesis. Methods Mol Biol. 1993;20:465-96.
Poster. Reimagine Genome Scale Research. 2016, 1 page. Available at http://www2.twistbioscience.com/Oligo_Pools_CRISPR_poster.
Powers et al.: Optimal strategies for the chemical and enzymatic synthesis of bihelical deoxyribonucleic acids. J Am Chem Soc., 97(4):875-884, 1975.
Pray. Discovery of DNA Structure and Function: Watson and Crick, Nature Education, 2008, 6 pages. available at: http://www.nature.com/scitable/topicpage/discovery-of-dna-structure-and-function-watson-397.
Prodromou et al.: Recursive PCR: a novel technique for total gene synthesis. Protein Eng. Dec. 1992;5(8):827-9.
PubChem Data Sheet Acetonitrile. Printed from website https://pubchem.ncbi.nlm.nig.gov/ pp. 1-124 (2020).
PubChem Data Sheet Methylene Chloride. Printed from website https://pubchem.ncbi.nlm.nih.gov/ pp. 1-140 (2020).
Puigbo. Optimizer: a web server for optimizing the codon usage of DNA sequences. Nucleic Acid Research, 35(14):126-131, 2007.
Qian and Winfree. Scaling up digital circuit computation with DNA strand displacement cascades. Science, 332(6034):196-1201, 2011.
Qian et al.: Neural network computation with DNA strand displacement cascades, Nature, 475(7356):368-372, 2011.
Quan et al.: Parallel on-chip gene synthesis and application to optimization of protein expression. Nature Biotechnology. 2011; 29:449-452.
Rafalski and Morgante. Corn and humans: recombination and linkage disequilibrium in two genomes of similar size. Trends in Genetics, 20(2):103-111, 2004.
Raje and Murma. A Review of electrohydrodynamic-inkjet printing technology. International Journal of Emerging Technology and Advanced Engineering, 4(5):174-183, 2014.
Rajpal et al.: A general method for greatly improving the affinity of antibodies by using combinatorial libraries. Proc. Natl. Acad. Sci. 102(24):8466-8471 (2005).
Rastegari et al.: XNOR-Net: ImageNet Classification Using Binary Convolutional Neural Networks, in ECCV 2016, Part IV, LNCS 9908, p. 525-542, 2016.
Reimagine SequenceSpace. Reimagine Research, Twist Bioscience, Product Brochure, Published Apr. 6, 2016 online at: www2.twistbioscience.com/TB_Product_Brochure_04.2016, 8 pages.
RF Electric discharge type excimer lamp. Products Catalog. Excimer lamp light source flat excimer, 16 pages dated Jan. 2016. From: http://www.hamamatsu.com/jp/en/product/category/1001/3026/index.html.
Richmond et al.: Amplification and assembly of chip-eluted DNA (AACED): a method for high-throughput gene synthesis. Nucleic Acids Res. Sep. 24, 2004;32(17):5011-8. Print 2004.
Roche. Restriction Enzymes from Roche Applied Science—A Tradition of Premium Quality and Scientific Support. FAQS and Ordering Guide. Roche Applied Science. Accessed Jan. 12, 2015, 37 pages.
Rogozin et al.: Origin and evolution of spliceosomal introns. Biology Direct, 7:11, 2012.
Ruminy et al.: Long-range identification of hepatocyte nuclear factor-3 (FoxA) high and low-affinity binding Sites with a chimeric nuclease, J. Mol. Bioi., vol. 310, 523-535 (2001).
Saaem et al.: In situ synthesis of DNA microarray on functionalized cyclic olefin copolymer substrate ACS Applied Materials & Interfaces, 2(2):491-497, 2010.
Saboulard et al.: High-throughput site-directed mutagenesis using oligonucleotides synthesized on DNA chips. Biotechniques. Sep. 2005;39(3):363-8.

(56) References Cited

OTHER PUBLICATIONS

Sacconi et al.: Three-dimensional magneto-optic trap for microobject manipulation, Optics Letters, vol. 26, No. 17, 1359-1361 (Sep. 1, 2001).
Saiki et al.: Analysis of enzymatically amplified beta-globin and HLA-DQ alpha DNA with allele-specific oligonucleotide probes. Nature 324:163-166 (1986).
Sandhu et al.: Dual asymmetric PCR: one-step construction of synthetic genes. Biotechniques. Jan. 1992;12(1):14-6.
Sargolzaei et al.: Extent of linkage disequilibrium in Holstein cattle in North America. J.Dairy Science, 91:2106-2117, 2007.
Schaller et al.: Studies on Polynucleotides. XXV.1 The Stepwise Synthesis of Specific Deoxyribopolynucleotides (5). Further Studies on the Synthesis of Internucleotide Bond by the Carbodiimide Method. The Synthesis of Suitably Protected Dinucleotides as Intermediates in the Synthesis of Higher Oligonucleotides. J. Am. Chem. Soc. 1963; 85(23):3828-3835.
Schmalzing et al.: Microchip electrophoresis: a method for high-speed SNP detection. Nucleic Acids Res 28(9):E43 (2000).
Schmitt et al.: New strategies in engineering T-cell receptor gene-modified T cells to more effectively target malignancies. Clinical Cancer Research, 21(23):5191-5197, 2015.
Seelig et al.: Enzyme-Free Nucleic Acid Logic Circuits, Science 314(5805):1585-1588, 2006.
Sharan et al.: Recombineering: a homologous recombination-based method of genetic engineering. Nat Profile 4(2):1-37 (originally pp. 206-223) (2009).
Sharpe and Mount. Genetically modified T cells in cancer therapy: opportunities and challenges. Disease Models and Mechanisms, 8:337-350, 2015.
Sierzchala et al.: Solid-phase oligodeoxynucleotide synthesis : a two-step cycle using peroxy anion deprotection, J. Am. Chem. Soc., vol. 125, No. 44, 13427-13441 (2003).
Simonyan and Zisserman. Very Deep Convolutional Networks for Large-Scale Image Recognition, Published as a conference paper at Int. Conf. Learn. Represent., pp. 1-14, 2015.
Singh-Gasson et al.: Maskless fabrication of light-directed oligonucleotide microarrays using a digital micromirror array, Nature Biotechnology, vol. 17, 974-978 (Oct. 1999).
Skerra. Phosphorothioate primers improve the amplification of DNA sequences by DNA polymerases with proofreading activity. Nucleic Acids Res. Jul. 25, 1992; 20(14):3551-4.
Smith et al.: Generating a synthetic genome by whole genome assembly: phix174 bacteriophage from synthetic oligonucleotides. Proc Natl Acad Sci U S A. Dec. 23, 2003;100(26):15440-5. Epub Dec. 2, 2003.
Smith et al.: Generation of cohesive ends on PCR products by UDG-mediated excision of dU, and application for cloning into restriction digest-linearized vectors. PCR Methods Appl. May 1993;2(4):328-32.
Smith et al.: Mutation detection with MutH, MutL, and MutS mismatch repair proteins, Proc. Natl. Acad. Sci. USA, vol. 93, 4374-4379 (Apr. 1996).
Smith et al.: Removal of Polymerase-Produced mutant sequences from PCR products, Proc. Natl. Acad. Sci. USA, vol. 94, 6847-6850 (Jun. 1997).
Smith et al.: Direct mechanical measurements of the elasticity of single DNA molecules using magnetic beads, Science, vol. 258, 1122-1126 (Nov. 13, 1992).
Solomon et al.: Genomics at Agilent: Driving Value in DNA Sequencing.https://www.agilent.com/labs/features/2010_genomics.html, 8 pages (Aug. 5, 2010).
Soni et al.: Progress toward ultrafast DNA sequencing using solid-state nanopores. Clin Chem. Nov. 2007;53(11):1996-2001. Epub Sep. 21, 2007.
Southern et al.: Analyzing and comparing nucleic acid sequences by hybridization to arrays of oligonucleotides: evaluation using experimental models. Genomics. Aug. 1992;13(4):1008-17.
Sproat et al.: An efficient method for the isolation and purification of oligoribonucleotides. Nucleosides & Nucleotides. 1995; 14(1 &2):255-273.
Srivannavit et al.: Design and fabrication of microwell array chips for a solution-based, photogenerated acid-catalyzed parallel oligonuclotide DNA synthesis. Sensors and Actuators A, 116:150-160, 2004.
Srivastava et al.: RNA synthesis: phosphoramidites for RNA synthesis in the reverse direction. Highly efficient synthesis and application to convenient introduction of ligands, chromophores and modifications of synthetic RNA at the 3'-end, Nucleic Acids Symposium Series, 52(1):103-104, 2008.
Steel. The Flow-Thru Chip A Three-dimensional biochip platform. In: Schena, Microarray Biochip Technology, Chapter 5, Natick, MA: Eaton Publishing, 2000, 33 pages.
Stemmer et al.: Single-step assembly of a gene and entire plasmid from large numbers of oligodeoxyribonucleotides. Gene. Oct. 16, 1995;164(1):49-53.
Stryer. DNA Probes and genes can be synthesized by automated solid-phase methods. Biochemistry, 3rd edition, New York: W.H. Freeman and Company, 1988; 123-125.
Stutz et al.: Novel fluoride-labile nucleobase-protecting groups for the synthesis of 3'(2')-O-amino-acylated RNA sequences. Helv. Chim. Acta. 2000; 83(9):2477-2503.
Sullivan et al.: Library construction and evaluation for site saturation mutagenesis. Enzyme Microb. Technol. 53:70-77 (2013).
Sun et al.: Structure-Guided Triple-Code Saturation Mutagenesis: Efficient Tuning of the Stereoselectivity of an Epoxide Hydrolase. ACS Catal. 6:1590-1597 (2016).
Takahashi. Cell-free cloning using multiply-primed rolling circle amplification with modified RNA primers. Biotechniques. Jul. 2009;47(1):609-15. doi: 10.2144/000113155.
Tanase et al.: Magnetic trapping of multicomponent nanowires, The Johns Hopkins University, Baltimore, Maryland, p. 1-3 (Jun. 25, 2001).
Taylor et al.: Impact of surface chemistry and blocking strategies on DNA microarrays. Nucleic Acids Research, 31(16):e87, 19 pages, 2003.
The Hood Laboratory, Beta Group. Assembly Manual for the POSaM: The ISB Piezoelelctric Oligonucleotide Synthesizer and Microarrayer, Inkjet Microarrayer Manual Version 1.2, 50 pages, May 28, 2004.
The SLIC. Gibson, CPEC and SLiCE assembly methods (and GeneArt Seamless, In-Fusion Cloning). 5 pages, available online Sep. 2, 2010.
Tian et al.: Accurate multiplex gene synthesis from programmable DNA microchips. Nature. Dec. 23, 2004;432(7020):1050-4.
Tsai et al.: Dimeric CRISPR RNA-guided FokI nucleases for highly specific genome editing Nat. Biotechnol., 32(6):569-576, 2014.
Twist Bioscience | White Paper. DNA-Based Digital Storage. Retrieved from the internet, Twistbioscience.com, Mar. 27, 2018, 5 pages.
Unger et al.: Monolithic microfabricated valves and pumps by multilayer soft lithography. Science. Apr. 7, 2000;288(5463):113-6.
U.S. Appl. No. 14/241,874 Final Office Action dated Jan. 28, 2019.
U.S. Appl. No. 14/241,874 Office Action dated Feb. 27, 2017.
U.S. Appl. No. 14/241,874 Office Action dated Jul. 14, 2016.
U.S. Appl. No. 14/241,874 Office Action dated May 4, 2018.
U.S. Appl. No. 14/452,429 Notice of Allowance dated Jun. 7, 2016.
U.S. Appl. No. 14/452,429 Office Action mailed Oct. 21, 2015.
U.S. Appl. No. 14/452,429 Restriction Requirement mailed Dec. 12, 2014.
U.S. Appl. No. 14/885,962 Notice of Allowance dated Nov. 8, 2017 and Sep. 29, 2017.
U.S. Appl. No. 14/885,962 Office Action dated Dec. 16, 2016.
U.S. Appl. No. 14/885,962 Office Action dated Sep. 8, 2016.
U.S. Appl. No. 14/885,962 Restriction Requirement dated Mar. 1, 2016.
U.S. Appl. No. 14/885,963 Notice of Allowance dated May 24, 2016.
U.S. Appl. No. 14/885,963 Office Action dated Feb. 5, 2016.
U.S. Appl. No. 14/885,965 Office Action dated Aug. 28, 2018.
U.S. Appl. No. 14/885,965 Office Action dated Aug. 30, 2017.
U.S. Appl. No. 14/885,965 Office Action dated Feb. 10, 2017.

(56) References Cited

OTHER PUBLICATIONS

U.S. Appl. No. 14/885,965 Office Action dated Feb. 18, 2016.
U.S. Appl. No. 14/885,965 Office Action dated Jan. 4, 2018.
U.S. Appl. No. 14/885,965 Office Action dated Jul. 7, 2016.
U.S. Appl. No. 15/015,059 Final Office Action dated Jul. 17, 2019.
U.S. Appl. No. 15/015,059 Office Action dated Aug. 19, 2019.
U.S. Appl. No. 15/015,059 Office Action dated Feb. 7, 2019.
U.S. Appl. No. 15/135,434 Notice of Allowance dated Feb. 9, 2018.
U.S. Appl. No. 15/135,434 Office Action dated Nov. 30, 2017.
U.S. Appl. No. 15/135,434 Restriction Requirement dated Jul. 12, 2017.
U.S. Appl. No. 15/151,316 Office Action dated Jun. 7, 2018.
U.S. Appl. No. 15/151,316 Office Action dated Oct. 4, 2019.
U.S. Appl. No. 15/154,879 Notice of Allowance dated Feb. 1, 2017.
U.S. Appl. No. 15/156,134 Final Office Action dated Jan. 3, 2020.
U.S. Appl. No. 15/156,134 Office Action dated Apr. 4, 2019.
U.S. Appl. No. 15/187,714 Final Office Action dated Sep. 17, 2019.
U.S. Appl. No. 15/187,714 Office Action dated Apr. 4, 2019.
U.S. Appl. No. 15/187,714 Restriction Requirement dated Sep. 17, 2018.
U.S. Appl. No. 15/187,721 Notice of Allowance dated Dec. 7, 2016.
U.S. Appl. No. 15/187,721 Office Action dated Oct. 14, 2016.
U.S. Appl. No. 15/233,835 Notice of Allowance dated Oct. 4, 2017.
U.S. Appl. No. 15/233,835 Office Action dated Feb. 8, 2017.
U.S. Appl. No. 15/233,835 Office Action dated Jul. 26, 2017.
U.S. Appl. No. 15/233,835 Restriction Requirement dated Nov. 4, 2016.
U.S. Appl. No. 15/245,054 Office Action dated Mar. 21, 2017.
U.S. Appl. No. 15/245,054 Office Action dated Oct. 19, 2016.
U.S. Appl. No. 15/268,422 Final Office Action dated Oct. 3, 2019.
U.S. Appl. No. 15/268,422 Office Action dated Mar. 1, 2019.
U.S. Appl. No. 15/268,422 Restriction Requirement dated Oct. 4, 2018.
U.S. Appl. No. 15/377,547 Final Office Action dated Feb. 8, 2019.
U.S. Appl. No. 15/377,547 Office Action dated Jul. 27, 2018.
U.S. Appl. No. 15/377,547 Office Action dated Mar. 24, 2017.
U.S. Appl. No. 15/377,547 Office Action dated Nov. 30, 2017.
U.S. Appl. No. 15/433,909 Non-Final Office Action dated Feb. 8, 2019.
U.S. Appl. No. 15/433,909 Restriction Requirement dated Sep. 17, 2018.
U.S. Appl. No. 15/921,537 Office Action dated Apr. 1, 2020.
U.S. Appl. No. 15/602,991 Final Office Action dated Dec. 13, 2018.
U.S. Appl. No. 15/602,991 Notice of Allowance dated Oct. 25, 2017.
U.S. Appl. No. 15/602,991 Office Action dated May 31, 2018.
U.S. Appl. No. 15/602,991 Office Action dated May 31, 2019.
U.S. Appl. No. 15/602,991 Office Action dated Sep. 21, 2017.
U.S. Appl. No. 15/603,013 Final Office Action dated Nov. 6, 2019.
U.S. Appl. No. 15/603,013 Office Action dated Jan. 30, 2018.
U.S. Appl. No. 15/603,013 Office Action dated Jul. 10, 2018.
U.S. Appl. No. 15/603,013 Office Action dated Oct. 20, 2017.
U.S. Appl. No. 15/619,322 Office Action dated Aug. 14, 2019.
U.S. Appl. No. 15/619,322 Final Office Action dated Mar. 30, 2020.
U.S. Appl. No. 15/682,100 Office Action dated Jan. 2, 2018.
U.S. Appl. No. 15/682,100 Restriction Requirement dated Nov. 8, 2017.
U.S. Appl. No. 15/709,274 Notice of Allowance dated Apr. 3, 2019.
U.S. Appl. No. 15/729,564 Final Office Action dated Dec. 13, 2018.
U.S. Appl. No. 15/729,564 Office Action dated Jan. 8, 2018.
U.S. Appl. No. 15/729,564 Office Action dated Jun. 6, 2018.
U.S. Appl. No. 15/729,564 Office Action dated May 30, 2019.
U.S. Appl. No. 15/816,995 Office Action dated Sep. 20, 2019.
U.S. Appl. No. 15/816,995 Restriction Requirement dated Apr. 4, 2019.
U.S. Appl. No. 15/835,342 Office Action dated Dec. 2, 2019.
U.S. Appl. No. 15/835,342 Restriction Requirement dated Sep. 10, 2019.
U.S. Appl. No. 15/844,395 Office Action dated Jan. 24, 2020.
U.S. Appl. No. 15/844,395 Restriction Requirement dated May 17, 2019.
U.S. Appl. No. 15/860,445 Final Office Action dated Dec. 13, 2018.
U.S. Appl. No. 15/860,445 Office Action dated May 30, 2018.
U.S. Appl. No. 15/921,479 Office Action dated Nov. 12, 2019.
U.S. Appl. No. 15/921,479 Restriction Requirement dated May 24, 2019.
U.S. Appl. No. 15/960,319 Office Action dated Aug. 16, 2019.
U.S. Appl. No. 15/991,992 Restriction Requirement dated Mar. 10, 2020.
U.S. Appl. No. 16/006,581 Office Action dated Sep. 25, 2019.
U.S. Appl. No. 16/165,952 Office Action dated Mar. 12, 2020.
U.S. Appl. No. 16/239,453 Office Action dated Nov. 7, 2019.
U.S. Appl. No. 16/384,678 Office Action dated Jan. 21, 2020.
U.S. Appl. No. 16/409,608 Office Action dated Sep. 9, 2019.
U.S. Appl. No. 16/530,717 Office Action dated Sep. 6, 2019.
U.S. Appl. No. 16/535,777 Office Action dated Jan. 23, 2020.
U.S. Appl. No. 16/535,779 First Action Interview dated Feb. 10, 2020.
U.S. Appl. No. 14/452,429 Office Action mailed Apr. 9, 2015.
U.S. Appl. No. 15/151,316 Final Office Action dated Feb. 21, 2019.
U.S. Appl. No. 15/603,013 Office Action dated Jun. 26, 2019.
Vaijayanthi et al.: Recent advances in oligonucleotide synthesis and their applications. Indian J Biochem Biophys. Dec. 2003;40(6):377-91.
Van Den Brulle et al.: A novel solid phase technology for high-throughput gene synthesis. Biotechniques. 2008; 45(3):340-343.
Van Der Werf et al.: Limonene-1,2-epoxide hydrolase from Rhodococcus erythropolis DCL14 belongs to a novel class of epoxide hydrolases. J. Bacteriol. 180:5052-5057 (1998).
Van Tassell et al.: SNP discovery and allele frequency estimation by deep sequencing of reduced representation libraries. Nature Methods, 5:247-252, 2008.
Vargeese et al.: Efficient activation of nucleoside phosphoramidites with 4,5-dicyanoimidazole during oligonucleotide synthesis. Nucleic Acids Res. Feb. 15, 1998;26(4):1046-50.
Verma et al.: Modified oligonucleotides: synthesis and strategy for users. Annu Rev Biochem 67:99-134 (1998).
Vincent et al.: Helicase-dependent isothermal DNA amplification. EMBO Rep. Aug. 2004;5(8):795-800.
Visscher et al.: Construction of multiple-beam optical traps with nanometer-resolution position sensing, IEEE Journal of Selected Topics in Quantum Electronics, vol. 2, No. 4, 1066-1076 (Dec. 1996).
Voldmans et al.: Holding forces of single-particle dielectrophoretic traps. Biophysical Journal, vol. 80, No. 1, 531-541 (Jan. 2001).
Vos et al.: AFLP: A new technique for DNA fingerprinting. Nucleic Acids Res. Nov. 11, 1995;23(21):4407-14.
Wagner et al.: Nucleotides, Part LXV, Synthesis of 2'-Deoxyribonucleoside 5'-Phosphoramidites: New Building Blocks for the Inverse (5'-3')-Oligonucleotide Approach. Helvetica Chimica Acta, 83(8):2023-2035, 2000.
Wah et al.: Structure of Fok I has implications for DNA cleavage, Proc. Natl. Acad. Sci. USA, vol. 95, 10564-10569 (Sep. 1998).
Wah et al.: Structure of the multimodular endonuclease Fok I bound to DNA, Nature, vol. 388, 97-100 ( Jul. 1997).
Walker et al.: Strand displacement amplification—an isothermal, in vitro DNA amplification technique. Nucleic Acids Res. Apr. 11, 1992;20(7):1691-6.
Wan et al.: Deep Learning for Content-Based Image Retrieval: A comprehensive study. in Proceedings of the 22nd ACM International Conference on Multimedia—Nov. 3-7, 2014, Orlando, FL, p. 157-166, 2014.
Warr et al.: Exome Sequencing: current and future perspectives. G3: (Bethesda) 5(8):1543-1550 (2015).
Weber et al.: A modular cloning system for standardized assembly of multigene constructs. PLoS One. Feb. 18, 2011;6(2):e16765. doi: 10.1371/journal.pone.0016765.
Weiler et al.: Combining the Preparation of Oligonucleotide Arrays and Synthesis of High-Quality Primers. Analytical Biochemistry. 243:218-227 (1996).

(56) References Cited

OTHER PUBLICATIONS

Welz et al.: 5-(Benzylmercapto)-1H-tetrazole as activator for 2'-O-TBDMS phosphoramidite building blocks in RNA synthesis. Tetrahedron Lett. 2002; 43(5):795-797.
Westin et al.: Anchored multiplex amplification on a microelectronic chip array Nature Biotechnology, 18:199-202 (2000) (abstract only).
Whitehouse et al.: Analysis of the mismatch and insertion/deletion binding properties of Thermus thermophilus, HB8, MutS, Biochemical and Biophysical Research Communications, vol. 233, 834-837 (1997).
Wiedenheft et al.: RNA-guided genetic silencing systems in bacteria and archaea. Nature 482:331-338 (2012).
Wijshoff. Structure and fluid-dynamics in Piezo inkjet printheads. Thesis. Venio, The Netherlands, published 2008, p. 1-185.
Wirtz. Direct measurement of the transport properties of a single DNA molecule, Physical Review Letters, vol. 75, No. 12, 2436-2439 (Sep. 18, 1995).
Withers-Martinez et al.: PCR-based gene synthesis as an efficient approach for expression of the A+ T-rich malaria genome, Protein Engineering, vol. 12, No. 12, 1113-1120 (1999).
Wood et al.: Human DNA repair genes, Science, vol. 291, 1284-1289 (Feb. 16, 2001).
Wosnick et al.: Rapid construction of large synthetic genes: total chemical synthesis of two different versions of the bovine prochymosin gene. Gene. 1987;60(1):115-27.
Wright and Church. An open-source oligomicroarray standard for human and mouse. Nature Biotechnology, 20:1082-1083, 2002.
Wu et al.: Sequence-Specific Capture of Protein-DNA Complexes for Mass Spectrometric Protein Identification PLoS ONE. Oct. 20, 2011, vol. 6, No. 10.
Wu et al.: RNA-mediated gene assembly from DNA arrays. Angew Chem Int Ed Engl. May 7, 2012;51(19):4628-32. doi: 10.1002/anie. 201109058.
Wu et al.: Specificity of the nick-closing activity of bacteriophage T4 DNA ligase. Gene. 1989;76(2):245-54.
Wu et al.: An improvement of the on-line electrophoretic concentration method for capillary electrophoresis of proteins an experimental factors affecting he concentration effect, Analytical Sciences, vol. 16, 329-331 (Mar. 2000).
Xiong et al.: A simple, rapid, high-fidelity and cost-effective PCR-based two-step DNA synthesis method for long gene sequences. Nucleic Acids Res. 2004, 32(12):e98.
Xiong et al.: Chemical gene synthesis: Strategies, softwares, error corrections, and applications. FEMS Microbiol. Rev., 32:522-540, 2008.
Xiong et al.: Non-polymerase-cycling-assembly-based chemical gene synthesis: Strategies, methods, and progress. Biotechnology Advances. 26(2):121-134, 2008.
Xu et al.: Design of 240,000 orthogonal 25mer DNA barcode probes. PNAS, 106(7):2289-2294, 2009.
Yang et al.: Purification, cloning, and characterization of the CEL I nuclease, Biochemistry, 39(13):3533-35, 2000.
Yazdi et al.: A Rewritable, Random-Access DNA-Based Storage System, Scientific Reports, 5, Article No. 14138, 27 pages, 2015.
Yehezkel et al.: De novo DNA synthesis using single molecule PCR Nucleic Acids Research, 36(17):e107, 2008.
Yes HMDS vapor prime process application note Prepared by UC Berkeley and University of Texas at Dallas and re-printed by Yield Engineering Systems, Inc., 6 pages (http://www.yieldengineering.com/Portals/0/HMDS%20Application%20Note.pdf (Published online Aug. 23, 2013).
Youil et al.: Detection of 81 of 81 known mouse Beta-Globin promoter mutations with T4 Endonuclease VII• The EMC Method. Genomics, 32:431-435, 1996.
Young et al.: Two-step total gene synthesis method. Nucleic Acids Res. 32(7):e59, 2004.
Zhang and Seelig. Dynamic DNA nanotechnology using strand-displacement reactions, Nat. Chem., 3(2):103-113, 2011.
Zheleznaya et al.: Nicking endonucleases. Biochemistry (Mosc). 74(13):1457-66, 2009.
Zheng et al.: Manipulating the Stereoselectivity of Limonene Epoxide Hydrolase by Directed Evolution Based on Iterative Saturation Mutagenesis. J. Am. Chem. Soc. 132:15744-15751 (2010).
Zhirnov et al.: Nucleic acid memory. Nature Materials, 15:366, 2016.
Zhou et al.: Establishment and application of a loop-mediated isothermal amplification (LAMP) system for detection of cry1Ac transgenic sugarcane Scientific Reports May 9, 2014, vol. 4, No. 4912.
Zhou et al.: Microfluidic PicoArray synthesis of oligodeoxynucleotides and simultaneous assembling of multiple DNA sequences Nucleic Acids Research, 32(18):5409-5417, 2004.
Alberts et al.: Molecular Biology of the Cell. 4th edition. New York: Garland Science; 2002. The Generation of Antibody Diversity. https://www.ncbi.nlm.nih.gov/books/NBK26860/.
Almagro et al.: Progress and Challenges in the Design and Clinical Development of Antibodies for Cancer Therapy. Frontiers in immunology; 8, 1751 (2018) doi:10.3389/fimmu.2017.01751 https://www.frontiersin.org/articles/10.3389/fimmu.2017.01751/full.
Bai. A Novel Human scFv Library with Non-Combinatorial Synthetic CDR Diversity. PLoS One. 10(10):1-18 (2015).
Berg: Biochemistry. 5th ED. New York (2002) 148-149.
Borda et al.: Secret writing by DNA hybridization. Acta Technica Napocensis Electronics and Telecommunications. 50(2):21-24 (2008).
Chervin et al.: Design of T-cell receptor libraries with diverse binding properties to examine adoptive T-cell responses. Gene Therapy. 20(6):634-644 (2012).
Cui et al.: Information Security Technology Based on DNA Computing. International Workshop on Anti-Counterfeiting, Security and Identification (ASID); IEEE Xplore 4 pages (2007).
Fernández-Quintero et al.: Characterizing the Diversity of the CDR-H3 Loop Conformational Ensembles in Relationship to Antibody Binding Properties. Front. Immunol. 9:1-11 (2019).
GE Healthcare. AKTA oligopilot plus. Data File 18-114-66 AD ©. 8 pages (2006).
GE Healthcare. Robust and cost-efficient oligonucleotide synthesis. Application Note 28-4058-08 AA. 4 pages (2005).
Geetha et al.: Survey on Security Mechanisms for Public Cloud Data. 2016 International Conference on Emerging Trends in Engineering, Technology and Science (ICETETS). 8 pages (2016).
Goodwin et al.: immunoglobulin heavy chain variable region, partial [*Homo sapiens*]. Genbank entry (online). National Institute of Biotechnology Information. (2018) https://www.ncbi.nim.nih.gov/protein/AXA12486.1.
Hauser et al.: Trends in GPCR drug discovery: new agents, targets and indications. Nature Reviews Drug Discovery, 16, 829-842 (2017). doi:10.1038/nrd.2017.178 https://www.nature.com/articles/nrd.2017.178.
Hopcroft et al.: What is the Young's Modulus of Silicon?. Journal of Microelectromechanical Systems. 19(2):229-238 (2010).
Hötzel et al.: A strategy for risk mitigation of antibodies with fast clearance. mAbs, 4(6), 753-760 (2012). doi:10.4161/mabs.22189 https://www.ncbi.nlm.nih.gov/pubmed/23778268.
Hudson: Matrix Assisted Synthetic Transformations: A Mosaic of Diverse Contributions. Journal of Combinatorial Chemistry. 1(6):403-457 (1999).
Jaiswal et al.: An architecture for creating collaborative semantically capable scientific data sharing infrastructures. Proceeding WIDM '06 Proceedings of the 8th annual ACM international workshop on Web information and data management. ACM Digital Library pp. 75-82 (2006).
Jang et al.: Characterization of T cell repertoire of blood, tumor, and ascites in ovarian cancer patients using next generation sequencing. Oncoimmunology, 4(11):e1030561:1-10 (2015).
Kalva et al.: Gibson Deletion: a novel application of isothermal in vitro recombination. Biological Procedures Online. 20(1):1-10 (2018).
Kosuri et al.: A scalable gene synthesis platform using high-fidelity DNA microchips Nat.Biotechnol. 28(12):1295-1299 (2010).
Lebl et al.: Economical Parallel Oligonucleotide and Peptide Synthesizer—Pet Oligator. Int. J. Peptide Res. Ther. 13(1-2):367-376 (2007).

(56) References Cited

OTHER PUBLICATIONS

Malecek et al.: Engineering improved T cell receptors using an alanine-scan guided T cell display selection system. Journal of Immunological Methods. Elsevier Science Publishers. 392(1):1-11 (2013).
MLAB 2321 Molecular Diagnostics for Clinical Laboratory Science. Mar. 6, 2015.
Momentiv. Technical Data Sheet. Silquest A-1100. Momentiv. 1-6 (2020).
Novartis Institutes for Biomedical Research) Immunoglobulin Heavy Chain [*Homo sapiens*]. National Center for Biotechnology Information. Genbank Entry. pp. 1-2 (2018) https://www.ncbi.nlm.nih.gov/nuccore/MH975524.1ttps://https://www.ncbi.nlm.nih.gov/nuccore/MH975524.1.
Novartis Institutes for Biomedical Research) Immunoglobulin Lambda Chain [*Homo sapiens*]. National Center for Biotechnology Information. Genbank Entry. pp. 1-2 (2018) https://www.ncbi.nlm.nih.gov/nuccore/MH975524.1.
Nucleic acid thermodynamics. Wikipedia. Feb. 4, 2021.
O'Driscoll et al.: Synthetic DNA: The next generation of big data storage. Bioengineered. 4(3):123-125 (2013).
Opposition to European Patent No. 3030682 filed Mar. 3, 2021.
PCT/US2018/037152 International Preliminary Report on Patentability dated Dec. 17, 2019.
PCT/US2018/037161 International Preliminary Report on Patentability dated Dec. 17, 2019.
PCT/US2018/050511 International Preliminary Report on Patentability dated Mar. 17, 2020.
PCT/US2018/056783 International Preliminary Report on Patentability dated Apr. 30, 2020.
PCT/US2018/057857 International Preliminary Report on Patentability dated Apr. 28, 2020.
PCT/US2019/012218 International Preliminary Report on Patentability dated Jul. 16, 2020.
PCT/US2019/032992 International Preliminary Report on Patentability dated Nov. 24, 2020.
PCT/US2019/068435 International Preliminary Report on Patentability dated Jul. 8, 2021.
PCT/US2020/019371 International Search Report and Written Opinion dated Jun. 25, 2020.
PCT/US2020/019986 International Search Report and Written Opinion dated Jul. 29, 2020.
PCT/US2020/019986 Invitation to Pay Additional Fees dated Jun. 5, 2020.
PCT/US2020/019988 International Search Report and Written Opinion dated Jul. 29, 2020.
PCT/US2020/019988 Invitation to Pay Additional Fees dated Jun. 8, 2020.
PCT/US2020/038679 International Search Report and Written Opinion dated Oct. 28, 2020.
PCT/US2020/052291 International Search Report and Written Opinion dated Mar. 10, 2021.
PCT/US2020/052291 Invitation to Pay Additional Fees dated Dec. 31, 2020.
PCT/US2020/052306 International Search Report and Written Opinion dated Mar. 2, 2021.
PCT/US2020/052306 Invitation to Pay Additional Fees dated Dec. 18, 2020.
PCT/US2020/064106 International Search Report and Written Opinion dated Jun. 3, 2021.
PCT/US2020/064106 Invitation to Pay Additional Fees dated Apr. 9, 2021.
Pigott et al.: The Use of a Novel Discovery Platform to Identify Peptide-Grafted Antibodies that Activate GLP-1 Receptor Signaling. Innovative Targeting Solutions Inc. (2013) XP055327428 retrieved from the internet: http://www.innovativetargeting.com/wo-content/uploads/2013/12/Pigott-et-al-Antibody-Engineering-2013.pdf.
Ponsel. High Affinity, Developability and Functional Size: The Holy Grail of Combinatorial Antibody Library Generation. Molecules. 16:3675-3700 (2011).
PubChem Data Sheet Dichloromethane. Printed from website https://pubchem.ncbi.nlm.nih.gov/compound/Dichloromethane (2020).
Regep et al.: The H3 loop of antibodies shows unique structural characteristics. Proteins. 85(7):1311-1318 (2017).
Shipman et al.: Molecular recordings by directed CRISPR spacer acquisition. Science. 353(6298):1-16 (2016).
U.S. Appl. No. 15/151,316 Final Office Action dated Jul. 9, 2020.
U.S. Appl. No. 15/156,134 Final Office Action dated Aug. 18, 2021.
U.S. Appl. No. 15/156,134 Office Action dated Nov. 25, 2020.
U.S. Appl. No. 15/245,054 Notice of Allowance dated Dec. 14, 2017.
U.S. Appl. No. 15/272,004 Final Office Action dated Mar. 18, 2021.
U.S. Appl. No. 15/272,004 Office Action dated Jun. 12, 2020.
U.S. Appl. No. 15/619,322 Final Office Action dated Jul. 9, 2021.
U.S. Appl. No. 15/619,322 Office Action dated Nov. 4, 2020.
U.S. Appl. No. 15/816,995 Office Action dated May 19, 2020.
U.S. Appl. No. 15/835,342 Final Office Action dated Sep. 8, 2020.
U.S. Appl. No. 15/835,342 Office Action dated Apr. 16, 2021.
U.S. Appl. No. 15/902,855 Restriction Requirement dated Apr. 6, 2021.
U.S. Appl. No. 15/921,479 Final Office Action dated Jun. 15, 2020.
U.S. Appl. No. 15/921,479 Office Action dated Apr. 27, 2021.
U.S. Appl. No. 15/991,992 Office Action dated May 21, 2020.
U.S. Appl. No. 16/031,784 Office Action dated May 12, 2020.
U.S. Appl. No. 16/039,256 Final Office Action dated Mar. 30, 2021.
U.S. Appl. No. 16/039,256 Office Action dated Aug. 20, 2020.
U.S. Appl. No. 16/039,256 Restriction Requirement dated May 18, 2020.
U.S. Appl. No. 16/128,372 Final Office Action dated Mar. 18, 2021.
U.S. Appl. No. 16/128,372 Office Action dated Oct. 8, 2020.
U.S. Appl. No. 16/128,372 Restriction Requirement dated May 18, 2020.
U.S. Appl. No. 16/239,453 Office Action dated May 11, 2020.
U.S. Appl. No. 16/384,678 Final Office Action dated Oct. 15, 2020.
U.S. Appl. No. 16/535,777 Final Office Action dated Oct. 20, 2020.
U.S. Appl. No. 16/535,777 Office Action dated Feb. 8, 2021.
U.S. Appl. No. 16/712,678 Restriction Requirement dated Aug. 25, 2021.
U.S. Appl. No. 16/798,275 Office Action dated Feb. 10, 2021.
U.S. Appl. No. 16/854,719 Restriction Requirement dated Jul. 28, 2021.
U.S. Appl. No. 16/906,555 Office Action dated Aug. 17, 2021.
U.S. Appl. No. 17/154,906 Restriction Requirement dated Jul. 26, 2021.
Van der Velde: Thesis. Finding the Strength of Glass. Delft University of Technology. 1-16 (2015).
Xu et al.: Coordination between the Polymerase and 5'-Nuclease Components of DNA Polymerase I of *Escherichia coli*. The Journal of Biological Chemistry. 275(27):20949-20955 (2000).
Yazdi et al.: DNA-Based Storage: Trends and Methods. IEEE Transactions on Molecular, Biological and Multi-Scale Communications. IEEE. 1(3):230-248 (2016).
PCT/US2019/068435 International Search Report and Written Opinion dated Apr. 23, 2020.
U.S. Appl. No. 16/530,717 Final Office Action dated Apr. 15, 2020.
Agbavwe et al.: Efficiency, Error and Yield in Light-Directed Maskless Synthesis of DNA Microarrays. Journal of Nanobiotechnology. 9(57):1-17 (2011).
Altshuler et al.: Generation of Recombinant Antibodies and Means for Increasing Their Affinity. Biochemistry (Moscow). 75(13:1584-1605 (2010).
De Graff et al.: Glucagon-Like Peptide-1 and its Class B G Protein-Coupled Receptors: A Long March to Therapeutic Successes. Pharmacol Rev. 68(4):954-1013 (2016).
Diehl et al.: BEAMING: single-molecule PCR on microparticles in water-in-oil emulsions. Nature Methods. 3(7):551-559 (2006).
Hood et al.: The digital code of DNA. Nature 421.6921:444-448 (2003).
PCT/US2020/019371 International Preliminary Report on Patentability dated Sep. 2, 2021.
PCT/US2020/019986 International Preliminary Report on Patentability dated Sep. 10, 2021.

(56) References Cited

OTHER PUBLICATIONS

PCT/US2020/019988 International Preliminary Report on Patentability dated Sep. 10, 2021.
PCT/US2020/052291 International Preliminary Report on Patentability dated Apr. 7, 2022.
PCT/US2020/052306 International Preliminary Report on Patentability dated Mar. 15, 2022.
PCT/US2022/023936 International Search Report and Written Opinion dated Jul. 14, 2022.
Smith et al.: Changing the peptide specificity of a human T-cell receptor by directed evolution. Nature Communications. 5:1-13 (2014).
Sommermeyer et al.: Minimal Amino Acid Exchange in Human TCR Constant Regions Fosters Improved Function of TCR Gene-Modified T Cells. Journal of Immunology. 184:6223-6231 (2010).
U.S. Appl. No. 16/737,401 Final Office Action dated Jun. 13, 2022.
U.S. Appl. No. 15/272,004 Office Action dated Apr. 13, 2022.
U.S. Appl. No. 15/835,342 Office Action dated Jun. 17, 2022.
U.S. Appl. No. 15/902,855 Final Office Action dated Aug. 11, 2022.
U.S. Appl. No. 15/902,855 Office Action dated Dec. 9, 2021.
U.S. Appl. No. 15/902,855 Office Action dated Oct. 5, 2022.
U.S. Appl. No. 15/921,479 Final Office Action dated Dec. 20, 2021.
U.S. Appl. No. 15/921,479 Office Action dated Apr. 28, 2022.
U.S. Appl. No. 16/039,256 Office Action dated May 10, 2022.
U.S. Appl. No. 16/128,372 Office Action dated Dec. 13, 2021.
U.S. Appl. No. 16/417,023 Final Office Action dated Aug. 2, 2022.
U.S. Appl. No. 16/417,023 Office Action dated Feb. 22, 2022.
U.S. Appl. No. 16/590,301 Office Action dated Jul. 20, 2022.
U.S. Appl. No. 16/590,301 Restriction Requirement dated Apr. 28, 2022.
U.S. Appl. No. 16/712,678 Office Action dated Nov. 26, 2021.
U.S. Appl. No. 16/737,401 Office Action dated Jan. 5, 2022.
U.S. Appl. No. 16/737,401 Restriction Requirement dated Nov. 15, 2021.
U.S. Appl. No. 16/798,275 Final Office Action dated Aug. 30, 2021.
U.S. Appl. No. 16/802,423 Notice of Allowance dated Jul. 25, 2022.
U.S. Appl. No. 16/802,423 Restriction Requirement dated Dec. 29, 2021.
U.S. Appl. No. 16/802,439 Office Action dated Mar. 17, 2022.
U.S. Appl. No. 16/802,439 Restriction Requirement dated Oct. 1, 2021.
U.S. Appl. No. 16/854,719 Office Action dated Jun. 2, 2022.
U.S. Appl. No. 16/854,719 Office Action dated Nov. 24, 2021.
U.S. Appl. No. 16/879,705 Office Action dated Sep. 9, 2021.
U.S. Appl. No. 17/154,906 Office Action dated May 17, 2022.
U.S. Appl. No. 17/154,906 Office Action dated Nov. 10, 2021.
U.S. Appl. No. 17/180,614 Office Action dated Oct. 5, 2022.
Wikipedia. Central dogma of molecular biology. URL: https://en.wikipedia.org/wiki/Central_dogma_of_molecular_biology. 9 pages (2021).
Williams et al.: Amplification of complex gene libraries by emulsion PCR. Nature Methods. 3(7):545-550(2006).
Frederickson et al.: A rationally designed agonist antibody fragment that funxtionally mimics thrombopoietin. Proceedings of the National Academy of Sciences. National Academy of Sciences. 103(39):14307-14312 (2006).
Legault-Demare et al.: Studies on Hybrid Molecules of Nucleic Acids. Biochemical and Biophysical Research Communications. 28(4):1-16 (1967).
Liu et al.: Functional GLP-1R antibodies identified from a synthetic GPCR-focused library demonstrate potent blood glucose control. MABS. 13(1):15 pages (2021).
U.S. Appl. No. 15/156,134 Office Action dated Dec. 8, 2022.
U.S. Appl. No. 15/619,322 Office Action dated Nov. 10, 2022.
U.S. Appl. No. 15/921,479 Final Office Action dated Jan. 9, 2023.
U.S. Appl. No. 16/590,301 Office Action dated Dec. 5, 2022.
U.S. Appl. No. 16/798,275 Office Action dated Feb. 3, 2023.
U.S. Appl. No. 16/921,712 Non-Final Office Action dated Nov. 25, 2022.
U.S. Appl. No. 17/030,216 Restriction Requirement dated Dec. 23, 2022.
U.S. Appl. No. 17/030,232 Restriction Requirement dated Jan. 26, 2023.
U.S. Appl. No. 17/068,551 Restriction Requirement dated Dec. 23, 2022.
U.S. Appl. No. 17/116,939 Restriction Requirement dated Dec. 27, 2022.
U.S. Appl. No. 17/120,037 Office Action dated Feb. 2, 2023.
U.S. Appl. No. 17/154,906 Office Action dated Jan. 20, 2023.
U.S. Appl. No. 17/578,356 Notice of Allowance dated Dec. 5, 2022.
Bode et al.: TmPrime: fast, flexible oligonucleotide design software for gene synthesis. Nucleic Acids Research 37:W214-W221 (2009).
Cohen et al.: Enhanced Antitumor Activity of Murine-Human Hybrid T-Cell Receptor (TCR) in Human Lymphocytes is Associated with Improved Pairing and TCR/CD3 Stability. Cancer Research. American Association for Cancer Research. US. 66(17):8878-8886 (2006).
Heemskerk et al.: Efficiency of T-cell receptor expression in dual-specific T cells is controlled by the intrinsic qualities of the TCR chains within the TCR-CD3 complex. Blood. 109(1):235-243 (2007).
Hu et al.: Selection of long oligonucleotides for gene expression microarrays using weighted rank-sum strategy. BMC Bioinformatics 8(350):1-13 (2007).
Kalendar et al.: Java web tools for PCR, in silico PCR, and oligonucleotide assembly and analysis. Genomics 98:137-144 (2011).
Lyons et al.: Large-scale DNA Barcode Library Generation for Biomolecule Identification in High-throughput Screens. Scientific Reports. 7:13899 p. 1-7 (2017).
U.S. Appl. No. 15/835,342 Final Office Action dated Apr. 25, 2023.
U.S. Appl. No. 16/759,282 Office Action dated May 10, 2023.
U.S. Appl. No. 17/133,408 Office Action dated Apr. 13, 2023.
U.S. Appl. No. 17/180,614 Final Office Action dated Apr. 5, 2023.
Voss et al.: Molecular Design of the C[alpha][beta] Interface Favors Specific Pairing of Introduced TCR[alpha][beta] in Human T Cells. The Journal of Immunology. 180(1):391-401 (2008).

* cited by examiner

HIGHLY ACCURATE DE NOVO POLYNUCLEOTIDE SYNTHESIS

CROSS-REFERENCE

This application claims the benefit of U.S. provisional patent application No. 62/785,015 filed on Dec. 26, 2018 which is incorporated by reference in its entirety.

BACKGROUND

De novo gene synthesis is a powerful tool for basic biological research and biotechnology applications. While various methods are known for the design and synthesis of relatively short fragments in a small scale, these techniques often suffer from predictability, scalability, automation, speed, accuracy, and cost.

BRIEF SUMMARY

Provided herein are systems, methods, and compositions for the efficient de novo synthesis of highly accurate and uniform polynucleotide libraries.

Provided herein are methods for polynucleotide synthesis, comprising: a) providing a structure comprising a surface; b) coupling at least one nucleoside to a polynucleotide attached to the surface; c) depositing an oxidizing solution on the surface; d) depositing a wash solvent on the surface, wherein the wash solvent comprises a ketone, an ester, an ether, a hydrocarbon, or a functional equivalent thereof; and e) repeating steps b-d to synthesize a plurality of polynucleotides. Further provided herein, the wash solvent comprises acetone, tetrahydrofuran, ethyl acetate, toluene, benzene, ethanol, or a combination thereof. Further provided herein, the wash solvent comprises a ketone, an ether, or a functional equivalent thereof. Further provided herein, the wash solvent comprises acetone, or a functional equivalent thereof. Further provided herein, the wash solvent is functionally equivalent to a primary constituent by volume of a previously contacted reagent solution. Further provided herein, one or more of steps b) to d) is followed by washing the surface with the wash solvent. Further provided herein, one or more steps b) to d) is followed by washing the surface with acetonitrile. Further provided herein, each step subsequent to the coupling step is followed by washing the surface with the wash solvent. Further provided herein, each step subsequent to the deblocking step is followed by washing the surface with the wash solvent. Further provided herein, the method further comprises depositing a capping solution on the surface, wherein capping prevents coupling of unblocked nucleosides. Further provided herein, the capping solution comprises an acid halide or an anhydride. Further provided herein, the capping solution comprises acetyl chloride or acetic anhydride. Further provided herein, the capping solution comprises an amine base. Further provided herein, each step subsequent to the capping step is followed by washing the surface with the wash solvent. Further provided herein, the method further comprises depositing a deblocking solution on the surface, wherein deblocking allows coupling of the polynucleotide to a nucleoside. Further provided herein, the at least one nucleoside comprises a phosphoramidite. Further provided herein, the at least one nucleoside comprises a 5' blocking group. Further provided herein, the at least one nucleoside comprises a 3' blocking group. Further provided herein, the structure is a plate, a tape, a belt, or a bead. Further provided herein, the method further comprises depositing a deblocking solution on the surface, wherein deblocking allows coupling of the polynucleotide to a nucleoside. Further provided herein, the method further comprises depositing a capping solution on the surface before or after depositing the oxidizing solution on the surface. Provided herein are methods further comprising depositing the capping solution on the surface before and after depositing the oxidizing solution on the surface. Further provided herein, are methods further comprising depositing a wash solvent after (i) coupling the at least one nucleoside to the polynucleotide attached to the surface; (ii) depositing the capping solution; and (iii) depositing the oxidizing solution. Further provided herein, the oxidizing solution comprises iodine. Further provided herein, the oxidizing solution comprises $I_2$ or iodine salts, and the $I_2$ or iodine salts have a greater solubility or increased rate of dissolution in the wash solvent compared to acetonitrile. Further provided herein, are methods wherein the oxidizing solution further comprises an amine base. Further provided herein, the amine base is selected from pyridine, lutidine, collidine, N-methyl morpholine, or a functional equivalent thereof. Provided herein are methods further comprising: providing predetermined sequences for a plurality of preselected polynucleotides before step (a); and assembling the plurality of preselected polynucleotides after step (e), wherein the wash solvent dissolves an active component or byproduct of the oxidizing solution. Further provided herein, the method further comprises additional washing before or after depositing the oxidizing solution on the surface, wherein washing comprises depositing the wash solvent on the surface. Further provided herein, the polynucleotide or nucleoside comprises DNA or RNA.

Provided herein are compositions for polynucleotide synthesis comprising: a) at least one base; b) at least one 0-nucleophile; and c) at least one solvent. Further provided herein, the at least one base is selected from the group consisting of pyridine, lutidine, and collidine. Further provided herein, the at least one nucleophile is an O-nucleophile selected from group consisting of acetic acid, formic acid, propionic acid, methoxyacetic acid, phenoxyacetic acid, and water. Further provided herein, the O-nucleophile is selected from group consisting of acetic acid, and water. Further provided herein, the concentration of the O-nucleophile is 0.01-3 M. Further provided herein, the concentration of the O-nucleophile is 0.1-0.5 M. Further provided herein, the at least one solvent is acetonitrile, acetone, or THF. Further provided herein, the concentration of the at least one base is 0.01-3 M. Further provided herein, the concentration of the at least one base is 0.1-0.5 M.

Provided herein are methods of polynucleotide synthesis comprising: a) providing a structure comprising a surface; b) coupling at least one nucleoside to a polynucleotide attached to the surface; c) depositing an oxidizing solution on the surface; and d) repeating steps (b)-(c) to synthesize a plurality of polynucleotides, wherein the method comprises depositing a composition of any one of the compositions described herein. Further provided herein, depositing occurs during any of steps (a)-(d). Further provided herein, depositing occurs after step (b). Provided herein are methods further comprising at least one washing step with a wash solvent, wherein the wash solvent comprises acetone or THF.

Provided herein are compositions for polynucleotide synthesis comprising: a) at least one base; b) at least one 0-nucleophile; c) at least one electrophile; and d) at least one solvent. Further provided herein, the at least one base is selected from the group consisting of pyridine, lutidine, and collidine. Further provided herein, the O-nucleophile is selected from group consisting of acetic acid, formic acid, propionic acid, methoxyacetic acid, phenoxyacetic acid, and water. Further provided herein, the O-nucleophile is selected from group consisting of acetic acid, methoxyacetic acid, phenoxyacetic acid, and water. Further provided herein, the concentration of the O-nucleophile is 0.01-3 M. Further provided herein, the concentration of the O-nucleophile is 0.1-0.5 M. Further provided herein, the electrophile is an anhydride, NHS ester, or acid halide. Further provided herein, the at least one electrophile is an anhydride or acid halide. Further provided herein, the anhydride is acetic anhydride. Further provided herein, the composition further comprises an activator. Further provided herein, the activator is N-methylimidazole or DMAP. Further provided herein, the concentration of the activator is 0.001-0.05 M. Further provided herein, the at least one solvent is acetonitrile, acetone, or THF. Further provided herein, the concentration of the at least one base is 0.01-3 M. Further provided herein, the concentration of the at least one base is 0.1-0.5 M. Provided herein are methods of polynucleotide synthesis comprising: a) providing a structure comprising a surface; b) coupling at least one nucleoside to a polynucleotide attached to the surface; c) depositing an oxidizing solution on the surface; d) depositing a capping solution on the surface, wherein the capping solution comprises the composition described herein; and e) repeating steps (b)-(d) to synthesize a plurality of polynucleotides. Further provided herein, the method further comprises at least one washing step comprising acetone or THF. Further provided herein, the nucleoside comprises a protected nucleoside phosphoramidite. Further provided herein, the nucleoside comprises a protected base. Further provided herein, the protected nucleoside phosphoramidite comprises a protected guanine or thymine. Further provided herein, the protected nucleoside phosphoramidite is selected from the group consisting of:

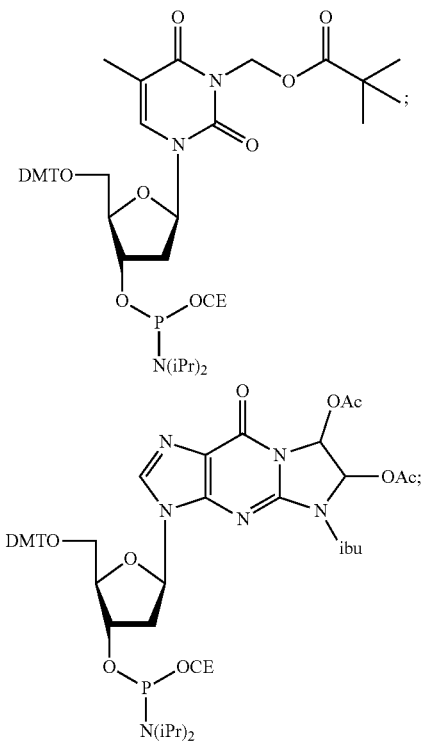

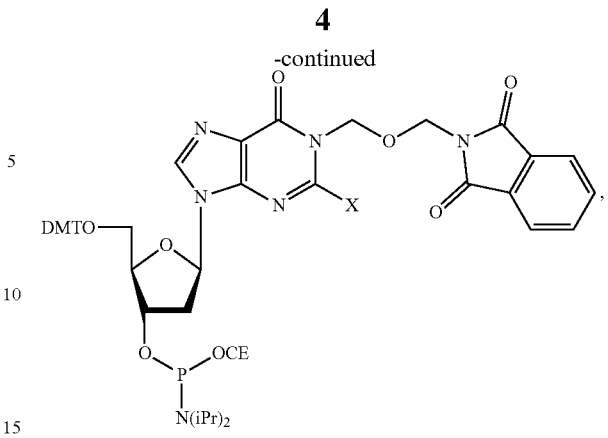

wherein X is —N=CHNR$^2$, and R is CH$_3$ or CH$_2$CH$_3$; and

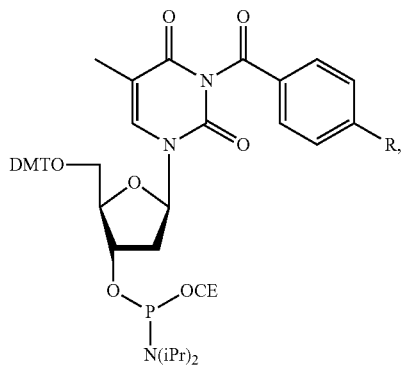

wherein R is H, OCH$_3$, F, or tert-butyl; wherein DMT is dimethoxytrityl; and CE is cyanoethyl.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
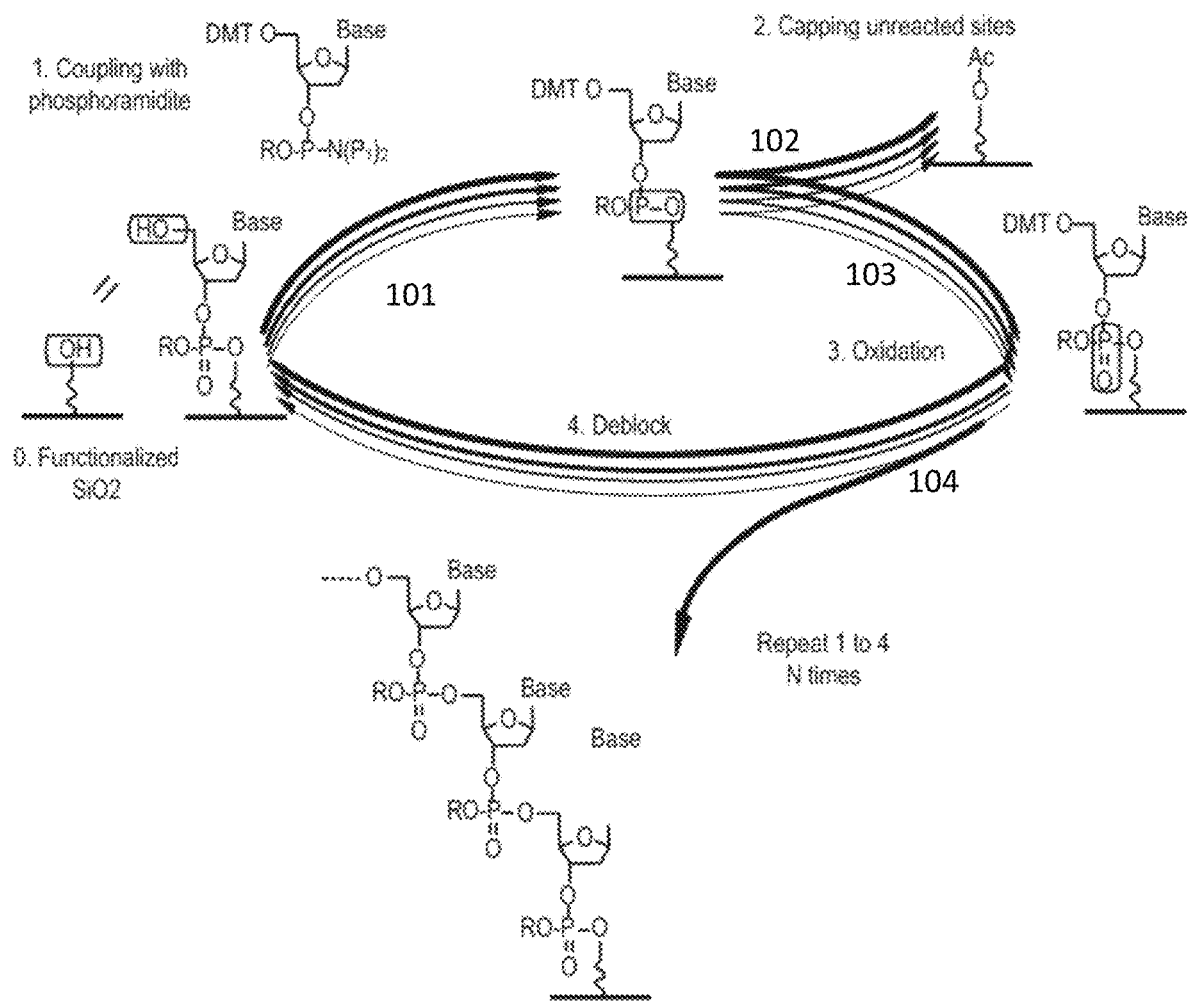
FIG. 1A depicts a workflow for nucleoside phosphoramidite based polynucleotide synthesis.
Figure 1B:
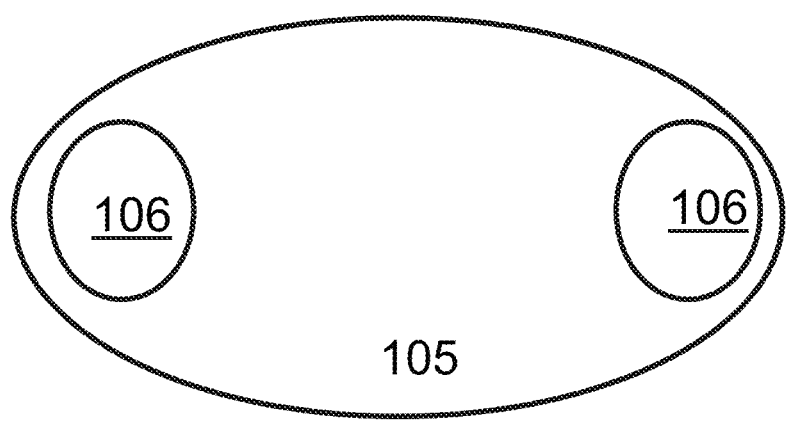
FIG. 1B depicts a continuous loop arrangement for polynucleotide synthesis structures.
Figure 1C:
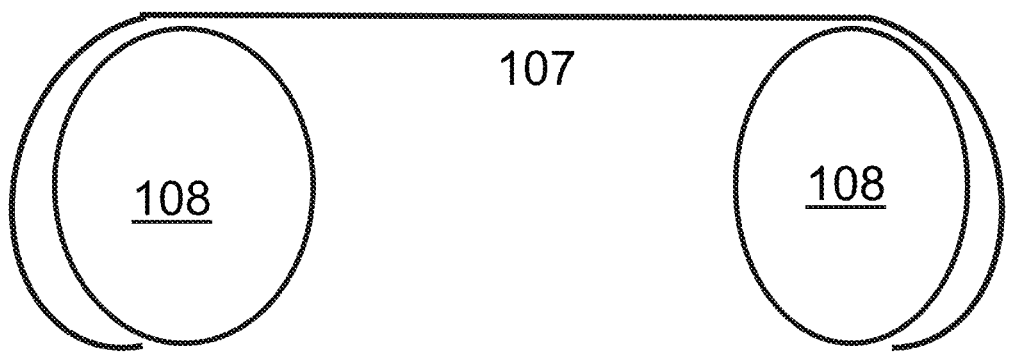
FIG. 1C depicts a reel-to-reel arrangement for polynucleotide synthesis structures.

Provided herein are systems, methods, and compositions for the efficient de novo synthesis of highly accurate and uniform polynucleotide libraries. Further provided herein are methods comprising post-oxidation step washing with a solvent, wherein the solvent dissolves a primary reagent or reagent byproduct of the oxidation step.

Definitions

Unless defined otherwise, all technical and scientific terms used herein have the same meaning as is commonly understood by one of ordinary skill in the art to which these inventions belong.

Throughout this disclosure, numerical features are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

As used herein, the terms "preselected sequence", "predefined sequence," or "predetermined sequence" are used interchangeably. The terms mean that the sequence of the polymer is known and chosen before synthesis or assembly of the polymer. In particular, various aspects of the invention are described herein primarily with regard to the preparation of polynucleotides, the sequence of the oligonucleotide or polynucleotide being known and chosen before the synthesis or assembly of the polynucleotides.

Methods, systems, devices, and compositions described herein in various aspects comprise contacting a surface with a solvent or solvent mixture, variously described as a "wash," "wash solvent," "wash buffer," "bath," "cleaning solvent," or "rinse". A wash step in some cases is used to push, flush, purge, remove, exchange, or replace other reagent solutions (comprising unreacted reagents (active components), solvents, or reagent byproducts (chemical products resulting from the reaction of the reagents) or previous wash solvents that are in contact with a surface. A residual reagent solution or solvent is in some cases used in the step immediately prior to the wash step.

The term "functional equivalent" used herein in regard to solvents describes an alternative solvent or solvent mixture that possess similar properties. These properties are in some cases physical properties (including e.g., boiling point, melting point, heat of vaporization, viscosity, miscibility, solubility, density, purity, or other physical property). Similar properties also optionally include performance measures, for example, a solvent and a functional equivalent both provide a similar outcome (reduced error rate, increase in error rate uniformity, dissolution of reagents or reagent byproducts, or other outcome) when used with the methods, systems, compositions, and devices described herein.

Provided herein are methods and compositions for production of synthetic (i.e. de novo synthesized or chemically synthesized) polynucleotides. The term oligonucleotide, oligo, and polynucleotide are defined to be synonymous throughout. Libraries of synthesized polynucleotides described herein may comprise a plurality of polynucleotides collectively encoding for one or more genes or gene fragments. In some instances, the polynucleotide library comprises coding or non-coding sequences. In some instances, the polynucleotide library encodes for a plurality of cDNA sequences. Reference gene sequences from which the cDNA sequences are based may contain introns, whereas cDNA sequences exclude introns. Polynucleotides described herein may encode for genes or gene fragments from an organism. Exemplary organisms include, without limitation, prokaryotes (e.g., bacteria) and eukaryotes (e.g., mice, rabbits, humans, and non-human primates). In some instances, the polynucleotide library comprises one or more polynucleotides, each of the one or more polynucleotides encoding sequences for multiple exons. Each polynucleotide within a library described herein may encode a different sequence, i.e., non-identical sequence. In some instances, each polynucleotide within a library described herein comprises at least one portion that is complementary to sequence of another polynucleotide within the library. Polynucleotide sequences described herein may, unless stated otherwise, comprise DNA or RNA.

Provided herein are methods and compositions for production of synthetic (i.e. de novo synthesized) genes. Libraries comprising synthetic genes may be constructed by a variety of methods described in further detail elsewhere herein, such as PCA, non-PCA gene assembly methods or hierarchical gene assembly, combining ("stitching") two or more double-stranded polynucleotides to produce larger DNA units (i.e., a chassis). Libraries of large constructs may involve polynucleotides that are at least 1, 1.5, 2, 3, 4, 5, 6, 7, 8, 9, 10, 15, 20, 30, 40, 50, 60, 70, 80, 90, 100, 125, 150, 175, 200, 250, 300, 400, 500 kb long or longer. The large constructs can be bounded by an independently selected upper limit of about 5000, 10000, 20000 or 50000 base pairs. The synthesis of any number of polypeptide-segment encoding nucleotide sequences, including sequences encoding non-ribosomal peptides (NRPs), sequences encoding non-ribosomal peptide-synthetase (NRPS) modules and synthetic variants, polypeptide segments of other modular proteins, such as antibodies, polypeptide segments from other protein families, including non-coding DNA or RNA, such as regulatory sequences e.g., promoters, transcription factors, enhancers, siRNA, shRNA, RNAi, miRNA, small nucleolar RNA derived from microRNA, or any functional or structural DNA or RNA unit of interest. The following are non-limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, complementary DNA (cDNA), which is a DNA representation of mRNA, usually obtained by reverse transcription of messenger RNA (mRNA) or by amplification DNA molecules produced synthetically or by amplification, genomic DNA, recombinant polynucleotides, branched polynucleotides, plasmids, vectors, isolated DNA of any sequence, isolated RNA of any sequence, nucleic acid probes, and primers. cDNA encoding for a gene or gene fragment referred to herein, may comprise at least one region encoding for exon sequence(s) without an intervening intron sequence found in the corresponding genomic sequence. Alternatively, the corresponding genomic sequence to a cDNA may lack an intron sequence in the first place.

De Novo Polynucleotide Synthesis

Provided herein are methods for the synthesis of polynucleotides that typically involve an iterating sequence of the following steps: application of a protected monomer to a surface of a substrate feature to link with either the surface, a linker, or with a previously deprotected monomer; deprotection of the applied monomer so that it can react with a subsequently applied protected monomer; and application of another protected monomer for linking. One or more intermediate steps include oxidation and/or sulfurization. Optionally, intermediate steps include a capping step to block previously deprotected monomers which have not reacted with a protected monomer. Further provided herein methods comprising one or more wash steps with a solvent or solvent mixture (e.g., wash formulation) that follow at least one or all of the polynucleotide synthesis steps, such as an oxidation step, wherein the solvent or solvent mixture dissolves the primary reagent or reagent byproduct of the previous step.

An exemplary synthetic scheme for polynucleotide synthesis in the 3' to 5' direction is shown in FIG. 1. In Step 0, a surface is functionalized with a blocked nucleoside and then deblocked (not shown) to provide an unblocked nucleoside attached to the surface. The unblocked nucleoside is then washed 101 with a wash solvent. In Step 1, a 5' DMT protected phosphoramidite nucleoside is coupled with the unblocked nucleoside on the surface to form a phosphite ester, resulting in a polynucleotide that is extended by one base. The surface is then washed 102 with a wash solvent, and a capping reagent (or reagents) is added to block all unreacted 5' OH groups on the surface with an acetate group. The surface is washed after capping 103, and further subjected to oxidation in Step 3 to generate a phosphate ester. The phosphate ester is washed 104 with a wash solvent, and deblocked by removal of the DMT group in Step 4 to generate an unblocked polynucleotide. The unblocked polynucleotide is washed 101 with a wash solvent, and Steps 1-4 are repeated to synthesize the polynucleotide. Alternatively, polynucleotides are synthesized in a 5' to 3' direction, wherein 3' blocked phosphoramidite nucleotides are coupled to the 3' OH position of the growing polynucleotide chain.

Further provided herein are methods comprising wash steps that are executed before or after another step in de novo synthesis of polynucleotides, for example, a wash step is executed after surface preparation, after phosphoramidite coupling, after oxidation, after capping, or after deblocking. Wash steps often are used to remove residual reagents, solutions, reaction byproducts, or solvents from a previous synthetic step or a previous wash. For example, in an oxidation step comprising iodine and an amine base, a subsequent wash step comprises a solvent that dissolves a primary component of the reagent (remaining iodine or amine base), or a primary byproduct of said reagent (an iodide salt of an amine base). A wash step is often executed before one or more steps, such as before surface preparation, before phosphoramidite coupling, before oxidation, before capping, or before cleavage. Multiple wash steps are often used during polynucleotide synthesis, such as a plurality of wash steps separated by additional steps synthetic steps, or sequential wash steps. A wash step is in some instances executed after a deblocking step. A wash step is in some instances executed after a coupling step. A wash step is in some instances executed after an oxidation step. A wash step is in some instances executed after a capping step. A wash step is in some instances executed after a deblocking step, a coupling step, an oxidation step, and a capping step. A wash step in some instances comprises washing with a solvent or a mixture of solvents. For a given method, a single solvent or a plurality of different solvents or solvent mixtures are in some instances used for each individual wash step, or for all wash steps in the method. Wash steps in between synthesis steps are optionally omitted in some instances. In some instances, wash steps are performed with wash solvents comprising one or more solutes.

Further provided herein are methods wherein following addition of a nucleoside phosphoramidite, and optionally after capping and one or more wash steps, the substrate-bound growing polynucleotide is oxidized with an oxidizing solution. The oxidation step comprises oxidizing the phosphite triester into a tetracoordinated phosphate triester, a protected precursor of the naturally occurring phosphate diester internucleoside linkage. The oxidizing solution often comprises one or more chemical components. For example, an oxidizing solution comprises components such as one or more solvents (such as acetonitrile, acetone, THF or other solvent), and one or more oxidants or catalysts as active components or reagents. Oxidants variously comprise I2, peroxides (e.g., hydrogen peroxide, mCPBA, TBHP, etc.), dioxiranes, or other oxidant known in the art capable of oxidizing a phosphate triester. Oxidation is sometimes carried out under anhydrous conditions using tert-butyl hydroperoxide or (1S)-(+)-(10-camphorsulfonyl)-oxaziridine (CSO). In some instances, the primary constituent (by mass) of an oxidizing solution is a solvent or solvent mixture. In some instances, the primary reagent of an oxidation solution is iodine. In some instances, oxidation of the growing polynucleotide is achieved by treatment with iodine and water, optionally in the presence of a weak base catalyst such as an amine base (e.g., pyridine, lutidine, collidine, N-methyl morpholine, or other amine base), or other weak base.

Washes with one or more solvents are often used to remove remaining oxidant or oxidation byproducts after an oxidation step. Without being bound by theory, solvent or solvent mixtures in some cases increases solubility of the oxidant, increase solubility of byproducts generated by the oxidant after oxidation, or in some instances react with the solvent to form a different oxidant. Alternately or in combination, a solvent or solvent mixture in some cases increases the rate of dissolution of the oxidant, or increases the rate of dissolution of byproducts generated by the oxidant after oxidation. Oxidation byproducts variously comprise salts, salts of a weak base (such as an amine), iodide salts, or reaction products of the oxidant and the solvent. In some instances, solvents that dissolve pyridinium iodide or other amine base salts of iodine are used as wash solvents following oxidation. In some instances, oxidation byproducts comprise iodide salts of pyridine, lutidine, collidine, N-methyl morpholine, or other weak base. The choice of solvent in some instances depends on the choice of oxidant; for example, an oxidizing solution comprises an oxidant $I_2$ and a solvent comprising acetone.

Reactions can occur at the O6 oxygen atom of guanosine and at the O4 oxygen atoms of thymidine/uridine nucleotides. The resulting activated nucleotide derivatives can be further modified by oxidation and nucleophilic aromatic substitution with additional reagents. In some instances, the activated nucleotide derivatives can be further modified by reagents used in capping, such as N-methylimidazole or DMAP. In some instances, the activated nucleotide derivatives can be further modified by reagents used in oxidation, such as pyridine. In some instances, the activated nucleotide derivatives can be further modified by reagents used in deprotection, such as methylamine, ammonia, or ethylenediamine. Products obtained after oxidation and capping can also react with amines used for deprotections to further generate unwanted products. The reaction between phosphoramidites with O-containing nucleotides can lead to N-substituted guanosine and thymidine/uridine nucleotides, which can form Watson-Crick base pairs with thymidine/uridine and guanosine nucleotides, respectively. The final consequences of undesired reactivity are G→A and T/U→C mutations.

Further provided herein are wash solutions that remove unwanted G→A and T/U→C mutations resulting from phosphoramidite-coupling to nucleobases by selectively removing undesired adducts directly after the coupling step and before the oxidation step. In some instances, wash solutions improve synthesis uniformity (e.g., yields, error rates, or other performance metric) across a solid support (e.g., a chip). The wash solutions of the disclosure in some instances comprise a solvent, a base, and an O-nucleophile. In some instances, the solvent is acetonitrile or THF. In some instances, the base is pyridine, lutidine, or collidine. In some instances, the O-nucleophile is water or an organic acid (such as acetic acid, formic acid, propionic acid). In some instances, the O-nucleophile is water. In some instances, a wash solution comprises THF, pyridine, water, or a combination thereof. In some instances, reagent concentration in such wash solutions is measured by ratios of various components. In some instances, a wash solution comprises a ratio of volumes. In some instances, a wash solution comprises a solvent, a base, and an O-nucleophile in a ratio of about 95:3:1, 90:7:3, 80:10:10, 80:20:10, 85:10:5, or 70:20:10. In some instances, a wash solution comprises a solvent, a base, and an O-nucleophile in a ratio of 60-90% solvent, 5-30% base, and 5-30% O-nucleophile. In some instances, a wash solution comprises a solvent, a base, and an O-nucleophile, wherein the ratio of base to O-nucleophile is at least about 0.5:1, 1:1, 1.5:1, 2:1, 2.5:1, 3:1, 4:1, 5:1, 7:1, 9:1, 10:1, 12:1, or 15:1. In some instances, a wash solution comprises a solvent, a base, and an O-nucleophile, wherein the ratio of base to O-nucleophile is about 0.5:1-15:1, 0.5:1-3:1, 1:1-5:1, 1:1-9:1, or 2:1-12:1. In some instances, reagent concentration is measured by molarity (M=mol/L). In some instances, the O-nucleophile concentration is about 0.01 M, 0.02 M, 0.05 M, 0.08 M, 0.1 M, 0.2 M, 0.5 M, 0.8 M, 1.0 M, 1.2 M, 1.2 M, 1.5 M, 1.8 M, 2 M, 2.5 M, or about 3 M. In some instances, the O-nucleophile concentration is no more than 0.01 M, 0.02 M, 0.05 M, 0.08 M, 0.1 M, 0.2 M, 0.5 M, 0.8 M, 1.0 M, 1.2 M, 1.2 M, 1.5 M, 1.8 M, 2 M, 2.5 M, or no more than 3 M. In some instances, the O-nucleophile concentration is at least 0.01 M, 0.02 M, 0.05 M, 0.08 M, 0.1 M, 0.2 M, 0.5 M, 0.8 M, 1.0 M, 1.2 M, 1.2 M, 1.5 M, 1.8 M, 2 M, 2.5 M, or at least 3 M. In some instances, the O-nucleophile concentration is 0.01-0.1 M, 0.01-0.5 M, 0.01-1.5 M, 0.5-2 M, 0.5-1.0 M, 0.2-1.2 M, 0.8-2.0 M, or 0.5-1 M. In some instances, the base concentration is about 0.01 M, 0.02 M, 0.05 M, 0.08 M, 0.1 M, 0.2 M, 0.5 M, 0.8 M, 1.0 M, 1.2 M, 1.2 M, 1.5 M, 1.8 M, 2 M, 2.5 M, or about 3 M. In some instances, the base concentration is no more than 0.01 M, 0.02 M, 0.05 M, 0.08 M, 0.1 M, 0.2 M, 0.5 M, 0.8 M, 1.0 M, 1.2 M, 1.2 M, 1.5 M, 1.8 M, 2 M, 2.5 M, or no more than 3 M. In some instances, the base concentration is at least 0.01 M, 0.02 M, 0.05 M, 0.08 M, 0.1 M, 0.2 M, 0.5 M, 0.8 M, 1.0 M, 1.2 M, 1.2 M, 1.5 M, 1.8 M, 2 M, 2.5 M, or at least 3 M. In some instances, the base concentration is 0.01-0.1 M, 0.01-0.5 M, 0.01-1.5 M, 0.5-2 M, 0.5-1.0 M, 0.2-1.2 M, 0.8-2.0 M, or 0.5-1 M.

Provided herein are chemical polynucleotide synthesis methods wherein a wash solvent following an oxidation step comprises a solvent with high solubility for oxidant $I_2$ or iodine salts. Exemplary solvents with high solubility for oxidant $I_2$ or iodine salts are listed in Table 1. Provided herein are chemical polynucleotide synthesis methods wherein a wash solvent following the oxidation reaction comprises a solvent listed in Table 1. In some instances, a wash step following the oxidation reaction comprises use of a solvent comprising THF, acetone, or other solvent described herein. In some instances, a wash step following the oxidation reaction comprises use of a solvent comprising acetone. In some instances, a wash step following the oxidation reaction comprises use of a solvent comprising a mixture of acetone and THF. In some instances, the same solvent selected for use as a wash after oxidation reaction is also used as a washing reagent following additional reactions in the chemical synthesis workflow. In some instances, at least one wash step comprising THF, acetone, or another solvent described herein, is employed after an oxidation reaction, and all other wash steps in the chemical polynucleotide synthesis workflow comprise deposition of acetonitrile. Further described herein are methods wherein a washing solvent is used for its ability to dissolve iodine or iodine salts. Exemplary solubilities of iodine in various solvents used with the methods described herein at various temperatures are listed in Table 1.

TABLE 1

Solvents and associated solubility of iodine

| Solvent | Solubility in g/mL (at Deg C.)* |
|---|---|
| Ethyl alcohol | 0.1618 (8) |
| Toluene | 0.1012 (8) |
| Ethyl Acetate | 0.987 (8) |
| Benzene | 0.893 (8) |
| Chloroform | 0.269 (8) |
| Carbon Disulfide | 16.49 (25); 21.63 (35) |
| Carbon tetrachloride | 0.02603 (35) |
| 2,2-dimethyl butane | 1.369 (25); 1.989 (35) |
| ethyl alcohol | 21.48 (25); 24.51 (35) |
| ethyl ether | 25.18 (25); 28.50 (35) |
| p-Xylene | 16.56 (25); 20.11 (35) |

TABLE 1-continued

Solvents and associated solubility of iodine

| Solvent | Solubility in g/mL (at Deg C.)* |
|---|---|
| Mesitylene | 20.27 (25) |
| Perfluoroheptane | 0.0119 (25); 0.0179 (35) |

*Note temperature in degrees Celsius are in parentheses.

Further described herein are methods wherein the coupling comprises use of protected nucleoside phosphoramidites, such as base protected nucleoside phosphoramidites. In some instances, phosphoramidite building blocks give rise to unwanted reactions at the nucleobases, leading to branching and mutations. In some instances, methods and reagents block the reaction of guanosine and thymidine/uridine nucleotides with activated phosphoramidites. After activation, phosphoramidites are highly reactive (electrophilic) reagents which preferentially react with oxygen nucleophiles due to the strength of the thereby resulting P—O bonds. During reaction with 5'-OH groups of growing nucleic acid strands, the desired chain elongation reaction takes place. To some extent, however, this reaction in some instances also occurs at oxygen atoms O6 and O4 of guanosine and thymidine/uridine nucleotides, respectively. The resulting activated nucleotide derivative may, at least partially, be further modified by oxidation and nucleophilic aromatic substitution with N-methylimidazole (used in capping), DMAP (used also in capping), pyridine (used in oxidation) and various amines used in deprotection (e.g., methylamine, ammonia or ethylenediamine). The products obtained after oxidation and capping in some instances also react with the various amines used for deprotection. The above-mentioned reaction of phosphoramidites with O-containing nucleotides will often lead to N-substituted guanosine and thymidine/uridine nucleotides able to form Watson-Crick base pairs with thymidine/uridine and guanosine nucleotides, respectively. In context with duplex formation, the consequence is an apparent G->A and T/U->C mutation, respectively. In the context of the preparation of high-quality (e.g., low error-rate) polynucleotides, a minimal number of such mutations are desirable. Nucleic acid syntheses in flow cells are commonly carried out with an extremely large excess of activated phosphoramidites. As a result, only neglectable amounts of these expensive reagents are actually consumed. To increase efficiency and minimize chemical waste, it is in some instances desirable to use these activated phosphoramidite solutions in consecutive flow cell reactions. However, since activated G and T/U phosphoramidites undergo side-reactions described above, the longer these solutions are exposed to the growing polynucleotide, an increasing amount of branching and mutations are in some instances introduced. In some instances, this reactivity prevents the utilization of money and waste saving multiple-coupling/phosphoramidite recycling strategies in high quality nucleic acid syntheses. In some instances, undesired side reactions are partially or fully suppressed by the attachment of protecting groups which are stable during the synthesis of the polynucleotide, but can be cleaved at the end, preferentially under the same conditions as the other protecting groups present in the primary synthesis product (protected and immobilized polynucleotide). In some instances, a protected nucleoside phosphoramidite base comprises a protected nitrogen atom. In some instances, the protected nucleoside phosphoramidite base comprises cytosine, adenine, thymine, uracil, or guanine. In some instances, the protected nucleoside phosphoramidite base comprises thymine or guanine. Exemplary protected dT and dG phosphoramidite building blocks A-I containing a protecting group at nitrogen atoms N3 and N1, respectively, are shown below:

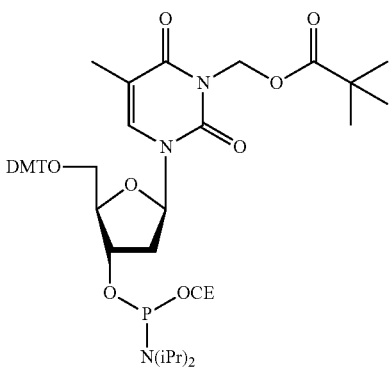

A

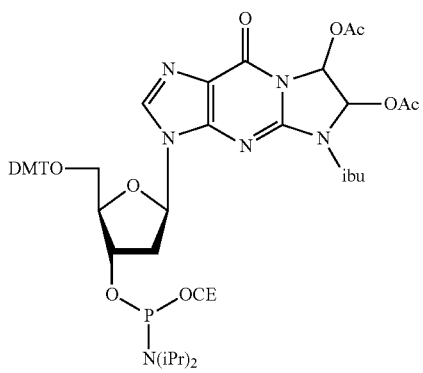

F

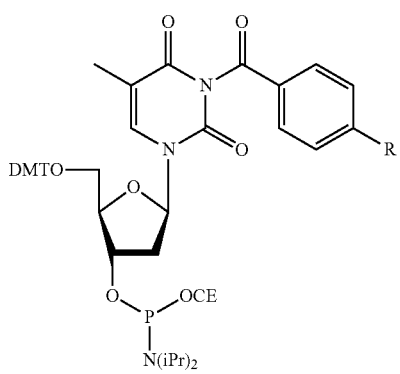

R = H    B
    OMe  C
    F    D
    tBu  E

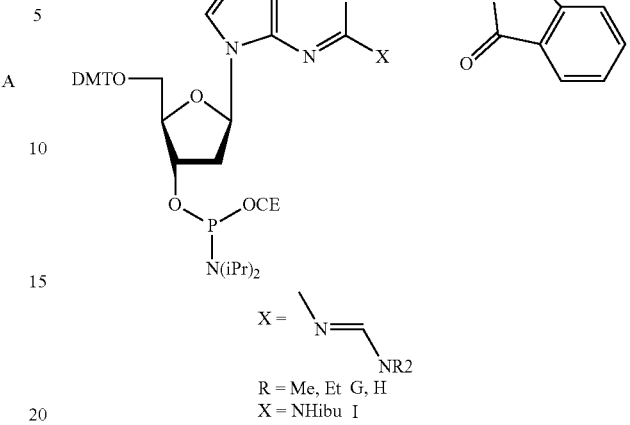

R = Me, Et  G, H
X = NHibu   I

Further described herein are methods wherein following coupling, phosphoramidite polynucleotide synthesis methods comprise a capping step. In a capping step, the growing polynucleotide is treated with a capping agent. A capping step generally serves to block unreacted substrate-bound 5'-OH groups after coupling from further chain elongation, preventing the formation of polynucleotides with internal base deletions. Further, phosphoramidites activated with 1H-tetrazole often react, to a small extent, with the O6 position of guanosine. Without being bound by theory, upon oxidation with I$_2$/water, this side product, possibly via O6-N7 migration, undergoes depurination. The apurinic sites can end up being cleaved in the course of the final deprotection of the polynucleotide thus reducing the yield of the full-length product. The O6 modifications may be removed by treatment with the capping reagent prior to oxidation with I$_2$/water. In some instances, inclusion of a capping step during polynucleotide synthesis decreases the error rate as compared to synthesis without capping. As an example, the capping step comprises treating the substrate-bound polynucleotide with a mixture of acetic anhydride and 1-methylimidazole. Following a capping step, the substrate is optionally washed. The capping reaction in DNA synthesis blocks non-coupled DNA fragments from being further elongated in later coupling steps, which suppresses the formation of n–1mer sequences. Capping reactions are carried out by coupling reactive phosphoramidites ("Uncap") or by reacting a carboxylic acid anhydride in the presence of a base and an activator. In some instances, the carboxylic acid anhydride is acetic anhydride. In some instances, the base is lutidine. In some instances, the activator is N-methylimidazole or DMAP). Capping by reacting a carboxylic acid anhydride in the presence of a base and an activator can result in G→A and T→C mutation reactions, as a result of an electrophilic activation of the O6 and O4 oxygen atoms of guanosine and thymidine nucleotides, respectively, by acylation. The resulting activated nucleotide derivatives can then be further modified by nucleophilic aromatic substitution with N-methylimidazole or DMAP. The further modified products can react with various amines used for deprotection, which results in the formation of N-substituted guanosine and thymidine nucleotides able to form Watson-Crick base pairs with thymidine and guanosine nucleotides (i.e., G→A and T/U→C mutations).

Further provided herein are capping formulations that inhibit the formation of unwanted G→A and T→C mutations resulting from carboxylic acid-promoted activation of nucleobases. The capping formulations of the disclosure comprise a solvent, base, anhydride, and nucleophile. In some instances, the capping formulations comprise a solvent, base, anhydride, and O-nucleophile. In some instances, the capping formulations of the disclosure comprise a solvent, such as acetonitrile or THF. In some instances, the capping formulations of the disclosure comprise a base, such as lutidine or collidine. In some instances, the capping formulations of the disclosure comprise an anhydride, such as acetic anhydride. In some instances, the capping formulations of the disclosure comprise an activator, such as N-methylimidazole or DMAP. In some instances, the capping formulations of the disclosure comprise an O-nucleophile, such as acetic acid, methoxyacetic acid, or phenoxyacetic acid. A capping solution often comprises components such as one or more solvents (such as acetonitrile, acetone, THF or other solvent), one or more capping reagents, and one or more activators (N-methyl imidazole or other activator known in the art). Capping reagents variously comprise acid halides (e.g., acetyl chloride, or other acid halide), anhydrides (e.g., acetic anhydride, or other anhydride) or other capping reagent known in the art capable of reacting with the 5' OH of an unprotected nucleobase. In some instances, the primary constituent (by mass) of a capping solution is a solvent or solvent mixture. In some instances, one or more washes with one or more solvents is used to remove remaining capping reagents or activators after a capping step. Without being bound by theory, solvent or solvent mixtures in some cases increases solubility of capping reagents or activator, increases solubility of byproducts generated by the capping reagents, activator, or other reagent, or in some instances reacts with the capping reagent or activator to form a different capping or activating reagent. Alternately or in combination, a solvent or solvent mixture in some cases increases the rate of dissolution of the capping reagent or activator, or increases the rate of dissolution of byproducts generated by the capping reagent or activator. The choice of solvent in some instances depends on the choice of capping reagent or activator; for example, a capping solution comprises acetic anhydride and a solvent comprising tetrahydrofuran. Any combination of capping reagents activator, or other reagent and solvent is in some instances used with the methods described herein. In some instances, two or more capping solutions are prepared, and then mixed during polynucleotide synthesis during a capping step. In some instances, a first capping solution comprises a solvent and an activator. In some instances, a first capping solution comprises acetonitrile/n-methylimidazole in a 90:10 ratio. In some instances, a second capping solution comprises a solvent, base, and capping reagent. In some instances, a second capping solution comprises THF/lutidine/acetic anhydride in an 80:10:10 ratio. In some instances, the first and the second capping solutions are mixed together during the capping step. In some instances, a capping solution comprises a ratio of volumes. In some instances, a capping solution comprises a solvent, a base, and a capping reagent in a ratio of about 95:3:1, 90:7:3, 80:10:10, 80:20:10, 85:10:5, or 70:20:10. In some instances, a wash solution comprises a solvent, a base, and an a capping reagent in a ratio of 60-90% solvent, 5-30% base, and 5-30% capping reagent. In some instances, a wash solution comprises a solvent, a base, and a capping reagent, wherein the ratio of base to a capping reagent is at least about 0.5:1, 1:1, 1.5:1, 2:1, 2.5:1, 3:1, 4:1, 5:1, 7:1, 9:1, 10:1, 12:1, or 15:1. In some instances, a wash solution comprises a solvent, a base, and a capping reagent, wherein the ratio of base to a capping reagent is about 0.5:1-15:1, 0.5:1-3:1, 1:1-5:1, 1:1-9:1, or 2:1-12:1. In some instances, reagent concentration is measured by molarity (M=mol/L). In some instances, the O-nucleophile concentration is about 0.01 M, 0.02 M, 0.05 M, 0.08 M, 0.1 M, 0.2 M, 0.5 M, 0.8 M, 1.0 M, 1.2 M, 1.2 M, 1.5 M, 1.8 M, 2 M, 2.5 M, or about 3 M. In some instances, the O-nucleophile concentration is no more than 0.01 M, 0.02 M, 0.05 M, 0.08 M, 0.1 M, 0.2 M, 0.5 M, 0.8 M, 1.0 M, 1.2 M, 1.2 M, 1.5 M, 1.8 M, 2 M, 2.5 M, or no more than 3 M. In some instances, the O-nucleophile concentration is at least 0.01 M, 0.02 M, 0.05 M, 0.08 M, 0.1 M, 0.2 M, 0.5 M, 0.8 M, 1.0 M, 1.2 M, 1.2 M, 1.5 M, 1.8 M, 2 M, 2.5 M, or at least 3 M. In some instances, the O-nucleophile concentration is 0.01-0.1 M, 0.01-0.5 M, 0.01-1.5 M, 0.5-2 M, 0.5-1.0 M, 0.2-1.2 M, 0.8-2.0 M, or 0.5-1 M. In some instances, the base concentration is about 0.01 M, 0.02 M, 0.05 M, 0.08 M, 0.1 M, 0.2 M, 0.5 M, 0.8 M, 1.0 M, 1.2 M, 1.2 M, 1.5 M, 1.8 M, 2 M, 2.5 M, or about 3 M. In some instances, the base concentration is no more than 0.01 M, 0.02 M, 0.05 M, 0.08 M, 0.1 M, 0.2 M, 0.5 M, 0.8 M, 1.0 M, 1.2 M, 1.2 M, 1.5 M, 1.8 M, 2 M, 2.5 M, or no more than 3 M. In some instances, the base concentration is at least 0.01 M, 0.02 M, 0.05 M, 0.08 M, 0.1 M, 0.2 M, 0.5 M, 0.8 M, 1.0 M, 1.2 M, 1.2 M, 1.5 M, 1.8 M, 2 M, 2.5 M, or at least 3 M. In some instances, the base concentration is 0.01-0.1 M, 0.01-0.5 M, 0.01-1.5 M, 0.5-2 M, 0.5-1.0 M, 0.2-1.2 M, 0.8-2.0 M, or 0.5-1 M. In some instances, the activator concentration is about 0.001 M, 0.002 M, 0.005 M, 0.008 M, 0.01 M, 0.02 M, 0.05 M, 0.08 M, 0.1 M, 0.12 M, 0.15 M, 0.18 M, 0.2 M, 0.3 M, or about 0.5 M. In some instances, the activator concentration is at least 0.001 M, 0.002 M, 0.005 M, 0.008 M, 0.01 M, 0.02 M, 0.05 M, 0.08 M, 0.1 M, 0.12 M, 0.15 M, 0.18 M, 0.2 M, 0.3 M, or at least 0.5 M. In some instances, the activator concentration is no more than 0.001 M, 0.002 M, 0.005 M, 0.008 M, 0.01 M, 0.02 M, 0.05 M, 0.08 M, 0.1 M, 0.12 M, 0.15 M, 0.18 M, 0.2 M, 0.3 M, or no more than 0.5 M. In some instances, the activator concentration is 0.001-0.01 M, 0.001-0.05 M, 0.001-0.15 M, 0.05-0.2 M, 0.005-0.02 M, 0.01-0.1 M, 0.08-0.2 M, or 0.05-0.1 M. In some instances, a capping step is performed following oxidation. In some instances a capping step is performed prior to oxidation. In some instances a capping step is performed prior to oxidation, and after oxidation. In some methods, a wash step is performed after oxidation. A second capping step allows for substrate drying, as residual water from oxidation that may persist can inhibit subsequent coupling. Following oxidation, the substrate and growing polynucleotide are optionally washed. In some instances, the step of oxidation is substituted with a sulfurization step to obtain polynucleotide phosphorothioates, wherein any capping steps can be performed after the sulfurization. Many reagents are capable of the efficient sulfur transfer, including, but not limited to, 3-(Dimethylaminomethylidene)amino)-3H-1,2,4-dithiazole-3-thione, DDTT, 3H-1,2-benzodithiol-3-one 1,1-dioxide, also known as Beaucage reagent, and N,N,N'N'-Tetraethylthiuram disulfide (TETD).

Further provided herein are methods comprising an elongation step that utilizes a coupling solution, wherein the coupling solution comprises one or more chemical components. For example, a coupling solution comprises components such as one or more solvents (such as acetonitrile, acetone, THF or other solvent), one or more monomers, and one or more activators (tetrazole or other activator known in the art). Monomers variously comprise phosphoramidite nucleosides, chlorophosphites, H-phosphonates, phosphodiesters, phosphotriesters, or other activated nucleoside known in the art capable of reacting with an unprotected monomer. In some instances, the primary constituent (by mass) of a coupling solution is a solvent or solvent mixture. In some instances, one or more washes with one or more solvents is used to remove remaining monomer, activator, or byproduct after a coupling step. Without being bound by theory, solvent or solvent mixtures in some cases increases solubility of monomer or activator, increases solubility of byproducts generated by the coupling reagents (monomers, activators, other reagent), or in some instances reacts with the solvent to form a different coupling or activating reagent. Alternately or in combination, a solvent or solvent mixture in some cases increases the rate of dissolution of the monomer or activator, or increases the rate of dissolution of byproducts generated by the monomer or activator. The choice of solvent in some instances depends on the choice of monomer or activator; for example, a coupling solution comprises a monomer phosphoramidite and a solvent comprising tetrahydrofuran. Any combination of coupling reagents (monomer, activator, or other reagent) and solvent is in some instances used with the systems, methods and compositions described herein. Polynucleotide synthesis methods used herein often comprise 1, 2, 3 or more sequential coupling steps.

Prior to coupling, the nucleoside bound to the substrate is often de-protected by removal of a protecting group, where the protecting group functions to prevent polymerization. Inability to completely remove one or more protecting groups in some instances leads to errors in polynucleotide synthesis products. In some instances, coupling steps are repeated two or more times without removal of a protecting group. Additional steps include but are not limited to capping, oxidation, or cleavage.

Further provided herein are methods comprising a deblocking (or deprotecting) step that utilizes a deblocking solution, wherein the deblocking solution comprises one or more chemical components. The deblocking solution often is used to remove protecting groups on the 5' OH of a polynucleotide or nucleoside. 5' OH protecting groups are well known in the art, and, in some cases comprise trityl, DMT (4,4'-dimethoxytrityl), or other protecting group (including triarylmethyl, triphenylmethyl, or other group) wherein removal of the protecting group does not otherwise cleave or modify the polynucleotide. In some instances, a deblocking solution comprises components such as one or more solvents (such as acetonitrile, acetone, THF, toluene, or other solvent), and one or more deblocking reagents. Deblocking reagents variously comprise acids (trifluoroacetic acid, or other acid), bases, light, heat, enzymes, or other reagent known in the art capable of removing a 5' OH protecting group. In some instances, the primary constituent (by mass) of a deblocking solution is a solvent or solvent mixture. In some instances, one or more washes with one or more solvents is used to remove remaining deblocking reagent after a deblocking step. Without being bound by theory, solvent or solvent mixtures in some cases increases solubility of deblocking reagents, increases solubility of byproducts generated by the deblocking reagents (cleaved protecting groups), or in some instances reacts with the solvent to form a different deblocking reagent. Alternately or in combination, a solvent or solvent mixture in some cases increases the rate of dissolution of the deblocking reagent, or increases the rate of dissolution of byproducts generated by the deblocking reagent (cleaved protecting group, or other byproduct). The choice of solvent in some instances depends on the choice of deblocking reagent or 5' protecting group; for example, a deblocking solution comprises a trifluoracetic acid and a solvent comprising toluene. Any combination of deblocking reagents, protecting groups, and solvent is in some instances used with the methods described herein.

For a subsequent cycle of nucleoside incorporation to occur through coupling, a protected 5' end of the substrate bound growing polynucleotide must be removed so that the primary hydroxyl group can react with a next nucleoside phosphoramidite. In some instances, the protecting group is DMT and deblocking occurs with trichloroacetic acid in dichloromethane. Conducting detritylation for an extended time or with stronger than recommended solutions of acids may lead to increased depurination of solid support-bound polynucleotide and thus reduces the yield of the desired full-length product. Methods and compositions described herein provide for controlled deblocking conditions limiting undesired depurination reactions. In some instances, the substrate bound polynucleotide is washed after deblocking. In some instances, efficient washing after deblocking contributes to synthesized polynucleotides having a reduced error rate, and/or higher yields.

Exemplary combinations, without limitation, for wash steps and solvents are provided in Table 2, where each different combination of washes is provided by a different number ("No.") reading from left to right in the table.

TABLE 2

Exemplary solvent wash steps during de novo polynucleotide synthesis.

| No. | Coupling reaction | Wash 1 | Capping Reaction (optional) | Wash 2 (optional) | Oxidation Reaction | Wash 3 | Deblocking Reaction | Wash 4 |
|---|---|---|---|---|---|---|---|---|
| 1 | | Acetone | | Acetone | | Acetone | | Acetone |
| 2 | | Acetonitrile | | Acetonitrile | | Acetone | | Acetonitrile |
| 3 | | THF | | THF | | THF | | THF |
| 4 | | Acetonitrile | | Acetonitrile | | THF | | Acetonitrile |
| 5 | | Methyl ethyl ketone | | Methyl ethyl ketone | | Methyl ethyl ketone | | Methyl ethyl ketone |
| 6 | | Acetonitrile | | Acetonitrile | | Methyl ethyl ketone | | Acetonitrile |

The surface or support-bound polynucleotides may be immobilized through their 3' end. It should be appreciated that by 3' end, it is meant the sequence downstream to the 5' end, for example 2, 3, 4, 5, 6, 7, 10, 15, 20 nucleotides or more downstream from the 5' end, for another example on the 3' half, third, or quarter of the sequence, for yet another example, less than 2, 3, 4, 5, 6, 7, 10, 15, or 20 nucleotides away from the absolute 3' end and by 5' end it is meant the sequence upstream to the 3' end, for example 2, 3, 4, 5, 6, 7, 10, 15, 20 nucleotides or more upstream from the 3' end, for another example on the 5' half, third, or quarter of the sequence, for yet another example, less than 2, 3, 4, 5, 6, 7, 10, 15, or 20 nucleotides away from the absolute 5' end. For example, a polynucleotide may be immobilized on the support via a nucleotide sequence (e.g., a degenerate binding sequence), a linker or spacer (e.g., a moiety that is not involved in hybridization). In some instances, a linker or spacer comprising nucleosides is homogeneous for a single base. In some instances, a linker or spacer comprising nucleosides is heterogeneous for a single base. In some embodiments, the polynucleotide comprises a spacer or linker to separate the polynucleotide sequence from the support. Useful spacers or linkers include photocleavable linkers, or other traditional chemical linkers. In one embodiment, polynucleotides may be attached to a solid support through a cleavable linkage moiety. For example, the solid support may be functionalized to provide cleavable linkers for covalent attachment to the polynucleotides. The linker moiety may be of six or more atoms in length. Alternatively, the cleavable moiety may be within a polynucleotide and may be introduced during in situ synthesis. A suitable cleavable moiety may be selected to be compatible with the nature of the protecting group of the nucleoside bases, the choice of solid support, and/or the mode of reagent delivery, among others. In an exemplary embodiment, the polynucleotides cleaved from the solid support contain a free 3'-OH end. Alternatively, the free 3'-OH end may also be obtained by chemical or enzymatic treatment, following the cleavage nucleoside comprising a 5' blocking group; 2) capping unreacted 5' OH groups of the polynucleotide by contacting the surface with a capping solution; 3) washing the surface at least once with a wash solvent; 4) contacting the surface with an oxidizing solution; 5) washing the surface at least once with a wash solvent; 6) capping unreacted 5' OH groups of the polynucleotide by contacting the surface with a capping solution; 7) removing the 5' blocking group with a deblocking solution; and 8) washing the surface at least once with a wash solvent. Steps 1-8 are in some instances repeated until a plurality of polynucleotide spacers are synthesized. The wash solvent may be a wash solvent described elsewhere herein.

Provided herein are methods wherein one or more capping steps are used to prevent subsequent reactions with unreacted hydroxyl groups. Capping steps are variously executed before or after any step of polynucleotide synthesis described herein. Often, capping steps are followed with a washing step comprising depositing a wash solvent on the synthesis surface. For example, a capping step is followed by washing with a wash solvent comprising acetone. In some instances, an oxidation step and a capping step are both followed by washing with a wash solvent, such as a wash solvent comprising acetone.

Exemplary combinations, without limitation, for capping steps, wash steps and solvents are provided in Table 3, where each different combination of reaction steps and washes is provided by a different number ("No.") reading from left to right in the table.

TABLE 3

Exemplary inclusion of capping steps during de novo polynucleotide synthesis.

| No. | Coupling Reaction | Wash 1 | Capping Reaction | Wash 2 (optional) | Oxidation Reaction | Wash 3 | Capping Reaction | Wash 4 | Deblocking Reaction | Wash 4 |
|---|---|---|---|---|---|---|---|---|---|---|
| 1 | | Acetone | | Acetone | | Acetone | | Acetone | | Acetone |
| 2 | | Acetonitrile | | Acetonitrile | | Acetone | | Acetonitrile | | Acetonitrile |
| 3 | | Acetonitrile | | Acetonitrile | | Acetone | | Acetone | | Acetonitrile |
| 4 | | THF | | THF | | THF | | THF | | THF |
| 5 | | Acetonitrile | | Acetonitrile | | THF | | Acetonitrile | | Acetonitrile |
| 6 | | Acetonitrile | | Acetonitrile | | THF | | THF | | Acetonitrile |
| 7 | | Methyl ethyl ketone | | Methyl ethyl ketone | | Methyl ethyl ketone | | Methyl ethyl ketone | | Methyl ethyl ketone |
| 8 | | Acetonitrile | | Acetonitrile | | Methyl ethyl ketone | | Acetonitrile | | Acetonitrile |
| 9 | | Acetonitrile | | Acetonitrile | | Methyl ethyl ketone | | Methyl ethyl ketone | | Acetonitrile | of polynucleotides. In various embodiments, the invention relates to methods and compositions for release of support or surface bound polynucleotides into solution. The cleavable moiety may be removed under conditions which do not degrade the polynucleotides. The linker may be cleaved using two approaches, either simultaneously under the same conditions as the deprotection step or subsequently utilizing a different condition or reagent for linker cleavage after the completion of the deprotection step. Optionally, a capping step is used after any step of linker/spacer synthesis to prevent additional functionalization of unreacted linkers or spacers. In some instances, two or more capping steps are used during synthesis of a polynucleotide spacer.

Provided herein are methods wherein a spacer region is synthesized by iteration of the following steps: 1) extension of a plurality of reactive molecules from a surface by contacting the surface with a base addition solution comprising at least one reactive monomer, wherein the at least one reactive monomer comprising a phosphoramidite Solvents Provided herein are methods, systems, compositions, and devices for chemical polynucleotide synthesis which comprise the use of solvents, or solvent mixtures. In some instances, a solvent or functional equivalent thereof is used as a wash solvent. In some instances, a solvent or functional equivalent thereof is used as a reaction solvent. Suitable solvents and functional equivalents are selected in some instances based on common inherent properties (density, heat capacity, solubility, polarity, miscibility, boiling point, melting point, viscosity, chemical structure, or other physical property), or performance characteristics (ability to dissolve a specific reagent or salt, reduction in error rate, resistance to degradation by a chemical reagent, heat of mixing with solvent of previous wash or reagent solution, or other performance outcome). Wash solvents are variously used in a wash step after any step in the polynucleotide synthesis, such as after deblocking, elongation, oxidation, capping, or any combination thereof.

Further described herein are exemplary solvents including hydrocarbons (e.g., hexane, decane, benzene, toluene, xylene, isomers thereof, and the like), ethers (e.g., THF, diethyl ether, methyl t-butyl ether, and the like), esters (e.g., methyl acetate, ethyl acetate, tert-butylacetate, etc.), lactones, ketones (e.g., acetone, methyl ethyl ketone, cyclopentanone, and the like), alcohols (e.g., ethanol, butanol, isopropanol, and the like), amides (e.g., DMF, N-methylpyrrolidinone, or other amides), ureas, carbonates (e.g., diethylcarbonate, or other carbonate), carbamates, aldehydes, amines, cyanates, isocyanates, sulfoxides, sulfones, aromatics, heteroaromatics, thiols, phosphoramides, nitriles (e.g., acetonitrile), alkynes, alkenes, alkanes, halogenated solvents (e.g., tetrachloromethane, dichloromethane, chloroform, or other halogenated solvent), silanes, perfluorocarbons ($C_2$-$C_{18}$ perfluorinated branched or straight alkanes such as perfluorohexane, perfluoroheptane, perfluorodecane, perfluoro aromatics such as perfluorobenzene, or other perfluorocarbon), supercritical fluids, ionic liquids, compressed gases, and the like. In some instances, wash solvents comprise a nitrile, such as acetonitrile. Solvents optionally comprise additional components such as acids, bases, or salts. In some instances, a solvent used for a non-wash step is the same solvent used for a prior or subsequent wash step.

Further described herein are methods, systems, compositions, and devices comprising solvents such as ethers. Exemplary ethers include diethyl ether, methyl ethyl ether, dibutyl ether, diisopropyl ether, di(n-propyl)ether, di(tert-butyl) ether, cyclopentyl methyl ether, dimethoxymethane, 1,4-dioxane, ethyl tert-butyl ether, 2-(2-methoxyethoxy)ethanol, morpholine, polyethylene glycol, 2-(2-methoxyethoxy)ethanol, tetrahydrofuran, tetrahydropyran, methyl tert-butylether, 2-methyl tetrahydrofuran, glyme, diglyme, and dimethoxyethane. In some instances, a wash solvent comprises tetrahydrofuran. In some instances, ethers comprise $C_2$-$C_8$ ethers.

Solvents often comprise ketones and are used with the methods, systems and compositions described herein. Exemplary ketones include acetone, acetophenone, butanone, cyclopentanone, cyclohexanone, cyclobutanone, cyclopropanone, ethyl isopropyl ketone, 2-hexanone, isophorone, mesityl oxide, methyl isobutyl ketone, methyl isopropyl ketone, 3-methyl-2-pentanone, 2-pentanone, and 3-pentanone. In some instances, a wash solvent comprises acetone. In some instances, ketones comprise $C_2$-$C_8$ ketones.

Further described herein are solvents that are in some instances "pure" substances wherein the solvent comprises only trace (<0.1%, w/v) of other chemical components (e.g., salts, solvents, other solutes). In some instances, solvents comprise water, for example a solvent comprises (v/v) no more than 0.01%, 0.1%, 0.2%, 0.3%, 0.5%, 1.0%, 2.0%, or no more than 5.0% water. In some instances the purity (w/w) of a solvent is at least 70%, 75%, 80%, 85%, 90%, 95%, 97%, 99%, or at least 99.9% pure. In some instances the purity (w/w) of a solvent is about 70%, 75%, 80%, 85%, 90%, 95%, 97%, 99%, or about 99.9% pure. In some instances, solvents comprise salts or buffers.

Further described herein are wash solvents comprising acetone with a purity of (<0.1%, w/v) of other chemical components (e.g., salts, solvents, other solutes). In some instances, wash solvents comprising acetone comprise water, for example a wash solvent comprising acetone comprises (v/v) no more than 0.01%, 0.1%, 0.2%, 0.3%, 0.5%, 1.0%, 2.0%, or no more than 5.0% water. In some instances the purity (w/w) of a wash solvent comprising acetone is at least 70%, 75%, 80%, 85%, 90%, 95%, 97%, 99%, or at least 99.9% pure. In some instances the purity (w/w) of a wash solvent comprising acetone is about 70%, 75%, 80%, 85%, 90%, 95%, 97%, 99%, or about 99.9% pure. In some instances, wash solvents comprising acetone comprise salts or buffers.

Further described herein are solvents comprising a mixture of two or more solvents. For example, a solvent comprises two solvents mixed at about a 1:1, 2:1, 3:1, 4:1, 5:1, 10:1, 20:1, 50:1, 80:10, 99:1 ratio (v/v). In some instances, a mixture of two solvents comprises at least 1%, 2%, 5%, 10%, 20%, 30%, 40%, 50%, 60%, 70%, 80% 90%, 95%, 97%, or at least 99% of one of the solvents (v/v). In some instances, a mixture of two solvents comprises about 1%, 2%, 5%, 10%, 20%, 30%, 40%, 50%, 60%, 70%, 80% 90%, 95%, 97%, or about 99% of one of the solvents (v/v). Solvents in some instances comprise a mixture of three or more solvents.

Further described herein are solvents comprising a mixture of a ketone and an additional solvent. For example, a solvent comprises a ketone and an additional solvent mixed at about a 1:1, 2:1, 3:1, 4:1, 5:1, 10:1, 20:1, 50:1, 80:10, 99:1 ratio (v/v). In some instances, a mixture of a ketone and an additional solvent comprises at least 1%, 2%, 5%, 10%, 20%, 30%, 40%, 50%, 60%, 70%, 80% 90%, 95%, 97%, or at least 99% a ketone (v/v). In some instances, a mixture of a ketone and an additional solvent comprises about 1%, 2%, 5%, 10%, 20%, 30%, 40%, 50%, 60%, 70%, 80% 90%, 95%, 97%, or about 99% a ketone (v/v). In some instances, the additional solvent is acetonitrile.

Further described herein are solvents comprising a mixture of acetone and an additional solvent. For example, a solvent comprises acetone and an additional solvent mixed at about a 1:1, 2:1, 3:1, 4:1, 5:1, 10:1, 20:1, 50:1, 80:10, 99:1 ratio (v/v). In some instances, a mixture of acetone and an additional solvent comprises at least 1%, 2%, 5%, 10%, 20%, 30%, 40%, 50%, 60%, 70%, 80% 90%, 95%, 97%, or at least 99% acetone (v/v). In some instances, a mixture of acetone and an additional solvent comprises about 1%, 2%, 5%, 10%, 20%, 30%, 40%, 50%, 60%, 70%, 80% 90%, 95%, 97%, or about 99% acetone (v/v). In some instances, the additional solvent is acetonitrile. In some instances, the additional solvent comprises THF. In some instances, the additional solvent is acetonitrile. In some instances, the additional solvent is a solvent mixture of two or more solvents.

Further described herein are various solvent temperatures that are optimized. Solvent temperatures can achieve low error rates and increased uniformity of error rate. In some instances, solvent temperatures increase the solubility of a primary reagent or byproduct from a previous step. For example, the temperature of a solvent for a wash or reagent solution is at least 0, 1, 5, 8, 10, 12, 15, 18, 20, 22, 25, 28, 30, 32, 35, 38, 40, 42, 45, 48, 50, 52, 55, 58, 60, 65, 70, 75, 80, 85, 90, or at least 90 degrees C. In some instances the temperature of a solvent for a wash or reagent solution is no more than 0, 1, 5, 8, 10, 12, 15, 18, 20, 22, 25, 28, 30, 32, 35, 38, 40, 42, 45, 48, 50, 52, 55, 58, 60, 65, 70, 75, 80, 85 or no more than 90 degrees C. In some instances the temperature of a solvent for a wash or reagent solution is about 0, 1, 5, 8, 10, 12, 15, 18, 20, 22, 25, 28, 30, 32, 35, 38, 40, 42, 45, 48, 50, 52, 55, 58, 60, 65, 70, 75, 80, 85 or about 90 degrees C. In some instances the temperature of a solvent for a wash or reagent solution is about 20 degrees C. In some instances the temperature of a solvent for a wash or reagent solution is about 25 degrees C. In some instances the temperature of a solvent for a wash or reagent solution is about 5 to 90, about 5 to 70, about 5 to 50, about 5 to 30, about 10 to 80, about 10 to 70, about 10 to 40, about 15 to 40, about 15 to 30, about 15 to 25, about 20 to 30, about 20 to 45, about 25 to 50, about 30 to 60, about 40 to 90, about 40 to 70, about 40 to 60, or about 60 to 90 degrees C. In some instances the temperature of a solvent for a wash or reagent solution is about 15 to about 25 degrees C. In some instances the temperature of a solvent for a wash or reagent solution is about 20 to 25 degrees C. In some instances the temperature of a solvent for a wash or reagent solution is about 20 to 35 degrees C. In some instances the temperature of a solvent for a wash or reagent solution is about 30 to 45 degrees C. In some instances, the temperature of a solvent is varied between two temperatures over time. In some instances, the temperature is varied across a surface to form a temperature gradient.

Further provided herein are solvents that are selected based on polarity index, or miscibility with other solvents or reagent solutions. For example, a wash solvent is selected that comprises a polarity index that is similar to the polarity of the primary constituent of a previous wash solvent or a reagent solution. Alternately or in combination, the viscosity of a solvent at a given temperature determines an optimum wash solvent. Another variable that is in some instances considered is miscibility. In some cases if two solvents are "miscible", only one phase will be produced at all proportions for a defined temperature. Polarity index, viscosity, water solubility, and miscibility (non-exhaustive) for various solvents used in the methods described herein are shown in Table 4. In some instances, solvents are combined to further adjust polarity, viscosity, or miscibility.

Further provided herein are methods, systems, compositions, and devices wherein the viscosity of a solvent for a wash or reagent solution is about 0.01, 0.05, 0.1, 0.2, 0.3, 0.4, 0.5, 0.6, 0.7, 0.8, or about 0.9 cP (centiPoise). In some instances the viscosity of a solvent for a wash or reagent solution is at least 0.01, 0.05, 0.1, 0.2, 0.3, 0.4, 0.5, 0.6, 0.7, 0.8, or at least 0.9 cP. In some instances the viscosity of a solvent for a wash or reagent solution is no more than 0.01, 0.05, 0.1, 0.2, 0.3, 0.4, 0.5, 0.6, 0.7, 0.8, or no more than 0.9 cP. In some instances the viscosity of a solvent for a wash or reagent solution is about 0.01 to 0.8, about 0.01 to 0.6, about 0.1 to 0.5, about 0.1 to 0.4, about 0.2 to 0.3, about 0.2 to 0.4, about 0.2 to 0.6, about 0.4 to 0.9, about 0.4 to 0.7, or about 0.5 to 0.9 cP. In some instances the viscosity of a solvent for a wash or reagent solution is about 0.2 to about 0.4 cP. In some instances the viscosity of a solvent for a wash or reagent solution is about 0.1 to about 0.5 cP. In some instances the viscosity of a solvent for a wash or reagent solution is about 0.3 to about 0.4 cP.

Further provided herein are methods, systems, compositions, and devices wherein the polarity index of a solvent for a wash or reagent solution is about 0, 0.5, 1, 1.5, 2, 2.5, 3, 3.5, 4, 4.5, 5, 5.5, 6, 7, 8, or about 9. In some instances the polarity index of a solvent for a wash or reagent solution is at least 0, 0.5, 1, 1.5, 2, 2.5, 3, 3.5, 4, 4.5, 5, 5.5, 6, 7, 8, or at least 9. In some instances the polarity index of a solvent for a wash or reagent solution is no more than 0, 0.5, 1, 1.5, 2, 2.5, 3, 3.5, 4, 4.5, 5, 5.5, 6, 7, 8, or no more than 9. In some instances the polarity index of a solvent for a wash or reagent solution is about 0 to 9, about 0 to 7, about 1 to 6,

TABLE 4

Solvent characteristics.

| Solvent Name | Polarity Index | Viscosity (cPoise) | Solubility in water (% w/w) | Immiscible in |
|---|---|---|---|---|
| acetic acid | 6.2 | 1.25 | 100 | pentane, hexane |
| acetone | 5.1 | 0.32 | 100 | |
| acetonitrile | 5.8 | 0.37 | 100 | pentane, hexane, heptane, cyclohexane |
| benzene | 2.7 | 0.66 | 0.18 | water |
| n-butanol | 4.0 | 0.73 | 0.43 | water |
| butyl acetate | 3.9 | 2.98 | 7.81 | water |
| carbon tetrachloride | 1.6 | 0.97 | 0.08 | water |
| chloroform | 4.1 | 0.57 | 0.815 | water |
| cyclohexane | 0.2 | 1.00 | 0.01 | water, methanol, dimethylsulfoxide, dimethylformamide |
| 1,2-dichloroethane | 3.5 | 0.79 | 0.81 | water |
| dichloromethane | 3.1 | 0.44 | 1.6 | water |
| dimethylformamide | 6.4 | 0.92 | 100 | heptane, hexane, pentane, diisopropyl ether, xylene |
| dimethyl sulfoxide | 7.2 | 2.00 | 100 | diethyl ether, heptane, hexane, pentane, xylene |
| dioxane | 4.8 | 1.54 | 100 | |
| ethanol | 5.2 | 1.20 | 100 | |
| ethyl acetate | 4.4 | 0.45 | 8.7 | water |
| diethyl ether | 2.8 | 0.32 | 6.89 | water |
| heptane | 0.0 | 0.39 | 0.0003 | water, methanol |
| hexane | 0.0 | 0.33 | 0.001 | water, methanol |
| methanol | 5.1 | 0.60 | 100 | pentane |
| methyl tert-butyl ether | 2.5 | 0.27 | 4.8 | water |
| methyl ethyl ketone | 4.7 | 0.45 | 24 | water |
| pentane | 0.0 | 0.23 | 0.004 | water |
| n-propanol | 4.0 | 2.27 | 100 | |
| isopropanol | 3.9 | 2.30 | 100 | |
| diisopropyl ether | 2.2 | 0.37 | — | water |
| tetrahydrofuran | 4.0 | 0.55 | 100 | |
| toluene | 2.4 | 0.59 | 0.051 | water |
| trichloroethylene | 1.0 | 0.57 | 0.11 | water, xylene |
| water | 9.0 | 1.00 | 100 | xylene |
| xylene | 2.5 | 0.51 | 0.018 | water | about 1 to 5, about 1 to 4, about 1 to 3, about 2 to 6, about 2 to 5, about 2 to 4, about 2 to 3, about 3 to 6, about 3 to 5, about 3 to 4, about 4 to 10, about 4 to 9, about 4 to 8, about 4 to 7, about 5 to 10, about 5 to 9, about 5 to 8, about 5 to 7, or about 5 to 6. In some instances the polarity index of a solvent for a wash or reagent solution is about 4 to about 6. In some instances the polarity index of a solvent for a wash or reagent solution is about 5 to about 6. In some instances the polarity index of a solvent for a wash or reagent solution is about 5 to about 7.

Error Rates of Large Polynucleotide Libraries

Described herein are several methods are used to evaluate the quality of polynucleotide libraries described herein, including Sanger sequencing, next generation sequencing, or other method for measuring the quality of a polynucleotide library. The quality of a polynucleotide library is may be measured by error rate, species representation, or drop outs frequency. Various metrics for error rates include deletions, insertions, substitutions, mismatches, dropouts, or other discrepancy between a predetermined sequence and a measured polynucleotide sequence. Capping is in some instances used to truncate unreacted molecules remaining after a coupling step, which prevents further growth of the polynucleotide into a full-length polynucleotide. In some instances, error rates are described by the number or percentage of full-length polynucleotides. This percentage is often determined by the efficiency of each coupling step, or an average efficiency of coupling over multiple steps.

Further provided herein are methods for synthesizing polynucleotide libraries wherein the average coupling efficiency is about 80%, 90%, 95%, 96%, 96.2%, 96.5%, 96.8%, 97%, 97.2%, 97.5%, 97.8%, 98%, 98.2%, 98.5%, 99.8%, 99%, 99.1%, 99.2%, 99.3%, 99.4%, 99.5%, 99.6%, 99.7%, 99.8%, 99.9%, 99.95%, or about 99.99%. In some instances the average coupling efficiency is at least 80%, 90%, 95%, 96%, 96.2%, 96.5%, 96.8%, 97%, 97.2%, 97.5%, 97.8%, 98%, 98.2%, 98.5%, 99.8%, 99%, 99.1%, 99.2%, 99.3%, 99.4%, 99.5%, 99.6%, 99.7%, 99.8%, 99.9%, 99.95%, or at least 99.99%. In some instances, such libraries comprise polynucleotides wherein each polynucleotide is at least 50, 100, 150, 200, 250, or at least 300 bases in length.

Further provided herein are error rates for polynucleotide libraries, wherein each polynucleotide comprises at least 50 bases, wherein the percentage of full-length sequences is about 40%, 45%, 50%, 52%, 55%, 58%, 60%, 62%, 65%, 68%, 70%, 72%, 75%, 78%, 80%, 82%, 85%, 88%, or about 90%. In some instances for polynucleotide libraries wherein each polynucleotide comprises at least 50 bases, the percentage of full-length sequences is at least 40%, 45%, 50%, 52%, 55%, 58%, 60%, 62%, 65%, 68%, 70%, 72%, 75%, 78%, 80%, 82%, 85%, 88%, or at least 90%. Further provided herein are error rates for polynucleotide libraries, wherein each polynucleotide comprises at least 100 bases, wherein the percentage of full-length sequences is about 40%, 45%, 50%, 52%, 55%, 58%, 60%, 62%, 65%, 68%, 70%, 72%, 75%, 78%, 80%, 82%, 85%, 88%, or about 90%. In some instances for polynucleotide libraries wherein each polynucleotide comprises at least 100 bases, the percentage of full-length sequences is at least 40%, 45%, 50%, 52%, 55%, 58%, 60%, 62%, 65%, 68%, 70%, 72%, 75%, 78%, 80%, 82%, 85%, 88%, or at least 90%. Further provided herein are error rates for polynucleotide libraries, wherein each polynucleotide comprises at least 150 bases, wherein the percentage of full-length sequences is about 40%, 45%, 50%, 52%, 55%, 58%, 60%, 62%, 65%, 68%, 70%, 72%, 75%, 78%, 80%, 82%, 85%, 88%, or about 90%. In some instances for polynucleotide libraries wherein each polynucleotide comprises at least 150 bases, the percentage of full-length sequences is at least 40%, 45%, 50%, 52%, 55%, 58%, 60%, 62%, 65%, 68%, 70%, 72%, 75%, 78%, 80%, 82%, 85%, 88%, or at least 90%. Further provided herein are error rates for polynucleotide libraries, wherein each polynucleotide comprises at least 200 bases, wherein the percentage of full-length sequences is about 40%, 45%, 50%, 52%, 55%, 58%, 60%, 62%, 65%, 68%, 70%, 72%, 75%, 78%, 80%, 82%, 85%, 88%, or about 90%. In some instances for polynucleotide libraries wherein each polynucleotide comprises at least 200 bases, the percentage of full-length sequences is at least 40%, 45%, 50%, 52%, 55%, 58%, 60%, 62%, 65%, 68%, 70%, 72%, 75%, 78%, 80%, 82%, 85%, 88%, or at least 90%. Further provided herein are error rates for polynucleotide libraries, wherein each polynucleotide comprises at least 300 bases, wherein the percentage of full-length sequences is about 40%, 45%, 50%, 52%, 55%, 58%, 60%, 62%, 65%, 68%, 70%, 72%, 75%, 78%, 80%, 82%, 85%, 88%, or about 90%. In some instances for polynucleotide libraries wherein each polynucleotide comprises at least 300 bases, the percentage of full-length sequences is at least 40%, 45%, 50%, 52%, 55%, 58%, 60%, 62%, 65%, 68%, 70%, 72%, 75%, 78%, 80%, 82%, 85%, 88%, or at least 90%.

Further provided herein are error rates for polynucleotide libraries. In some instances, overall error rates for three different sets of oligonucleotide libraries may be less than 1 error in 900, including 1 error in 1000 bases or less than 1 in 1000 bases—where the error rate is a comparison of synthesized sequences to instructions for synthesis of the polynucleotides. In some instances, one or more quality control steps are used in the workflow. For example, control polynucleotides of various sizes present on the surface are evaluated. Control polynucleotides in some instances are 10, 20, 30, 50, 70, 90, 100, 150, 200, 250, 300, or more than 300 bases in length. Control polynucleotides are of different sizes are often used. In some instances, control polynucleotides are 20 bases in length. In some instances, control polynucleotides are 90 bases in length. In some instances, control polynucleotides are 150 bases in length. In some instances, control polynucleotides are 250 bases in length.

Further described herein are methods for measuring error rates in polynucleotide libraries, such as Next Generation Sequencing. For example, error types (or classes) such as deletions, insertions, or mismatches are measured categorized. Error rates are often expressed for any number of error types. In some instances, mismatches are categorized based on the type of transition, for example base 1 to base 2 (e.g., A to T, T to G, C to G, etc.). In some instances, insertions are categorized based on bases adjacent to the insertion, such as base 1+base 2 (e.g., A+A corresponds to an insertion of A after a base A). In some instances, deletions are categorized based on the type of base deleted, for example Base— (e.g., A—corresponds to a deletion of an A). In some instances, deletion rates are measured as single base deletions, or block deletions. Alternately or in combination, error types are evaluated as a function of base position (relative to the order synthesizes) on the polynucleotide.

Average error rates for polynucleotides synthesized within a library using the systems and methods provided may be less than 1 in 800 bases, less than 1 in 900, 1 in 1000, less than 1 in 1250, less than 1 in 1500, less than 1 in 2000, less than 1 in 3000 or less often. In some instances, average error rates for polynucleotides synthesized within a library using the systems and methods provided are less than 1/1000. In some instances, average error rates for polynucleotides synthesized within a library using the systems and methods provided are less than 1/900. In some instances, average error rates for polynucleotides synthesized within a library using the systems and methods provided are less than 1/800. In some instances, average error rates for polynucleotides synthesized within a library using the systems and methods provided are less than 1/1100. In some instances, aggregate error rates for polynucleotides synthesized within a library using the systems and methods provided are less than 1/500, 1/600, 1/700, 1/800, 1/900, 1/1000, 1/1100, 1/1200, 1/1250, 1/1300, 1/1400, 1/1500, 1/1600, 1/1700, 1/1800, 1/1900, 1/2000, 1/3000, or less compared to the predetermined sequences. In some instances, aggregate error rates for polynucleotides synthesized within a library using the systems and methods provided are less than 1/1000. In some instances, aggregate error rates for polynucleotides synthesized within a library using the systems and methods provided are less than 1/900. In some instances, aggregate error rates for polynucleotides synthesized within a library using the systems and methods provided are less than 1/1100.

In some instances, an error correction enzyme may be used for polynucleotides synthesized within a library using the systems and methods provided can use. In some instances, aggregate error rates for polynucleotides with error correction can be less than 1/1000, 1/1500, 1/2000, 1/3000, 1/4000, 1/5000, 1/6000, 1/7000, 1/8000, 1/9000, 1/10000 or less compared to the predetermined sequences. In some instances, aggregate error rates with error correction for polynucleotides synthesized within a library using the systems and methods provided can be less than 1/1000, 1/1500, 1/2000, 1/3000, 1/4000, 1/5000, 1/6000, 1/7000, 1/8000, 1/9000, 1/10000.

Libraries may be synthesized with base insertion, deletion, substitution, or total error rates that are under 1/300, 1/400, 1/500, 1/600, 1/700, 1/800, 1/900, 1/1000, 1/1250, 1/1500, 1/2000, 1/2500, 1/3000, 1/4000, 1/5000, 1/6000, 1/7000, 1/8000, 1/9000, 1/10000, 1/12000, 1/15000, 1/20000, 1/25000, 1/30000, 1/40000, 1/50000, 1/60000, 1/70000, 1/80000, 1/90000, 1/100000, 1/125000, 1/150000, 1/200000, 1/300000, 1/400000, 1/500000, 1/600000, 1/700000, 1/800000, 1/900000, 1/1000000, or less, across the library, or across more than 80%, 85%, 90%, 93%, 95%, 96%, 97%, 98%, 99%, 99.5%, 99.8%, 99.9%, 99.95%, 99.98%, 99.99%, or more of the library. The methods and compositions of the disclosure further relate to large synthetic polynucleotide and gene libraries with low error rates associated with at least 30%, 40%, 50%, 60%, 70%, 75%, 80%, 85%, 90%, 93%, 95%, 96%, 97%, 98%, 99%, 99.5%, 99.8%, 99.9%, 99.95%, 99.98%, 99.99%, or more of the polynucleotides or genes in at least a subset of the library to relate to error free sequences in comparison to a predetermined/preselected sequence. In some instances, at least 30%, 40%, 50%, 60%, 70%, 75%, 80%, 85%, 90%, 93%, 95%, 96%, 97%, 98%, 99%, 99.5%, 99.8%, 99.9%, 99.95%, 99.98%, 99.99%, or more of the polynucleotides or genes in an isolated volume within the library have the same sequence. In some instances, at least 30%, 40%, 50%, 60%, 70%, 75%, 80%, 85%, 90%, 93%, 95%, 96%, 97%, 98%, 99%, 99.5%, 99.8%, 99.9%, 99.95%, 99.98%, 99.99%, or more of any polynucleotides or genes related with more than 95%, 96%, 97%, 98%, 99%, 99.5%, 99.6%, 99.7%, 99.8%, 99.9% or more similarity or identity have the same sequence. In some instances, the error rate related to a specified locus on a polynucleotide or gene is optimized.

Thus, a given locus or a plurality of selected loci of one or more polynucleotides or genes as part of a large library may each have an error rate that is less than 1/300, 1/400, 1/500, 1/600, 1/700, 1/800, 1/900, 1/1000, 1/1250, 1/1500, 1/2000, 1/2500, 1/3000, 1/4000, 1/5000, 1/6000, 1/7000, 1/8000, 1/9000, 1/10000, 1/12000, 1/15000, 1/20000, 1/25000, 1/30000, 1/40000, 1/50000, 1/60000, 1/70000, 1/80000, 1/90000, 1/100000, 1/125000, 1/150000, 1/200000, 1/300000, 1/400000, 1/500000, 1/600000, 1/700000, 1/800000, 1/900000, 1/1000000, or less. In various instances, such error optimized loci may comprise at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000, 1500, 2000, 2500, 3000, 4000, 5000, 6000, 7000, 8000, 9000, 10000, 30000, 50000, 75000, 100000, 500000, 1000000, 2000000, 3000000 or more loci. The error optimized loci may be distributed to at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000, 1500, 2000, 2500, 3000, 4000, 5000, 6000, 7000, 8000, 9000, 10000, 30000, 75000, 100000, 500000, 1000000, 2000000, 3000000 or more polynucleotides or genes.

The error rates can be achieved with or without error correction. The error rates can be achieved across the library, or across more than 80%, 85%, 90%, 93%, 95%, 96%, 97%, 98%, 99%, 99.5%, 99.8%, 99.9%, 99.95%, 99.98%, 99.99%, or more of the library.

Polynucleotide libraries described herein may be measured in terms of uniformity, a measure of polynucleotide species representation. Uniformity may be measured on both a per cluster and per device basis. In some instances, 99% of the polynucleotides have an abundance that is within about 0.05, 0.1, 0.2, 0.5, 0.7, 1, 1.2, 1.5, 1.7 or about within 2× of the mean abundance. In some instances, 97% of the polynucleotides have an abundance that is within about 0.05, 0.1, 0.2, 0.5, 0.7, 1, 1.2, 1.5, 1.7 or about within 2× of the mean abundance. In some instances, 60%, 75%, 80%, 85%, 90%, 95%, 97%, or 99% of the sequences have an abundance that is within 2× of the mean. In some instances, 60%, 75%, 80%, 85%, 90%, 95%, 97%, or 99% of the sequences have an abundance that is within 1.5× of the mean. In some instances, 60%, 75%, 80%, 85%, 90%, 95%, 97%, or 99% of the sequences have an abundance that is within 1× of the mean.

Use of a wash solvent provided herein may provide for a decreased error rate across a surface. For example, flow effects caused by a solvent moving over a surface in some cases lead to residual reagents left on the surface, or solubility effects that result in a difference in the local concentration of reagents across a surface. Flowing reagent solutions that contact a first portion the surface initially in some instances have different properties (reagent concentration, temperature, viscosity, or other property) than the same reagent solution contacting a second portion of the surface at a later time point; this leads to differences in error rates for the first and second portions of the surface (error gradient). This can lead to incomplete reactions, or in some cases unwanted side reactions in a non-uniform manner across the surface, resulting in errors for the synthesized polynucleotides. Wash solvents provided herein in some cases improve solubility of reagents or reagent byproducts, which decreases or eliminates a reagent concentration gradient across a surface Solid surfaces may be horizontal or vertical, where orientation is relative to the flow of a fluid across the solid surface. In other cases wash solvents provided herein facilitate favorable interactions with residual reagent solution in contact with the surface. In some cases, the difference in error rates across a surface are less than 1/100, 1/500, 1/600, 1/700, 1/800, 1/900, 1/1000, 1/1100, 1/1250, 1/1500, 1/2000, 1/5000, or less than 1/10000. In some cases, the difference in error rates across a surface are at least 1/100, 1/500, 1/600, 1/700, 1/800, 1/900, 1/1000, 1/1100, 1/1250, 1/1500, 1/2000, 1/5000, or less than 1/10000. In some cases, the difference in error rates across a surface are about 1/100, 1/500, 1/600, 1/700, 1/800, 1/900, 1/1000, 1/1100, 1/1250, 1/1500, 1/2000, 1/5000, or about 1/10000.

The methods, compositions, systems, and devices described herein in some cases comprise a surface such as a flow cell, wherein clusters are distributed between an inlet and an outlet that allow for exchange of reagent solution and washes with loci for polynucleotide synthesis. In some instances, a plurality of inlets and outlets are used. In some instances, the flow cell is horizontal, wherein the solvents and reagent solutions flow perpendicular relative to a vector defined by the force of gravity. In some instances, one or more washes with solvents described herein result in uniform error rates between clusters proximal to an inlet and clusters distal from an inlet. In some instances, the difference in error rate is about 0.0001%, 0.001%, 0.002%, 0.005%, 0.008%, 0.01%, 0.02%, 0.05%, 0.08%, 0.1%, 0.2%, 0.5%, 0.8%, or about 1.0% per micron between an inlet and an outlet. In some instances, the difference in error rate is no more than 0.0001%, 0.001%, 0.002%, 0.005%, 0.008%, 0.01%, 0.02%, 0.05%, 0.08%, 0.1%, 0.2%, 0.5%, 0.8%, or no more than 1.0% per micron between an inlet and an outlet. In some instances, the difference in error rate is at least 0.0001%, 0.001%, 0.002%, 0.005%, 0.008%, 0.01%, 0.02%, 0.05%, 0.08%, 0.1%, 0.2%, 0.5%, 0.8%, or at least 1.0% per micron between an inlet and an outlet.

As fluid flows from the inlet to the outlet, various rates of flow are used herein for reagent solutions or wash solvents. In some instances, the flow rate is about 5, 10, 15, 20, 50, 75, 100, 125, 150, 200, 250, 300, 350, 400, or about 500 uL/s. In some instances, the flow rate is at least 5, 10, 15, 20, 50, 75, 100, 125, 150, 200, 250, 300, 350, 400, or at least 500 uL/s. In some instances, the flow rate is no more than 5, 10, 15, 20, 50, 75, 100, 125, 150, 200, 250, 300, 350, 400, or no more than 500 uL/s. In some instances, the flow rate is about 5 to 500 uL/s, about 10 to 400 uL/s, about 20 to 300 uL/s, about 50 to 500 uL/s, about 50 to 400 uL/s, about 50 to 300 uL/s, about 75 to 300 uL/s, about 100 to 400 uL/s, about 200 to 500 uL/s, or about 40 to 350 uL/s. In some instances, the flow rate is about 40 to 350 uL/s. In some instances, the flow rate is about 75 to 250 uL/s. In some instances, the flow rate is about 50 to 400 uL/s.

Devices for Polynucleotide Synthesis

Figure 2:
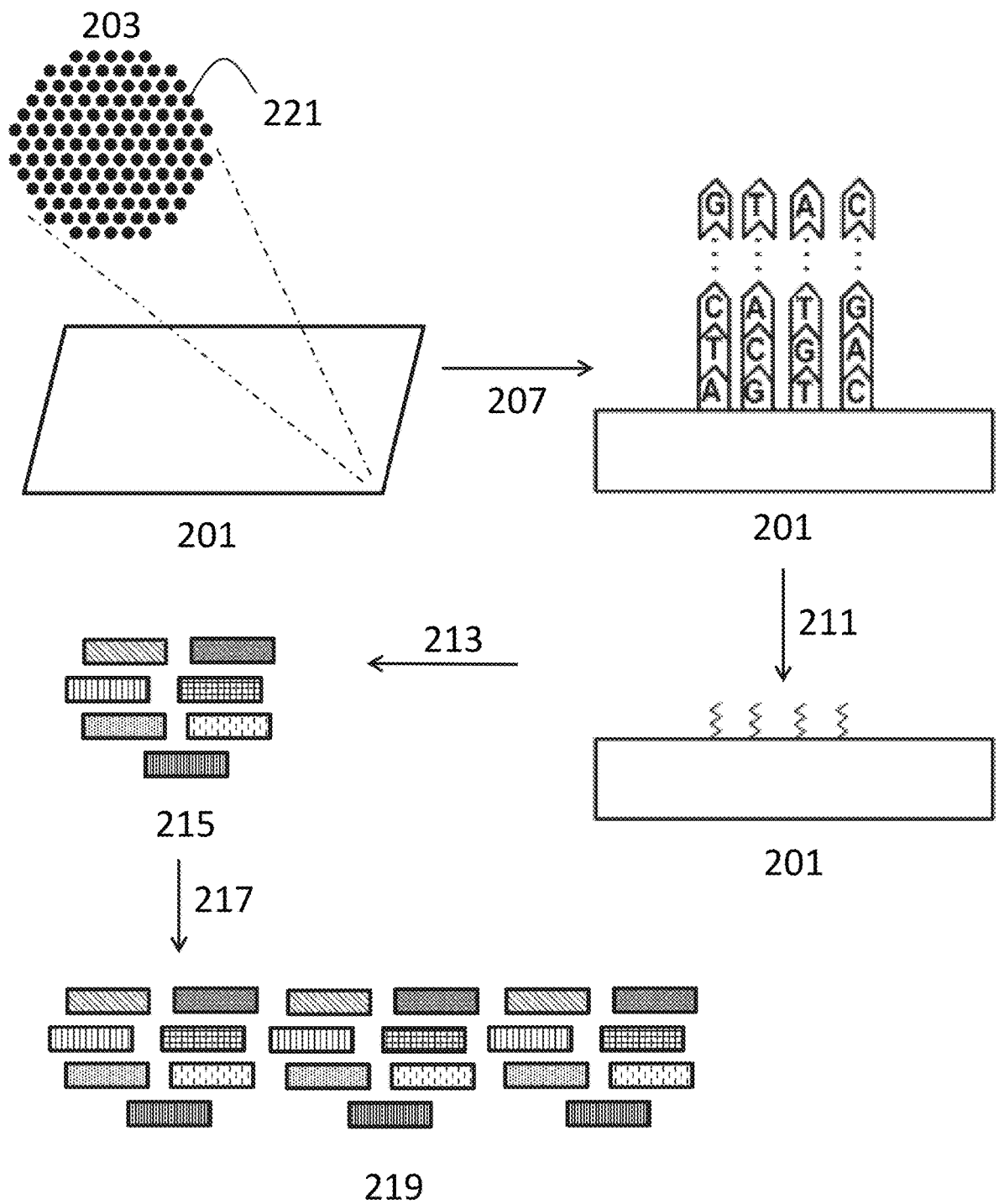
FIG. 2 depicts a schematic for the generation of polynucleotide libraries from cluster amplification.

Provided herein are structures having a surface with a plurality of features (loci) for polynucleotide synthesis or extension. Structure may comprise, without limitation, a plate, a film, a tape, a belt, or bead. With regard to structures in the form of an array, each feature in a portion of the structure may comprise a substantially planar feature, a well or a channel. In some instances, the polynucleotides are synthesized on a cluster of loci for polynucleotide extension, released and then subsequently subjected to an amplification reaction, e.g., PCR. An exemplary workflow of synthesis of polynucleotides from a cluster is depicted in FIG. 2. A silicon plate 201 includes multiple clusters 203. Within each cluster are multiple loci 221. Polynucleotides are synthesized 207 de novo on a plate 201 from the cluster 203. Polynucleotides are cleaved 211 and removed 213 from the plate to form a population of released polynucleotides 215. The population of released polynucleotides 215 are then amplified 217 to form a library of amplified polynucleotides 219.

In some instances, a well described herein has a width to depth (or height) ratio of 20 to 0.01, wherein the width is a measurement of the width at the narrowest segment of the well. In some instances, a well described herein has a width to depth (or height) ratio of 20 to 0.05, wherein the width is a measurement of the width at the narrowest segment of the well. In some instances, a well described herein has a width to depth (or height) ratio of 1 to 0.01, wherein the width is a measurement of the width at the narrowest segment of the well. In some instances, a well described herein has a width to depth (or height) ratio of 0.5 to 0.01, wherein the width is a measurement of the width at the narrowest segment of the well. In some instances, a well described herein has a width to depth (or height) ratio of about 0.01, 0.05, 0.1, 0.15, 0.16, 0.2, 0.5, 1, 2, 5, 10 or 20.

In some instances, a well described herein has a diameter to depth (or height) ratio of 20 to 0.01, wherein the diameter is a measurement of the diameter at the narrowest segment of the well. In some instances, a well described herein has a diameter to depth (or height) ratio of 20 to 0.05, wherein the diameter is a measurement of the diameter at the narrowest segment of the well. In some instances, a well described herein has a diameter to depth (or height) ratio of 1 to 0.01, wherein the diameter is a measurement of the diameter at the narrowest segment of the well. In some instances, a well described herein has a diameter to depth (or height) ratio of 0.5 to 0.01, wherein the diameter is a measurement of the diameter at the narrowest segment of the well. In some instances, a well described herein has a diameter to depth (or height) ratio of about 0.01, 0.05, 0.1, 0.15, 0.16, 0.2, 0.5, 1, 2, 5, 10, or 20.

In some instances, a structure described herein comprises a plurality of wells, wherein the height or depth of the well is from about 10 nm to about 10 μm, from about 10 nm to about 1 μm, from about 10 nm to about 500 nm, from about 10 nm to about 100 nm, from about 50 nm to about 700 nm, from about 50 nm to about 600 nm, from about 50 nm to about 500 nm, from about 50 nm to about 400 nm, from about 50 nm to about 300 nm, from about 50 nm to about 200 nm, or from about 50 nm to about 100 nm. In some instances, the height of a well is no more than 10 μm, 5 μm, 2 μm, 1 μm, 500 nm, 200 nm, 100 nm, 50 nm, 20 nm, or no more than 10 nm. In some instances, the well height is about 10 nm, 20 nm, 30 nm, 40 nm, 50 nm, 60 nm, 70 nm, 80 nm, 90 nm, 100 nm, 200 nm, 300 nm, 400 nm, 500 nm, 1 μm, 2 μm, 5 μm, 10 μm, or more than 10 μm.

In some instances, a structure described herein comprises a plurality of wells, wherein the width of the well is from about 10 nm to about 10 μm, from about 10 nm to about 1 μm, from about 10 nm to about 500 nm, from about 10 nm to about 100 nm, from about 50 nm to about 700 nm, from about 50 nm to about 600 nm, from about 50 nm to about 500 nm, from about 50 nm to about 400 nm, from about 50 nm to about 300 nm, from about 50 nm to about 200 nm, or from about 50 nm to about 100 nm. In some instances, the width of a well is no more than 10 μm, 5 μm, 2 μm, 1 μm, 500 nm, 200 nm, 100 nm, 50 nm, 20 nm, or no more than 10 nm. In some instances, well width is about 10 nm, 20 nm, 30 nm, 40 nm, 50 nm, 60 nm, 70 nm, 80 nm, 90 nm, 100 nm, 200 nm, 300 nm, 400 nm, 500 nm, 1 μm, 2 μm, 5 μm, 10 μm, or more than 10 μm.

In some instances, a structure described herein comprises a plurality of wells, wherein the diameter of the well is from about 10 nm to about 10 µm, from about 10 nm to about 1 µm, from about 10 nm to about 500 nm, from about 10 nm to about 100 nm, from about 50 nm to about 700 nm, from about 50 nm to about 600 nm, from about 50 nm to about 500 nm, from about 50 nm to about 400 nm, from about 50 nm to about 300 nm, from about 50 nm to about 200 nm, or from about 50 nm to about 100 nm. In some instances, the diameter of a well is no more than 10 µm, 5 µm, 2 µm, 1 µm, 500 nm, 200 nm, 100 nm, 50 nm, 20 nm, or no more than 10 nm. In some instances, well diameter is about 10 nm, 20 nm, 30 nm, 40 nm, 50 nm, 60 nm, 70 nm, 80 nm, 90 nm, 100 nm, 200 nm, 300 nm, 400 nm, 500 nm, 1 µm, 2 µm, 5 µm, 10 µm, or more than 10 µm.

In some instances, a spot or substantially planar feature described herein has a diameter from about 50 nm to about 1000 nm, from about 50 nm to about 900 nm, from about 50 nm to about 800 nm, from about 50 nm to about 700 nm, from about 50 nm to about 600 nm, from about 50 nm to about 500 nm, from about 50 nm to about 400 nm, from about 50 nm to about 300 nm, from about 50 nm to about 200 nm, or from about 50 nm to about 100 nm.

In some instances, a channel described herein has a width to depth (or height) ratio of 20 to 0.01, wherein the channel is a measurement of the width at the narrowest segment of the channel. In some instances, a channel described herein has a width to depth (or height) ratio of 20 to 0.05, wherein the width is a measurement of the width at the narrowest segment of the channel. In some instances, a channel described herein has a width to depth (or height) ratio of 1 to 0.01, wherein the width is a measurement of the width at the narrowest segment of the channel. In some instances, a channel described herein has a width to depth (or height) ratio of 0.5 to 0.01, wherein the width is a measurement of the width at the narrowest segment of the well. In some instances, a channel described herein has a width to depth (or height) ratio of about 0.01, 0.05, 0.1, 0.15, 0.16, 0.2, 0.5, 1, 2, 5, 10 or 20.

In some instances, a channel described herein has a diameter to depth (or height) ratio of 20 to 0.01, wherein the diameter is a measurement of the diameter at the narrowest segment of the channel. In some instances, a channel described herein has a diameter to depth (or height) ratio of 20 to 0.05, wherein the diameter is a measurement of the diameter at the narrowest segment of the channel. In some instances, a channel described herein has a diameter to depth (or height) ratio of 1 to 0.01, wherein the diameter is a measurement of the diameter at the narrowest segment of the channel. In some instances, a channel described herein has a diameter to depth (or height) ratio of 0.5 to 0.01, wherein the diameter is a measurement of the diameter at the narrowest segment of the channel. In some instances, a channel described herein has a diameter to depth (or height) ratio of about 0.01, 0.05, 0.1, 0.15, 0.16, 0.2, 0.5, 1, 2, 5, 10, or 20.

In some instances, a structure described herein comprises a plurality of channels, wherein the height or depth of the channel is from about 10 nm to about 10 µm, from about 10 nm to about 1 µm, from about 10 nm to about 500 nm, from about 10 nm to about 100 nm, from about 50 nm to about 700 nm, from about 50 nm to about 600 nm, from about 50 nm to about 500 nm, from about 50 nm to about 400 nm, from about 50 nm to about 300 nm, from about 50 nm to about 200 nm, or from about 50 nm to about 100 nm. In some instances, the height of a channel is no more than 10 µm, 5 µm, 2 µm, 1 µm, 500 nm, 200 nm, 100 nm, 50 nm, 20 nm, or no more than 10 nm. In some instances, channel height is about 10 nm, 20 nm, 30 nm, 40 nm, 50 nm, 60 nm, 70 nm, 80 nm, 90 nm, 100 nm, 200 nm, 300 nm, 400 nm, 500 nm, 1 µm, 2 µm, 5 µm, 10 µm, or more than 10 µm.

In some instances, a structure described herein comprises a plurality of channels, wherein the width of the channel is from about 10 nm to about 10 µm, from about 10 nm to about 1 µm, from about 10 nm to about 500 nm, from about 10 nm to about 100 nm, from about 50 nm to about 700 nm, from about 50 nm to about 600 nm, from about 50 nm to about 500 nm, from about 50 nm to about 400 nm, from about 50 nm to about 300 nm, from about 50 nm to about 200 nm, or from about 50 nm to about 100 nm. In some instances, the width of a channel is no more than 10 µm, 5 µm, 2 µm, 1 µm, 500 nm, 200 nm, 100 nm, 50 nm, 20 nm, or no more than 10 nm. In some instances, channel width is about 10 nm, 20 nm, 30 nm, 40 nm, 50 nm, 60 nm, 70 nm, 80 nm, 90 nm, 100 nm, 200 nm, 300 nm, 400 nm, 500 nm, 1 µm, 2 µm, 5 µm, 10 µm, or more than 10 µm.

In some instances, a structure described herein comprises a plurality of channels, wherein the diameter of the channel is from about 10 nm to about 10 µm, from about 10 nm to about 1 µm, from about 10 nm to about 500 nm, from about 10 nm to about 100 nm, from about 50 nm to about 700 nm, from about 50 nm to about 600 nm, from about 50 nm to about 500 nm, from about 50 nm to about 400 nm, from about 50 nm to about 300 nm, from about 50 nm to about 200 nm, or from about 50 nm to about 100 nm. In some instances, the diameter of a channel is no more than 10 µm, 5 µm, 2 µm, 1 µm, 500 nm, 200 nm, 100 nm, 50 nm, 20 nm, or no more than 10 nm. In some instances, well diameter is about 10 nm, 20 nm, 30 nm, 40 nm, 50 nm, 60 nm, 70 nm, 80 nm, 90 nm, 100 nm, 200 nm, 300 nm, 400 nm, 500 nm, 1 µm, 2 µm, 5 µm, 10 µm, or more than 10 µm.

In some instances, the width of a feature (e.g., substantially planar feature, well, channel, or other feature supporting polynucleotide synthesis) is from about 10 nm to about 10 µm, from about 100 nm to about 10 µm, from about 200 nm to about 1 µm, from about 50 nm to about 500 nm, from about 50 nm to about 200 µm, or from about 10 nm to about 100 nm, for example, about 10 µm, 5 µm, 2 µm, 1 µm, 500 nm, 200 nm, 100 nm, 50 nm, 20 nm, or 10 nm. In some instances, the width of a feature is no more than about 10 µm, 5 µm, 2 µm, 1 µm, 500 nm, 200 nm, 100 nm, 50 nm or 10 nm. In some instances, the distance between the center of two adjacent features is from about 10 nm to about 10 µm, 20 nm to about 5 µm, from about 50 nm to about 2 nm, from about 100 nm to about 1 µm, from about 200 nm to about 500 nm, from about 200 nm to about 1 µm, from about 200 nm to about 750 nm, or from about 300 nm to about 600 nm, for example, about 500 nm. In some instances, the total width of a feature is about 10 nm, 20 nm, 50 nm, 100 nm, 200 nm, 500 nm, 1 µm, 5 µm, 10 µm, 20 µm, 30 µm, 40 µm, 50 µm, 60 µm, 70 µm, 80 µm, 90 µm, or 100 µm. In some instances, the total width of a feature is about 10 nm to 1 µm, 20 nm to 500 nm, or 50 nm to 100 nm.

Surfaces for Polynucleotide Synthesis

Figure 1D:
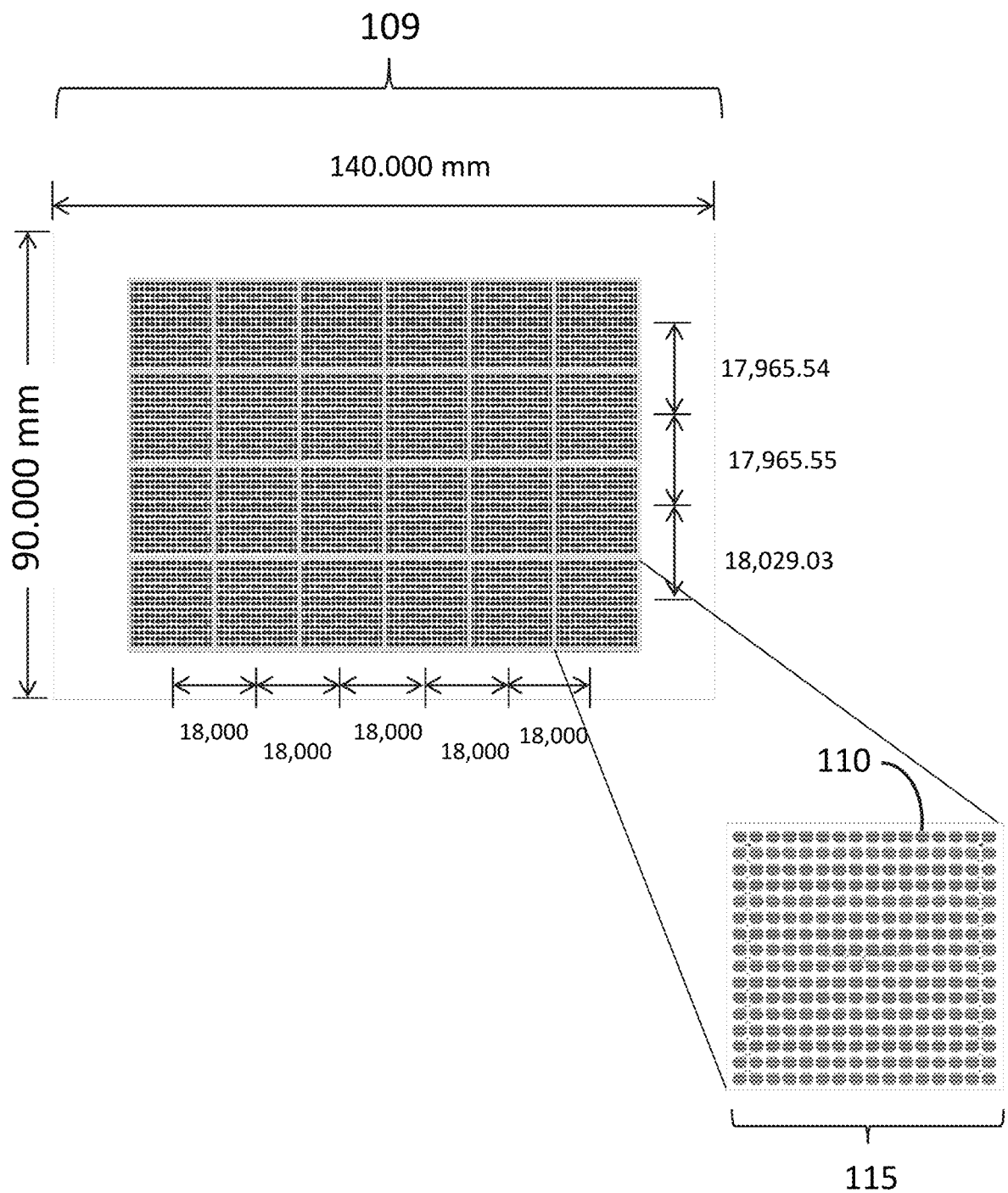
FIG. 1D illustrates a plate configured for polynucleotide synthesis comprising 24 regions, or sub-fields, each having an array of 256 clusters.
Figure 1E:
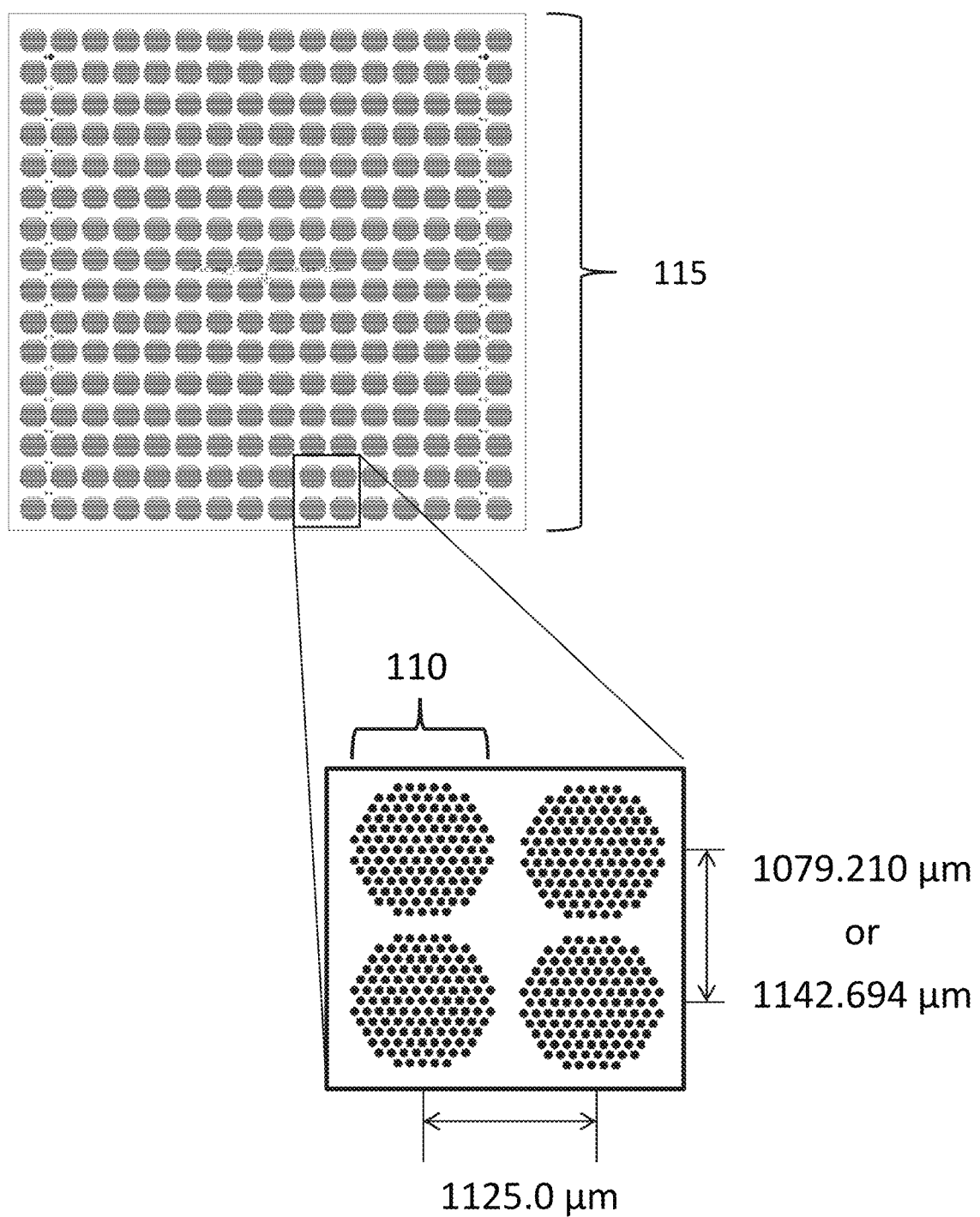
FIG. 1E illustrates a closer view of the sub-field in FIG. 1D having 16×16 of clusters, each cluster having 121 individual loci.
Figure 1F:
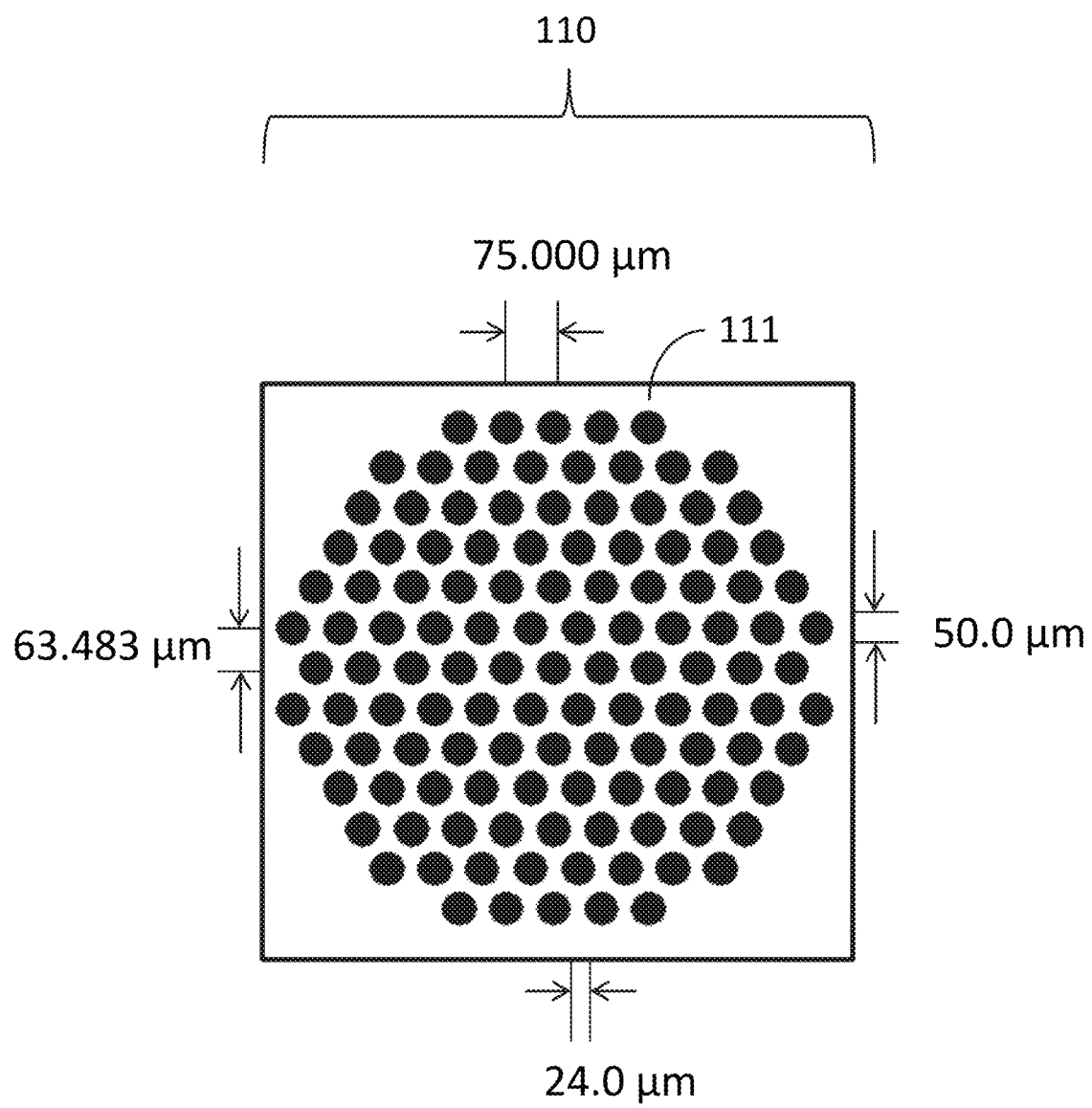
FIG. 1F illustrates a detailed view of the cluster in FIG. 1D, where the cluster has 121 loci.

Provided herein are rigid or flexibles structures for polynucleotide synthesis. In the case of rigid structures, provided herein are devices having a structure (e.g., a plate) for the generation of a library of polynucleotides. An exemplary structure 109 is illustrated in FIG. 1D, wherein the structure 109 has about the same size dimensions as a standard 96 well plate: 140 mm by 90 mm. The structure 109 comprises clusters grouped in 24 regions or sub-fields 115, each sub-field 115 comprising an array of 256 clusters 110. An expanded view of an exemplary sub-field 115 is shown in FIG. 1E. In the expanded view of four clusters (FIG. 1E), a single cluster 110, has a Y axis cluster pitch (distance from center to center of adjacent clusters) of 1079.210 μm or 1142.694 μm, and an X axis cluster pitch of 1125 μm. An illustrative cluster 110 is depicted in FIG. 1F, where the Y axis loci pitch (distance from center to center of adjacent loci) is 63.483 μm, and an X axis loci pitch is 75 μm. The locus width at the longest part, e.g., diameter for a circular locus, is 50 μm and the distance between loci is 24 μm. The number of loci 111 in the exemplary cluster in FIG. 1F is 121. The loci may be flat, wells, or channels.

In the case of flexible structures, provided herein are devices wherein the flexible structure comprises a continuous loop 105 wrapped around one or more fixed structures, e.g., a pair of rollers 106 or a non-continuous flexible structure 107 wrapped around separate fixed structures, e.g., a pair reels 108. See FIGS. 1B-1C. In some instances, the structures comprise multiple regions for polynucleotide synthesis.

In some instances, each feature supports the synthesis of a population of polynucleotides having a different sequence than a population of polynucleotides grown on another feature. Provided herein are surfaces which comprise at least 10, 100, 256, 500, 1,000, 2,000, 3,000, 4,000, 5,000, 6,000, 7,000, 8,000, 9,000, 10,000, 11,000, 12,000, 13,000, 14,000, 15,000, 20,000, 30,000, 40,000, 50,000 or more clusters. Provided herein are surfaces which comprise more than 2,000; 5,000; 10,000; 20,000; 30,000; 50,000; 100,000; 200,000; 300,000; 400,000; 500,000; 600,000; 700,000; 800,000; 900,000; 1,000,000; 5,000,000; or 10,000,000 or more distinct features. In some instances, each cluster includes 1, 2, 3, 4, 5, 6, 7, 8, 9, 10, 20, 30, 40, 50, 60, 70, 80, 90, 100, 120, 130, 150, 200, 500 or more features. In some instances, each cluster includes 50 to 500, 50 to 200, 50 to 150, or 100 to 150 features. In some instances, each cluster includes 100 to 150 features. In exemplary arrangements, each cluster includes 109, 121, 130 or 137 features. In some instances, each structure within a feature supports the synthesis of a population of polynucleotides having a different sequence than a population of polynucleotides grown on another structure, within the same feature. Provided herein are features which in some instances each comprise at least 1; 2; 5; 10; 20; 50; 100; 200, 500, 1,000, 2,000, 5,000, 10,000, 20,000 or more than 200,000 distinct structures. In some instances, each feature comprises about 10 to about 500, about 50 to about 250, about 10 to about 1000, or about 1 to about 50 structures.

In some instances, the distance from the centers of two adjacent loci within a cluster is from about 10 μm to about 500 μm, from about 10 μm to about 200 μm, or from about 10 μm to about 100 μm. In some instances, the distance from two centers of adjacent loci is greater than about 10 μm, 20 μm, 30 μm, 40 μm, 50 μm, 60 μm, 70 μm, 80 μm, 90 μm or 100 μm. In some instances, the distance from the centers of two adjacent loci is less than about 200 μm, 150 μm, 100 μm, 80 μm, 70 μm, 60 μm, 50 μm, 40 μm, 30 μm, 20 μm or 10 μm. In some instances, each locus has a width of about 0.5 μm, 1 μm, 2 μm, 3 μm, 4 μm, 5 μm, 6 μm, 7 μm, 8 μm, 9 μm, 10 μm, 20 μm, 30 μm, 40 μm, 50 μm, 60 μm, 70 μm, 80 μm, 90 μm or 100 μm. In some instances, each locus has a width of about 0.5 μm to 100 μm, about 0.5 μm to 50 μm, about 10 μm to 75 μm, or about 0.5 μm to 50 μm.

In some instances, the density of clusters within a device is at least or about 1 cluster per 100 $mm^2$, 1 cluster per 10 $mm^2$, 1 cluster per 5 $mm^2$, 1 cluster per 4 $mm^2$, 1 cluster per 3 $mm^2$, 1 cluster per 2 $mm^2$, 1 cluster per 1 $mm^2$, 2 clusters per 1 $mm^2$, 3 clusters per 1 $mm^2$, 4 clusters per 1 $mm^2$, 5 clusters per 1 $mm^2$, 10 clusters per 1 $mm^2$, 50 clusters per 1 $mm^2$ or more. In some instances, a device comprises from about 1 cluster per 10 $mm^2$ to about 10 clusters per 1 $mm^2$. In some instances, the distance from the centers of two adjacent clusters is less than about 50 μm, 100 μm, 200 μm, 500 μm, 1000 μm, or 2000 μm or 5000 μm. In some instances, the distance from the centers of two adjacent clusters is from about 50 μm and about 100 μm, from about 50 μm and about 200 μm, from about 50 μm and about 300 μm, from about 50 μm and about 500 μm, and from about 100 μm to about 2000 μm. In some instances, the distance from the centers of two adjacent clusters is from about 0.05 mm to about 50 mm, from about 0.05 mm to about 10 mm, from about 0.05 mm and about 5 mm, from about 0.05 mm and about 4 mm, from about 0.05 mm and about 3 mm, from about 0.05 mm and about 2 mm, from about 0.1 mm and 10 mm, from about 0.2 mm and 10 mm, from about 0.3 mm and about 10 mm, from about 0.4 mm and about 10 mm, from about 0.5 mm and 10 mm, from about 0.5 mm and about 5 mm, or from about 0.5 mm and about 2 mm. In some instances, each cluster has a diameter or width along one dimension of about 0.5 to 2 mm, about 0.5 to 1 mm, or about 1 to 2 mm. In some instances, each cluster has a diameter or width along one dimension of about 0.5, 0.6, 0.7, 0.8, 0.9, 1, 1.1, 1.2, 1.3, 1.4, 1.5, 1.6, 1.7, 1.8, 1.9 or 2 mm. In some instances, each cluster has an interior diameter or width along one dimension of about 0.5, 0.6, 0.7, 0.8, 0.9, 1, 1.1, 1.15, 1.2, 1.3, 1.4, 1.5, 1.6, 1.7, 1.8, 1.9 or 2 mm.

Provided herein are features having a width at the longest segment of 10 nm to 1 μm. In some instances, the features have a width at the longest segment of about 10, 20, 30, 35, 40, 45, 50, 55 or 60 nm. In some instances, the features are channels having multiple segments, wherein each segment has a center to center distance apart of 5 to 50 nm. In some instances, the center to center distance apart for each segment is about 5, 10, 15, 20 or 25 nm.

The number of distinct polynucleotides synthesized on the surface of a structure described herein is often dependent on the number of distinct features available in the substrate. In some instances, the density of features within a cluster of a substrate is at least or about 1 feature per $mm^2$, 10 features per $mm^2$, 25 features per $mm^2$, 50 features per $mm^2$, 65 features per $mm^2$, 75 features per $mm^2$, 100 features per $mm^2$, 130 features per $mm^2$, 150 features per $mm^2$, 175 features per $mm^2$, 200 features per $mm^2$, 300 features per $mm^2$, 400 features per $mm^2$, 500 features per $mm^2$, 1,000 features per $mm^2$, 2,000 features per $mm^2$, 5,000 features per $mm^2$, 10,000 features per $mm^2$, 100,000 features per $mm^2$, 1,000,000 features per $mm^2$ or more than 1,000,000 features per $mm^2$. In some instances, a substrate comprises from about 10 features per $mm^2$ to about 500 features per $mm^2$, from about 25 features per $mm^2$ to about 400 features per $mm^2$, from about 50 features per $mm^2$ to about 500 features per $mm^2$, from about 100 features per $mm^2$ to about 500 features per $mm^2$, from about 150 features per $mm^2$ to about 500 features per $mm^2$, from about 10 features per $mm^2$ to about 250 features per $mm^2$, from about 50 features per $mm^2$ to about 250 features per $mm^2$, from about 10 features per $mm^2$ to about 200 features per $mm^2$, or from about 50 features per $mm^2$ to about 200 features per $mm^2$.

In some instances, the density of features within a cluster of a substrate is at least or about 1 feature per $\mu m^2$, 10 features per $\mu m^2$, 25 features per $\mu m^2$, 50 features per $\mu m^2$, 65 features per $\mu m^2$, 75 features per $\mu m^2$, 100 features per $\mu m^2$, 130 features per $\mu m^2$, 150 features per $\mu m^2$, 175 features per $\mu m^2$, 200 features per $\mu m^2$, 300 features per $\mu m^2$, 400 features per $\mu m^2$, 500 features per $\mu m^2$, 1,000 features per µm², 2,000 features per µm², 5,000 features per µm², 10,000 features per µm², 100,000 features per µm², 1,000,000 features per µm² or more than 1,000,000 features per µm². In some instances, a substrate comprises from about 10 features per µm² to about 500 features per µm², from about 25 features per µm² to about 400 features per µm², from about 50 features per µm² to about 500 features per µm², from about 100 features per µm² to about 500 features per µm², from about 150 features per µm² to about 500 features per µm², from about 10 features per µm² to about 250 features per µm², from about 50 features per µm² to about 250 features per µm², from about 10 features per µm² to about 200 features per µm², or from about 50 features per µm² to about 200 features per µm². In some instances, the distance between the centers of two adjacent features within a cluster is from about 10 µm to about 500 µm, from about 10 µm to about 200 µm, or from about 10 µm to about 100 µm. In some instances, the distance between two centers of adjacent features is greater than about 10 µm, 20 µm, 30 µm, 40 µm, 50 µm, 60 µm, 70 µm, 80 µm, 90 µm or 100 µm. In some instances, the distance between the centers of two adjacent features is less than about 200 µm, 150 µm, 100 µm, 80 µm, 70 µm, 60 µm, 50 µm, 40 µm, 30 µm, 20 µm or 10 µm. In some instances, the distance between the centers of two adjacent features within a cluster is from about 10 nm to about 1000 nm, from about 10 nm to about 500 nm, 10 nm to about 200 nm, or from about 10 nm to about 100 nm. In some instances, the distance between two centers of adjacent features is greater than about 10 nm, 20 nm, 30 nm, 40 nm, 50 nm, 60 nm, 70 nm, 80 nm, 90 nm or 100 nm. In some instances, the distance between the centers of two adjacent features is less than about 500 nm, 200 nm, 150 nm, 100 nm, 80 nm, 70 nm, 60 nm, 50 nm, 40 nm, 30 nm, 20 nm or 10 nm. In some instances, each square meter of a structure described herein allows for at least about $10^7$, $10^8$, $10^9$, $10^{10}$, $10^{11}$, or at least about $10^{12}$ features, where each feature supports one polynucleotide. In some instances, each square meter of a structure described herein allows for at least about $10^7$, $10^8$, $10^9$, $10^{10}$, $10^{11}$, or at least about $10^{12}$ features, where each feature supports a plurality of different polynucleotides. In some instances, $10^9$ polynucleotides are supported on less than about 6, 5, 4, 3, 2 or 1 m² of a structure described herein.

In some instances, a structure described herein provides support for the synthesis of more than 2,000; 5,000; 10,000; 20,000; 30,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000; 100,000,000 or more non-identical polynucleotides. In some instances, the structure provides support for the synthesis of more than 2,000; 5,000; 10,000; 20,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000; 100,000,000 or more polynucleotides encoding for distinct sequences. In some instances, at least a portion of the polynucleotides have an identical sequence or are configured to be synthesized with an identical sequence. In some instances, the structure provides a surface environment for the growth of polynucleotides having at least about 50, 60, 70, 75, 80, 85, 90, 95, 100, 110, 120, 130, 140, 150, 160, 175, 200, 225, 250, 275, 300, 325, 350, 375, 400, 425, 450, 475, 500, 1,000, 2,000 bases or more than 2,000 bases. In some instances, the structure provides a surface environment for the growth of polynucleotides each having at least about 50, 60, 70, 75, 80, 85, 90, 95, 100, 110, 120, 130, 140, 150, 160, 175, 200, 225, 250, 275, 300, 325, 350, 375, 400, 425, 450, 475, 500, 1,000, 2,000 bases or more than 2,000 bases. In some instances, the structure provides a surface environment for the growth of polynucleotides having between 50 and 2,000, bases, 50 and 1,000, 50 and 500, 50 and 250, or between 100 and 1,000, 100 and 500, or between 100 and 300 bases.

In some instances, polynucleotides are synthesized on distinct features of a structure, wherein each feature supports the synthesis of a population of polynucleotides. In some instances, each feature supports the synthesis of a population of polynucleotides having a different sequence than a population of polynucleotides grown on another locus. In some instances, the features of a structure are located within a plurality of clusters. In some instances, a structure comprises at least 10, 500, 1,000, 2,000, 3,000, 4,000, 5,000, 6,000, 7,000, 8,000, 9,000, 10,000, 11,000, 12,000, 13,000, 14,000, 15,000, 20,000, 30,000, 40,000, 50,000 or more clusters. In some instances, a structure comprises more than 2,000; 5,000; 10,000; 100,000; 200,000; 300,000; 400,000; 500,000; 600,000; 700,000; 800,000; 900,000; 1,000,000; 1,100,000; 1,200,000; 1,300,000; 1,400,000; 1,500,000; 1,600,000; 1,700,000; 1,800,000; 1,900,000; 2,000,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; or 10,000,000 or more distinct features. In some instances, each cluster includes 1, 2, 3, 4, 5, 6, 7, 8, 9, 10, 20, 30, 40, 50, 60, 70, 80, 90, 100, 120, 130, 150 or more features (loci). In some instances, each cluster includes 50 to 500, 100 to 150, or 100 to 200 features. In some instances, each cluster includes 109, 121, 130 or 137 features. In some instances, each cluster includes 5, 6, 7, 8, 9, 10, 11 or 12 features.

In some instances, polynucleotides from distinct features within one cluster have sequences that, when assembled, encode for a contiguous longer polynucleotide of a predetermined sequence.

In some instances, a structure described herein is about the size of a standard 96 well plate, for example between about 100 and 200 mm by between about 50 and 150 mm. In some instances, a structure described herein has a diameter less than or equal to about 1000 mm, 500 mm, 450 mm, 400 mm, 300 mm, 250 mm, 200 mm, 150 mm, 100 mm or 50 mm. In some instances, the diameter of a substrate is between about 25 mm and 1000 mm, between about 25 mm and about 800 mm, between about 25 mm and about 600 mm, between about 25 mm and about 500 mm, between about 25 mm and about 400 mm, between about 25 mm and about 300 mm, or between about 25 mm and about 200. Non-limiting examples of substrate size include about 300 mm, 200 mm, 150 mm, 130 mm, 100 mm, 76 mm, 51 mm and 25 mm. In some instances, a substrate has a planar surface area of at least about 100 mm²; 200 mm²; 500 mm²; 1,000 mm²; 2,000 mm²; 5,000 mm²; 10,000 mm²; 12,000 mm²; 15,000 mm²; 20,000 mm²; 30,000 mm²; 40,000 mm²; 50,000 mm² or more. In some instances, a substrate has a thickness between about 50 mm and about 2000 mm, between about 50 mm and about 1000 mm, between about 100 mm and about 1000 mm, between about 200 mm and about 1000 mm, or between about 250 mm and about 1000 mm. Non-limiting examples of thickness include 275 mm, 375 mm, 525 mm, 625 mm, 675 mm, 725 mm, 775 mm and 925 mm. In some instances, the thickness of the substrate varies with diameter and depends on the composition of the substrate. For example, a structure comprising materials other than silicon may have a different thickness than a silicon structure of the same diameter. Structure thickness may be determined by the mechanical strength of the material used and the structure must be thick enough to support its own weight without cracking during handling. In some instances, a structure is more than about 1, 2, 3, 4, 5, 10, 15, 30, 40, 50 feet in any one dimension.

Surface Architecture

Provided herein are devices comprising raised and/or lowered features. One benefit of having such features is an increase in surface area to support polynucleotide synthesis. In some instances, a device having raised and/or lowered features is referred to as a three-dimensional substrate. In some instances, a three-dimensional device comprises one or more channels. In some instances, one or more loci comprise a channel. In some instances, the channels are accessible to reagent deposition via a deposition device such as a polynucleotide synthesizer. In some instances, reagents and/or fluids collect in a larger well in fluid communication one or more channels. For example, a device comprises a plurality of channels corresponding to a plurality of loci with a cluster, and the plurality of channels are in fluid communication with one well of the cluster. In some methods, a library of polynucleotides is synthesized in a plurality of loci of a cluster.

In some instances, the structure is configured to allow for controlled flow and mass transfer paths for polynucleotide synthesis on a surface. In some instances, the configuration of a device allows for the controlled and even distribution of mass transfer paths, chemical exposure times, and/or wash efficacy during polynucleotide synthesis. In some instances, the configuration of a device allows for increased sweep efficiency, for example by providing sufficient volume for a growing a polynucleotide such that the excluded volume by the growing polynucleotide does not take up more than 50, 45, 40, 35, 30, 25, 20, 15, 14, 13, 12, 11, 10, 9, 8, 7, 6, 5, 4, 3, 2, 1%, or less of the initially available volume that is available or suitable for growing the polynucleotide. In some instances, a three-dimensional structure allows for managed flow of fluid to allow for the rapid exchange of chemical exposure.

Provided herein are methods to synthesize an amount of nucleic acid, such as RNA or DNA, of 1 fM, 5 fM, 10 fM, 25 fM, 50 fM, 75 fM, 100 fM, 200 fM, 300 fM, 400 fM, 500 fM, 600 fM, 700 fM, 800 fM, 900 fM, 1 pM, 5 pM, 10 pM, 25 pM, 50 pM, 75 pM, 100 pM, 200 pM, 300 pM, 400 pM, 500 pM, 600 pM, 700 pM, 800 pM, 900 pM, or more. In some instances, a polynucleotide library may span the length of about 1%, 2%, 3%, 4%, 5%, 10%, 15%, 20%, 30%, 40%, 50%, 60%, 70%, 80%, 90%, 95%, or 100% of a gene. A gene may be varied up to about 1%, 2%, 3%, 4%, 5%, 10%, 15%, 20%, 30%, 40%, 50%, 60%, 70%, 80%, 85%, 90%, 95%, or 100%.

Non-identical polynucleotides may collectively encode a sequence for at least 1%, 2%, 3%, 4%, 5%, 10%, 15%, 20%, 30%, 40%, 50%, 60%, 70%, 80%, 85%, 90%, 95%, or 100% of a gene. In some instances, a polynucleotide may encode a sequence of 50%, 60%, 70%, 80%, 85%, 90%, 95%, or more of a gene. In some instances, a polynucleotide may encode a sequence of 80%, 85%, 90%, 95%, or more of a gene.

In some instances, segregation is achieved by physical structure. In some instances, segregation is achieved by differential functionalization of the surface generating active and passive regions for polynucleotide synthesis. Differential functionalization is also be achieved by alternating the hydrophobicity across the device surface, thereby creating water contact angle effects that cause beading or wetting of the deposited reagents. Employing larger structures can decrease splashing and cross-contamination of distinct polynucleotide synthesis locations with reagents of the neighboring spots. In some instances, a device, such as a polynucleotide synthesizer, is used to deposit reagents to distinct polynucleotide synthesis locations. Substrates having three-dimensional features are configured in a manner that allows for the synthesis of a large number of polynucleotides (e.g., more than about 10,000) with a low error rate (e.g., less than about 1:500, 1:1000, 1:1500, 1:2,000; 1:3,000; 1:5,000; or 1:10,000). In some instances, a device comprises features with a density of about or greater than about 1, 5, 10, 20, 30, 40, 50, 60, 70, 80, 100, 110, 120, 130, 140, 150, 160, 170, 180, 190, 200, 300, 400 or 500 features per $mm^2$.

A well of a device may have the same or different width, height, and/or volume as another well of the substrate. A channel of a device may have the same or different width, height, and/or volume as another channel of the substrate. In some instances, the width of a cluster is from about 0.05 mm to about 50 mm, from about 0.05 mm to about 10 mm, from about 0.05 mm and about 5 mm, from about 0.05 mm and about 4 mm, from about 0.05 mm and about 3 mm, from about 0.05 mm and about 2 mm, from about 0.05 mm and about 1 mm, from about 0.05 mm and about 0.5 mm, from about 0.05 mm and about 0.1 mm, from about 0.1 mm and 10 mm, from about 0.2 mm and 10 mm, from about 0.3 mm and about 10 mm, from about 0.4 mm and about 10 mm, from about 0.5 mm and 10 mm, from about 0.5 mm and about 5 mm, or from about 0.5 mm and about 2 mm. In some instances, the width of a well comprising a cluster is from about 0.05 mm to about 50 mm, from about 0.05 mm to about 10 mm, from about 0.05 mm and about 5 mm, from about 0.05 mm and about 4 mm, from about 0.05 mm and about 3 mm, from about 0.05 mm and about 2 mm, from about 0.05 mm and about 1 mm, from about 0.05 mm and about 0.5 mm, from about 0.05 mm and about 0.1 mm, from about 0.1 mm and 10 mm, from about 0.2 mm and 10 mm, from about 0.3 mm and about 10 mm, from about 0.4 mm and about 10 mm, from about 0.5 mm and 10 mm, from about 0.5 mm and about 5 mm, or from about 0.5 mm and about 2 mm. In some instances, the width of a cluster is less than or about 5 mm, 4 mm, 3 mm, 2 mm, 1 mm, 0.5 mm, 0.1 mm, 0.09 mm, 0.08 mm, 0.07 mm, 0.06 mm or 0.05 mm. In some instances, the width of a cluster is from about 1.0 and 1.3 mm. In some instances, the width of a cluster is about 1.150 mm. In some instances, the width of a well is less than or about 5 mm, 4 mm, 3 mm, 2 mm, 1 mm, 0.5 mm, 0.1 mm, 0.09 mm, 0.08 mm, 0.07 mm, 0.06 mm or 0.05 mm. In some instances, the width of a well is from about 1.0 and 1.3 mm. In some instances, the width of a well is about 1.150 mm. In some instances, the width of a cluster is about 0.08 mm. In some instances, the width of a well is about 0.08 mm. The width of a cluster may refer to clusters within a two-dimensional or three-dimensional substrate.

In some instances, the height of a well is from about 20 μm to about 1000 μm, from about 50 μm to about 1000 μm, from about 100 μm to about 1000 μm, from about 200 μm to about 1000 μm, from about 300 μm to about 1000 μm, from about 400 μm to about 1000 μm, or from about 500 μm to about 1000 μm. In some instances, the height of a well is less than about 1000 μm, less than about 900 μm, less than about 800 μm, less than about 700 μm, or less than about 600 μm.

In some instances, a device comprises a plurality of channels corresponding to a plurality of loci within a cluster, wherein the height or depth of a channel is from about 5 μm to about 500 μm, from about 5 μm to about 400 μm, from about 5 μm to about 300 μm, from about 5 μm to about 200 μm, from about 5 μm to about 100 μm, from about 5 μm to about 50 μm, or from about 10 μm to about 50 μm. In some instances, the height of a channel is less than 100 μm, less than 80 μm, less than 60 μm, less than 40 μm or less than 20 μm.

In some instances, the diameter of a channel, locus (e.g., in a substantially planar substrate) or both channel and locus (e.g., in a three-dimensional device wherein a locus corresponds to a channel) is from about 1 μm to about 1000 μm, from about 1 μm to about 500 μm, from about 1 μm to about 200 μm, from about 1 μm to about 100 μm, from about 5 μm to about 100 μm, or from about 10 μm to about 100 μm, for example, about 90 μm, 80 μm, 70 μm, 60 μm, 50 μm, 40 μm, 30 μm, 20 μm or 10 μm. In some instances, the diameter of a channel, locus, or both channel and locus is less than about 100 μm, 90 μm, 80 μm, 70 μm, 60 μm, 50 μm, 40 μm, 30 μm, 20 μm or 10 μm. In some instances, the distance from the center of two adjacent channels, loci, or channels and loci is from about 1 μm to about 500 μm, from about 1 μm to about 200 μm, from about 1 μm to about 100 μm, from about 5 μm to about 200 μm, from about 5 μm to about 100 μm, from about 5 μm to about 50 μm, or from about 5 μm to about 30 μm, for example, about 20 μm.

Surface Materials

Provided herein are devices comprising a surface, wherein the surface is modified to support polynucleotide synthesis at predetermined locations and with a resulting low error rate, a low dropout rate, a high yield, and a high oligo representation. In some instances, surfaces of a device for polynucleotide synthesis provided herein are fabricated from a variety of materials capable of modification to support a de novo polynucleotide synthesis reaction. In some instances, the devices are sufficiently conductive, e.g., are able to form uniform electric fields across all or a portion of the device. A device described herein may comprise a flexible material. Exemplary flexible materials include, without limitation, modified nylon, unmodified nylon, nitrocellulose, and polypropylene. A device described herein may comprise a rigid material. Exemplary rigid materials include, without limitation, glass, fuse silica, silicon, silicon dioxide, silicon nitride, metal nitride, metal silicide, metal carbide, metal oxide, plastics (for example, polytetrafluoroethylene, polypropylene, polystyrene, polycarbonate, and blends thereof), and metals (for example, gold, platinum). In some instances, metal oxides include $TiO_2$, $Ta_2O_5$, $Nb_2O_5$, $Al_2O_3$, BaO, $Y_2O_3$, $HfO_2$, SrO or other metal oxide known in the art. In some instances, metal carbides include TiC, WC, $ThC_2$, ThC, VC, $W_2C$, ZrC, HfC, NbC, TaC, $Ta_2C$, or other metal carbide known in the art. In some instances, metal nitrides include GaN, InN, BN, $Be_3N_2$, $Cr_2N$, MoN, $Si_3N_4$, TaN, $Th_2N_2$, VN, ZrN, TiN, HfN, NbC, WN, TaN, or other metal nitride known in the art. Devices disclosed herein are in some instances fabricated from a material comprising silicon, polystyrene, agarose, dextran, cellulosic polymers, polyacrylamides, polydimethylsiloxane (PDMS), glass, or any combination thereof. In some instances, a device disclosed herein is manufactured with a combination of materials listed herein or any other suitable material known in the art.

A listing of tensile strengths for exemplary materials described herein is provides as follows: nylon (70 MPa), nitrocellulose (1.5 MPa), polypropylene (40 MPa), silicon (268 MPa), polystyrene (40 MPa), agarose (1-10 MPa), polyacrylamide (1-10 MPa), polydimethylsiloxane (PDMS) (3.9-10.8 MPa). Solid supports described herein can have a tensile strength from 1 to 300, 1 to 40, 1 to 10, 1 to 5, or 3 to 11 MPa. Solid supports described herein can have a tensile strength of about 1, 1.5, 2, 3, 4, 5, 6, 7, 8, 9, 10, 11, 20, 25, 40, 50, 60, 70, 80, 90, 100, 150, 200, 250, 270, or more MPa. In some instances, a device described herein comprises a solid support for polynucleotide synthesis that is in the form of a flexible material capable of being stored in a continuous loop or reel, such as a tape or flexible sheet.

Young's modulus measures the resistance of a material to elastic (recoverable) deformation under load. A listing of Young's modulus for stiffness of exemplary materials described herein is provides as follows: nylon (3 GPa), nitrocellulose (1.5 GPa), polypropylene (2 GPa), silicon (150 GPa), polystyrene (3 GPa), agarose (1-10 GPa), polyacrylamide (1-10 GPa), polydimethylsiloxane (PDMS) (1-10 GPa). Solid supports described herein can have a Young's moduli from 1 to 500, 1 to 40, 1 to 10, 1 to 5, or 3 to 11 GPa. Solid supports described herein can have a Young's moduli of about 1, 1.5, 2, 3, 4, 5, 6, 7, 8, 9, 10, 11, 20, 25, 40, 50, 60, 70, 80, 90, 100, 150, 200, 250, 400, 500 GPa, or more. As the relationship between flexibility and stiffness are inverse to each other, a flexible material has a low Young's modulus and changes its shape considerably under load.

In some instances, a device disclosed herein comprises a silicon dioxide base and a surface layer of silicon oxide. Alternatively, the device may have a base of silicon oxide. Surface of the device provided here may be textured, resulting in an increase overall surface area for polynucleotide synthesis. Devices described herein may comprise at least 5%, 10%, 25%, 50%, 80%, 90%, 95%, or 99% silicon. A device disclosed herein may be fabricated from a silicon on insulator (SOI) wafer.

Surface Modifications

In various instances, surface modifications are employed for the chemical and/or physical alteration of a surface by an additive or subtractive process to change one or more chemical and/or physical properties of a device surface or a selected site or region of a device surface. For example, surface modifications include, without limitation, (1) changing the wetting properties of a surface, (2) functionalizing a surface, i.e., providing, modifying or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface.

In some instances, the addition of a chemical layer on top of a surface (referred to as adhesion promoter) facilitates structured patterning of loci on a surface of a substrate. Exemplary surfaces for application of adhesion promotion include, without limitation, glass, silicon, silicon dioxide and silicon nitride. In some instances, the adhesion promoter is a chemical with a high surface energy. In some instances, a second chemical layer is deposited on a surface of a substrate. In some instances, the second chemical layer has a low surface energy. In some instances, surface energy of a chemical layer coated on a surface supports localization of droplets on the surface. Depending on the patterning arrangement selected, the proximity of loci and/or area of fluid contact at the loci are alterable.

In some instances, a device surface, or resolved loci, onto which nucleic acids or other moieties are deposited, e.g., for polynucleotide synthesis, are smooth or substantially planar (e.g., two-dimensional) or have irregularities, such as raised or lowered features (e.g., three-dimensional features). In some instances, a device surface is modified with one or more different layers of compounds. Such modification layers of interest include, without limitation, inorganic and organic layers such as metals, metal oxides, polymers, small organic molecules and the like. Non-limiting polymeric layers include peptides, proteins, nucleic acids or mimetics thereof (e.g., peptide nucleic acids and the like), polysaccharides, phospholipids, polyurethanes, polyesters, polycarbonates, polyureas, polyamides, polyethyleneamines, polyarylene sulfides, polysiloxanes, polyimides, polyacetates, and any other suitable compounds described herein or otherwise known in the art. In some instances, polymers are heteropolymeric. In some instances, polymers are homopolymeric. In some instances, polymers comprise functional moieties or are conjugated.

In some instances, resolved loci of a device are functionalized with one or more moieties that increase and/or decrease surface energy. In some instances, a moiety is chemically inert. In some instances, a moiety is configured to support a desired chemical reaction, for example, one or more processes in a polynucleotide synthesis reaction. The surface energy, or hydrophobicity, of a surface is a factor for determining the affinity of a nucleotide to attach onto the surface. In some instances, a method for device functionalization may comprise: (a) providing a device having a surface that comprises silicon dioxide; and (b) silanizing the surface using, a suitable silanizing agent described herein or otherwise known in the art, for example, an organofunctional alkoxysilane molecule.

In some instances, the organofunctional alkoxysilane molecule comprises dimethylchloro-octodecyl-silane, methyldichloro-octodecyl-silane, trichloro-octodecyl-silane, trimethyl-octodecyl-silane, triethyl-octodecyl-silane, or any combination thereof. In some instances, a device surface comprises functionalized with polyethylene/polypropylene (functionalized by gamma irradiation or chromic acid oxidation, and reduction to hydroxyalkyl surface), highly cross-linked polystyrene-divinylbenzene (derivatized by chloromethylation, and aminated to benzylamine functional surface), nylon (the terminal aminohexyl groups are directly reactive), or etched with reduced polytetrafluoroethylene. Other methods and functionalizing agents are described in U.S. Pat. No. 5,474,796, which is herein incorporated by reference in its entirety.

In some instances, a device surface is functionalized by contact with a derivatizing composition that contains a mixture of silanes, under reaction conditions effective to couple the silanes to the device surface, typically via reactive hydrophilic moieties present on the device surface. Silanization generally covers a surface through self-assembly with organofunctional alkoxysilane molecules.

A variety of siloxane functionalizing reagents can further be used as currently known in the art, e.g., for lowering or increasing surface energy. The organofunctional alkoxysilanes can be classified according to their organic functions.

Provided herein are devices that may contain patterning of agents capable of coupling to a nucleoside. In some instances, a device may be coated with an active agent. In some instances, a device may be coated with a passive agent. Exemplary active agents for inclusion in coating materials described herein includes, without limitation, N-(3-triethoxysilylpropyl)-4-hydroxybutyramide (HAPS), 11-acetoxyundecyltriethoxysilane, n-decyltriethoxysilane, (3-aminopropyl)trimethoxysilane, (3-aminopropyl)triethoxysilane, 3-glycidoxypropyltrimethoxysilane (GOPS), 3-iodo-propyltrimethoxysilane, butyl-aldehyde-trimethoxysilane, dimeric secondary aminoalkyl siloxanes, (3-aminopropyl)-diethoxy-methylsilane, (3-aminopropyl)-dimethyl-ethoxysilane, and (3-aminopropyl)-trimethoxysilane, (3-glycidoxypropyl)-di-methyl-ethoxysilane, glycidoxy-trimethoxysilane, (3-mercaptopropyl)-trimethoxysilane, 3-4 epoxycyclohexyl-ethyl-trimethoxysilane, and (3-mercaptopropyl)-methyl-dimethoxysilane, allyl trichlorochlorosilane, 7-oct-1-enyl trichlorochlorosilane, or bis (3-trimethoxysilylpropyl) amine.

Exemplary passive agents for inclusion in a coating material described herein includes, without limitation, perfluorooctyltrichlorosilane; tridecafluoro-1,1,2,2-tetrahydrooctyl)trichlorosilane; 1H, 1H, 2H, 2H-fluorooctyltriethoxysilane (FOS); trichloro(1H, 1H, 2H, 2H-perfluorooctyl)silane; tert-butyl-[5-fluoro-4-(4,4,5,5-tetramethyl-1,3,2-dioxaborolan-2-yl)indol-1-yl]-dimethyl-silane; CYTOP™; Fluorinert™; perfluoroctyltrichlorosilane (PFOTCS); perfluorooctyldimethylchlorosilane (PFODCS); perfluorodecyltriethoxysilane (PFDTES); pentafluorophenyl-dimethylpropylchloro-silane (PFPTES); perfluorooctyltriethoxysilane; perfluorooctyltrimethoxysilane; octylchlorosilane; dimethylchloro-octodecyl-silane; methyldichloro-octodecyl-silane; trichloro-octodecyl-silane; trimethyl-octodecyl-silane; triethyl-octodecyl-silane; or octadecyltrichlorosilane.

In some instances, a functionalization agent comprises a hydrocarbon silane such as octadecyltrichlorosilane. In some instances, the functionalizing agent comprises 11-acetoxyundecyltriethoxysilane, n-decyltriethoxysilane, (3-aminopropyl)trimethoxysilane, (3-aminopropyl)triethoxysilane, glycidyloxypropyl/trimethoxysilane and N-(3-triethoxysilylpropyl)-4-hydroxybutyramide.

Provided herein are devices for polynucleotide synthesis comprising a structure fabricated from any one or more of a variety of materials. In certain instances, the materials from which the substrates/solid supports comprise are fabricated to exhibit a low level of polynucleotide binding. In some situations, materials that are transparent to visible and/or UV light can be employed. Materials that are sufficiently conductive (conductors), e.g., those that can form uniform electric fields across all or a portion of the substrates/solids support described herein, can be utilized. In some instances, such materials may be connected to an electric ground. In some instances, the substrate or solid support can be heat conductive or insulated. The materials can be chemical resistant and heat resistant to support chemical or biochemical reactions such as a series of polynucleotide synthesis reactions.

In some instances, conductive or semiconductive materials (semiconductors) include but are not limited to one or more of titanium silicon nitride, titanium nitride, tungsten nitride, tantulum nitride, tantulum silicon nitride, titanium, platinum silicide, or other conductive materials. In instances materials include but are not limited to one or more of aluminum carbides, carbides, nitrides, oxides, silicides, siliconitrides, phosphides, or other non-metal or metalloids used as components of conductive materials. In some instances, exemplary materials comprise (non-limiting) one or more of the elements of tungsten, cobalt, iridium, molybdenum, nickel, platinum, rhenium, ruthenium, tantulum, titanium, or other, metals used as components of conductive materials. In some instances, materials comprise mixtures of metals, non-metals, or metalloids. In some instances, dopants are added to the semiconductive material. Dopants include but are not limited to phosphorus, antimony, arsenic, boron, aluminum, indium, or other element consistent with the specification. Conductors, semiconductors, or insulators may be manufactured with a combination of materials listed herein or any other suitable material known in the art.

For rigid materials, specific materials of interest include: glass; fused silica; silicon, plastics (for example polytetrafluoroethylene, polypropylene, polystyrene, polycarbonate, and blends thereof, and the like); metals (for example, gold, platinum, and the like). The structure can be fabricated from a material selected from the group consisting of silicon, polystyrene, agarose, dextran, cellulosic polymers, polyacrylamides, polydimethylsiloxane (PDMS), and glass. The substrates/solid supports, microstructures, reactors, or other polynucleotide synthesis structure therein may be manufactured with a combination of materials listed herein or any other suitable material known in the art.

Exemplary flexible materials for structures described herein include, without limitation, nylon (unmodified nylon, modified nylon, clear nylon), nitrocellulose, polypropylene, polycarbonate, polyethylene, polyurethane, polystyrene, acetal, acrylic, acrylonitrile, butadiene styrene (ABS), polyester films such as polyethylene terephthalate, polymethyl methacrylate or other acrylics, polyvinyl chloride or other vinyl resin, transparent PVC foil, transparent foil for printers, Poly(methyl methacrylate) (PMMA), methacrylate copolymers, styrenic polymers, high refractive index polymers, fluorine-containing polymers, polyethersulfone, polyimides containing an alicyclic structure, rubber, fabric, metal foils, and any combination thereof. Various plasticizers and modifiers may be used with polymeric substrate materials to achieve selected flexibility characteristics.

Flexible structures described herein may comprise a plastic material. In some instances, the structure comprises a thermoplastic material. Non-limiting examples of thermoplastic materials include acrylic, acrylonitrile butadiene styrene, nylon, polylactic acid, polybenzimidazole, polycarbonate, polyether sulfone, polyetherether ketone, polyetherimide, polyethylene, polyphenylene oxide, polyphenylene sulfide, polypropylene, polystyrene, polyvinyl chloride, and polytetrafluoroethylene. In some instances, the substrate comprises a thermoplastic material in the polyaryletherketone (PEAK) family. Non-limiting examples of PEAK thermoplastics include polyetherketone (PEK), polyetherketoneketone (PEKK), poly(ether ketone ketone) (PEEKK), polyether ether ketone (PEEK), and polyetherketoneetherketoneketone (PEKEKK). In some instances, the structure comprises a thermoplastic material compatible with toluene. In some instances, the flexibility of the plastic material is increased by the addition of a plasticizer. An example of a plasticizer is an ester-based plasticizer, such as phthalate. Phthalate plasticizers include bis(2-ethylhexyl) phthalate (DEHP), diisononly phthalate (DINP), di-n-butyl phthalate (DnBP, DBP), butyl benzyl phthalate (BBzP), diisodecyl phthalate (DIDP), dioctyl phthalate (DOP, DnOP), diisooctyl phthalate (DIOP), diethyl phthalate (DEP), diisobutyl phthalate (DIBP), and di-n-hexyl phthalate. In some instances, modification of the thermoplastic polymer through copolymerization or through the addition of non-reactive side chains to monomers before polymerization also increases flexibility.

Provided herein are flexible structures which may further comprise a fluoroelastomer. Materials having about 80% fluoroelastomers are designated as FKMs. Fluoroelastomers include perfluoro-elastomers (FFKMs) and tetrafluoroethylene/propylene rubbers (FEPM).

Fluoroelastomers have five known types. Type 1 FKMs are composed of vinylidene fluoride (VDF) and hexafluoropropylene (HFP) and their fluorine content typically is around 66% by weight. Type 2 FKMs are composed of VDF, HFP, and tetrafluoroethylene (TFE) and typically have between about 68% and 69% fluorine. Type 3 FKMs are composed of VDF, TFE, and perfluoromethylvinylether (PMVE) and typically have between about 62% and 68% fluorine. Type 4 FKMs are composed of propylene, TFE, and VDF and typically have about 67% fluorine. Type 5 FKMs are composed of VDF, HFP, TFE, PMVE, and ethylene.

In some instances, a substrate disclosed herein comprises a computer readable material. Computer readable materials include, without limitation, magnetic media, reel-to-reel tape, cartridge tape, cassette tape, flexible disk, paper media, film, microfiche, continuous tape (e.g., a belt) and any media suitable for storing electronic instructions. In some instances, the substrate comprises magnetic reel-to-reel tape or a magnetic belt. In some instances, the substrate comprises a flexible printed circuit board.

Structures described herein may be transparent to visible and/or UV light. In some instances, structures described herein are sufficiently conductive to form uniform electric fields across all or a portion of a structure. In some instances, structures described herein are heat conductive or insulated. In some instances, the structures are chemical resistant and heat resistant to support a chemical reaction such as a polynucleotide synthesis reaction. In some instances, the substrate is magnetic. In some instances, the structures comprise a metal or a metal alloy.

Structures for polynucleotide synthesis may be over 1, 2, 5, 10, 30, 50 or more feet long in any dimension. In the case of a flexible structure, the flexible structure is optionally stored in a wound state, e.g., in a reel. In the case of a large structure, e.g., greater than 1 foot in length, the structure can be stored vertically or horizontally.

Material Deposition Systems

Provided herein are systems and devices for the deposition and storage of biomolecules on a structure described herein. In some instances, the biomolecules are polynucleotides that store encoded information in their sequences. In some instances, the system comprises a surface of a structure to support biomolecule attachment and/or a device for application of a biomolecule to the surface of the substrate. In an example, the device for biomolecule application is a polynucleotide synthesizer. In some instances, the system comprises a device for treating the substrate with a fluid, for example, a flow cell. In some instances, the system comprises a device for moving the substrate between the application device and the treatment device. For instances where the substrate is a reel-to-reel tape, the system may comprise two or more reels that allow for access of different portions of the substrate to the application and optional treatment device at different times.

Figure 3:
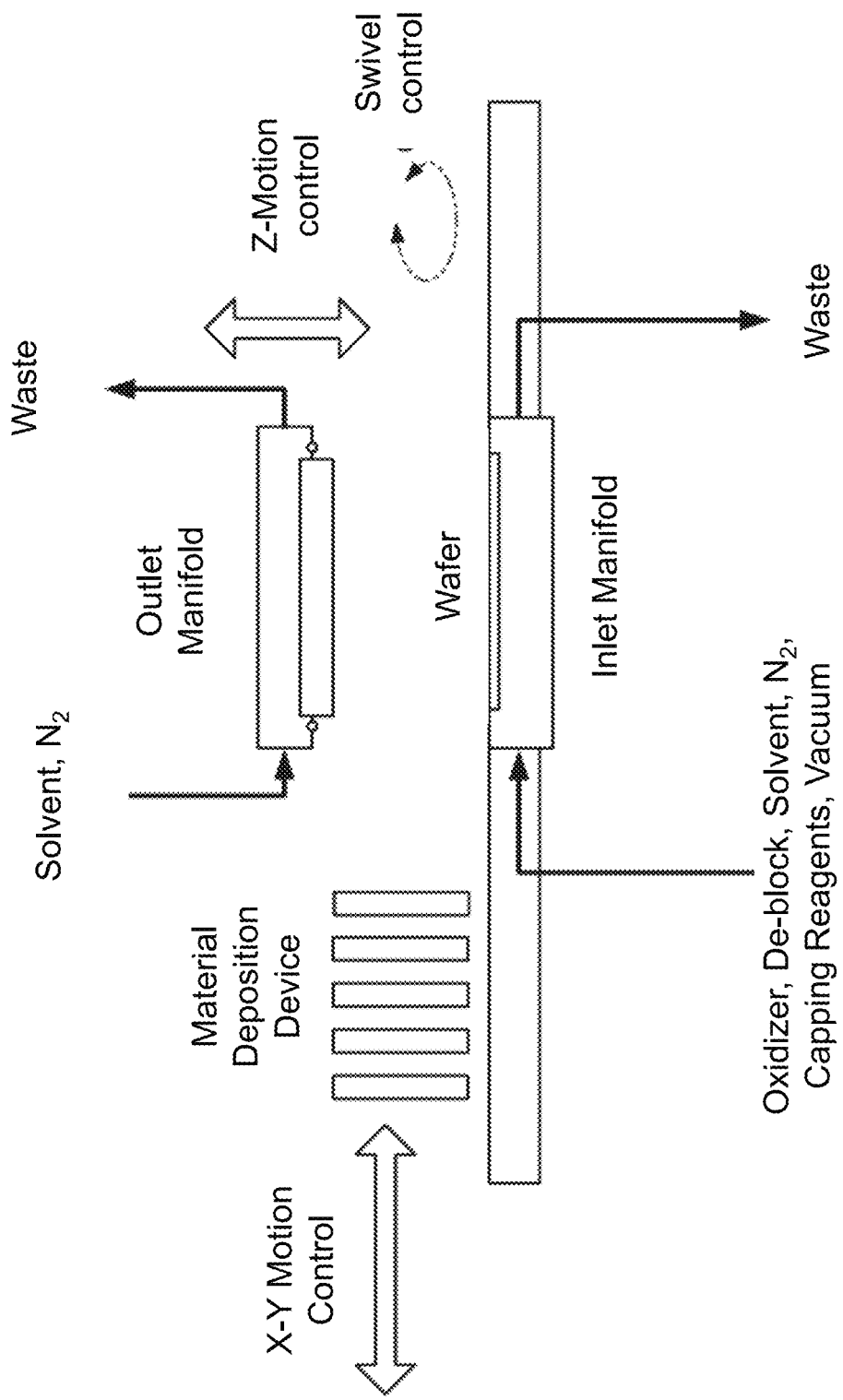
FIG. 3 depicts a polynucleotide synthesis material deposition device.

A first example of a polynucleotide material deposition system for polynucleotide synthesis is shown in FIG. 3. The system includes a material deposition device that moves in the X-Y direction to align with the location of the substrate. The material deposition device can also move in the Z direction to seal with the substrate, forming a resolved reactor. A resolved reactor is configured to allow for the transfer of fluid, including polynucleotides and/or reagents, from the substrate to a capping element and/or vice versa. As shown in FIG. 3, fluid may pass through either or both the substrate and the capping element and includes, without limitation, coupling reagents, capping reagents, oxidizers, de-blocking agents, acetonitrile and nitrogen gas. Examples of devices that are capable of high resolution droplet deposition include the printhead of inkjet printers and laser printers. The devices useful in the systems and methods described herein achieve a resolution from about 100 dots per inch (DPI) to about 50,000 DPI; from about 100 DPI to about 20,000 DPI; from about 100 DPI to about 10,000 DPI; from about 100 DPI to about 5,000 DPI; from about 1,000 DPI to about 20,000 DPI; or from about 1,000 DPI to about 10,000 DPI. In some instances, the devices have a resolution at least about 1,000; 2,000; 3,000; 4,000; 5,000; 10,000; 12,000 DPI, or 20,000 DPI. The high resolution deposition performed by the device is related to the number and density of each nozzle that corresponds to a feature of the substrate.

Figure 4:
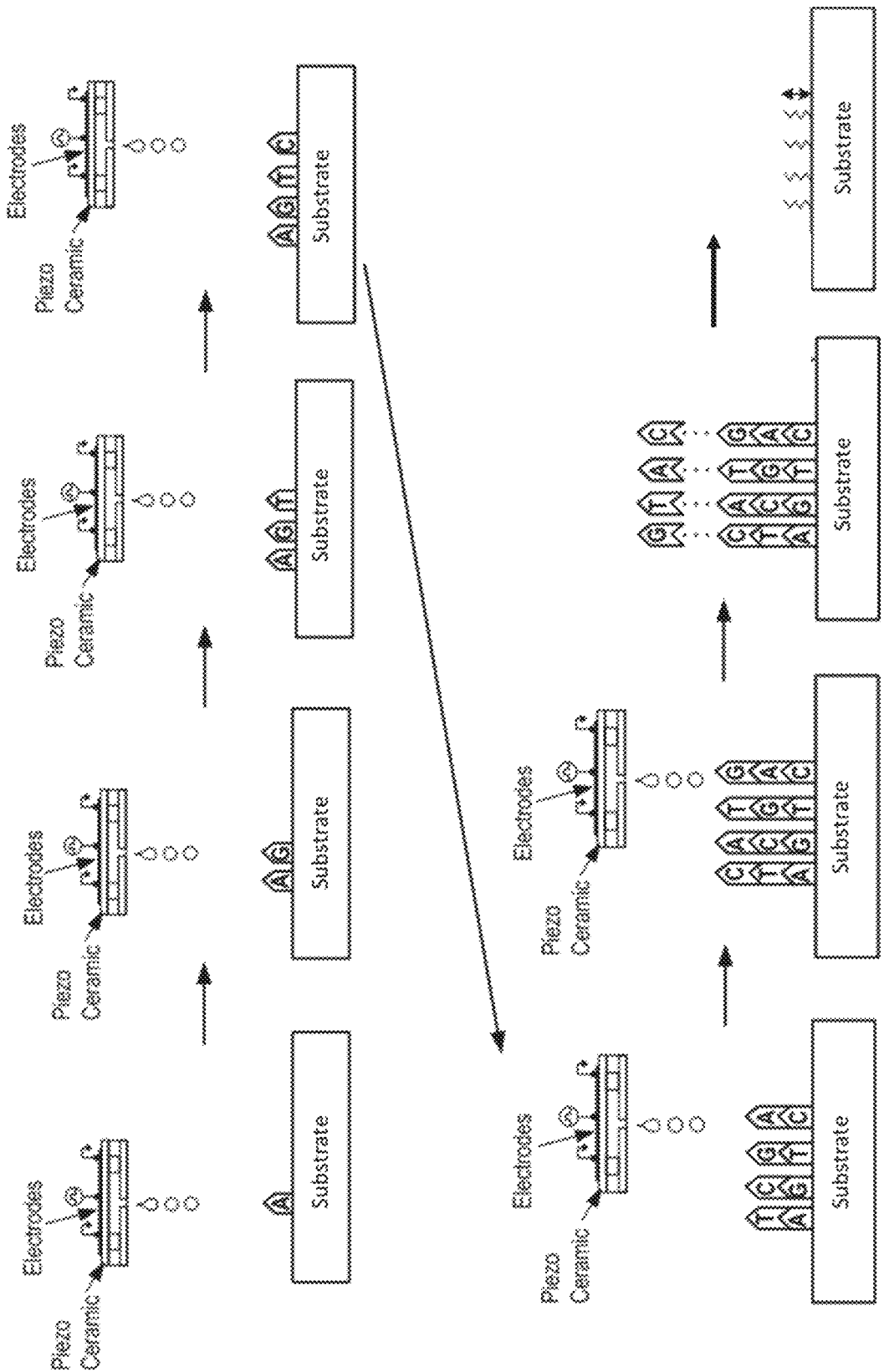
FIG. 4 depicts a polynucleotide synthesis workflow.

An exemplary process workflow for de novo synthesis of a polynucleotide on a substrate using a polynucleotide synthesizer is shown in FIG. 4. Droplets comprising polynucleotide synthesis reagents are released from the material deposition device to the substrate in a stepwise manner, wherein the material deposition device has a piezo ceramic material and electrodes to convert electrical signals into a mechanical signal for releasing the droplets. The droplets are released to specific locations on the surface of the substrate one nucleobase at a time to generate a plurality of synthesized polynucleotides having predetermined sequences that encode data. In some instances, the synthesized polynucleotides are stored on the substrate. Polynucleotide reagents may be deposited on the substrate surface in a non-continuous, or drop-on-demand method. Examples of such methods include the electromechanical transfer method, electric thermal transfer method, and electrostatic attraction method. In the electromechanical transfer method, piezoelectric elements deformed by electrical pulses cause the droplets to be ejected. In the electric thermal transfer method, bubbles are generated in a chamber of the device, and the expansive force of the bubbles causes the droplets to be ejected. In the electrostatic attraction method, electrostatic force of attraction is used to eject the droplets onto the substrate. In some instances, the drop frequency is from about 5 KHz to about 500 KHz; from about 5 KHz to about 100 KHz; from about 10 KHz to about 500 KHz; from about 10 KHz to about 100 KHz; or from about 50 KHz to about 500 KHz. In some instances, the frequency is less than about 500 KHz, 200 KHz, 100 KHz, or 50 KHz.

The size of the droplets dispensed correlates to the resolution of the device. In some instances, the devices deposit droplets of reagents at sizes from about 0.01 pl to about 20 pl, from about 0.01 pl to about 10 pl, from about 0.01 pl to about 1 pl, from about 0.01 pl to about 0.5 pl, from about 0.01 pl to about 0.01 pl, or from about 0.05 pl to about 1 pl. In some instances, the droplet size is less than about 1 pl, 0.5 pl, 0.2 pl, 0.1 pl, or 0.05 pl. The size of droplets dispensed by the device is correlated to the diameters of deposition nozzles, wherein each nozzle is capable of depositing a reagent onto a feature of the substrate. In some instances, a deposition device of a polynucleotide synthesizer comprises from about 100 to about 10,000 nozzles; from about 100 to about 5,000 nozzles; from about 100 to about 3,000 nozzles; from about 500 to about 10,000 nozzles; or from about 100 to about 5,000 nozzles. In some instances, the deposition device comprises greater than 1,000; 2,000; 3,000; 4,000; 5,000; or 10,000 nozzles. In some instances, each material deposition device comprises a plurality of nozzles, where each nozzle is optionally configured to correspond to a feature on a substrate. Each nozzle may deposit a reagent component that is different from another nozzle. In some instances, each nozzle deposits a droplet that covers one or more features of the substrate. In some instances, one or more nozzles are angled. In some instances, multiple deposition devices are stacked side by side to achieve a fold increase in throughput. In some instances, the gain is 2×, 4×, 8× or more. An example of a deposition device is Samba Printhead (Fujifilm). A Samba Printhead may be used with the Samba Web Administration Tool (SWAT).

The number of deposition sites may be increased by using and rotating the same deposition device by a certain degree or saber angle. By rotating the deposition device, each nozzle is jetted with a certain amount of delay time corresponding to the saber angle. This unsynchronized jetting creates a cross talk among the nozzles. Therefore, when the droplets are jetting at a certain saber angle different from 0 degrees, the droplet volume from the nozzle could be different.

In some arrangements, the configuration of a polynucleotide synthesis system allows for a continuous polynucleotide synthesis process that exploits the flexibility of a substrate for traveling in a reel-to-reel type process. This synthesis process operates in a continuous production line manner with the substrate travelling through various stages of polynucleotide synthesis using one or more reels to rotate the position of the substrate. In an exemplary embodiment, a polynucleotide synthesis reaction comprises rolling a substrate: through a solvent bath, beneath a deposition device for phosphoramidite deposition, through a bath of oxidizing agent, through an acetonitrile wash bath, and through a deblock bath. Alternatively, other wash baths comprising alternative wash solvents are employed, such as acetone, toluene, THF, or other wash solvent. Optionally, the tape is also traversed through a capping bath. A reel-to-reel type process allows for the finished product of a substrate comprising synthesized polynucleotides to be easily gathered on a take-up reel, where it can be transported for further processing or storage.

In some arrangements, polynucleotide synthesis proceeds in a continuous process as a continuous flexible tape is conveyed along a conveyor belt system. Similar to the reel-to-reel type process, polynucleotide synthesis on a continuous tape operates in a production line manner, with the substrate travelling through various stages of polynucleotide synthesis during conveyance. However, in a conveyor belt process, the continuous tape revisits a polynucleotide synthesis step without rolling and unrolling of the tape, as in a reel-to-reel process. In some arrangements, polynucleotide synthesis steps are partitioned into zones and a continuous tape is conveyed through each zone one or more times in a cycle. For example, a polynucleotide synthesis reaction may comprise (1) conveying a substrate through a solvent bath, beneath a deposition device for phosphoramidite deposition, through a bath of oxidizing agent, through an acetonitrile wash bath, and through a block bath in a cycle; and then (2) repeating the cycles to achieve synthesized polynucleotides of a predetermined length. Alternatively, other wash baths comprising alternative wash solvents are employed, such as acetone, THF, or other wash solvent. After polynucleotide synthesis, the flexible substrate is removed from the conveyor belt system and, optionally, rolled for storage. Rolling may be around a reel, for storage.

In an exemplary arrangement, a flexible substrate comprising thermoplastic material is coated with nucleoside coupling reagent. The coating is patterned into features such that each feature has diameter of about 10 µm, with a center-to-center distance between two adjacent features of about 21 µm. In this instance, the feature size is sufficient to accommodate a sessile drop volume of 0.2 pl during a polynucleotide synthesis deposition step. In some instances, the feature density is about 2.2 billion features per $m^2$ (1 feature/$441 \times 10^{-12}$ $m^2$). In some instances, a 4.5 $m^2$ substrate comprise about 10 billion features, each with a 10 µm diameter.

In another exemplary arrangement, a substrate comprising nanostructures is coated with nucleoside coupling reagent. The coating is patterned into features such that each feature has diameter of about 10 nm to about 200 nm, with a center-to-center distance between two adjacent features of about 10 nm to about 200 nm. In this instance, a plurality of features accommodates a sessile drop volume of 0.2 pl during a polynucleotide synthesis deposition step. In some instances, a feature diameter of about 50 nm and a center-to-center distance between two adjacent features of about 100 nm results in a feature density of about 10 billion features per $m^2$ (1 feature/$100 \times 10^{-12}$ $m^2$).

A material deposition device described herein may comprises about 2,048 nozzles that each deposit about 100,000 droplets per second at 1 nucleobase per droplet. For each deposition device, at least about $1.75 \times 10^{13}$ nucleobases are deposited on the substrate per day. In some instances, 100 to 500 nucleobase polynucleotides are synthesized. In some instances, 200 nucleobase polynucleotides are synthesized. Optionally, over 3 days, at a rate of about $1.75 \times 10^{13}$ bases per day, at least about $262.5 \times 10^9$ polynucleotides are synthesized.

In some arrangements, a device for application of one or more reagents to a substrate during a synthesis reaction is configured to deposit reagents and/or nucleotide monomers for nucleoside phosphoramidite based synthesis. Reagents for polynucleotide synthesis include reagents for polynucleotide extension and wash buffers. As non-limiting examples, the device deposits cleaning reagents, coupling reagents, capping reagents, oxidizers, de-blocking agents, acetonitrile, wash solvents, gases such as nitrogen gas, and any combination thereof. In addition, the device optionally deposits reagents for the preparation and/or maintenance of substrate integrity. In some instances, the polynucleotide synthesizer deposits a drop having a diameter less than about 200 µm, 100 µm, or 50 µm in a volume less than about 1000, 500, 100, 50, or 20 pl. In some instances, the polynucleotide synthesizer deposits between about 1 and 10,000, 1 and 5,000, 100 and 5,000, or 1,000 and 5,000 droplets per second.

In some arrangement, during polynucleotide synthesis, the substrate is positioned within and/or sealed within a flow cell. The flow cell may provide continuous or discontinuous flow of liquids such as those comprising reagents necessary for reactions within the substrate, for example, oxidizers and/or solvents. The flow cell may provide continuous or discontinuous flow of a gas, such as nitrogen, for drying the substrate typically through enhanced evaporation of a volatile substrate. A variety of auxiliary devices are useful to improve drying and reduce residual moisture on the surface of the substrate. Examples of such auxiliary drying devices include, without limitation, a vacuum source, depressurizing pump and a vacuum tank. In some instances, a polynucleotide synthesis system comprises one or more flow cells, such as 2, 3, 4, 5, 6, 7, 8, 9, 10, or 20 and one or more substrates, such as 2, 3, 4, 5, 6, 7, 8, 9, 10 or 20. In some instances, a flow cell is configured to hold and provide reagents to the substrate during one or more steps in a synthesis reaction. In some instances, a flowcell comprises a lid that slides over the top of a substrate and can be clamped into place to form a pressure tight seal around the edge of the substrate. An adequate seal includes, without limitation, a seal that allows for about 1, 2, 3, 4, 5, 6, 7, 8, 9 or 10 atmospheres of pressure. In some instances, the lid of the flow cell is opened to allow for access to an application device such as a polynucleotide synthesizer. In some instances, one or more steps of a polynucleotide synthesis method are performed on a substrate within a flow cell, without the transport of the substrate. The flowcell is optionally used/operated in any orientation, including vertically or horizontally. In some instances, the use of one or more washes in a horizontally orientated flowcell leads to reduced error rates of polynucleotide products.

In some arrangements, a device for treating a substrate with a fluid comprises a spray bar. Nucleotide monomers may be applied onto a substrate surface, and then a spray bar sprays the substrate surface with one or more treatment reagents using spray nozzles of the spray bar. In some arrangements, the spray nozzles are sequentially ordered to correlate with different treatment steps during polynucleotide synthesis. The chemicals used in different process steps may be changed in the spray bar to readily accommodate changes in a synthesis method or between steps of a synthesis method. In some instances, the spray bar continuously sprays a given chemistry on a surface of a substrate as the substrate moves past the spray bar. In some instances, the spray bar deposits over a wide area of a substrate, much like the spray bars used in lawn sprinklers. In some instances, the spray bar nozzles are positioned to provide a uniform coat of treatment material to a given area of a substrate.

In some instances, a polynucleotide synthesis system comprises one or more elements useful for downstream processing of synthesized polynucleotides. As an example, the system comprises a temperature control element such as a thermal cycling device. In some instances, the temperature control element is used with a plurality of resolved reactors to perform polynucleotide assembly such as PCA and/or polynucleotide amplification such as PCR.

In some instances, polynucleotides are synthesized with photolabile protecting groups, where the hydroxyl groups generated on the surface are blocked by photolabile-protecting groups. When the surface is exposed to UV light, such as through a photolithographic mask, a pattern of free hydroxyl groups on the surface may be generated. These hydroxyl groups can react with photoprotected nucleoside phosphoramidites, according to phosphoramidite chemistry. A second photolithographic mask can be applied and the surface can be exposed to UV light to generate second pattern of hydroxyl groups, followed by coupling with 5'-photoprotected nucleoside phosphoramidite. Likewise, patterns can be generated and oligomer chains can be extended. Without being bound by theory, the lability of a photocleavable group depends on the wavelength and polarity of a solvent employed and the rate of photocleavage may be affected by the duration of exposure and the intensity of light. This method can leverage a number of factors such as accuracy in alignment of the masks, efficiency of removal of photo-protecting groups, and the yields of the phosphoramidite coupling step. Further, unintended leakage of light into neighboring sites can be minimized. The density of synthesized oligomer per spot can be monitored by adjusting loading of the leader nucleoside on the surface of synthesis.

The surface of the substrate that provides support for polynucleotide synthesis may be chemically modified to allow for the synthesized polynucleotide chain to be cleaved from the surface. In some instances, the polynucleotide chain is cleaved at the same time as the polynucleotide is deprotected. In some instances, the polynucleotide chain is cleaved after the polynucleotide is deprotected. In an exemplary scheme, a trialkoxysilyl amine such as $(CH_3CH_2O)_3Si—(CH_2)_2—NH_2$ is reacted with surface SiOH groups of a substrate, followed by reaction with succinic anhydride with the amine to create an amide linkage and a free OH on which the polynucleotide chain growth is supported. Cleavage includes gas cleavage with a base, such as ammonia or methylamine. In some instances, once released from the surface, polynucleotides are assembled into larger polynucleotides that are sequenced and decoded to extract stored information.

Provided herein are systems and methods for synthesis of a high density of polynucleotides on a substrate in a short amount of time. In some instances, the substrate is a flexible substrate. In some instances, at least about $10^{10}$, $10^{11}$, $10^{12}$, $10^{13}$, $10^{14}$, or $10^{15}$ bases are synthesized in one day. In some instances, at least about $10\times10^8$, $10\times10^9$, $10\times10^{10}$, $10\times10^{11}$, or $10\times10^{12}$ polynucleotides are synthesized in one day. In some instances, each polynucleotide synthesized comprises at least about 20, 50, 100, 200, 300, 400 or 500 nucleobases. In some instances, these bases are synthesized with a total average error rate of less than about 1 in 100; 200; 300; 400; 500; 1000; 2000; 5000; 10000; 15000; 20000 bases. In some instances, these error rates are for at least 50%, 60%, 70%, 80%, 90%, 95%, 98%, 99%, 99.5%, or more of the polynucleotides synthesized. In some instances, these at least 90%, 95%, 98%, 99%, 99.5%, or more of the polynucleotides synthesized do not differ from a predetermined sequence for which they encode. In some instances, the error rate for synthesized polynucleotides on a substrate using the methods and systems described herein is less than about 1 in 200. In some instances, the error rate for synthesized polynucleotides on a substrate using the methods and systems described herein is less than about 1 in 1,000. In some instances, the error rate for synthesized polynucleotides on a substrate using the methods and systems described herein is less than about 1 in 2,000. In some instances, the error rate for synthesized polynucleotides on a substrate using the methods and systems described herein is less than about 1 in 3,000. In some instances, the error rate for synthesized polynucleotides on a substrate using the methods and systems described herein is less than about 1 in 5,000. Individual types of error rates include mismatches, deletions, insertions, and/or substitutions for the polynucleotides synthesized on the substrate. The term "error rate" refers to a comparison of the collective amount of synthesized polynucleotide to an aggregate of predetermined polynucleotide sequences. In some instances, synthesized polynucleotides disclosed herein comprise a tether of 12 to 25 bases. In some instances, the tether comprises 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more bases.

A suitable method for polynucleotide synthesis on a substrate of this disclosure is a phosphoramidite method comprising the controlled addition of a phosphoramidite building block, i.e. nucleoside phosphoramidite, to a growing polynucleotide chain in a coupling step that forms a phosphite triester linkage between the phosphoramidite building block and a nucleoside bound to the substrate (for example, an elongation step). In some instances, the nucleoside phosphoramidite is provided to the substrate activated. In some instances, the nucleoside phosphoramidite is provided to the substrate with an activator. In some instances, nucleoside phosphoramidites are provided to the substrate in a 1.5, 2, 3, 4, 5, 6, 7, 8, 9, 10, 11, 12, 13, 14, 15, 16, 17, 18, 19, 20, 25, 30, 35, 40, 50, 60, 70, 80, 90, 100-fold excess or more over the substrate-bound nucleosides. In some instances, the addition of nucleoside phosphoramidite is performed in an anhydrous environment, for example, in anhydrous acetonitrile. Following addition and linkage of a nucleoside phosphoramidite in the coupling step, the substrate is optionally washed. In some instances, the coupling step is repeated one or more additional times, optionally with a wash step between nucleoside phosphoramidite additions to the substrate.

Polynucleotide Assembly

Polynucleotides may be designed to collectively span a large region of a predetermined sequence that encodes for information. In some instances, larger polynucleotides are generated through ligation reactions to join the synthesized polynucleotides. One example of a ligation reaction is polymerase chain assembly (PCA). In some instances, at least of a portion of the polynucleotides are designed to include an appended region that is a substrate for universal primer binding. For PCA reactions, the presynthesized polynucleotides include overlaps with each other (e.g., 4, 20, 40 or more bases with overlapping sequence). During the polymerase cycles, the polynucleotides anneal to complementary fragments and then are filled in by polymerase. Each cycle thus increases the length of various fragments randomly depending on which polynucleotides find each other. Complementarity amongst the fragments allows for forming a complete large span of double-stranded DNA. In some instances, after the PCA reaction is complete, an error correction step is conducted using mismatch repair detecting enzymes to remove mismatches in the sequence. Once larger fragments of a target sequence are generated, they can be amplified. For example, in some instances, a target sequence comprising 5' and 3' terminal adapter sequences is amplified in a polymerase chain reaction (PCR) which includes modified primers that hybridize to the adapter sequences. In some instances, the modified primers comprise one or more uracil bases. The use of modified primers allows for removal of the primers through enzymatic reactions centered on targeting the modified base and/or gaps left by enzymes which cleave the modified base pair from the fragment. What remains is a double-stranded amplification product that lacks remnants of adapter sequence. In this way, multiple amplification products can be generated in parallel with the same set of primers to generate different fragments of double-stranded DNA.

Error correction may be performed on synthesized polynucleotides and/or assembled products. An example strategy for error correction involves site-directed mutagenesis by overlap extension PCR to correct errors, which is optionally coupled with two or more rounds of cloning and sequencing. In certain instances, double-stranded polynucleotides with mismatches, bulges and small loops, chemically altered bases and/or other heteroduplexes are selectively removed from populations of correctly synthesized polynucleotides. In some instances, error correction is performed using proteins/enzymes that recognize and bind to or next to mismatched or unpaired bases within double-stranded polynucleotides to create a single or double-strand break or to initiate a strand transfer transposition event. Non-limiting examples of proteins/enzymes for error correction include endonucleases (T7 Endonuclease I, *E. coli* Endonuclease V, T4 Endonuclease VII, mung bean nuclease, Cel1, *E. coli* Endonuclease IV, UVDE), restriction enzymes, glycosylases, ribonucleases, mismatch repair enzymes, resolvases, helicases, ligases, antibodies specific for mismatches, and their variants. Examples of specific error correction enzymes include T4 endonuclease 7, T7 endonuclease 1, S1, mung bean endonuclease, MutY, MutS, MutH, MutL, cleavase, CELI, and HINF1. In some instances, DNA mismatch-binding protein MutS (*Thermus aquaticus*) is used to remove failure products from a population of synthesized products. In some instances, error correction is performed using the enzyme Correctase. In some instances, error correction is performed using SURVEYOR endonuclease (Transgenomic), a mismatch-specific DNA endonuclease that scans for known and unknown mutations and polymorphisms for heteroduplex DNA.

Computer Systems

In various aspects, any of the systems described herein are operably linked to a computer and are optionally automated through a computer either locally or remotely. In various instances, the methods and systems of the invention further comprise software programs on computer systems and use thereof. Accordingly, computerized control for the synchronization of the dispense/vacuum/refill functions such as orchestrating and synchronizing the material deposition device movement, dispense action and vacuum actuation are within the bounds of the invention. In some instances, the computer systems are programmed to interface between the user specified base sequence and the position of a material deposition device to deliver the correct reagents to specified regions of the substrate.

Figure 5:
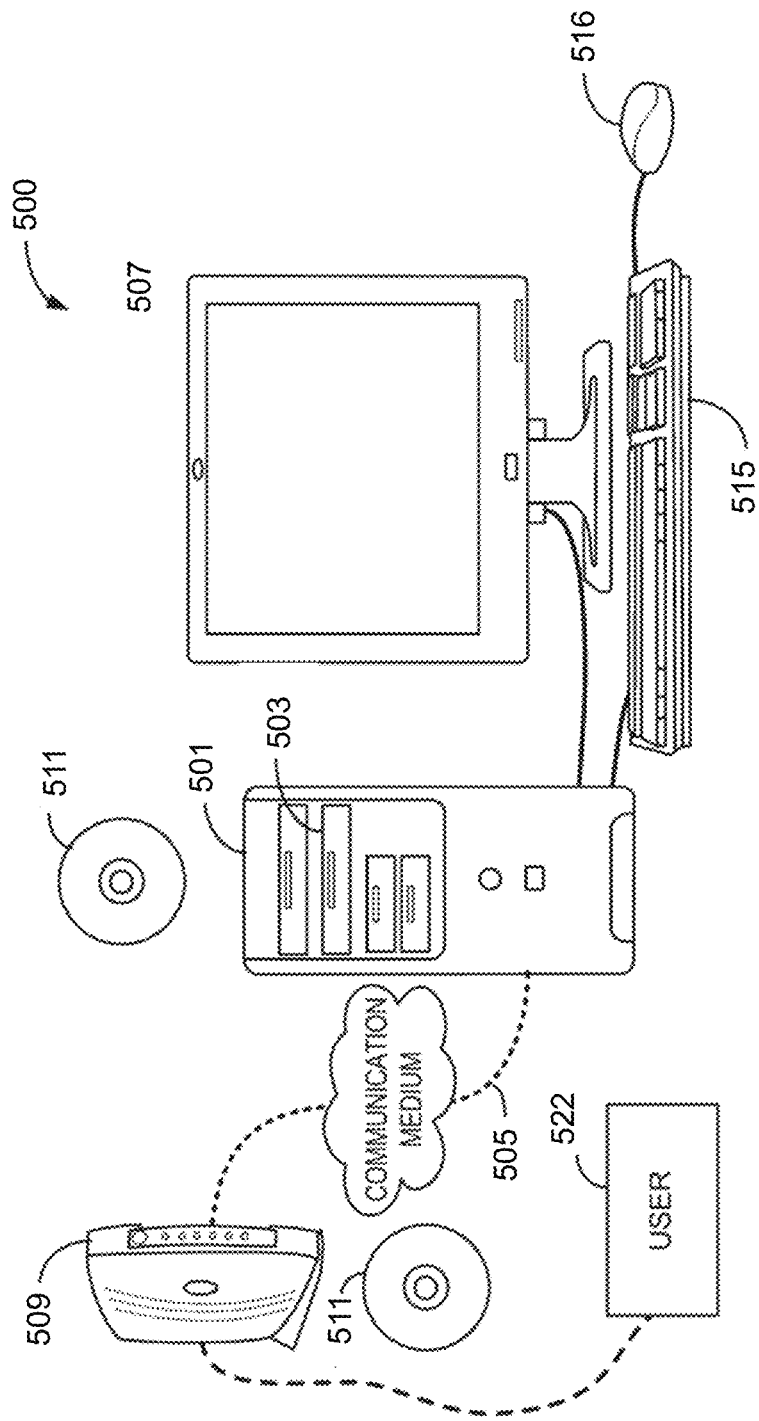
FIG. 5 depicts a computer system.

The computer system 500 illustrated in FIG. 5 may be understood as a logical apparatus that can read instructions from media 511 and/or a network port 505, which can optionally be connected to server 509. The system, such as shown in FIG. 5 can include a CPU 501, disk drives 503, optional input devices such as keyboard 515 and/or mouse 516 and optional monitor 507. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 522.

Figure 6:
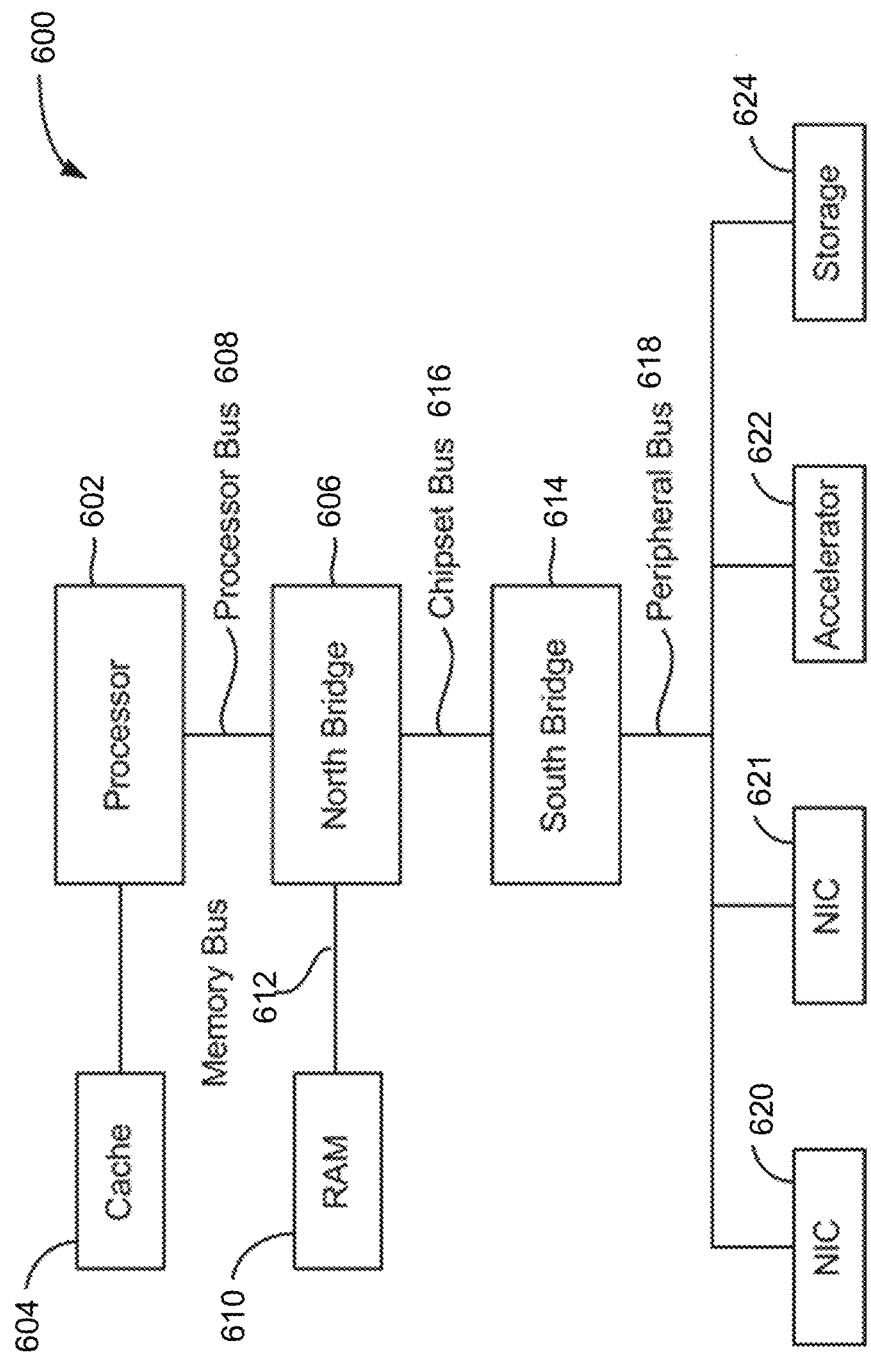
FIG. 6 depicts a block diagram illustrating the architecture of a computer system.

FIG. 6 is a block diagram illustrating a first example architecture of a computer system 1000 that can be used in connection with example instances of the present invention. As depicted in FIG. 6, the example computer system can include a processor 602 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some instances, multiple processors or processors with multiple cores can also be used, whether in a single computer system, in a cluster, or distributed across systems over a network comprising a plurality of computers, cell phones, and/or personal data assistant devices.

As illustrated in FIG. 6, a high speed cache 604 can be connected to, or incorporated in, the processor 602 to provide a high speed memory for instructions or data that have been recently, or are frequently, used by processor 602. The processor 602 is connected to a north bridge 606 by a processor bus 608. The north bridge 606 is connected to random access memory (RAM) 610 by a memory bus 612 and manages access to the RAM 610 by the processor 602. The north bridge 606 is also connected to a south bridge 614 by a chipset bus 616. The south bridge 614 is, in turn, connected to a peripheral bus 618. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 618. In some alternative architectures, the functionality of the north bridge can be incorporated into the processor instead of using a separate north bridge chip.

In some instances, system 600 can include an accelerator card 622 attached to the peripheral bus 618. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 624 and can be loaded into RAM 610 and/or cache 604 for use by the processor. The system 600 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example instances of the present invention.

In this example, system 600 also includes network interface cards (NICs) 620 and 621 connected to the peripheral bus for providing network interfaces to external storage, such as Network Attached Storage (NAS) and other computer systems that can be used for distributed parallel processing.

Figure 7:
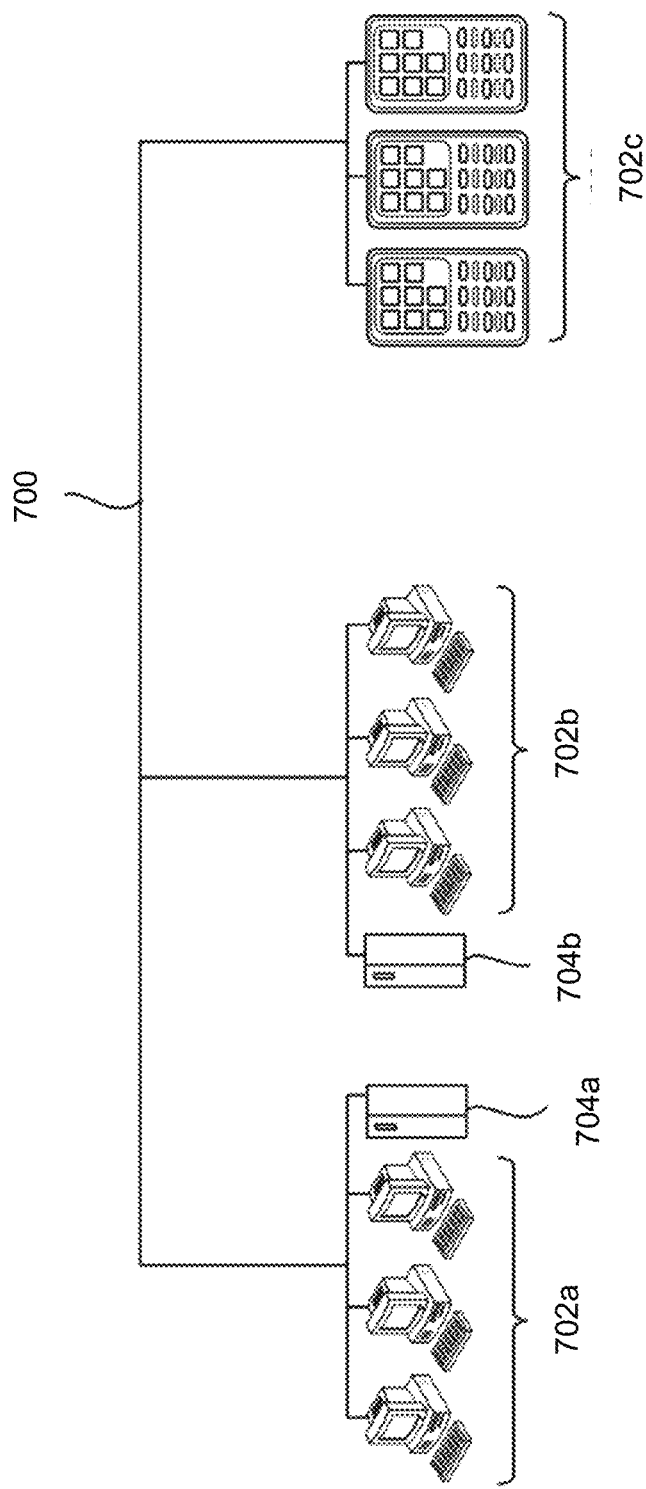
FIG. 7 depicts a network configured to incorporate a plurality of computer systems, a plurality of cell phones and personal data assistants, and Network Attached Storage (NAS).

FIG. 7 is a diagram showing a network 700 with a plurality of computer systems 702*a*, and 702*b*, a plurality of cell phones and personal data assistants 702*c*, and Network Attached Storage (NAS) 704*a*, and 704*b*. In example instances, systems 702*a*, 702*b*, and 702*c* can manage data storage and optimize data access for data stored in Network Attached Storage (NAS) 704*a* and 704*b*. A mathematical model can be used for the data and be evaluated using distributed parallel processing across computer systems 702*a*, and 702*b*, and cell phone and personal data assistant systems 702*c*. Computer systems 702*a*, and 702*b*, and cell phone and personal data assistant systems 702*c* can also provide parallel processing for adaptive data restructuring of the data stored in Network Attached Storage (NAS) 704*a* and 704*b*. FIG. 7 illustrates an example only, and a wide variety of other computer architectures and systems can be used in conjunction with the various instances of the present invention. For example, a blade server can be used to provide parallel processing. Processor blades can be connected through a back plane to provide parallel processing. Storage can also be connected to the back plane or as Network Attached Storage (NAS) through a separate network interface.

In some example instances, processors can maintain separate memory spaces and transmit data through network interfaces, back plane or other connectors for parallel processing by other processors. In other instances, some or all of the processors can use a shared virtual address memory space.

Figure 8:
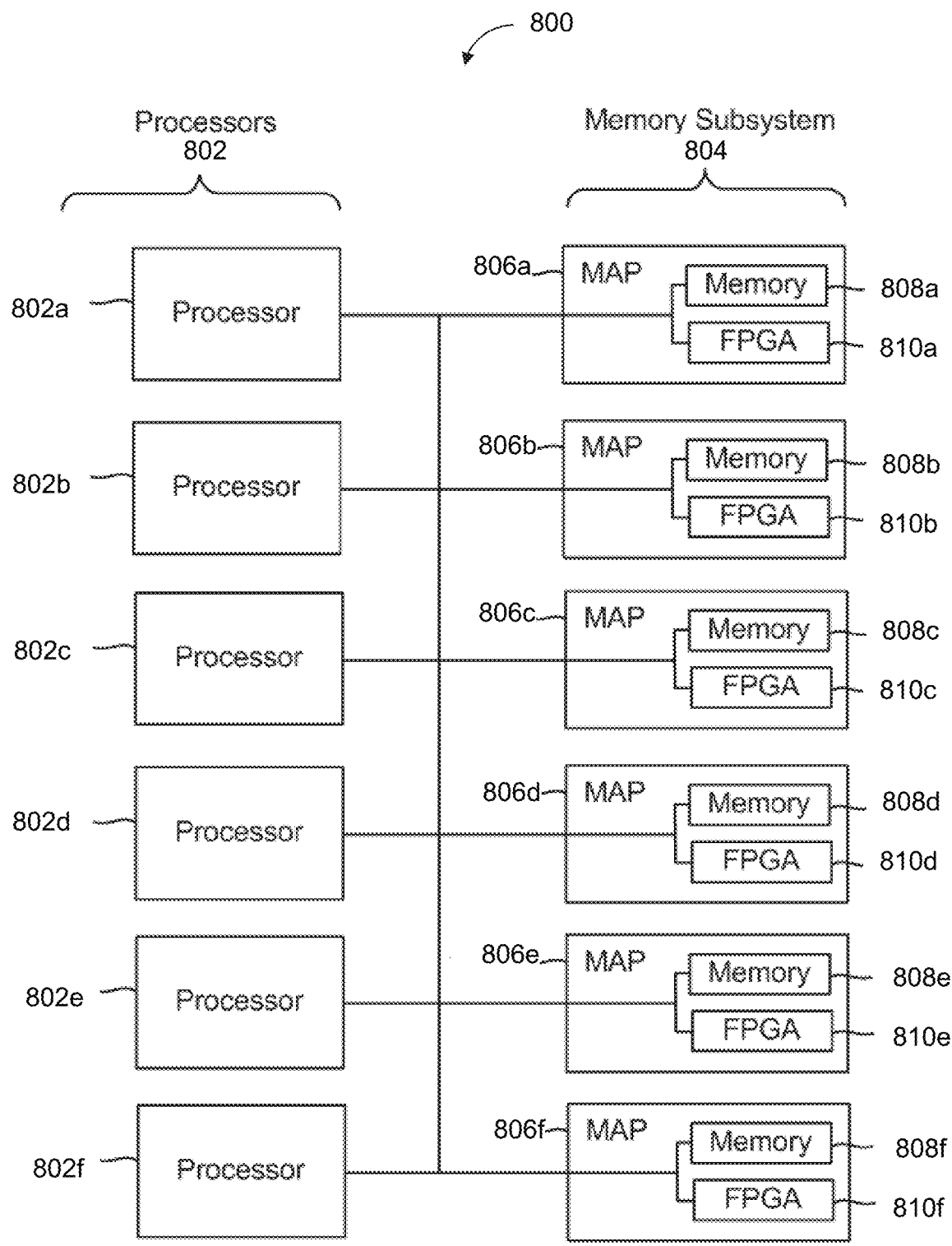
FIG. 8 depicts a multiprocessor computer system using a shared virtual address memory space.

FIG. 8 is a block diagram of a multiprocessor computer system 800 using a shared virtual address memory space in accordance with an example embodiment. The system includes a plurality of processors 802a-f that can access a shared memory subsystem 804. The system incorporates a plurality of programmable hardware memory algorithm processors (MAPs) 806a-f in the memory subsystem 804. Each MAP 806a-f can comprise a memory 808a-f and one or more field programmable gate arrays (FPGAs) 810a-f The MAP provides a configurable functional unit and particular algorithms or portions of algorithms can be provided to the FPGAs 810a-f for processing in close coordination with a respective processor. For example, the MAPs can be used to evaluate algebraic expressions regarding the data model and to perform adaptive data restructuring in example instances. In this example, each MAP is globally accessible by all of the processors for these purposes. In one configuration, each MAP can use Direct Memory Access (DMA) to access an associated memory 808a-f, allowing it to execute tasks independently of, and asynchronously from, the respective microprocessor 802a-f In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example instances, including systems using any combination of general processors, co-processors, FPGAs and other programmable logic devices, system on chips (SOCs), application specific integrated circuits (ASICs), and other processing and logic elements. In some instances, all or part of the computer system can be implemented in software or hardware. Any variety of data storage media can be used in connection with example instances, including random access memory, hard drives, flash memory, tape drives, disk arrays, Network Attached Storage (NAS) and other local or distributed data storage devices and systems.

Embodiments

Provided herein are methods for polynucleotide synthesis, comprising: a) providing a structure comprising a surface; b) coupling at least one nucleoside to a polynucleotide attached to the surface; c) depositing an oxidizing solution on the surface; d) depositing a wash solvent on the surface, wherein the wash solvent comprises a ketone, an ester, an ether, a hydrocarbon, or a functional equivalent thereof; and e) repeating steps b-d to synthesize a plurality of polynucleotides. Further provided herein are methods wherein the method further comprises depositing a capping solution on the surface, wherein capping prevents coupling of unblocked nucleosides. Further provided herein are methods wherein the method further comprises depositing a deblocking solution on the surface, wherein deblocking allows coupling of the polynucleotide to a nucleoside. Further provided herein are methods wherein one or more steps is followed by washing the surface with the wash solvent. Further provided herein are methods wherein one or more steps is followed by washing the surface with acetonitrile. Further provided herein are methods wherein each step subsequent to a coupling step is followed by washing the surface with the wash solvent. Further provided herein are methods wherein each step subsequent to a capping step is followed by washing the surface with the wash solvent. Further provided herein are methods wherein each step subsequent to a deblocking step is followed by washing the surface with the wash solvent. Further provided herein are methods wherein the at least one nucleoside comprises a phosphoramidite. Further provided herein are methods wherein the at least one nucleoside comprises a 5' blocking group. Further provided herein are methods wherein the at least one nucleoside comprises a 3' blocking group. Further provided herein are methods wherein the wash solvent is functionally equivalent to a primary constituent by volume of a previously contacted reagent solution. Further provided herein are methods wherein the wash solvent comprises acetone, tetrahydrofuran, ethyl acetate, toluene, benzene, ethanol, or a combination thereof. Further provided herein are methods wherein the wash solvent comprises a ketone, an ether, or a functional equivalent thereof. Further provided herein are methods wherein the structure is a plate, a tape, a belt, or a bead. Further provided herein are methods wherein the oxidizing solution comprises iodine. Further provided herein are methods wherein the polynucleotide or nucleoside comprises DNA or RNA.

Provided herein are methods for polynucleotide synthesis, comprising: a) providing a structure comprising a surface; b) coupling at least one nucleoside to a polynucleotide attached to the surface, wherein each of the at least one nucleosides comprises a blocking group; c) depositing an oxidizing solution on the surface; d) depositing a wash solvent on the surface, wherein the wash solvent comprises acetone or a functional equivalent thereof, or wherein the wash solvent comprises tetrahydrofuran or a functional equivalent thereof, e) depositing a deblocking solution on the surface to remove the blocking group, wherein removal of the blocking group allows coupling of nucleosides to the polynucleotide; and f) repeating steps b-e to synthesize a plurality of polynucleotides. Further provided herein are methods wherein the method further comprises contacting the surface with a capping solution, wherein capping prevents extension of unblocked nucleosides. Further provided herein are methods wherein the wash solvent is functionally equivalent to a primary constituent by volume of a previously contacted reagent solution. Further provided herein are methods wherein one or more steps is followed by washing the surface with the wash solvent. Further provided herein are methods wherein one or more steps is followed by washing the surface with acetonitrile. Further provided herein are methods wherein each step subsequent to a coupling, capping, or deblocking step is followed by washing the surface with the wash solvent. Further provided herein are methods wherein the at least one nucleoside comprises a phosphoramidite. Further provided herein are methods wherein the at least one nucleoside comprises a 5' blocking group. Further provided herein are methods wherein the at least one nucleoside comprises a 3' blocking group. Further provided herein are methods wherein the structure is a plate, a tape, a belt, or a bead. Further provided herein are methods wherein the oxidizing solution comprises iodine. Further provided herein are methods wherein the polynucleotide or nucleoside comprises DNA or RNA.

Provided herein are methods for polynucleotide synthesis, comprising: a) providing a structure comprising a surface; b) coupling at least one nucleoside to a polynucleotide attached to the surface; c) depositing an oxidizing solution on the surface; d) depositing a wash solvent on the surface, wherein 12 or iodine salts have a greater solubility or increased rate of dissolution in the wash solvent compared to acetonitrile; e) repeating steps b-d to synthesize a plurality of polynucleotides. Further provided herein are methods wherein the method further comprises depositing a deblocking solution on the surface, wherein deblocking allows coupling of the polynucleotide to a nucleoside. Further provided herein are methods wherein one or more steps is followed by washing the surface with the wash solvent. Further provided herein are methods wherein one or more steps is followed by washing the surface with acetonitrile. Further provided herein are methods wherein each step subsequent to a coupling or deblocking step is followed by washing the surface with the wash solvent. Further provided herein are methods wherein the wash solvent is functionally equivalent to a primary constituent by volume of a previously contacted reagent solution. Further provided herein are methods wherein the at least one nucleoside comprises a phosphoramidite. Further provided herein are methods wherein the at least one nucleoside comprises a 5' blocking group. Further provided herein are methods wherein the at least one nucleoside comprises a 3' blocking group. Further provided herein are methods wherein the structure is a plate, a tape, a belt, or a bead. Further provided herein are methods wherein the oxidizing solution comprises iodine. Further provided herein are methods wherein the oxidizing solution further comprises an amine base. Further provided herein are methods wherein the amine base is selected from pyridine, lutidine, collidine, N-methyl morpholine, or a functional equivalent thereof.

Further provided herein are methods wherein the polynucleotide or nucleoside comprises DNA or RNA.

Provided herein are methods of synthesizing polynucleotides, comprising: a) providing predetermined sequences for a plurality of preselected polynucleotides; b) providing a substrate comprising a surface; c) synthesizing the plurality of preselected polynucleotides extending from the surface, wherein synthesizing comprises one or more wash steps with a wash solvent after depositing an oxidizing solution on the surface, wherein the wash solvent dissolves an active component or byproduct of the oxidizing solution, wherein the wash solvent comprises a ketone, an ester, an ether, a hydrocarbon, or a functional equivalent thereof and d) assembling the plurality of preselected polynucleotides. Further provided herein are methods wherein the method further comprises washing before or after depositing the oxidizing solution on the surface, wherein washing comprises depositing the wash solvent on the surface. Further provided herein are methods wherein the wash solvent comprises a ketone, ether, or a functional equivalent thereof. Further provided herein are methods wherein the wash solvent comprises acetone, tetrahydrofuran, or a functional equivalent thereof. Further provided herein are methods wherein the oxidizing solution comprises iodine. Further provided herein are methods wherein the oxidizing solution further comprises an amine base. Further provided herein are methods wherein the amine base is selected from pyridine, lutidine, collidine, N-methyl morpholine, or a functional equivalent thereof. Further provided herein are methods wherein the polynucleotide or nucleoside comprises DNA or RNA.

Provided herein are methods for polynucleotide synthesis, comprising: a) providing a structure comprising a surface; b) coupling at least one nucleoside to a polynucleotide attached to the surface; c) depositing an oxidizing solution on the surface; d) depositing a capping solution on the surface before or after depositing the oxidizing solution on the surface; e) repeating steps b-d to synthesize a plurality of polynucleotides. Further provided are methods further comprising depositing the capping solution on the surface before and after depositing the oxidizing solution on the surface. Further provided are methods further comprising depositing a wash solvent after (i) coupling the at least one nucleoside to the polynucleotide attached to the surface; (ii) depositing the capping solution; and (iii) depositing the oxidizing solution. Further provided are methods wherein the wash solvent deposited after depositing the oxidizing solution comprises a ketone, an ester, an ether, a hydrocarbon, or a functional equivalent thereof. Further provided are methods wherein the wash solvent deposited after depositing the oxidizing solution comprises a ketone, ether or a functional equivalent thereof. Further provided are methods wherein the wash solvent deposited after depositing the oxidizing solution comprises acetone, THF or a functional equivalent thereof. Further provided are methods wherein the wash solvent deposited after the coupling step or the capping step comprises acetonitrile. Further provided are methods wherein the wash solvent deposited after the coupling step or the capping step comprises acetone, tetrahydrofuran, or a functional equivalent thereof. Further provided are methods wherein the wash solvent comprises a ketone, an ester, an ether, a hydrocarbon, or a functional equivalent thereof. Further provided are methods wherein the wash solvent comprises a ketone, an ether, or a functional equivalent thereof. Further provided are methods wherein the wash solvent comprises acetone, tetrahydrofuran, or a functional equivalent thereof. Further provided are methods wherein the capping solution comprises an acid halide or an anhydride. Further provided are methods wherein the capping solution comprises acetyl chloride or acetic anhydride. Further provided are methods wherein the capping solution comprises an amine base. Further provided are methods wherein the polynucleotide or nucleoside comprises DNA or RNA.

The following examples are set forth to illustrate more clearly the principle and practice of instances disclosed herein to those skilled in the art and are not to be construed as limiting the scope of any claimed instances. Unless otherwise stated, all parts and percentages are on a weight basis.

EXAMPLES

Example 1: Polynucleotide Synthesis with Acetone Wash Steps

A substrate surface (such as a silicon plate) was functionalized with 3-glycidoxypropyltrimethoxysilane (GOPS), a chemical group capable of reacting with a phosphoramidite to support the attachment and synthesis of a library of polynucleotides. Synthesis of polynucleotides was accomplished through iteration of the following steps: 1) extension of a plurality of polynucleotides from the surface by contacting the surface with a base addition solution comprising at least one reactive monomer, wherein the at least one reactive monomer was a 3' phosphoramidite nucleobase (A, T, G, or C) comprising a 5' blocking group; 2) washing the surface at least once; 3) contacting the surface with an oxidizing solution comprising iodine; 4) washing the surface at least once; and 5) removing the 5' blocking group with a deblocking solution; and 6) washing the surface at least once. Steps 1-6 were repeated until the plurality of polynucleotides were synthesized.

Two different sets of conditions were used with the above polynucleotide synthesis method. In conditions A, washing steps were completed using acetone as the wash reagent. In conditions B, washing steps were completed using acetonitrile as the wash reagent. Polynucleotide library error rates for both conditions were analyzed with Next Generation Sequencing, and the results by error type are shown in Table 5. Error rates were decreased for Conditions A, with the largest percent decrease observed for single base deletions.

TABLE 5

Comparison of error rates for Conditions A and B.

| Error Type | Conditions A | Conditions B |
| --- | --- | --- |
| Insertion Rate | 0.000227 | 0.000315 |
| Mismatch Rate | 0.000798 | 0.000905 |
| Single Base Deletion Rate | 0.000539 | 0.001117 |
| Total Error Rate | 0.001564 | 0.002337 |

Figure 9A:
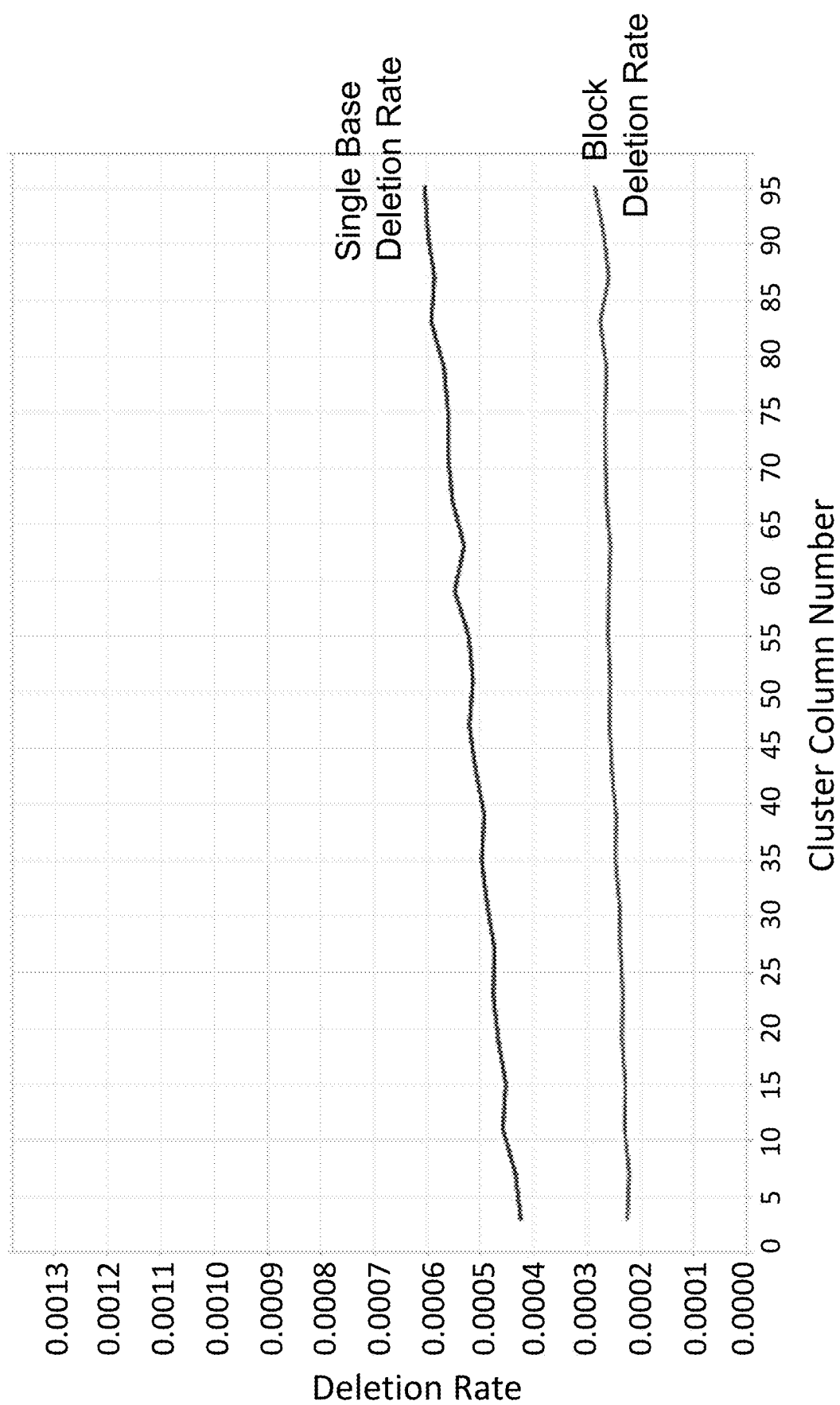
FIG. 9A depicts block deletion and single base deletion rates across columns of clusters on a surface for polynucleotides synthesized using washing Conditions A with acetone.
Figure 9B:
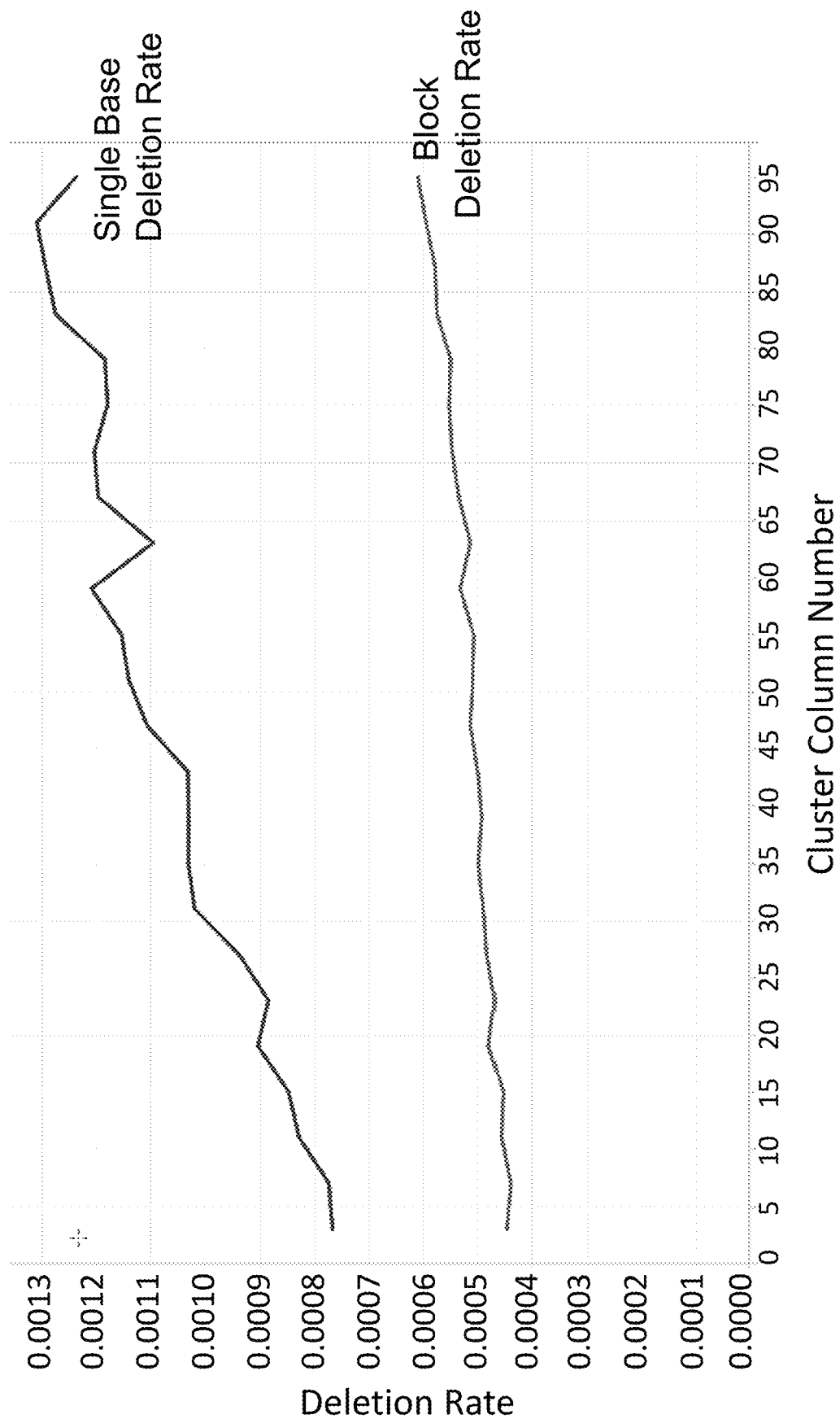
FIG. 9B depicts block deletion and single base deletion rates across columns of clusters on a surface for polynucleotides synthesized using washing Conditions B with acetonitrile.
Figure 9C:
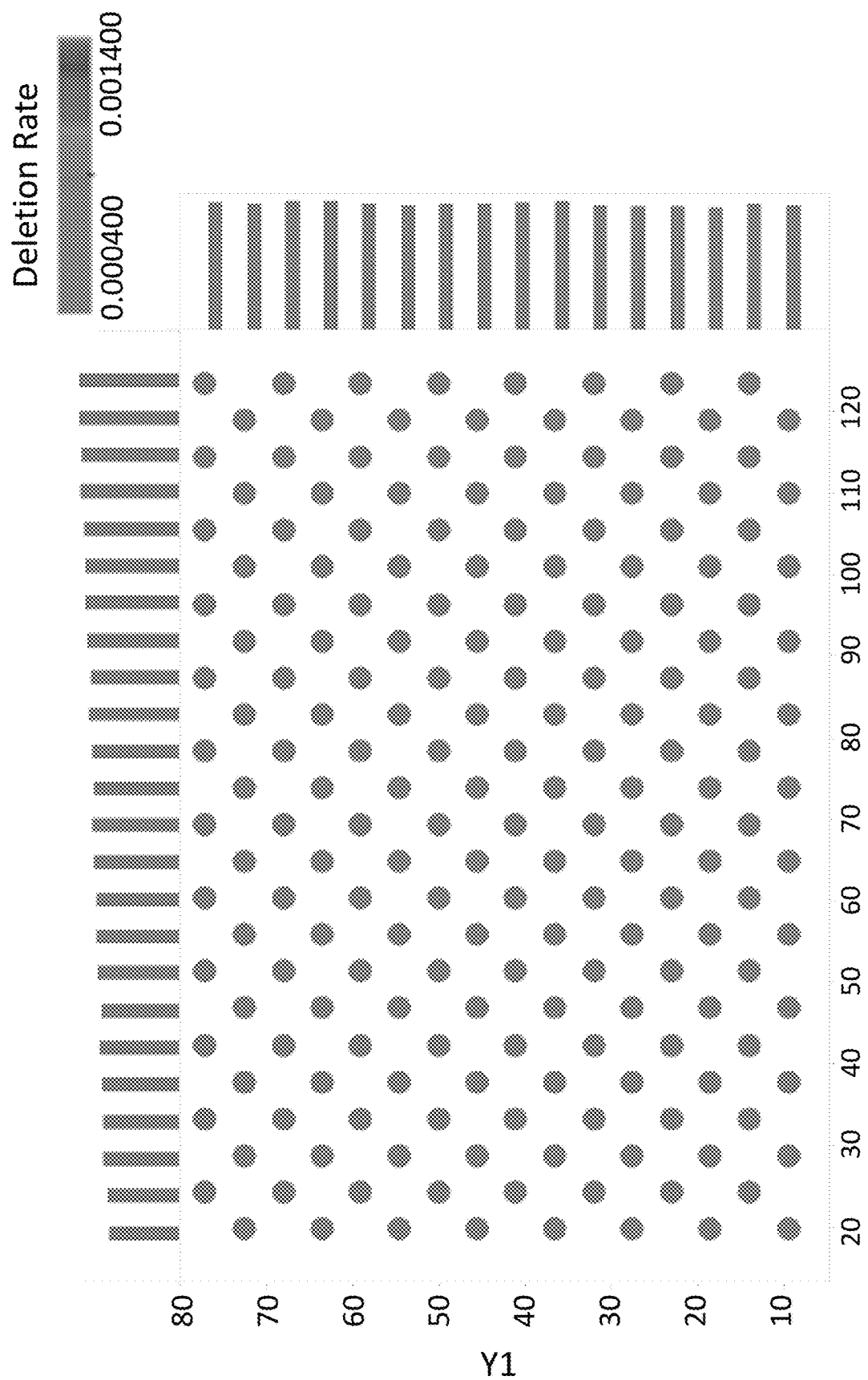
FIG. 9C depicts single base deletion rates across clusters on a surface for polynucleotides synthesized using washing Conditions A with acetone. Darker shaded circles indicate a higher deletion rate.
Figure 9D:
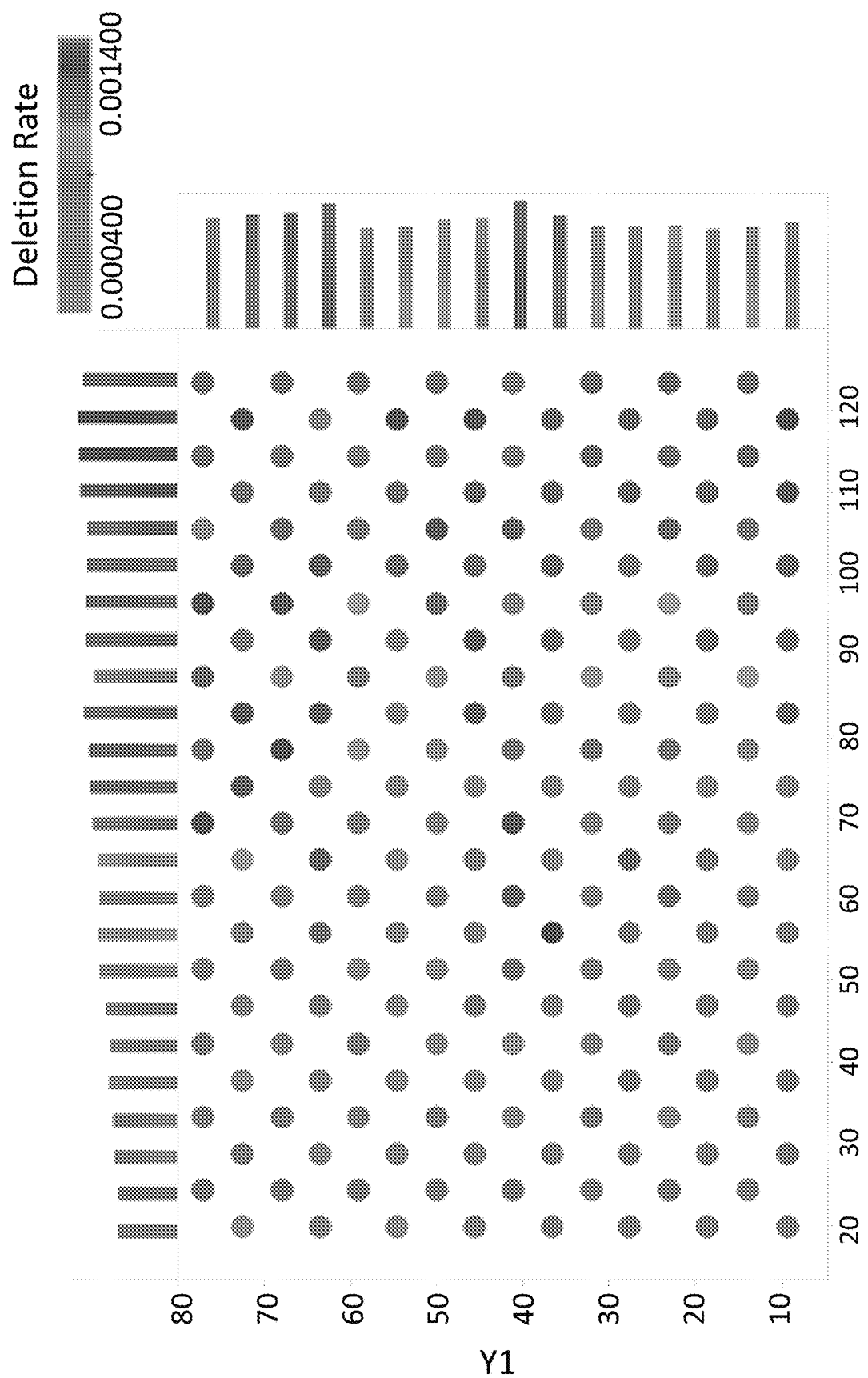
FIG. 9D depicts single base deletion rates across clusters on a surface for polynucleotides synthesized using washing Conditions B with acetonitrile. Darker shaded circles indicate a higher deletion rate.

Error rates for single base deletions and block deletions were further examined as a function of columns across the surfaces, wherein each column comprises a series of clusters. Condition A (FIG. 9A) provided lower deletion rates than Condition B (FIG. 9B), and the uniformity of deletions across cluster columns was higher for Conditions A. An examination of all clusters on the surface (plate) also demonstrated higher uniformity of single base deletion rates for Condition A (FIG. 9C) vs. Condition B (FIG. 9D) across clusters on the surface.

Example 2: Synthesis of Polynucleotides Using an Acetone Wash after Oxidation

A two dimensional polynucleotide synthesis device was assembled into a flowcell, which was connected to a flowcell (Applied Biosystems ("ABI394 DNA Synthesizer"). The surface of the polynucleotide synthesis device was functionalized with 3-glycidoxypropyltrimethoxysilane (GOPS), and was used to synthesize a library of polynucleotides using the synthesis methods described herein. The generic sequence of the nucleic acid synthesized on the surface was 5'-[polynucleotide]##[TTTTTTTTTT]-3', where # denotes Thymidine-succinyl hexamide CED phosphoramidite (CLP-2244 from ChemGenes), which is a cleavable linker enabling the release of the polynucleotides from the surface during deprotection. The 3' end of the polynucleotide was attached to the surface, and the TTTTTTTTTT sequence between the linker and the surface represents a polynucleotide spacer. Synthesis of the spacer region was performed by iteration of the following steps: 1) extension of a plurality of reactive molecules from the surface (initially GOPS, then nucleic acids or polynucleotides in subsequent steps) by contacting the surface with a base addition solution comprising at least one reactive monomer, wherein the at least one reactive monomer was a 3' phosphoramidite thymine comprising a 5' blocking group; 2) capping unreacted 5' OH groups of the thymine by contacting the surface with a capping solution; 3) washing the surface at least once with acetone; 4) contacting the surface with an oxidizing solution comprising iodine; 5) washing the surface at least once with acetone; 6) capping unreacted 5' OH groups of the thymine by contacting the surface with a capping solution; 7) removing the 5' blocking group with a deblocking solution; and 8) washing the surface at least once with acetone. Steps 1-8 were repeated until the plurality of polynucleotide spacers were synthesized. The cleavable linker group (##) was then coupled to the 5' end of the polynucleotide spacer, followed by washing the surface at least once with acetone.

Extension beyond the linker/spacer region to synthesize polynucleotides was performed by iteration of the following steps: 1) contacting the surface with a base addition solution comprising at least one reactive monomer, wherein the at least one reactive monomer was a 3' phosphoramidite nucleobase (A, T, G, or C) comprising a 5' blocking group; 2) contacting the surface with an oxidizing solution comprising iodine; 3) washing the surface at least once with acetone; and 4) removing the 5' blocking group with a deblocking solution; and 5) washing the surface at least once with acetone. Steps 1-5 were repeated until the plurality of polynucleotides were synthesized. After polynucleotide synthesis, polynucleotides were cleaved from the surface by deprotection in gaseous ammonia overnight for further analysis.

Figure 10:
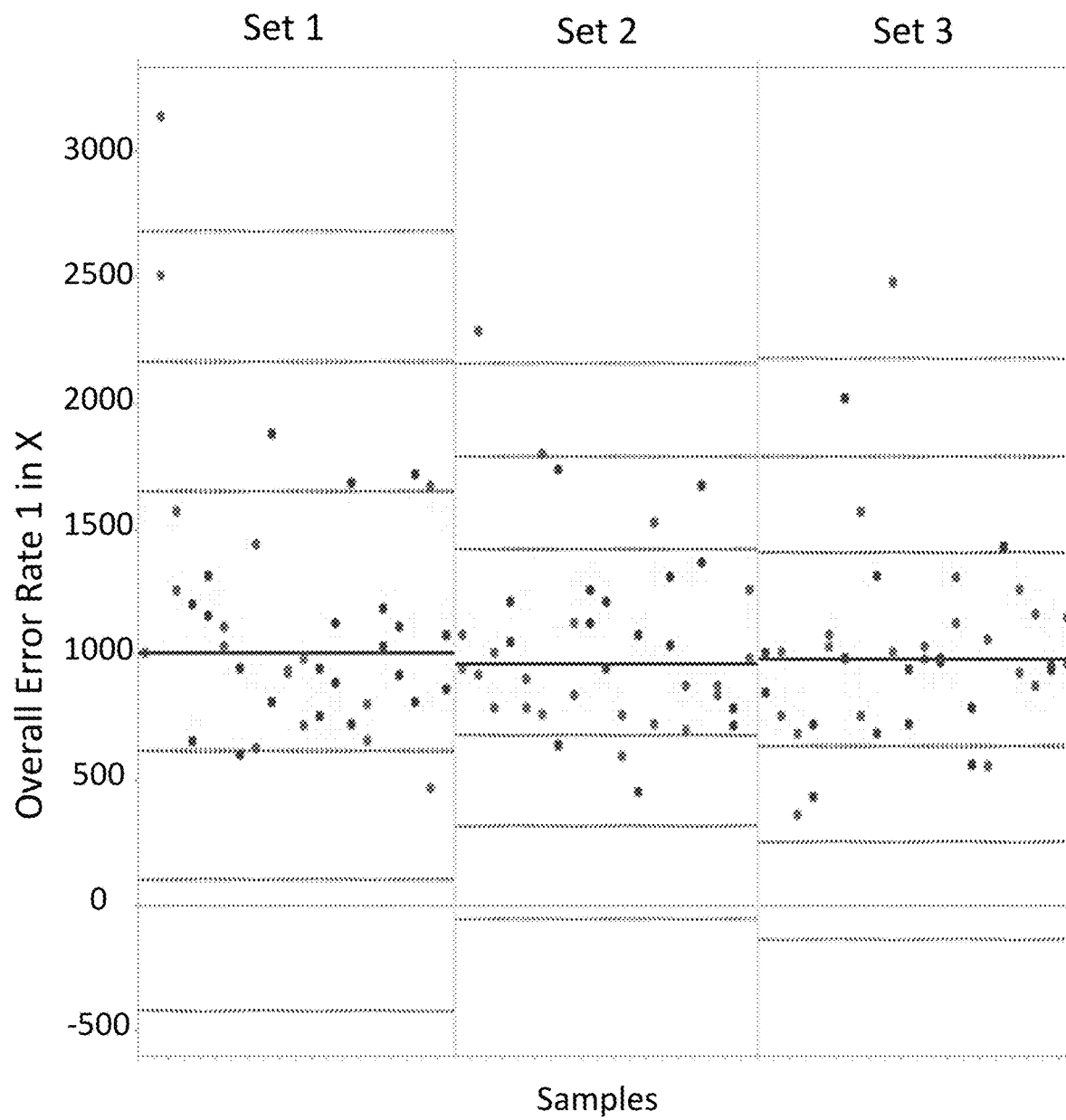
FIG. 10 depicts overall error rates for three different sets of samples determined using Sanger sequencing.
Figure 11A:
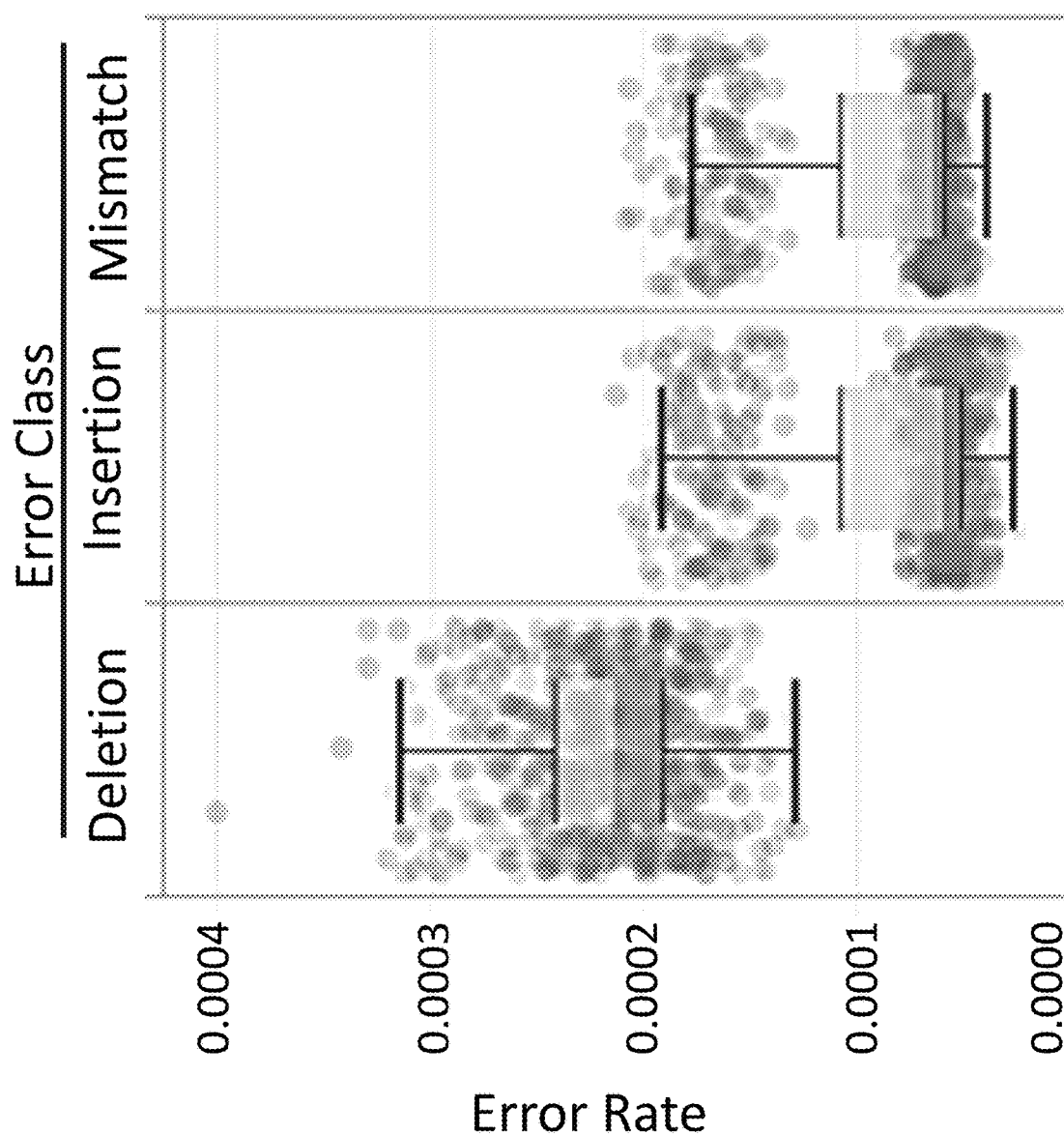
FIG. 11A depicts polynucleotide error rates by error class (deletion, insertion, or mismatch) determined using Next Generation Sequencing (NGS).
Figure 11B:
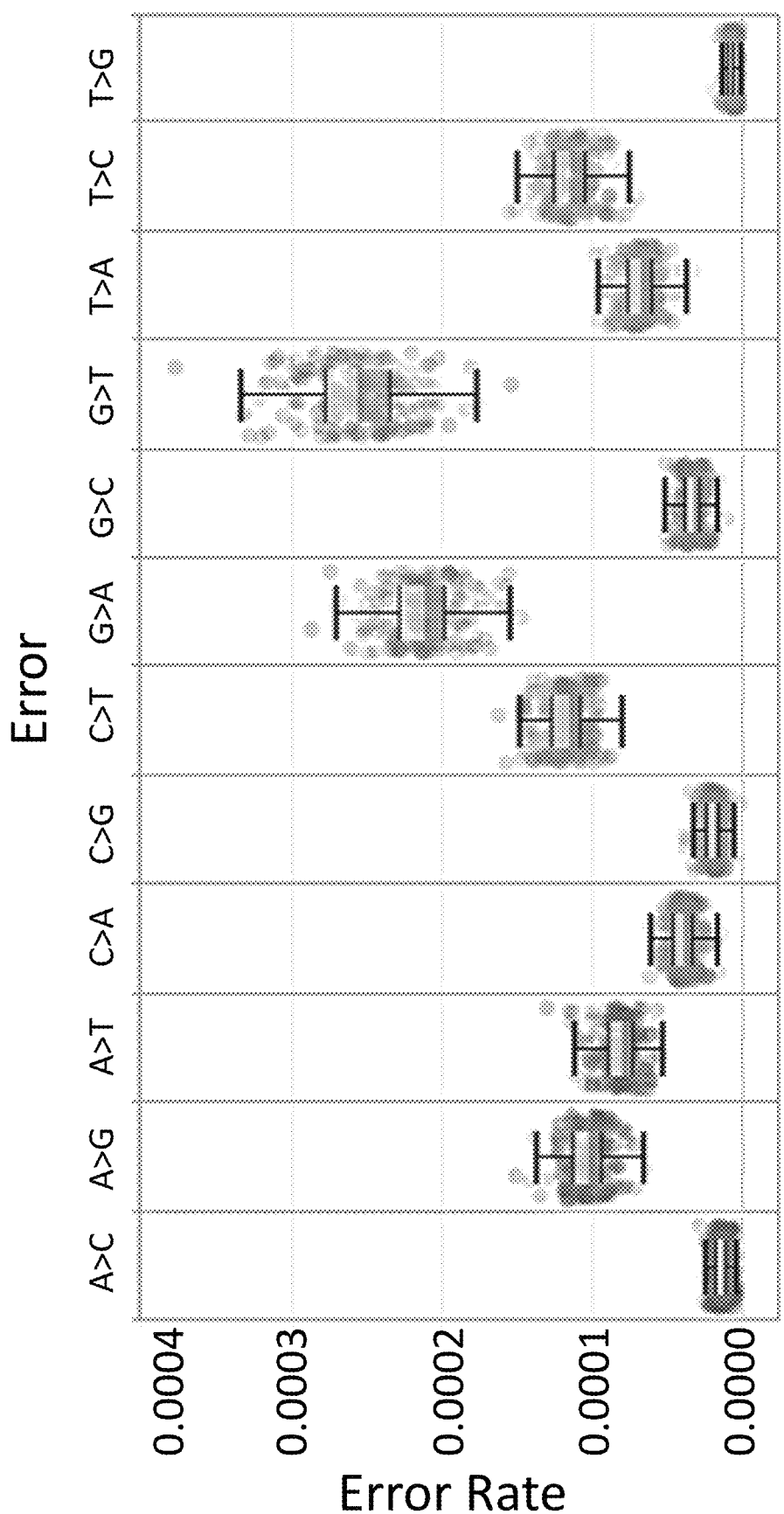
FIG. 11B depicts polynucleotide error rates for various substitutions determined using Next-Generation Sequencing (NGS).
Figure 11C:
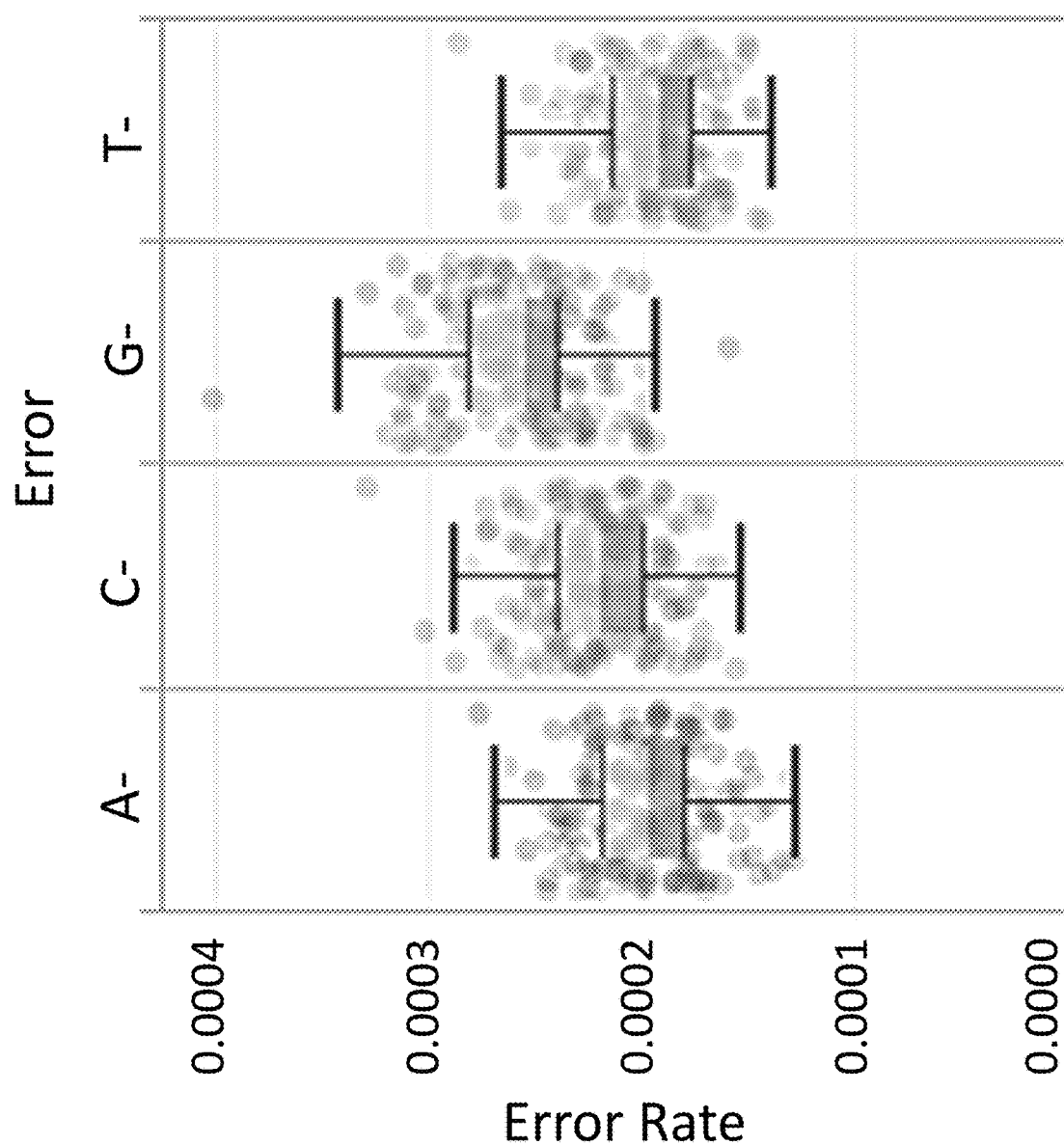
FIG. 11C depicts polynucleotide error rates for deletions determined using NGS.
Figure 11D:
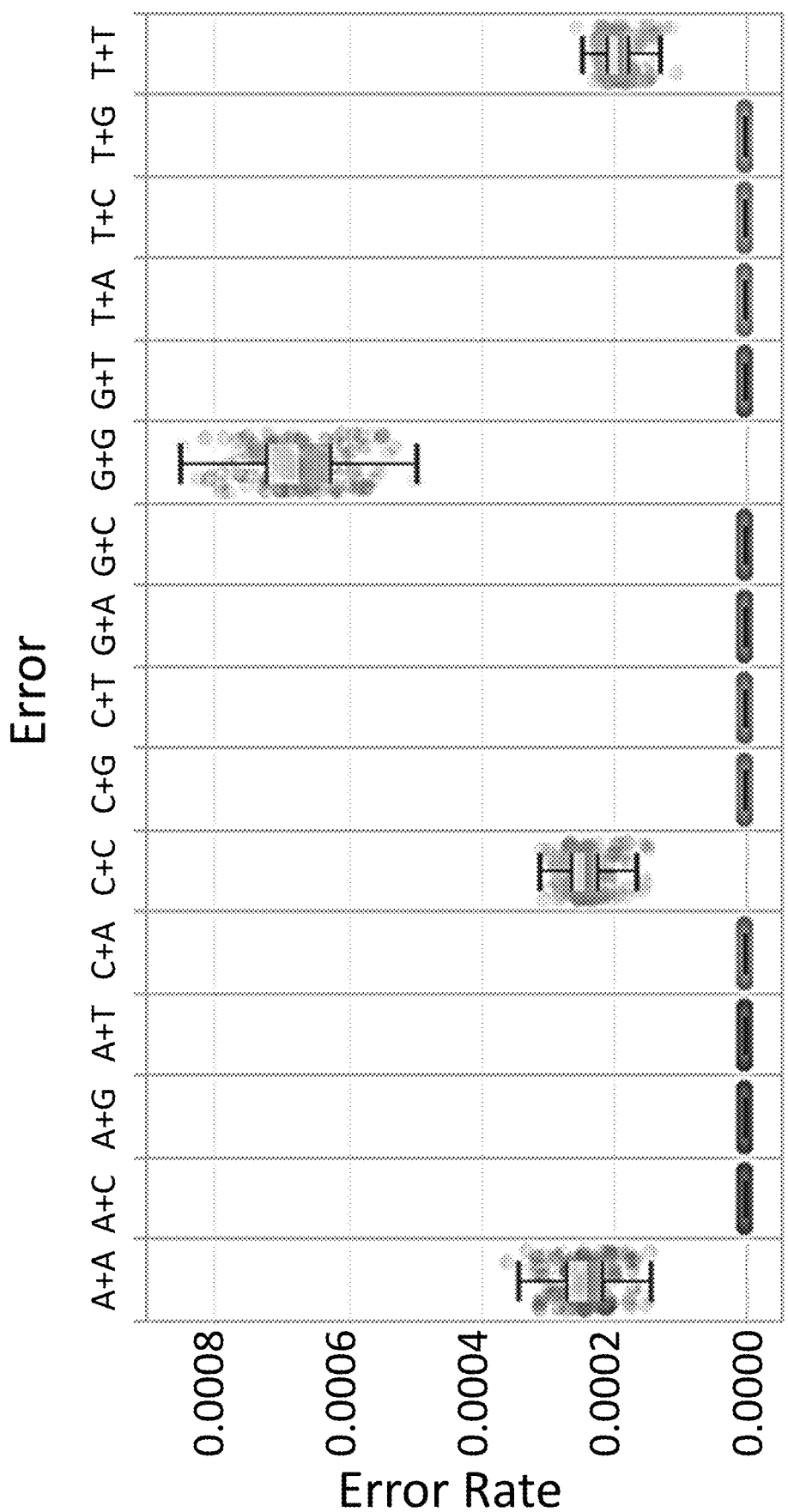
FIG. 11D depicts polynucleotide error rates for insertions determined using NGS.
Figure 11E:
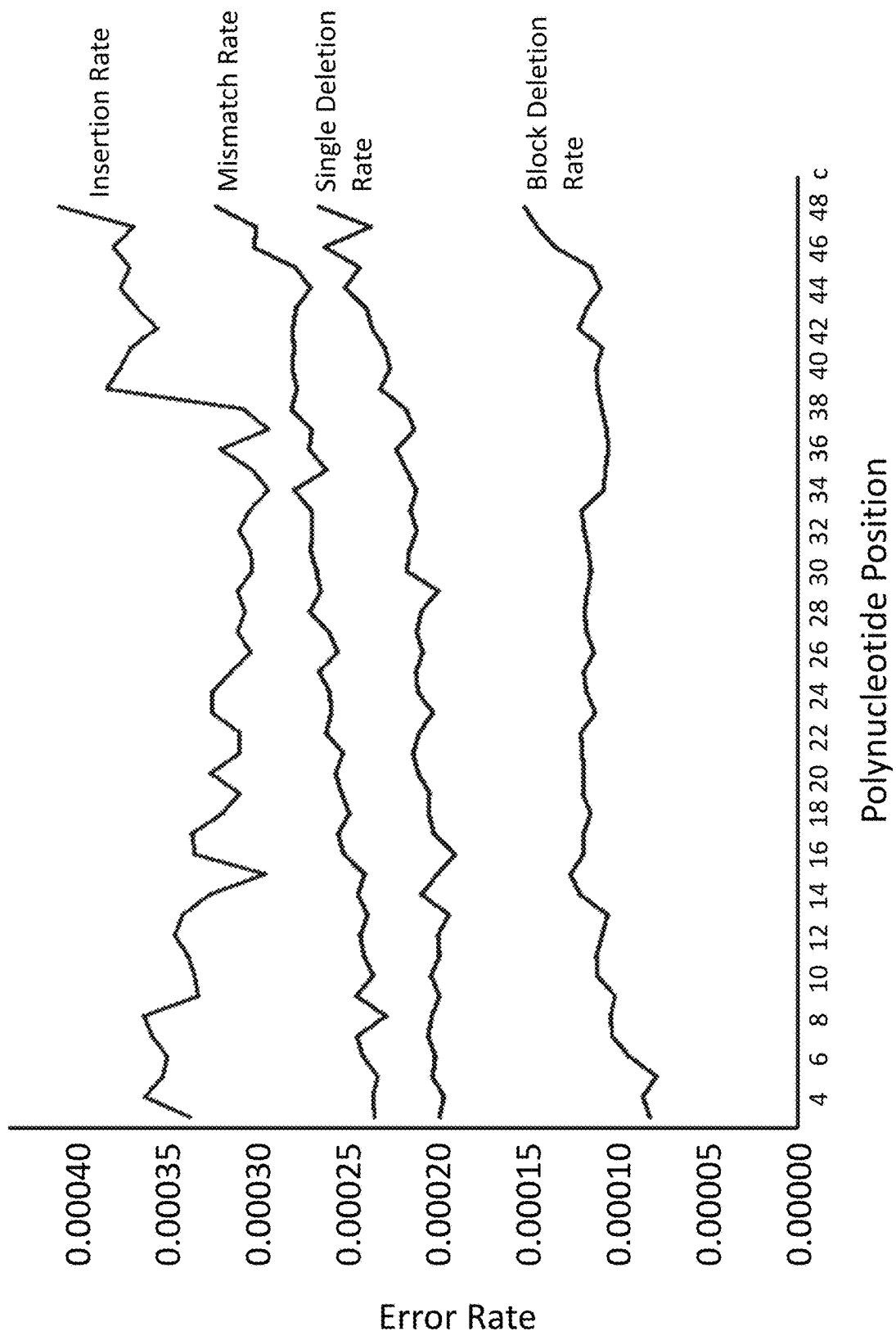
FIG. 11E depicts error rates for various error classes (insertions, mismatches, single deletions, and block deletions) at different base positions on a synthesized polynucleotide, determined using NGS. The base at position one is furthest from the synthesis surface, and therefore was added last to the synthesized polynucleotide chain.
Figure 12A:
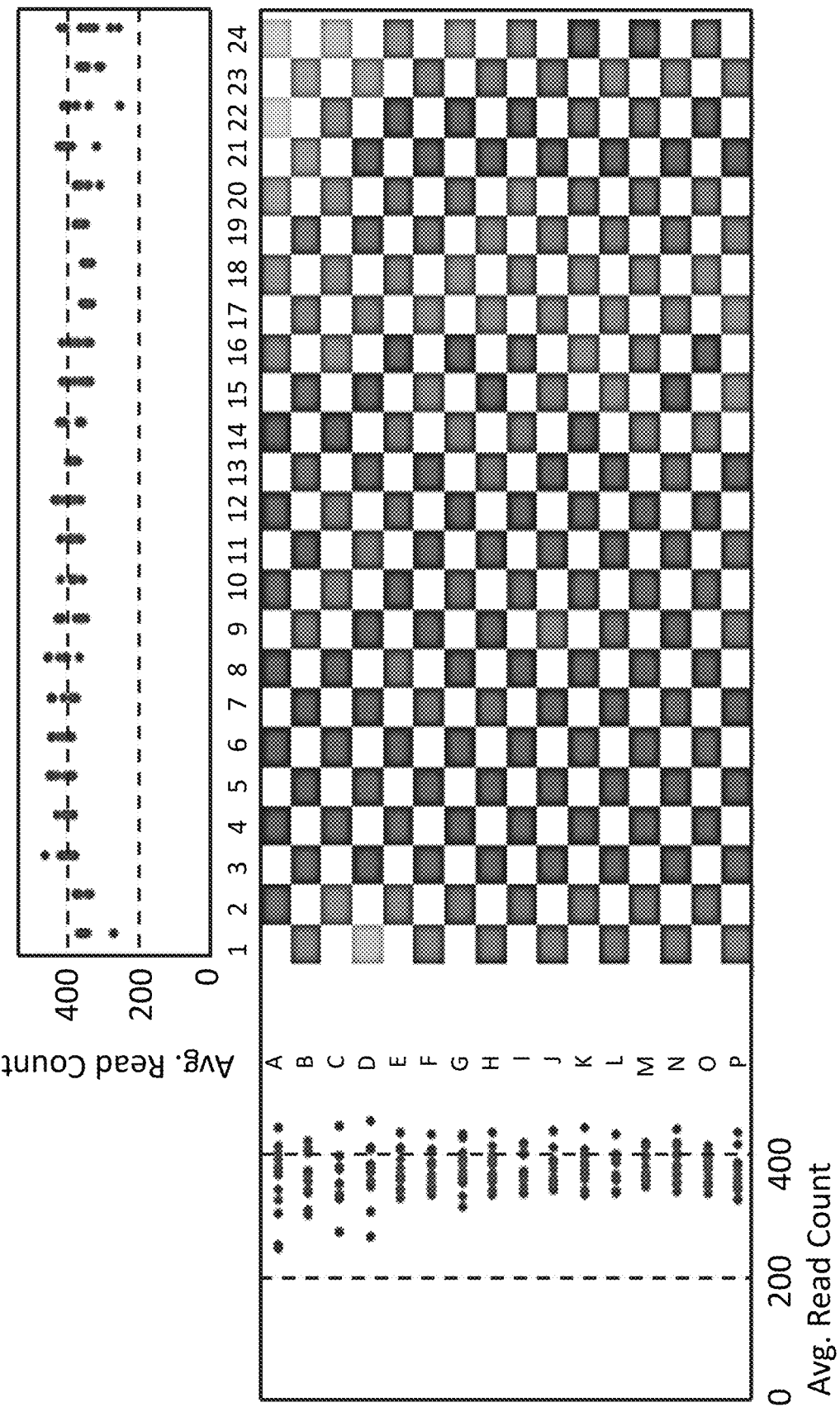
FIG. 12A depicts representation uniformity, dropout rate, and total reads of synthesized polynucleotides at various positions on a synthesis surface. Lighter shaded squares on the surface indicate lower average read count, and darker shaded squares indicate higher average read count.
Figure 12B:
FIG. 12B depicts representation uniformity of a synthesized polynucleotide library.
Figure 12B:
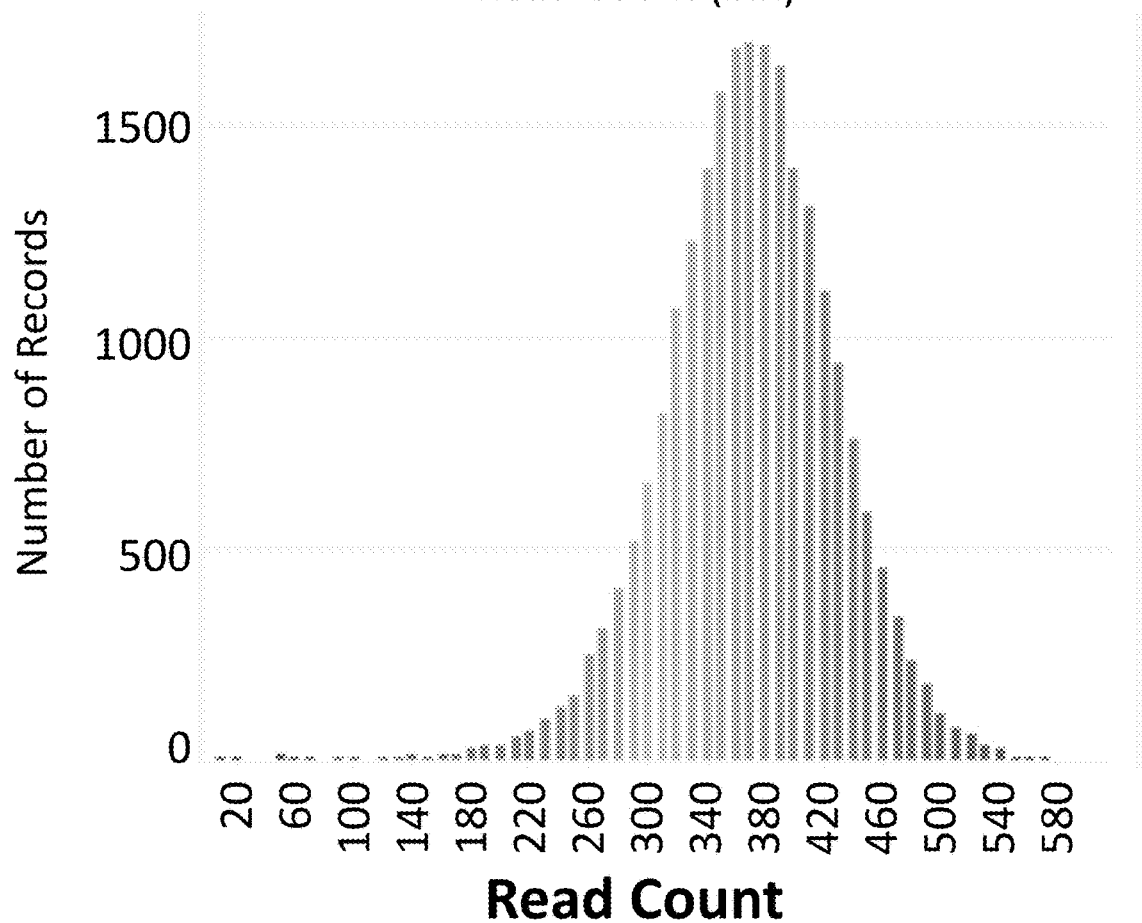
Figure 12C:
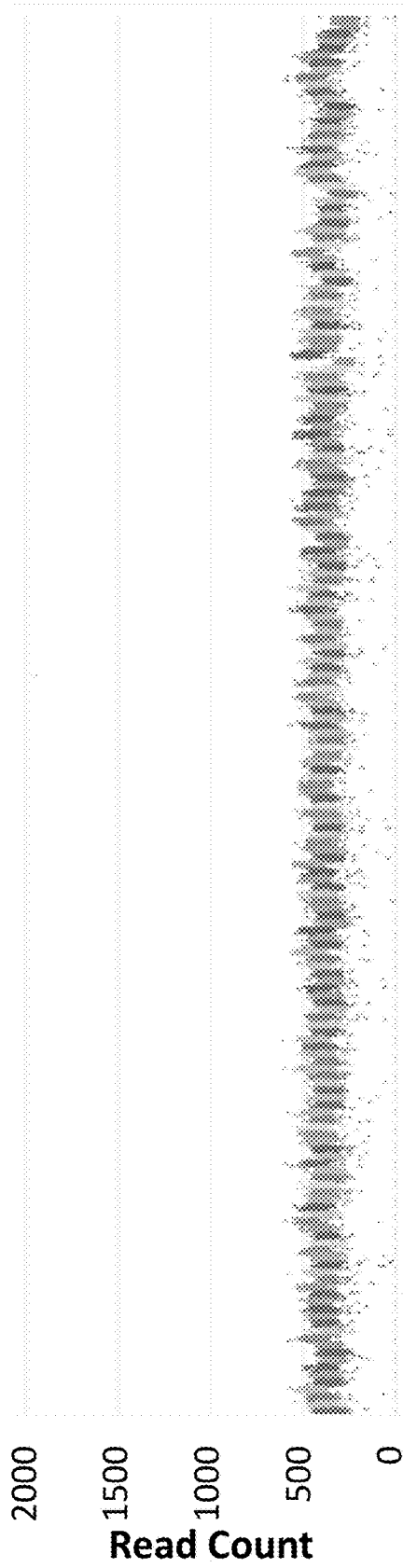
FIG. 12C depicts representation uniformity of a synthesized polynucleotide library as a function of cluster (top) and device (bottom). Different levels of shading indicate individual clusters (top) or devices (bottom).
Figure 12C:
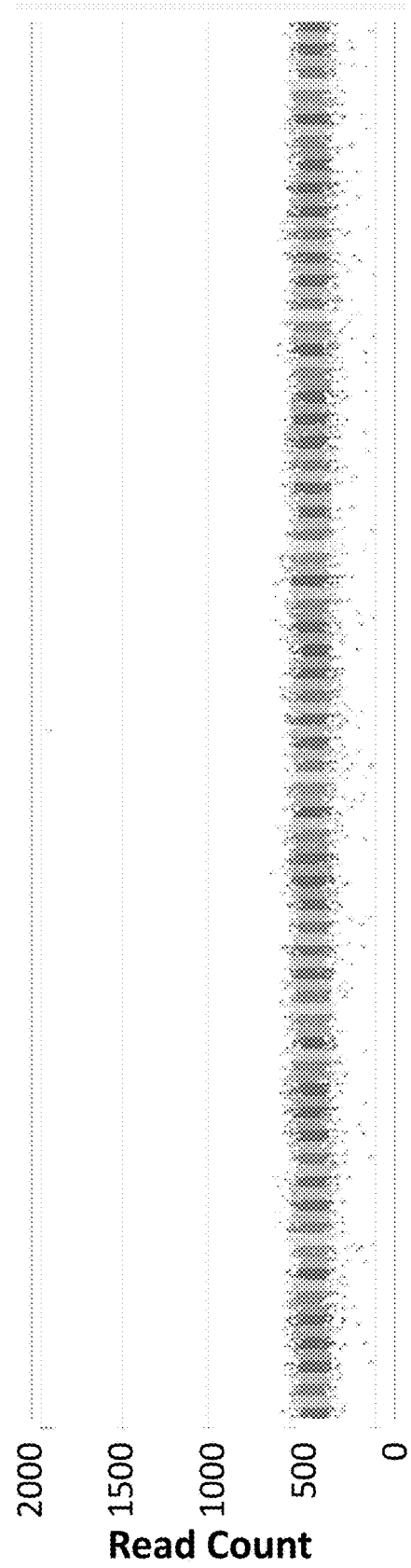

Polynucleotide libraries were synthesized at high uniformity. Several methods were used to evaluate the quality of the polynucleotide library, including Sanger sequencing and Next generation sequencing. The overall error rates for three different sets of oligonucleotide libraries were about 1/1000 or less (FIG. 10). Next generation sequencing was used to evaluate the quality of the polynucleotide library. Error rates for error classes deletions, insertions, and mismatches were measured (FIG. 11A). For example, substitution rates were further evaluated as function of a reference base verses observed base. Substitutions occurred at a uniform rate, with a slightly increased rate of substitution for G to A and G to T substitutions. (FIG. 11B). Deletion rates for each base type were measured; rates were comparable for all bases, about 0.002 (FIG. 11C). G+G insertions increased verses A+A, C+C, and T+T insertion errors (FIG. 11D). Insertion, mismatch, single deletion and block deletion rates were also evaluated as a function of base position on the polynucleotide. Observed error rates were uniform across all positions in the synthesized polynucleotide, with x axis correlating to bases distanced from the surface (FIG. 11E). To evaluate dropouts, clusters from each area of the plate (FIG. 12A) were evaluated for average read count, with a total of 8.7 million reads (Table 6). Mean read counts across all clusters were about 400, and were highly uniform in both the x (1-24) and y (A-P) directions of the plate. The dropout rate was less than 0.0%, with a uniformity of 1.7× of the mean in the distribution curve in FIG. 12B. In another depiction of error rate, read count was highly uniform across clusters (FIG. 12C, top) and across multiple devices (FIG. 12C, bottom).

TABLE 6

Polynucleotide Library Measurements

| Metric | Value |
| --- | --- |
| Dropouts | 0.0% |
| Uniformity | 1.7x |
| Total Reads | 8.7 million |
| Mean ± SD | 374 ± 61 |

Example 3: Wash Solutions to Remove Undesired G→a and T/U→C Mutations

A wash solution was prepared as described herein comprising THF, pyridine, and water in an 80:20:10 ratio. Following the general procedure of Examples 1 and 2, phosphoramidite chemistry was used to synthesize samples of polynucleotides. Sample A used a post-coupling wash with the wash solution comprising THF/pyridine/water, followed by acetone, and a second sample B utilized a post-coupling wash of acetone. Deprotection of the first sample with methylamine and a wash step with the wash solution comprising THF, pyridine, and the O-nucleophile (water) resulted in no T→C and G→A mutation rate above the noise level (rates less than 1/5000), as detected by NGS. Deprotection of the second sample with methylamine and a wash step with acetonitrile or acetone resulted in T→C and G→A mutation rates greater than 1/1500. Uniformity of syntheses carried out using the wash solution was highly improved. The results showed complete removal, within the detection limit, of the phosphoramidite/tetrazole material deposited in the previous coupling reaction by printing. Uniformity of the resulting polynucleotides was improved for Sample A. For sample A, approximately >90% of all records had between 220 and 670 reads. For sample B, approximately >90% of all records had between 30 and 940 reads.

TABLE 7

Wash solution results

| Sample | Dropouts (%) | Uniformity | Total Reads (millions) | Mean ± SD |
|---|---|---|---|---|
| A | 0.1 | 6.9 | 12 | 518 ± 229 |
| B | 0.1 | 1.9 | 10.1 | 436 ± 88 |

Example 4: Capping to Remove Undesired G→a and T/U→C Mutations

A capping solution 1 was prepared as described herein comprising THF, lutidine, acetic anhydride in an 80:10:10 ratio, with added acetic acid (10 g/L). A capping solution 2 comprising acetonitrile and n-methylimidazole in a 90:10 ratio was also prepared. Following the general procedure of Examples 1 and 2, phosphoramidite chemistry was used to synthesize samples of polynucleotides. Sample A was washed a mix of solutions 1 and 2, and a second sample B was washed using a capping solution in the absence of the acetic acid. Deprotection of the first sample with methylamine and a wash step with the capping solution comprising the O-nucleophile (acetic acid) resulted in no T→C and G→A mutation rate above the noise level (rates of 1/10101), as detected by NGS. Deprotection of the second sample with methylamine and a wash step with a capping solution without the O-nucleoside resulted in T→C and G→A mutation rates of 1/3058. The addition of alternative O-nucleophiles such as sigma-acceptor-substituted acetic acid derivatives, such as methoxyacetic acid and phenoxyacetic acid, also increased the efficiency of the capping reaction.

Example 5: Capping Order

Following the general procedures of Examples 1 and 2, sample A was washed with a capping solution after oxidation, and sample B was washed with a capping solution before oxidation. For sample A, the procedure was Wash—Acetone—Ox—Acetone—CapMix (from Example 4)—Acetone—Deblock—Acetone. Sample B had a single base deletion rate of 1/1196, while Sample A had a single base deletion rate of 1/5450.

Example 6: Base Protected Phosphoramidites

Protected dT and dG phosphoramidite building blocks A-I containing a protecting group at nitrogen atoms N3 and N1, were incorporated into polynucleotides using the general procedure of Examples 1 and 2. After deprotection of the resulting polynucleotide products with MeNH$_2$, no T->C and G->A mutation above the noise-level (rates less than 1/5000) could be detected by the limits of NGS, whereas a control experiment using standard, unprotected nucleoside phosphoramidites resulted in mutation rates of greater than 1/1500 were obtained. The use of base protected nucleoside phosphoramidites led to lower error rates.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of polynucleotide synthesis comprising:
   providing predetermined sequences for a plurality of preselected polynucleotides;
   providing a structure comprising a silicon surface;
   coupling at least one nucleoside to a polynucleotide attached to the silicon surface;
   washing the silicon surface with a wash solvent, wherein the wash solvent consists essentially of acetone;
   washing the silicon surface with a capping solution, the capping solution comprising:
   (i) at least one base;
   (ii) at least one O-nucleophile selected from a group consisting of acetic acid, formic acid, propionic acid, methoxyacetic acid, phenoxyacetic acid, and water; and
   (iii) tetrahydrofuran;
   oxidizing a linkage between the at least one nucleoside and the polynucleotide with an oxidizing solution; and
   repeating the coupling, washing, capping, and oxidizing steps to synthesize a plurality of polynucleotides.

2. The method of claim 1, wherein the silicon surface is washed with the wash solvent after the coupling step.

3. The method of claim 1, wherein the at least one base is selected from the group consisting of pyridine, lutidine, and collidine.

4. The method of claim 1, wherein a concentration of the at least one O-nucleophile is 0.01-3 M.

5. The method of claim 1, wherein the capping solution further comprises at least one electrophile, and wherein the at least one electrophile is an anhydride, NHS ester, or acid halide.

6. The method of claim 1, wherein a concentration of the at least one base is 0.01-3 M.

7. The method of claim 1, wherein the capping solution comprises the at least one base at about 5-30%, the at least one O-nucleophile at about 5-30%, and the tetrahydrofuran at about 60-90%.

8. The method of claim 1, wherein the oxidizing solution comprises I$_2$ or iodine salts, and the I$_2$ or iodine salts have a greater solubility or increased rate of dissolution in the wash solvent compared to acetonitrile.

9. The method of claim 1, wherein the capping solution further comprises an activator, wherein the activator is N-methylimidazole or DMAP.

10. The method of claim 9, wherein concentration of the activator in the capping solution is 0.001-0.05 M.

11. The method of claim 1, wherein oxidizing the linkage between the at least one nucleoside and the polynucleotide with the oxidizing solution includes depositing the oxidizing solution on the silicon surface and the method further comprises a washing step with the wash solvent after depositing the oxidizing solution on the silicon surface.

12. The method of claim 1, wherein the polynucleotide or nucleoside comprises DNA or RNA.

13. The method of claim 1, wherein the structure is a plate, a tape, or a belt, and the silicon surface is functionalized with 3-glycidoxypropyltimethoxysilane.

14. A method for polynucleotide synthesis, comprising:
providing predetermined sequences for a plurality of polynucleotides;
providing a structure comprising a silicon surface, wherein the silicon surface comprises a plurality of discrete loci configured for polynucleotide synthesis;
coupling at least one nucleoside to a polynucleotide attached to the silicon surface, according to the predetermined sequences;
oxidizing a linkage between the at least one nucleoside and the polynucleotide with an oxidizing solution; and
washing the silicon surface with a wash solvent, wherein the wash solvent consists essentially of acetone.

15. A method for polynucleotide synthesis, the method comprising repeating the steps of claim 14 to synthesize a plurality of polynucleotides, wherein the plurality of polynucleotides are synthesized at an error rate of about 1/5000 or less.

16. The method of claim 14, wherein the silicon surface is washed with the wash solvent after the at least one nucleoside is coupled to the polynucleotide.

17. The method of claim 16, further comprising depositing a capping solution on the silicon surface, wherein the capping solution comprises acetyl chloride, acetic anhydride, or an amine base.

18. The method of claim 17, wherein washing the silicon surface with the wash solvent occurs after oxidizing the linkage and prior to depositing the capping solution, and where the method further comprises,
after depositing the capping solution, washing the silicon surface with the wash solvent.

19. The method of claim 14, wherein the silicon surface is functionalized with 3-glycidoxypropyltrimethoxysilane.

20. The method of claim 14, wherein the oxidizing solution comprises $I_2$ or iodine salts, and the $I_2$ or iodine salts have a greater solubility or increased rate of dissolution in the wash solvent compared to acetonitrile.

21. The method of claim 14, further comprising depositing a deblocking solution on the silicon surface, wherein the deblocking solution includes a deblocking reagent configured to remove a 5' OH protecting group.

22. The method of claim 21, wherein the deblocking solution comprises:
acetonitrile, acetone, tetrahydrofuran, or toluene; and
an acid.

* * * * *